(12) United States Patent
Lees et al.

US007807384B2

(10) Patent No.: US 7,807,384 B2
(45) Date of Patent: Oct. 5, 2010

(54) LOW DENSITY LIPOPROTEIN BINDING PROTEINS AND THEIR USE IN DIAGNOSING AND TREATING ATHEROSCLEROSIS

(75) Inventors: Ann M. Lees, Brookline, MA (US);
Robert S. Lees, Brookline, MA (US);
Simon W. Law, Lexington, MA (US);
Anibal A. Arjona, Boston, MA (US)

(73) Assignee: Boston Heart Foundation, Inc., Cambridge, MA (US)

( * ) Notice: Subject to any disclaimer, the term of this patent is extended or adjusted under 35 U.S.C. 154(b) by 189 days.

(21) Appl. No.: 12/137,832

(22) Filed: Jun. 12, 2008

(65) Prior Publication Data

US 2010/0028327 A1 Feb. 4, 2010

Related U.S. Application Data

(60) Division of application No. 10/671,242, filed on Sep. 24, 2003, now Pat. No. 7,402,395, which is a continuation of application No. 09/616,289, filed on Jul. 14, 2000, now Pat. No. 6,632,923, which is a continuation-in-part of application No. 09/517,849, filed on Mar. 2, 2000, now Pat. No. 6,605,588, which is a continuation-in-part of application No. 08/979,608, filed on Nov. 26, 1997, now Pat. No. 6,355,451.

(60) Provisional application No. 60/031,930, filed on Nov. 27, 1996, provisional application No. 60/048,547, filed on Jun. 3, 1997.

(51) Int. Cl.
*G01N 33/53* (2006.01)
*C07K 1/00* (2006.01)

(52) U.S. Cl. .................................. 435/7.1; 530/359

(58) Field of Classification Search .................... None
See application file for complete search history.

(56) References Cited

U.S. PATENT DOCUMENTS

| 4,660,563 A | 4/1987 | Lees |
| 4,877,599 A | 10/1989 | Lees |
| 5,196,324 A | 3/1993 | Bumol et al. |
| 5,661,015 A | 8/1997 | Binger et al. |
| 5,665,872 A | 9/1997 | Saito et al. |
| 5,726,153 A | 3/1998 | Lees et al. |

FOREIGN PATENT DOCUMENTS

| DE | 4222385 | 1/1994 |
| EP | 0586094 | 3/1994 |
| EP | 0773290 | 5/1997 |
| JP | 59206046 | 11/1984 |
| WO | WO 91/06011 | 5/1991 |
| WO | WO 91/16919 | 11/1991 |
| WO | WO 94/16074 | 7/1994 |
| WO | WO 96/12811 | 5/1996 |
| WO | WO 98/23282 | 6/1998 |

OTHER PUBLICATIONS

Accession AF006088, GenBank, Dec. 15, 1999.
Accession AF017807, GenBank, Sep. 18, 1997.
Accession AL022098, GenBank, Nov. 23, 1999.
Accession AL049795, GenBank, Feb. 18, 2000.
Accession AL137800, GenBank, Jun. 20, 2000.
Accession L15344, GenBank, May 25, 1995.
Accession NM005717, GenBank, Jun. 9, 1999.
Altenburger et al., Database: A_Geneseq_0601, Accession No. AAW33626 (May 21, 1998).
Ambrus et al., Identification of a cDNA for a human high-molecular-weight B-cell growth factor, PNAS 93:8154 (1996).
Ambrus, Jr. et al., "Identification of a cDNA for a human high-molecular-weight B-cell growth factor," Proc. Natl. Acad. Sci. USA, 90:6630-6334, (Jul. 1993).
Bendayan, M., J. "Possibilities of False Immunocytochemical Results Generated by the Use of Monoclonal Antibodies: The Example of the Anti-proinsulin Antibody," Histochem. Cytochem. (1995), 43:9, pp. 881-886.
Camejo et al., "Characterization and Properties of a Lipoprotein-Complexing Proteoglycan from Human Aorta," Atherosclerosis, 35:307-320, (1980).
Chang et al., "Low-Density Lipoprotein Modification and Arterial Wall accumulation In a Rabbit Model of Atherosclerosis," Biochemistry, 32(33):8518-8524, (1993).
Chang et al., "Time Course of $^{125}$I-Labeled LDL Accumulation in the Healing, Balloon-Deendothelialized Rabbit Aorta," Arteriosclerosis and Thrombosis, 12(9):1088-1098, (Sep. 1992).
Daikin Kogyo Kk, Database: A_Geneseq_0601, Accession No. AAR30641 (May 6, 1993).
Davies, "Flow-Mediated Endothelial Mechanotransduction," Physiological Reviews, 75(3):519-560, (Jul. 1995).
de Rijke et al., "Rat Liver Kupffer and Endothelial Cells Express Different Binding Proteins for Modified Low Density Lipoproteins," The Journal of Biological Chemistry, 269(2):824-827, (Jan. 14, 1994).
DePaola et al., "Vascular Endothelium Responds to Fluid Shear Stress Gradients," Arteriosclerosis and Thrombosis, 12(11):1254-1257, (Nov. 1992).
Esterbauer et al., "The Role of Lipid Peroxidation and Antioxidants in Oxidative Modification of LDL," Free Radical Biology & Medicine, 13:341-390, (1992).
Fischman et al., "Accumulation of Native and Methylated Low Density Lipoproteins by Healing Rabbit Arterial Wall," Arteriosclerosis, 7(4):361-366, (Jul./Aug. 1987).

(Continued)

*Primary Examiner*—Karen Cochrane Carlson
(74) *Attorney, Agent, or Firm*—Fish & Richardson P.C.

(57) ABSTRACT

Isolated polynucleotides encoding novel polypeptides which are capable of binding to native and methylated LDL (low density lipoprotein), the isolated polypeptides, called LBPs (LDL binding proteins), and biologically active fragments and analogs thereof, are described. Also described are methods for determining if an animal is at risk for atherosclerosis, methods for evaluating an agent for use in treating atherosclerosis, methods for treating atherosclerosis, and methods for treating a cell having an abnormality in structure or metabolism of LBP. Pharmaceutical compositions and vaccine compositions are also provided.

41 Claims, 67 Drawing Sheets

OTHER PUBLICATIONS

GenBank™ Accession No. AA287095 (Aug. 14, 1997).
GenBank™ Accession No. R76498 (Jun. 6, 1995).
GenBank™ Accession No. W07246 (Apr. 25, 1996).
Gimbrone, Jr. et al., "Vascular Endothelium an Integrator of Pathophysiological Stimuli in Atherogenesis," Annals New York Academy of Sciences, 748:122-131, (1995).
Gofman et al., "Blood Lipids and Human Atherosclerosis," The Journal of the American Heart Association, II(2):161-178, (Aug. 1950).
Gottschling et al., Database: A_Geneseq_0601, Accession No. AAR95607 (Oct. 12, 1996).
Hoff et al., "Apolipoprotein B Retention in the Grossly Normal and Atherosclerotic Human Aorta," Circulation Research, 41(5):684-690, (Nov. 1977).
Hoff et al., "Detergent Extraction of Tightly-Bound apoB from Extracts of Normal Aortic Intima and Plaques," Experimental and Molecular Pathology, 28:290-300, (1978).
Holliger, P. et al., "Engineered Antibody Fragments and the Rise of Single Domains," Nature Biotechnology (2005), 23:9, pp. 1126-1136.
Kuzmenko et al., "Characteristics of Smooth Muscle Cell Lipoprotein Binding Proteins (p105/p130) as T-Cadherin and Regulation by Positive and Negative Growth Regulators," Biochemical and Biophysical Research Communications, 246:489-494, (1998).
Lee et al., "Nucleotide sequence of the rat low density lipoportein receptor cDNA," Nucleic Acids Res. 17(3):1259-1260 (1989).
Lees et al., "$^{99m}$Technetium-labeled low density lipoprotein: receptor recognition and intracellular sequestration of radiolabel," Journal of Lipid Research, 32(1):1-8 (1991).
Lees et al.,. "Imaging Human Atherosclerosis with $^{99m}$ Tc-labeled Low Density Lipoproteins," Arteriosclerosis, 8(5):461-470, (Sep./Oct. 1988).
Miki et al., "N-WASP, a novel actin-depolymerizing protein, regulates the cortical cytoskeletal rearrangement in a PIP2-dependent manner downstream of tyrosine kinases," The EMBO Journal, vol. 15(19):5326-5335 (1996).
Miki et al., Database: SPTREMBL_16, Accession No. Q95107 (Feb. 1, 1997).
Minick et al., "Role of Endothelium and Hypercholesterolemia in Intimal Thickening and Lipid Accumulation," American Journal of Pathology, 95(1):131-151, Figs. 1-7, (Apr. 1979).
Morel et al., "Endothelial and Smooth Muscle Cells Alter Low Density Lipoprotein In Vitro by Free Radical Oxidation," Arteriosclerosis, 4(4):357-364, (Jul./Aug. 1984).
Nielsen, "Transfer of Low Density Lipoprotein Into the Arterial Wall and Risk of Atherosclerosis," Atherosclerosis, 123:1-15, (1996).
Nievelstein et al., "Lipid accumulation in Rabbit Aortic Intima 2 Hours After Bolus Infusion of Low Density Lipoprotein," Arteriosclerosis and Thrombosis, 11(6):1795-1805, (Nov./Dec. 1991).
Ramprasad et al., "Cell Surface Expression of Mouse Macrosialin and Human CD68 and Their Role As Macrophage Receptors for Oxidized Low Density Lipoprotein," Proc. Natl. Acad. Sci. USA, 93:14833-14838, (Dec. 1996).
Roberts et al., "Selective Accumulation of Low Density Lipoproteins In Damaged Arterial Wall," Journal of Lipid Research, 24:1160-1167, (1983).
Scandinavian Simvastatin Survival Study Group, Randomised Trial of Cholesterol Lowering in 4444 Patients with Coronary Heart Disease: the Scandinavian Simvastatin Survival Study (4S), The Lancet, 344:1383-1389, (Nov. 19, 1994).
Schwenke et al., "Initiation of Atherosclerotic Lesions in Cholesterol-fed Rabbits," Arteriosclerosis, 9(6):895-907, (Nov./Dec. 1989).
Schwenke et al., "Initiation of Atherosclerotic Lesions in Cholesterol-fed Rabbits," Arteriosclerosis, 9(6):908-918, (Nov./Dec. 1989).
Shepherd et al., "Prevention of Coronary Heart Disease with Pravastatin In Men with Hypercholesterolemia," The New England Journal of Medicine, 333(20):1301-1307, (Nov. 16, 1995).
Shih, "Focal Accumulation of an Apolipoprotein B-based Synthetic Oligopeptide in the Healing Rabbit Arterial Wall," Proc. Natl. Acad. Sci. USA, 87:1436-1440, (Feb. 1990).
Sigma Chemical Company, Biochemicals Organic Compounds for Research and Diagnostic Reagents, p. 1906 (1995).
Smith, "The Relationship Between Plasma and Tissue Lipids in human Atherosclerosis," Adv. Lipid Res., 12:1-49, (1974).
Srinivasan et al., "Isolation of Lipoprotein-Acid Mucopolysaccharide Complexes from Fatty Streaks of Human Aortas," Atherosclerosis, 16:95-104, (1972).
Stamler et al., "Is Relationship Between Serum Cholesterol and Risk of Premature Death From Coronary Heart Disease Continuous and Graded?," JAMA, 256(20):2823-2828, (Nov. 28, 1986).
Stampfer et al., "A Prospective Study of Cholesterol, Apolipoproteins, and the Risk of Myocardial Infarction," New England Journal of Medicine, 325:373-381, (Aug. 8, 1991).
Stary et al., "A Definition of Initial, Fatth Streak, and Intermediate Lesions of Atherosclerosis," Arteriosclerosis and Thrombosis, 14(5):840-856, (May 1994).
Steinberg et al., "Beyond Cholesterol Modifications of Low-Density Lipoprotein That Increase Its Atherogenicity," The New England Journal of Medicine, 320(14):915-924, (Apr. 6, 1989).
Steinbrecher et al., "Modification of Low Density Lipoprotein by Endothelial Cells Involves Lipid Peroxidation and Degradation of Low Density Lipoprotein Phospholipids," Proc. Natl. Acad. Sci. USA, 81:3883-3887, (Jun. 1984).
Tkachuk, "Identification of an atypical lipoprotein-binding protein from human aortic smooth muscle as T-cadherin," Federation of European Biochemical Societies, 421:208-212, (1998).
Weisgraber et al., "Role of the Lysine Residues of Plasma Lipoproteins in High Affinity Binding to Cell Surface Receptors on Human Fibroblasts," The Journal of Biological Chemistry, 253:9053-9062, (1978).
Welch et al., "Actin Polymerization is Induced by Arp2/3 Protein Complex at the Surface of Listeria Monocytogenes," Nature, 385:265-269, (Jan. 16, 1997).
Welch et al., "The Human Arp2/3 Complex Is Composed of Evolutionarily Conserved Subunits and Is Localized to Cellular Regions of Dynamic Actin Filament Assembly," the Journal of Cell Biology, 138(2):375-384, (Jul. 28, 1997).
Williams, "The Response-to-Retention Hypothesis of Early Atherogenesis," Arteriosclerosis, Thrombosis, and Vascular Biology, 15(5):551-561, (May 1995).
Yang et al., "Protein farnesyltransferase in plants. Molecular cloning and expression of a homolog of the beta subunit from the garden pea," Plant Physiol. 101:667-674 (1993).

```
                                        met ser lys asn thr
val ser ser ala arg phe arg lys val asp val asp
glu tyr asp glu asn lys phe val asp glu glu asp
gly gly asp gly gln ala gly pro asp glu gly glu
val asp ser cys leu arg gln gly asn met thr ala
ala leu gln ala ala leu lys asn pro pro ile asn
thr arg ser gln ala val lys asp arg ala gly ser
ile val leu lys val leu ile ser phe lys ala gly
asp ile glu lys ala val gln ser leu asp arg asn
gly val asp leu leu met lys tyr ile tyr lys gly
phe glu ser pro ser asp asn ser ser ala val leu
leu gln trp his glu lys ala leu ala ala gly gly
val gly ser ile val arg val leu thr ala arg lys
thr val
```

FIG. 1

```
ggtctgtgtg tgcgtgcgtg cgagtgagtg agtgtgtgca tattttttt tctcttttct      60
ttctctctct tttttttttt tttgcaaaga aacagcagcg ccgccgccgc tccgccgagg     120
cgctgcgccc cccgggggg ggaggcggag gaggcgggca gcggcggagg gaggggagcc      180
ggggaggggg gcgccgcgct gggagggagg cagcgcgcac ggtgcagccg ggccgggcgg     240
gaggc atg gcg ggg ccc ccg gcc cta ccc ccg ccg gag acg gcg gcg gcc    290
      Met Ala Gly Pro Pro Ala Leu Pro Pro Pro Glu Thr Ala Ala Ala
       1               5                  10                  15
```

```
gcc acc acg gcc gcg gcc gcc gcc tcg tcg tcc gcc gct tcc ccg cac      338
Ala Thr Thr Ala Ala Ala Ala Ala Ser Ser Ser Ala Ala Ser Pro His
                  20                  25                  30
```

```
tac caa gag tgg att ctg gac acc atc gac tcg ctg cgc tcg cgc aag      386
Tyr Gln Glu Trp Ile Leu Asp Thr Ile Asp Ser Leu Arg Ser Arg Lys
                  35                  40                  45
```

```
gcg cgg ccg gac ctg gag cgc atc tgc cgg atg gtg cgg cgg cgg cac      434
Ala Arg Pro Asp Leu Glu Arg Ile Cys Arg Met Val Arg Arg Arg His
         50                   55                   60
```

```
ggc ccg gag ccg gag cgc acg cgc gcc gag ctc gag aaa ctg atc cag      482
Gly Pro Glu Pro Glu Arg Thr Arg Ala Glu Leu Glu Lys Leu Ile Gln
     65                   70                   75
```

```
cag cgc gcc gtg ctc cgg gtc agc tac aag ggg agc atc tcg tac cgc      530
Gln Arg Ala Val Leu Arg Val Ser Tyr Lys Gly Ser Ile Ser Tyr Arg
 80                   85                   90                   95
```

```
aac gcg gcg cgc gtc cag ccg ccc cgg cgc gga gcc acc ccg ccg gcc      578
Asn Ala Ala Arg Val Gln Pro Pro Arg Arg Gly Ala Thr Pro Pro Ala
                  100                 105                 110
```

```
ccg ccg cgc gcc ccc cgc ggg ggc ccc gcc gcc gcc gcc gcg ccg ccg      626
Pro Pro Arg Ala Pro Arg Gly Gly Pro Ala Ala Ala Ala Ala Pro Pro
                  115                 120                 125
```

```
ccc acg ccc gcc ccg ccg ccg ccc gcg ccc gtc gcc gcc gcc gcc          674
Pro Thr Pro Ala Pro Pro Pro Pro Ala Pro Val Ala Ala Ala Ala
                  130                 135                 140
```

```
gcc ccg gcc cgg gcg ccc cgc gcg gcc gcc gcc gct gcc gcc aca          722
Ala Pro Ala Arg Ala Pro Arg Ala Ala Ala Ala Ala Ala Ala Thr
                  145                 150                 155
```

```
gcg ccc ccc tcg ccc ggc ccc gcg cag ccg ggc ccc cgc gcg cag cgg      770
Ala Pro Pro Ser Pro Gly Pro Ala Gln Pro Gly Pro Arg Ala Gln Arg
 160                 165                 170                 175
```

```
gcc gcg ccc ctg gcc gcg ccg ccg ccc gcg ccc gcc gct ccc ccg gcg      818
Ala Ala Pro Leu Ala Ala Pro Pro Pro Ala Pro Ala Ala Pro Pro Ala
                  180                 185                 190
```

FIG. 2A-1

| | | |
|---|---|---|
| gcg gcg ccc ccg gcc ggc ccg cgc cgc gcc ccc ccg ccc gcc gcc gcc<br>Ala Ala Pro Pro Ala Gly Pro Arg Arg Ala Pro Pro Pro Ala Ala Ala<br>             195                     200                    205 | | 866 |
| gtc gcc gcc cgg gag tcg ccg ctg ccg ccg cca cag ccg ccg gcg<br>Val Ala Ala Arg Glu Ser Pro Leu Pro Pro Pro Gln Pro Pro Ala<br>          210                   215                 220 | | 914 |
| ccg cca cag cag cag cag cag ccg ccg ccg cca ccg ccg ccg cag cag<br>Pro Pro Gln Gln Gln Gln Gln Pro Pro Pro Pro Pro Pro Pro Gln Gln<br>225                     230                     235 | | 962 |
| cca cag ccg ccg ccg gag ggg ggc gcg gcg cgg gcc ggc ggc ccg gcg<br>Pro Gln Pro Pro Pro Glu Gly Gly Ala Ala Arg Ala Gly Gly Pro Ala<br>240                     245                    250                 255 | | 1010 |
| cgg ccc gtg agc ctg cgg gaa gtc gtg cgc tac ctc ggg ggt agc agc<br>Arg Pro Val Ser Leu Arg Glu Val Val Arg Tyr Leu Gly Gly Ser Ser<br>                  260                     265                 270 | | 1058 |
| ggc gct ggc ggc cgc ctg acc cgc ggc cgc gtg cag ggt ctg ctg gaa<br>Gly Ala Gly Gly Arg Leu Thr Arg Gly Arg Val Gln Gly Leu Leu Glu<br>             275                     280                    285 | | 1106 |
| gag gag gcg gcg gcg cgg ggc cgc ctg gag cgc acc cgt ctc gga gcg<br>Glu Glu Ala Ala Ala Arg Gly Arg Leu Glu Arg Thr Arg Leu Gly Ala<br>       290                     295                    300 | | 1154 |
| ctt gcg ctg ccc cgc ggg gac agg ccc gga cgg gcg cca ccg gcc gcc<br>Leu Ala Leu Pro Arg Gly Asp Arg Pro Gly Arg Ala Pro Pro Ala Ala<br>       305                     310                    315 | | 1202 |
| agc gcc cgc gcg gcg cgg aac aag aga gct ggc gag gag cga gtg ctt<br>Ser Ala Arg Ala Ala Arg Asn Lys Arg Ala Gly Glu Glu Arg Val Leu<br>320                     325                    330                335 | | 1250 |
| gaa aag gag gag gag gag gag gag gag gaa gac gac gag gac gac gac<br>Glu Lys Glu Glu Glu Glu Glu Glu Glu Glu Asp Asp Glu Asp Asp Asp<br>                  340                     345                   350 | | 1298 |
| gac gac gtc gtg tcc gag ggc tcg gag gtg ccc gag agc gat cgt ccc<br>Asp Asp Val Val Ser Glu Gly Ser Glu Val Pro Glu Ser Asp Arg Pro<br>               355                     360                   365 | | 1346 |
| gcg ggt gcg cag cat cac cag ctg aat ggc ggc gag cgc ggc ccg cag<br>Ala Gly Ala Gln His His Gln Leu Asn Gly Gly Glu Arg Gly Pro Gln<br>          370                     375                    380 | | 1394 |
| acc gcc aag gag cgg gcc aag gag tgg tcg ctg tgt ggc ccc cac cct<br>Thr Ala Lys Glu Arg Ala Lys Glu Trp Ser Leu Cys Gly Pro His Pro<br>385                     390                    395 | | 1442 |
| ggc cag gag gaa ggg cgg ggg ccg gcc gcg ggc agt ggc acc cgc cag<br>Gly Gln Glu Glu Gly Arg Gly Pro Ala Ala Gly Ser Gly Thr Arg Gln<br>400                     405                    410                415 | | 1490 |

FIG. 2A-2

| | | | | | | | | | | | | | | | |
|---|---|---|---|---|---|---|---|---|---|---|---|---|---|---|---|
| gtg | ttc | tcc | atg | gcg | gcc | ttg | agt | aag | gag | ggg | gga | tca | gcc | tct | tcg | 1538 |
| Val | Phe | Ser | Met | Ala | Ala | Leu | Ser | Lys | Glu | Gly | Gly | Ser | Ala | Ser | Ser | |
| | | | | 420 | | | | | 425 | | | | | 430 | | |

| acc | acc | ggg | cct | gac | tcc | ccg | tcc | ccg | gtg | cct | ttg | ccc | ccc | ggg | aag | 1586 |
|---|---|---|---|---|---|---|---|---|---|---|---|---|---|---|---|---|
| Thr | Thr | Gly | Pro | Asp | Ser | Pro | Ser | Pro | Val | Pro | Leu | Pro | Pro | Gly | Lys | |
| | | | 435 | | | | | 440 | | | | | 445 | | | |

| cca | gcc | ctc | cca | gga | gcc | gat | ggg | acc | ccc | ttt | ggc | tgc | cct | gcc | ggg | 1634 |
|---|---|---|---|---|---|---|---|---|---|---|---|---|---|---|---|---|
| Pro | Ala | Leu | Pro | Gly | Ala | Asp | Gly | Thr | Pro | Phe | Gly | Cys | Pro | Ala | Gly | |
| | | 450 | | | | | 455 | | | | | 460 | | | | |

| cgc | aaa | gag | aag | ccg | gca | gac | ccc | gtg | gag | tgg | aca | gtc | atg | gac | gtc | 1682 |
|---|---|---|---|---|---|---|---|---|---|---|---|---|---|---|---|---|
| Arg | Lys | Glu | Lys | Pro | Ala | Asp | Pro | Val | Glu | Trp | Thr | Val | Met | Asp | Val | |
| | 465 | | | | | 470 | | | | | 475 | | | | | |

| gtg | gag | tac | ttc | acc | gag | gcg | ggc | ttc | cct | gag | caa | gcc | acg | gct | ttc | 1730 |
|---|---|---|---|---|---|---|---|---|---|---|---|---|---|---|---|---|
| Val | Glu | Tyr | Phe | Thr | Glu | Ala | Gly | Phe | Pro | Glu | Gln | Ala | Thr | Ala | Phe | |
| 480 | | | | | 485 | | | | | 490 | | | | | 495 | |

| cag | gag | cag | gag | atc | gac | ggc | aag | tcc | ctg | ctg | ctc | atg | cag | cgc | acc | 1778 |
|---|---|---|---|---|---|---|---|---|---|---|---|---|---|---|---|---|
| Gln | Glu | Gln | Glu | Ile | Asp | Gly | Lys | Ser | Leu | Leu | Leu | Met | Gln | Arg | Thr | |
| | | | | 500 | | | | | 505 | | | | | 510 | | |

| gat | gtc | ctc | acc | ggc | ctg | tcc | atc | cgc | ctg | ggg | cca | gcg | ttg | aaa | atc | 1826 |
|---|---|---|---|---|---|---|---|---|---|---|---|---|---|---|---|---|
| Asp | Val | Leu | Thr | Gly | Leu | Ser | Ile | Arg | Leu | Gly | Pro | Ala | Leu | Lys | Ile | |
| | | | 515 | | | | | 520 | | | | | 525 | | | |

| tat | gag | cac | cat | atc | aag | gtg | ctg | cag | cag | ggt | cac | ttc | gag | gac | gat | 1874 |
|---|---|---|---|---|---|---|---|---|---|---|---|---|---|---|---|---|
| Tyr | Glu | His | His | Ile | Lys | Val | Leu | Gln | Gln | Gly | His | Phe | Glu | Asp | Asp | |
| | | 530 | | | | | 535 | | | | | 540 | | | | |

| gac | ccg | gaa | ggc | ttc | ctg | gga | t gagcacagag ccgccgcgcc ccttgtcccc | 1926 |
|---|---|---|---|---|---|---|---|---|
| Asp | Pro | Glu | Gly | Phe | Leu | Gly | | |
| 545 | | | | | 550 | | | |

```
acccccaccc  cgcctggacc  cattcctgcc  tccatgtcac  ccaaggtgtc  ccagaggcca   1986
ggagctggac  tgggcaggcg  aggggtgcgg  acctaccctg  attctggtag  ggggcggggc   2046
cttgctgtgc  tcattgctac  ccccccaccc  cgtgtgtgtc  tctgcacctg  ccccagcac   2106
acccctcccg  gagcctggat  gtcgcctggg  actctggcct  gctcatttg   ccccagatc   2166
agcccctcc   ctccctcctg  tccaggaca   ttttttaaaa  gaaaaaaagg  aaaaaaaaaa   2226
attggggagg  gggctggaa   ggtgccccaa  gatcctcctc  ggcccaacca  ggtgtttatt   2286
cctatatata  tatatatatg  ttttgttctg  cctgttttc   gttttttggt  gcgtggcctt   2346
tcttccctcc  caccaccact  catggcccca  gcctgctcg   ccctgtcggc  gggagcagct   2406
gggaatggga  ggagggtggg  aacttgggtc  tgtctcccac  cctctctccc  gttggttctg   2466
ttgtcgctcc  agctggctgt  attgcttttt  aatattgcac  cgaagggttg  tttttttttt   2526
tttaaataaa  attttaaaaa  aaggaaaaaa  aaaaa                                2561
```

FIG. 2A-3 asp cys arg ser ser ser asn asn arg Xaa pro lys
gly gly ala ala arg ala gly gly pro ala arg pro
val ser leu arg glu val val arg tyr leu gly gly
ser ser gly ala gly gly arg leu thr arg gly arg
val gln gly leu leu glu glu glu ala ala ala arg
gly arg leu glu arg thr arg leu gly ala leu ala
leu pro arg gly asp arg pro gly arg ala pro pro
ala ala ser ala arg ala ala arg asn lys arg ala
gly glu glu arg val leu glu lys glu glu glu glu
glu glu glu glu asp asp glu asp asp asp asp asp
val val ser glu gly ser glu val pro glu ser asp
arg pro ala gly ala gln his his gln leu asn gly
gly glu arg gly pro gln thr ala lys glu arg ala
lys glu trp ser leu cys gly pro his pro gly gln
glu glu gly arg gly pro ala ala gly ser gly thr
arg gln val phe ser met ala ala leu ser lys glu
gly gly ser ala ser ser thr thr gly pro asp ser
pro ser pro val pro leu pro pro gly lys pro ala
leu pro gly ala asp gly thr pro phe gly cys pro
ala gly arg lys glu lys pro ala asp pro val glu
trp thr val met asp val val glu tyr phe thr glu
ala gly phe pro glu gln ala thr ala phe gln glu
gln glu ile asp gly lys ser leu leu leu met gln
arg thr asp val leu thr gly leu ser ile arg leu
gly pro ala leu lys ile tyr glu his his ile lys
val leu gln gln gly his phe glu asp asp asp pro
glu gly phe leu gly

FIG. 2B ala ser ala arg ala ala arg asn lys arg ala
gly glu glu arg val leu glu lys glu glu glu
glu glu glu glu asp asp glu asp asp asp asp asp
val val ser glu gly ser glu val pro glu ser asp
arg pro ala gly ala gln his his gln leu asn gly
gly glu arg gly pro gln thr ala lys glu arg ala
lys glu trp ser leu cys gly pro his pro gly gln
glu glu gly arg gly pro ala ala gly ser gly thr
arg gln val phe ser met ala ala leu ser lys glu
gly gly ser ala ser ser thr thr gly pro asp ser
pro ser pro val pro leu pro pro gly lys pro ala
leu pro gly ala asp gly thr pro phe gly cys pro
ala gly arg lys glu lys pro ala asp pro val glu
trp thr val met asp val val glu tyr phe thr glu
ala gly phe pro glu gln ala thr ala phe gln glu
gln glu ile asp gly lys ser leu leu leu met gln
arg thr asp val leu thr gly leu ser ile arg leu
gly pro ala leu lys ile tyr glu his his ile lys
val leu gln gln gly his phe glu asp asp asp pro
glu gly phe leu gly

FIG. 3

```
                              thr arg leu gly ala leu ala
leu pro arg gly asp arg pro gly arg ala pro pro
ala ala ser ala arg ala ala arg asn lys arg ala
gly glu glu arg val leu glu lys glu glu glu glu
glu glu glu glu asp asp glu asp asp asp asp asp
val val ser glu gly ser glu val pro glu ser asp
arg pro ala gly ala gln his his gln leu asn gly
gly glu arg gly pro gln thr ala lys glu arg ala
lys glu trp ser leu cys gly pro his pro gly gln
glu glu gly arg gly pro ala ala gly ser gly thr
arg gln val phe ser met ala ala leu ser lys glu
gly gly ser ala ser ser thr thr gly pro asp ser
pro ser pro val pro leu pro pro gly lys pro ala
leu pro gly ala asp gly thr pro phe gly cys pro
ala gly arg lys glu lys pro ala asp pro val glu
trp thr val met asp val val glu tyr phe thr glu
ala gly phe pro glu gln ala thr ala phe gln glu
gln glu ile asp gly lys ser leu leu leu met gln
arg thr asp val leu thr gly leu ser ile arg leu
gly pro ala leu lys ile tyr glu his his ile lys
val leu gln gln gly his phe glu asp asp asp pro
glu gly phe leu gly
```

FIG. 4

```
                                        met lys asn gln
asp lys lys asn gly ala ala lys gln pro asn pro
lys ser ser pro gly gln pro glu ala gly ala glu
gly ala gln gly arg pro gly arg pro ala pro ala
arg glu ala glu gly ala ser ser gln ala pro gly
arg pro glu gly ala gln ala lys thr ala gln pro
gly ala leu cys asp val ser glu glu leu ser arg
gln leu glu asp ile leu ser thr tyr cys val asp
asn asn gln gly ala pro gly glu asp gly val gln
gly glu pro pro glu pro glu asp ala glu lys ser
arg ala tyr val ala arg asn gly glu pro glu pro
gly thr pro val val asn gly glu lys glu thr ser
lys ala glu pro gly thr glu glu ile arg thr ser
asp glu val gly asp arg asp his arg arg pro gln
glu lys lys lys ala lys gly leu gly lys glu ile
thr leu leu met gln thr leu asn thr leu ser thr
pro glu glu lys leu ala ala leu cys lys lys tyr
ala glu leu leu glu glu his arg asn ser gln lys
gln met lys leu leu gln lys lys gln ser gln leu
val gln glu lys asp his leu arg gly glu his ser
lys ala ile leu ala arg ser lys leu glu ser leu
cys arg glu leu gln arg his asn arg ser leu lys
glu glu gly val gln arg ala arg glu glu glu glu
lys arg lys glu val thr ser his phe gln met thr
leu asn asp ile gln leu gln met glu gln his asn
glu arg asn ser lys leu arg gln glu asn met glu
```

FIG. 5A

```
leu ala glu arg leu lys lys leu ile glu gln tyr
glu leu arg glu glu his ile asp lys val phe lys
his lys asp leu gln gln gln leu val asp ala lys
leu gln gln ala gln glu met leu lys glu ala glu
glu arg his gln arg glu lys asp phe leu leu lys
glu ala val glu ser gln arg met cys glu leu met
lys gln gln glu thr his leu lys gln gln leu ala
leu tyr thr glu lys phe glu glu phe gln asn thr
leu ser lys ser ser glu val phe thr thr phe lys
gln glu met glu lys met thr lys lys ile lys lys
leu glu lys glu thr thr met tyr arg ser arg trp
glu ser ser asn lys ala leu leu glu met ala glu
glu lys thr leu arg asp lys glu leu glu gly leu
gln val lys ile gln arg leu glu lys leu cys arg
ala leu gln thr glu arg asn asp leu asn lys arg
val gln asp leu ser ala gly gly gln gly pro val
ser asp ser gly pro glu arg arg pro glu pro ala
thr thr ser lys glu gln gly val glu gly pro gly
ala gln val pro asn ser pro arg ala thr asp ala
ser cys cys ala gly ala pro ser thr glu ala ser
gly gln thr gly pro gln glu pro thr thr ala thr
ala
```

FIG. 5B met ser lys asn thr val ser ser ala
arg phe arg lys val asp val asp glu tyr asp glu
asn lys phe val asp glu glu asp gly gly asp gly
gln ala gly pro asp glu gly glu val asp ser cys
leu arg gln gly asn met thr ala ala leu gln ala
ala leu lys asn pro pro ile asn thr lys ser gln
ala val lys asp arg ala gly ser ile val leu lys
val leu ile ser phe lys ala asn asp ile glu lys
ala val gln ser leu asp lys asn gly val asp leu
leu met lys tyr ile tyr lys gly phe glu ser pro
ser asp asn ser ser ala met leu leu gln trp his
glu lys ala leu ala ala gly gly val gly ser ile
val arg val leu thr ala arg lys thr val

FIG. 6

```
atg gcg ggg ccc ccg gcc cta ccc ccg ccg gag acg gcg gcg gcc gcc        48
Met Ala Gly Pro Pro Ala Leu Pro Pro Pro Glu Thr Ala Ala Ala Ala
 1               5                  10                  15 acc acg gcg gcc gcc gcc tcg tcg tcc gcc gct tcc ccg cac tac caa        96
Thr Thr Ala Ala Ala Ala Ser Ser Ser Ala Ala Ser Pro His Tyr Gln
            20                  25                  30 gag tgg atc ctg gac acc atc gac tcg ctg cgc tcg cgc aag gcg cgg       144
Glu Trp Ile Leu Asp Thr Ile Asp Ser Leu Arg Ser Arg Lys Ala Arg
        35                  40                  45 ccg gac ctg gag cgc atc tgc cgg atg gtg cgg cgg cgg cac ggc ccg       192
Pro Asp Leu Glu Arg Ile Cys Arg Met Val Arg Arg Arg His Gly Pro
 50                  55                  60 gag ccg gag cgc acg cgc gcc gag ctc gag aaa ctg atc cag cag cgc       240
Glu Pro Glu Arg Thr Arg Ala Glu Leu Glu Lys Leu Ile Gln Gln Arg
 65                  70                  75                  80 gcc gtg ctc cgg gtc agc tac aag ggg agc atc tcg tac cgc aac gcg       288
Ala Val Leu Arg Val Ser Tyr Lys Gly Ser Ile Ser Tyr Arg Asn Ala
                85                  90                  95 gcg cgc gtc cag ccg ccc cgg cgc gga gcc acc ccg ccg gcc ccg ccg       336
Ala Arg Val Gln Pro Pro Arg Arg Gly Ala Thr Pro Pro Ala Pro Pro
            100                 105                 110 cgc gcc ccc cgc ggg gcc ccc gcc gcc gcc gcc gcc gcc gcg ccg ccg       384
Arg Ala Pro Arg Gly Ala Pro Ala Ala Ala Ala Ala Ala Ala Pro Pro
        115                 120                 125 ccc acg ccc gcc ccg ccg cca ccg ccc gcg ccc gtc gcc gcc gcc gcc       432
Pro Thr Pro Ala Pro Pro Pro Pro Ala Pro Val Ala Ala Ala Ala
 130                 135                 140 ccg gcc cgg gcg ccc cgc gcg gcc gcc gcc gcc gcc aca gcg ccc ccc       480
Pro Ala Arg Ala Pro Arg Ala Ala Ala Ala Ala Thr Ala Pro Pro
145                 150                 155                 160 tcg cct ggc ccc gcg cag ccg ggc ccc cgc gcg cag cgg gcc gcg ccc       528
Ser Pro Gly Pro Ala Gln Pro Gly Pro Arg Ala Gln Arg Ala Ala Pro
                165                 170                 175 ctg gcc gcg ccg ccg ccc gcg cca gcc gct ccc ccg gcg gtg gcg ccc       576
Leu Ala Ala Pro Pro Pro Ala Pro Ala Ala Pro Pro Ala Val Ala Pro
            180                 185                 190 ccg gcc ggc ccg cgc cgc gcc ccc ccg ccc gtc gcc gcc cgg gag           624
Pro Ala Gly Pro Arg Arg Ala Pro Pro Ala Val Ala Ala Arg Glu
        195                 200                 205 ccg ccg ctg ccg ccg ccg cca cag ccg ccg gcg ccg cca cag cag cag       672
Pro Pro Leu Pro Pro Pro Pro Gln Pro Pro Ala Pro Pro Gln Gln Gln
 210                 215                 220
```

FIG. 7A-1

```
cag ccg ccg ccg ccg cag cca cag ccg ccg ccg gag ggg ggc gcg gtg    720
Gln Pro Pro Pro Pro Gln Pro Gln Pro Pro Pro Glu Gly Gly Ala Val
225             230                 235                 240 cgg gcc ggc ggc gcg gcg cgg ccc gtg agc ctg cgg gaa gtc gtg cgc    768
Arg Ala Gly Gly Ala Ala Arg Pro Val Ser Leu Arg Glu Val Val Arg
            245                 250                 255 tac ctc ggg ggc agc ggc ggc gcc ggc ggt cgc cta acc cgc ggc cgc    816
Tyr Leu Gly Gly Ser Gly Gly Ala Gly Gly Arg Leu Thr Arg Gly Arg
            260                 265                 270 gtg cag ggg ctg ctg gag gag gag gcg gcg gct cga ggc cgt ctg gag    864
Val Gln Gly Leu Leu Glu Glu Glu Ala Ala Ala Arg Gly Arg Leu Glu
        275                 280                 285 cgc acc cgt ctc gga gcg ctt gcg ctg ccc cgc ggg gac agg ccc gga    912
Arg Thr Arg Leu Gly Ala Leu Ala Leu Pro Arg Gly Asp Arg Pro Gly
        290                 295                 300 cgg gcg ccg ccg gcc gcc agc gcc cgc ccg tct cgc agc aag aga ggt    960
Arg Ala Pro Pro Ala Ala Ser Ala Arg Pro Ser Arg Ser Lys Arg Gly
305             310                 315                 320 gga gaa gag cga gta ctt gag aaa gaa gag gaa gaa gat gat gat gaa   1008
Gly Glu Glu Arg Val Leu Glu Lys Glu Glu Glu Glu Asp Asp Asp Glu
            325                 330                 335 gat gaa gat gaa gaa gat gat gtg tca gag ggc tct gaa gtg ccc gag   1056
Asp Glu Asp Glu Glu Asp Asp Val Ser Glu Gly Ser Glu Val Pro Glu
        340                 345                 350 agt gac cgt cct gca ggt gcc cag cac cac cag ctt aac ggc gag cgg   1104
Ser Asp Arg Pro Ala Gly Ala Gln His His Gln Leu Asn Gly Glu Arg
        355                 360                 365 gga cct cag agt gcc aag gag agg gtc aag gag tgg acc ccc tgc gga   1152
Gly Pro Gln Ser Ala Lys Glu Arg Val Lys Glu Trp Thr Pro Cys Gly
370                 375                 380 ccg cac cag ggc cag gat gaa ggg cgg ggg cca gcc ccg ggc agc ggc   1200
Pro His Gln Gly Gln Asp Glu Gly Arg Gly Pro Ala Pro Gly Ser Gly
385             390                 395                 400 acc cgc cag gtg ttc tcc atg gca gcc atg aac aag gaa ggg gga aca   1248
Thr Arg Gln Val Phe Ser Met Ala Ala Met Asn Lys Glu Gly Gly Thr
            405                 410                 415 gct tct gtt gcc acc ggg cca gac tcc ccg tcc ccc gtg cct ttg ccc   1296
Ala Ser Val Ala Thr Gly Pro Asp Ser Pro Ser Pro Val Pro Leu Pro
        420                 425                 430 cca ggc aaa cca gcc cta cct ggg gcc gac ggg acc ccc ttt ggc tgt   1344
Pro Gly Lys Pro Ala Leu Pro Gly Ala Asp Gly Thr Pro Phe Gly Cys
        435                 440                 445
```

FIG. 7A-2

```
ccg ccc ggg cgc aaa gag aag cca tct gat ccc gtc gag tgg acc gtg    1392
Pro Pro Gly Arg Lys Glu Lys Pro Ser Asp Pro Val Glu Trp Thr Val
450             455                 460 atg gat gtc gtc gaa tat ttt act gag gct gga ttc ccg gag cag gcg    1440
Met Asp Val Val Glu Tyr Phe Thr Glu Ala Gly Phe Pro Glu Gln Ala
465             470                 475                 480 aca gct ttc caa gag cag gaa att gat ggc aaa tct ttg ctg ctc atg    1488
Thr Ala Phe Gln Glu Gln Glu Ile Asp Gly Lys Ser Leu Leu Leu Met
                485                 490                 495 cag cgc aca gat gtg ctc acc ggc ctg tcc atc cgc ctc ggg cca gcc    1536
Gln Arg Thr Asp Val Leu Thr Gly Leu Ser Ile Arg Leu Gly Pro Ala
            500                 505                 510 ctg aaa atc tac gag cac cac atc aag gtg ctt cag caa ggc cac ttt    1584
Leu Lys Ile Tyr Glu His His Ile Lys Val Leu Gln Gln Gly His Phe
        515                 520                 525 gag gat gat gac ccc gat ggc ttc tta ggc                            1614
Glu Asp Asp Asp Pro Asp Gly Phe Leu Gly
530                 535
```

FIG. 7A-3 glu glu arg val leu glu lys glu glu glu asp asp asp glu asp glu asp glu glu asp asp val ser glu gly ser glu val pro glu ser asp arg pro ala gly ala gln his his gln leu asn gly glu arg gly pro gln ser ala lys glu arg val lys glu trp thr pro cys gly pro his gln gly gln asp glu gly arg gly pro ala pro gly ser gly thr arg gln val phe ser met ala ala met asn lys glu gly gly thr ala ser val ala thr gly pro asp ser pro ser pro val pro leu pro pro gly lys pro ala leu pro gly ala asp gly thr pro phe gly cys pro pro gly arg lys glu lys pro ser asp pro val glu trp thr val met asp val val glu tyr phe thr glu ala gly phe pro glu gln ala thr ala phe gln glu gln glu ile asp gly lys ser leu leu leu met gln arg thr asp val leu thr gly leu ser ile arg leu gly pro ala leu lys ile tyr glu his his ile lys val leu gln gln gly his phe glu asp asp asp pro asp gly phe leu gly

FIG. 7B

```
atg aag aac caa gac aaa aag aac ggg gct gcc aaa caa tcc aat cca      48
Met Lys Asn Gln Asp Lys Lys Asn Gly Ala Ala Lys Gln Ser Asn Pro
1               5                   10                  15 aaa agc agc cca gga caa ccg gaa gca gga ccc gag gga gcc cag gag      96
Lys Ser Ser Pro Gly Gln Pro Glu Ala Gly Pro Glu Gly Ala Gln Glu
            20                  25                  30 cgg ccc agc cag gcg gct cct gca gta gaa gca gaa ggt ccc ggc agc     144
Arg Pro Ser Gln Ala Ala Pro Ala Val Glu Ala Glu Gly Pro Gly Ser
        35                  40                  45 agc cag gct cct cgg aag ccg gag ggt gct caa gcc aga acg gct cag     192
Ser Gln Ala Pro Arg Lys Pro Glu Gly Ala Gln Ala Arg Thr Ala Gln
    50                  55                  60 tct ggg gcc ctt cgt gat gtc tct gag gag ctg agc cgc caa ctg gaa     240
Ser Gly Ala Leu Arg Asp Val Ser Glu Glu Leu Ser Arg Gln Leu Glu
65                  70                  75                  80 gac ata ctg agc aca tac tgt gtg gac aat aac cag ggg ggc ccc ggc     288
Asp Ile Leu Ser Thr Tyr Cys Val Asp Asn Asn Gln Gly Gly Pro Gly
                85                  90                  95 gag gat ggg gca cag ggt gag ccg gct gaa ccc gaa gat gca gag aag     336
Glu Asp Gly Ala Gln Gly Glu Pro Ala Glu Pro Glu Asp Ala Glu Lys
            100                 105                 110 tcc cgg acc tat gtg gca agg aat ggg gag cct gaa cca act cca gta     384
Ser Arg Thr Tyr Val Ala Arg Asn Gly Glu Pro Glu Pro Thr Pro Val
        115                 120                 125 gtc aat gga gag aag gaa ccc tcc aag ggg gat cca aac aca gaa gag     432
Val Asn Gly Glu Lys Glu Pro Ser Lys Gly Asp Pro Asn Thr Glu Glu
    130                 135                 140 atc cgg cag agt gac gag gtc gga gac cga gac cat cga agg cca cag     480
Ile Arg Gln Ser Asp Glu Val Gly Asp Arg Asp His Arg Arg Pro Gln
145                 150                 155                 160 gag aag aaa aaa gcc aag ggt ttg ggt aag gag atc acg ttg ctg atg     528
Glu Lys Lys Lys Ala Lys Gly Leu Gly Lys Glu Ile Thr Leu Leu Met
                165                 170                 175 cag aca ttg aat act ctg agt acc cca gag gag aag ctg gct gct ctg     576
Gln Thr Leu Asn Thr Leu Ser Thr Pro Glu Glu Lys Leu Ala Ala Leu
            180                 185                 190 tgc aag aag tat gct gaa ctg ctg gag gag cac cgg aat tca cag aag     624
Cys Lys Lys Tyr Ala Glu Leu Leu Glu Glu His Arg Asn Ser Gln Lys
        195                 200                 205
```

FIG. 8A-1

```
cag atg aag ctc cta cag aaa aag cag agc cag ctg gtg caa gag aag        672
Gln Met Lys Leu Leu Gln Lys Lys Gln Ser Gln Leu Val Gln Glu Lys
    210             215                 220 gac cac ctg cgc ggt gag cac agc aag gcc gtc ctg gcc cgc agc aag        720
Asp His Leu Arg Gly Glu His Ser Lys Ala Val Leu Ala Arg Ser Lys
225             230                 235                 240 ctt gag agc cta tgc cgt gag ctg cag cgg cac aac cgc tcc ctc aag        768
Leu Glu Ser Leu Cys Arg Glu Leu Gln Arg His Asn Arg Ser Leu Lys
                245                 250                 255 gaa gaa ggt gtg cag cgg gcc cgg gag gag gag gag aag cgc aag gag        816
Glu Glu Gly Val Gln Arg Ala Arg Glu Glu Glu Lys Arg Lys Glu
            260                 265                 270 gtg acc tcg cac ttc cag gtg aca ctg aat gac att cag ctg cag atg        864
Val Thr Ser His Phe Gln Val Thr Leu Asn Asp Ile Gln Leu Gln Met
        275                 280                 285 gaa cag cac aat gag cgc aac tcc aag ctg cgc caa gag aac atg gag        912
Glu Gln His Asn Glu Arg Asn Ser Lys Leu Arg Gln Glu Asn Met Glu
    290                 295                 300 ctg gct gag agg ctc aag aag ctg att gag cag tat gag ctg cgc gag        960
Leu Ala Glu Arg Leu Lys Lys Leu Ile Glu Gln Tyr Glu Leu Arg Glu
305             310                 315                 320 gag cat atc gac aaa gtc ttc aaa cac aag gac cta caa cag cag ctg       1008
Glu His Ile Asp Lys Val Phe Lys His Lys Asp Leu Gln Gln Gln Leu
                325                 330                 335 gtg gat gcc aag ctc cag cag gcc cag gag atg cta aag gag gca gaa       1056
Val Asp Ala Lys Leu Gln Gln Ala Gln Glu Met Leu Lys Glu Ala Glu
            340                 345                 350 gag cgg cac cag cgg gag aag gat ttt ctc ctg aaa gag gca gta gag       1104
Glu Arg His Gln Arg Glu Lys Asp Phe Leu Leu Lys Glu Ala Val Glu
        355                 360                 365 tcc cag agg atg tgt gag ctg atg aag cag caa gag acc cac ctg aag       1152
Ser Gln Arg Met Cys Glu Leu Met Lys Gln Gln Glu Thr His Leu Lys
370             375                 380 caa cag ctt gcc cta tac aca gag aag ttt gag gag ttc cag aac aca       1200
Gln Gln Leu Ala Leu Tyr Thr Glu Lys Phe Glu Glu Phe Gln Asn Thr
385                 390                 395                 400 ctt tcc aaa agc agc gag gta ttc acc aca ttc aag cag gag atg gaa       1248
Leu Ser Lys Ser Ser Glu Val Phe Thr Thr Phe Lys Gln Glu Met Glu
                405                 410                 415
```

FIG. 8A-2

```
aag atg act aag aag atc aag aag ctg gag aaa gaa acc acc atg tac      1296
Lys Met Thr Lys Lys Ile Lys Lys Leu Glu Lys Glu Thr Thr Met Tyr
            420             425             430 cgg tcc cgg tgg gag agc agc aac aag gcc ctg ctt gag atg gct gag      1344
Arg Ser Arg Trp Glu Ser Ser Asn Lys Ala Leu Leu Glu Met Ala Glu
            435             440             445 gag aaa aca gtc cgg gat aaa gaa ctg gag ggc ctg cag gta aaa atc      1392
Glu Lys Thr Val Arg Asp Lys Glu Leu Glu Gly Leu Gln Val Lys Ile
    450             455             460 caa cgg ctg gag aag ctg tgc cgg gca ctg cag aca gag cgc aat gac      1440
Gln Arg Leu Glu Lys Leu Cys Arg Ala Leu Gln Thr Glu Arg Asn Asp
465             470             475             480 ctg aac aag agg gta cag gac ctg agt gct ggt ggc cag ggc tcc ctc      1488
Leu Asn Lys Arg Val Gln Asp Leu Ser Ala Gly Gly Gln Gly Ser Leu
            485             490             495 act gac agt ggc cct gag agg agg cca gag ggg cct ggg gct caa gca      1536
Thr Asp Ser Gly Pro Glu Arg Arg Pro Glu Gly Pro Gly Ala Gln Ala
            500             505             510 ccc agc tcc ccc agg gtc aca gaa gcg cct tgc tac cca gga gca ccg      1584
Pro Ser Ser Pro Arg Val Thr Glu Ala Pro Cys Tyr Pro Gly Ala Pro
            515             520             525 agc aca gaa gca tca ggc cag act ggg cct caa gag ccc acc tcc gcc      1632
Ser Thr Glu Ala Ser Gly Gln Thr Gly Pro Gln Glu Pro Thr Ser Ala
            530             535             540 agg gcc                                                              1638
Arg Ala
545
```

FIG. 8A-3

```
      lys ser ser pro gly gln pro glu ala gly pro glu gly ala gln glu arg pro ser gln ala ala pro ala val glu ala glu gly pro gly ser ser gln ala pro arg lys pro glu gly ala gln ala arg thr ala gln ser gly ala leu arg asp val ser glu glu leu ser arg gln leu glu asp ile leu ser thr tyr cys val asp asn asn gln gly gly pro gly glu asp gly ala gln gly glu pro ala glu pro glu asp ala glu lys ser arg thr tyr val ala arg asn gly glu pro glu pro thr pro val val tyr gly glu lys glu pro ser lys gly asp pro asn thr glu glu ile arg gln ser asp glu val gly asp arg asp his arg arg pro gln glu lys lys lys ala lys gly leu gly lys glu ile thr leu leu met gln thr leu asn thr leu ser thr pro glu glu lys leu ala ala leu cys lys lys tyr ala glu leu leu glu glu his arg asn ser gln lys gln met lys leu leu gln lys lys gln ser gln leu val gln glu lys asp his leu arg gly glu his ser lys ala val leu ala arg ser lys leu glu ser leu cys arg glu leu gln arg his asn arg ser leu lys glu glu gly val gln arg ala arg glu glu glu glu lys arg lys glu val thr ser his phe gln val thr leu asn asp ile gln leu gln met glu gln his asn glu arg asn ser lys leu arg gln glu asn met glu leu ala glu arg leu lys lys leu ile glu gln tyr glu leu arg glu glu his ile asp lys val phe lys his lys asp leu gln gln gln leu val asp ala lys leu gln gln ala gln glu met leu lys glu ala glu glu arg his gln arg glu lys asp phe leu leu lys glu ala val glu ser gln arg met cys glu leu met lys gln gln glu thr his leu lys gln gln leu ala leu tyr thr glu lys phe glu glu phe gln asn thr leu ser lys ser ser
```

FIG. 8B-1

```
glu val phe thr thr phe lys gln glu met glu lys met thr lys
lys ile lys lys leu glu lys glu thr thr met tyr arg ser arg
trp glu ser ser asn lys ala leu leu glu met ala glu glu lys
thr val arg asp lys glu leu glu gly leu gln val lys ile gln
arg leu glu lys leu cys arg ala leu gln thr glu arg asn asp
leu asn lys arg val gln asp leu ser ala gly gly gln gly ser
leu thr asp ser gly pro glu arg arg pro glu gly pro gly ala
gln ala pro ser ser pro arg val thr glu ala pro cys tyr pro
gly ala pro ser thr glu ala ser gly gln thr gly pro gln glu
pro thr ser ala arg ala ***
```

FIG. 8B-2 val asp val asp glu tyr asp glu asn lys phe val asp glu glu asp gly gly asp gly

FIG. 9

```
  1  AAG CCT CGC AGC GGT CGG GGC GGC GCC GCG GAG GCT
 37  CGA GGG CGG CGG GCG GCG GCG ATG TCG AAG AAC ACG
                                 met ser lys asn thr 73  GTG TCG TCG GCG CGG TTC CGG AAG GTG GAC GTG GAT
     val ser ser ala arg phe arg lys val asp val asp 109  GAG TAC GAC GAG AAC AAG TTC GTG GAC GAG GAA GAC
     glu tyr asp glu asn lys phe val asp glu glu asp 145  GGC GGC GAC GGC CAG GCG GGC CCG GAC GAG GGC GAG
     gly gly asp gly gln ala gly pro asp glu gly glu 181  GTG GAC TCG TGC CTG CGG CAA GGG AAC ATG ACA GCC
     val asp ser cys leu arg gln gly asn met thr ala 217  GCC CTG CAG GCG GCG CTG AAG AAC CCT CCC ATC AAC
     ala leu gln ala ala leu lys asn pro pro ile asn 253  ACC AGG AGC CAG GCG GTG AAG GAC CGG GCA GGC AGC
     thr arg ser gln ala val lys asp arg ala gly ser 289  ATC GTG CTG AAG GTG CTC ATC TCC TTC AAG GCC GGC
     ile val leu lys val leu ile ser phe lys ala gly

325  GAC ATA GAA AAG GCC GTG CAG TCC CTG GAC AGG AAC
     asp ile glu lys ala val gln ser leu asp arg asn 361  GGC GTG GAC CTG CTC ATG AAG TAC ATC TAC AAG GGC
     gly val asp leu leu met lys tyr ile tyr lys gly 397  TTC GAG AGC CCC TCC GAC AAC AGC AGC GCC GTG CTC
     phe glu ser pro ser asp asn ser ser ala val leu 433  CTG CAG TGG CAC GAG AAG GCG CTG GCT GCA GGA GGA
     leu gln trp his glu lys ala leu ala ala gly gly 469  GTG GGC TCC ATC GTC CGT GTC CTG ACT GCA AGG AAA
     val gly ser ile val arg val leu thr ala arg lys 505  ACC GTG TAG CCT GGC AGG AAC GGG TGC CTG CCG GGG
     thr val
```

FIG. 10A

```
541   AGC GGG AGC TGC CGG TAC AAA GAC CAA AAC GCC CAG
577   ATG CCG CCG CTG CCC TGT GGG CGG CGT CTG TTC CCA
613   GCT TCG CTT TTT CCC TTT CCC GTG TCT GTC AGG ATT
649   ACA TAA GGT TTC CCT TCG TGA GAA TCG GAG TGG CGC
685   AGA GGG TCC TGT TCA TAC GCG CCG TGC GTC CGG CTG
721   TGT AAG ACC CCT GCC TTC AGT GTC CTT GAG CAA CGG
757   TAG CGT GTC GCC GGC TGG GTT TGG TTT TGT CGT GGA
793   GGG ATC TGG TCA GAA TTT GAG CCA GTT TTC CTA ACT
829   CAT TGC TGG TCA GGA AAT GAT CTT CAT TTA AAA AAA
865   AAA AAA AGA CTG GCA GCT ATT ATG CAA AAC TGG ACC
901   CTC TTC CCT TAT TTA AGC AGA GTG AGT TTC TGG AAC
937   CAG TGG TGC CCC CCC CCC CGC CCC GGC CGC CGT CCT
973   GCT CAA GGG AAG CCT CCC TGC AGA GCA GCA GAG CCC
1009  CTG GGC AGG AGC GCC GCG TCC GCC TCC AGA GAG ACA
1045  GCA TGC GCG GTC ACG CGG CAC TTC CTG TGC CTC CCA
1081  GCC CCA GTG CCC CGG AGT TCT TCA GGG CGA CAG GGA
1117  CCT CAG AAG ACT GGA TCC GAT CCA GAC AGA CGC CCA
1153  TTC TTG GTT CAG CTC AGT GTT TTC AAA AGG AAC GTG
1189  CTA CCG TGG GTA GAG CAC ACT GGT TCT CAG AAC ACG
1225  GCC GGC GCT TGA CGG TTG TCA CAG CTC CAG AAC AAA
1261  TCC TGG GAG ACA GGC GAG CGC GAG TCG CCG GGC AGG
1297  AAT TCC ACA CAC TCG TGC TGT TTT TGA TAC CTG CTT
1333  TTT GTT TTG TTT TGT AAA AAT GAT GCA CTT GAG AAA
1369  ATA AAA CGT CAG TGT TGA CAA AAA AAA AAA AAA
```

FIG. 10B

```
  1  GAC TGC CGC AGC AGC AGC AAC AAC CGC TAG CCG AAG
     asp cys arg ser ser ser asn asn arg Xaa pro lys 37  GGT GGC GCG GCG CGG GCC GGC GGC CCG GCG CGG CCC
     gly gly ala ala arg ala gly gly pro ala arg pro 73  GTG AGC CTG CGG GAA GTC GTG CGC TAC CTC GGG GGT
     val ser leu arg glu val val arg tyr leu gly gly 109  AGC AGC GGC GCT GGC GGC CGC CTG ACC CGC GGC CGC
     ser ser gly ala gly gly arg leu thr arg gly arg 145  GTG CAG GGT CTG CTG GAA GAG GAG GCG GCG GCG CGG
     val gln gly leu leu glu glu glu ala ala ala arg 181  GGC CGC CTG GAG CGC ACC CGT CTC GGA GCG CTT GCG
     gly arg leu glu arg thr arg leu gly ala leu ala 217  CTG CCC CGC GGG GAC AGG CCC GGA CGG GCG CCA CCG
     leu pro arg gly asp arg pro gly arg ala pro pro 253  GCC GCC AGC GCC CGC GCG GCG CGG AAC AAG AGA GCT
     ala ala ser ala arg ala ala arg asn lys arg ala 289  GGC GAG GAG CGA GTG CTT GAA AAG GAG GAG GAG GAG
     gly glu glu arg val leu glu lys glu glu glu glu 325  GAG GAG GAG GAA GAC GAC GAG GAC GAC GAC GAC GAC
     glu glu glu glu asp asp glu asp asp asp asp asp 361  GTC GTG TCC GAG GGC TCG GAG GTG CCC GAG AGC GAT
     val val ser glu gly ser glu val pro glu ser asp 397  CGT CCC GCG GGT GCG CAG CAT CAC CAG CTG AAT GGC
     arg pro ala gly ala gln his his gln leu asn gly 433  GGC GAG CGC GGC CCG CAG ACC GCC AAG GAG CGG GCC
     gly glu arg gly pro gln thr ala lys glu arg ala 469  AAG GAG TGG TCG CTG TGT GGC CCC CAC CCT GGC CAG
     lys glu trp ser leu cys gly pro his pro gly gln
```

FIG. 11A

```
505   GAG GAA GGG CGG GGG CCG GCC GCG GGC AGT GGC ACC
      glu glu gly arg gly pro ala ala gly ser gly thr 541   CGC CAG GTG TTC TCC ATG GCG GCC TTG AGT AAG GAG
      arg gln val phe ser met ala ala leu ser lys glu 577   GGG GGA TCA GCC TCT TCG ACC ACC GGG CCT GAC TCC
      gly gly ser ala ser ser thr thr gly pro asp ser 613   CCG TCC CCG GTG CCT TTG CCC CCC GGG AAG CCA GCC
      pro ser pro val pro leu pro pro gly lys pro ala 649   CTC CCA GGA GCC GAT GGG ACC CCC TTT GGC TGC CCT
      leu pro gly ala asp gly thr pro phe gly cys pro 685   GCC GGG CGC AAA GAG AAG CCG GCA GAC CCC GTG GAG
      ala gly arg lys glu lys pro ala asp pro val glu 721   TGG ACA GTC ATG GAC GTC GTG GAG TAC TTC ACC GAG
      trp thr val met asp val val glu tyr phe thr glu 757   GCG GGC TTC CCT GAG CAA GCC ACG GCT TTC CAG GAG
      ala gly phe pro glu gln ala thr ala phe gln glu 793   CAG GAG ATC GAC GGC AAG TCC CTG CTG CTC ATG CAG
      gln glu ile asp gly lys ser leu leu leu met gln 829   CGC ACC GAT GTC CTC ACC GGC CTG TCC ATC CGC CTG
      arg thr asp val leu thr gly leu ser ile arg leu 865   GGG CCA GCG TTG AAA ATC TAT GAG CAC CAT ATC AAG
      gly pro ala leu lys ile tyr glu his his ile lys 901   GTG CTG CAG CAG GGT CAC TTC GAG GAC GAT GAC CCG
      val leu gln gln gly his phe glu asp asp asp pro 937   GAA GGC TTC CTG GGA TGA GCA CAG AGC CGC CGC GCC
      glu gly phe leu gly 973   CCT TGT CCC CAC CCC CAC CCC GCC TGG ACC CAT TCC
1009  TGC CTC CAT GTC ACC CAA GGT GTC CCA GAG GCC AGG
1045  AGC TGG ACT GGG CAG GCG AGG GGT GCG GAC CTA CCC
1081  TGA TTC TGG TAG GGG GCG GGG CCT TGC TGT GCT CAT
```

FIG. 11B

```
1117  TGC TAC CCC CCC ACC CCG TGT GTG TCT CTG CAC CTG
1153  CCC CCA GCA CAC CCC TCC CGG AGC CTG GAT GTC GCC
1189  TGG GAC TCT GGC CTG CTC ATT TTG CCC CCA GAT CAG
1225  CCC CCT CCC TCC CTC CTG TCC CAG GAC ATT TTT TAA
1261  AAG AAA AAA AGG AAA AAA AAA AAT TGG GGA GGG GGC
1297  TGG GAA GGT GCC CCA AGA TCC TCC TCG GCC CAA CCA
1333  GGT GTT TAT TCC TAT ATA TAT ATA TAT ATG TTT TGT
1369  TCT GCC TGT TTT TCG TTT TTT GGT GCG TGG CCT TTC
1405  TTC CCT CCC ACC ACC ACT CAT GGC CCC AGC CCT GCT
1441  CGC CCT GTC GGC GGG AGC AGC TGG AAA TGG GAG GAG
1477  GGT GGG ACC TTG GGT CTG TCT CCC ACC CTC TCT CCC
1513  GTT GGT TCT GTT GTC GCT CCA GCT GGC TGT ATT GCT
1549  TTT TAA TAT TGC ACC GAA GGG TTG TTT TTT TTT TTT
1585  TAA ATA AAA TTT TAA AAA AAG AAA AAA AAA
```

FIG. 11C

```
256     GCC AGC GCC CGC GCG GCG CGG AAC AAG AGA GCT
        ala ser ala arg ala ala arg asn lys arg ala 289     GGC GAG GAG CGA GTG CTT GAA AAG GAG GAG GAG GAG
        gly glu glu arg val leu glu lys glu glu glu glu 325     GAG GAG GAG GAA GAC GAC GAG GAC GAC GAC GAC GAC
        glu glu glu glu asp asp glu asp asp asp asp asp 361     GTC GTG TCC GAG GGC TCG GAG GTG CCC GAG AGC GAT
        val val ser glu gly ser glu val pro glu ser asp 397     CGT CCC GCG GGT GCG CAG CAT CAC CAG CTG AAT GGC
        arg pro ala gly ala gln his his gln leu asn gly 433     GGC GAG CGC GGC CCG CAG ACC GCC AAG GAG CGG GCC
        gly glu arg gly pro gln thr ala lys glu arg ala 469     AAG GAG TGG TCG CTG TGT GGC CCC CAC CCT GGC CAG
        lys glu trp ser leu cys gly pro his pro gly gln 505     GAG GAA GGG CGG GGG CCG GCC GCG GGC AGT GGC ACC
        glu glu gly arg gly pro ala ala gly ser gly thr 541     CGC CAG GTG TTC TCC ATG GCG GCC TTG AGT AAG GAG
        arg gln val phe ser met ala ala leu ser lys glu 577     GGG GGA TCA GCC TCT TCG ACC ACC GGG CCT GAC TCC
        gly gly ser ala ser ser thr thr gly pro asp ser 613     CCG TCC CCG GTG CCT TTG CCC CCC GGG AAG CCA GCC
        pro ser pro val pro leu pro pro gly lys pro ala 649     CTC CCA GGA GCC GAT GGG ACC CCC TTT GGC TGC CCT
        leu pro gly ala asp gly thr pro phe gly cys pro 685     GCC GGG CGC AAA GAG AAG CCG GCA GAC CCC GTG GAG
        ala gly arg lys glu lys pro ala asp pro val glu 721     TGG ACA GTC ATG GAC GTC GTG GAG TAC TTC ACC GAG
        trp thr val met asp val val glu tyr phe thr glu
```

FIG. 12A

```
757   GCG GGC TTC CCT GAG CAA GCC ACG GCT TTC CAG GAG
      ala gly phe pro glu gln ala thr ala phe gln glu 793   CAG GAG ATC GAC GGC AAG TCC CTG CTG CTC ATG CAG
      gln glu ile asp gly lys ser leu leu leu met gln 829   CGC ACC GAT GTC CTC ACC GGC CTG TCC ATC CGC CTG
      arg thr asp val leu thr gly leu ser ile arg leu 865   GGG CCA GCG TTG AAA ATC TAT GAG CAC CAT ATC AAG
      gly pro ala leu lys ile tyr glu his his ile lys 901   GTG CTG CAG CAG GGT CAC TTC GAG GAC GAT GAC CCG
      val leu gln gln gly his phe glu asp asp asp pro 937   GAA GGC TTC CTG GGA TGA GCA CAG AGC CGC CGC GCC
      glu gly phe leu gly 973   CCT TGT CCC CAC CCC CAC CCC GCC TGG ACC CAT TCC
1009  TGC CTC CAT GTC ACC CAA GGT GTC CCA GAG GCC AGG
1045  AGC TGG ACT GGG CAG GCG AGG GGT GCG GAC CTA CCC
1081  TGA TTC TGG TAG GGG GCG GGG CCT GCT GTG CT CAT
1117  TGC TAC CCC CCC ACC CCG TGT GTG TCT CTG CAC CTG
1153  CCC CCA GCA CAC CCC TCC CGG AGC TGG ATG TC GCC
1189  TGG GAC TCT GGC CTG CTC ATT TTG CCC CCA GAT CAG
1225  CCC CCT CCC TCC CTC CTG TCC CAG GAC ATT TTT TAA
1261  AAG AAA AAA AGG AAA AAA AAA AAT TGG GGA GGG GGC
1297  TGG GAA GGT GCC CCA AGA TCC TCC TCG GCC CAA CCA
1333  GGT GTT TAT TCC TAT ATA TAT ATA TAT ATG TTT TGT
1369  TCT GCC TGT TTT TCG TTT TTT GGT GCG TGG CCT TTC
1405  TTC CCT CCC ACC ACC ACT CAT GGC CCC AGC CCT GCT
1441  CGC CCT GTC GGC GGG AGC AGC TGG AAT GGG AGG AGG
1477  GGT GGG ACC TTG GGT CTG TCT CCC ACC CTC TCT CCC
1513  GTT GGT TCT GTT GTC GCT CCA GCT GGC TGT ATT GCT
1549  TTT TAA TAT TGC ACC GAA GGG TTG TTT TTT TTT TTT
1585  TAA ATA AAA TTT TAA AAA AAG GAA AAA AAA AAA
```

FIG. 12B

```
196                         ACC CGT CTC GGA GCG CTT GCG
                            thr arg leu gly ala leu ala 217  CTG CCC CGC GGG GAC AGG CCC GGA CGG GCG CCA CCG
     leu pro arg gly asp arg pro gly arg ala pro pro 253  GCC GCC AGC GCC CGC GCG GCG CGG AAC AAG AGA GCT
     ala ala ser ala arg ala ala arg asn lys arg ala 289  GGC GAG GAG CGA GTG CTT GAA AAG GAG GAG GAG GAG
     gly glu glu arg val leu glu lys glu glu glu glu 325  GAG GAG GAG GAA GAC GAC GAG GAC GAC GAC GAC GAC
     glu glu glu glu asp asp glu asp asp asp asp asp 361  GTC GTG TCC GAG GGC TCG GAG GTG CCC GAG AGC GAT
     val val ser glu gly ser glu val pro glu ser asp 397  CGT CCC GCG GGT GCG CAG CAT CAC CAG CTG AAT GGC
     arg pro ala gly ala gln his his gln leu asn gly 433  GGC GAG CGC GGC CCG CAG ACC GCC AAG GAG CGG GCC
     gly glu arg gly pro gln thr ala lys glu arg ala 469  AAG GAG TGG TCG CTG TGT GGC CCC CAC CCT GGC CAG
     lys glu trp ser leu cys gly pro his pro gly gln 505  GAG GAA GGG CGG GGG CCG GCC GCG GGC AGT GGC ACC
     glu glu gly arg gly pro ala ala gly ser gly thr 541  CGC CAG GTG TTC TCC ATG GCG GCC TTG AGT AAG GAG
     arg gln val phe ser met ala ala leu ser lys glu 577  GGG GGA TCA GCC TCT TCG ACC ACC GGG CCT GAC TCC
     gly gly ser ala ser ser thr thr gly pro asp ser 613  CCG TCC CCG GTG CCT TTG CCC CCC GGG AAG CCA GCC
     pro ser pro val pro leu pro pro gly lys pro ala 649  CTC CCA GGA GCC GAT GGG ACC CCC TTT GGC TGC CCT
     leu pro gly ala asp gly thr pro phe gly cys pro
```

FIG. 13A

```
685   GCC GGG CGC AAA GAG AAG CCG GCA GAC CCC GTG GAG
      ala gly arg lys glu lys pro ala asp pro val glu 721   TGG ACA GTC ATG GAC GTC GTG GAG TAC TTC ACC GAG
      trp thr val met asp val val glu tyr phe thr glu 757   GCG GGC TTC CCT GAG CAA GCC ACG GCT TTC CAG GAG
      ala gly phe pro glu gln ala thr ala phe gln glu 793   CAG GAG ATC GAC GGC AAG TCC CTG CTG CTC ATG CAG
      gln glu ile asp gly lys ser leu leu leu met gln 829   CGC ACC GAT GTC CTC ACC GGC CTG TCC ATC CGC CTG
      arg thr asp val leu thr gly leu ser ile arg leu 865   GGG CCA GCG TTG AAA ATC TAT GAG CAC CAT ATC AAG
      gly pro ala leu lys ile tyr glu his his ile lys 901   GTG CTG CAG CAG GGT CAC TTC GAG GAC GAT GAC CCG
      val leu gln gln gly his phe glu asp asp asp pro 937   GAA GGC TTC CTG GGA TGA GCA CAG AGC CGC CGC GCC
      glu gly phe leu gly 973   CCT TGT CCC CAC CCC CAC CCC GCC TGG ACC CAT TCC
1009  TGC CTC CAT GTC ACC CAA GGT GTC CCA GAG GCC AGG
1045  AGC TGG ACT GGG CAG GCG AGG GGT GCG GAC CTA CCC
1081  TGA TTC TGG TAG GGG GCG GGG CCT TGC TGT GCT CAT
1117  TGC TAC CCC CCC ACC CCG TGT GTG TCT CTG CAC CTG
1153  CCC CCA GCA CAC CCC TCC CGG AGC CTG GAT GTC GCC
1189  TGG GAC TCT GGC CTG CTC ATT TTG CCC CCA GAT CAG
1225  CCC CCT CCC TCC CTC CTG TCC CAG GAC ATT TTT TAA
1261  AAG AAA AAA AGG AAA AAA AAA AAT TGG GGA GGG GGC
1297  TGG GAA GGT GCC CCA AGA TCC TCC TCG GCC CAA CCA
1333  GGT GTT TAT TCC TAT ATA TAT ATA TAT ATG TTT TGT
1369  TCT GCC TGT TTT TCG TTT TTT GGT GCG TGG CCT TTC
1405  TTC CCT CCC ACC ACC ACT CAT GGC CCC AGC CCT GCT
1441  CGC CCT GTC GGC GGG AGC AGC TGG GAA TGG GAG GAG
1477  GGT GGG ACC TTG GGT CTG TCT CCC ACC CTC TCT CCC
1513  GTT GGT TCT GTT GTC GCT CCA GCT GGC TGT ATT GCT
1549  TTT TAA TAT TGC ACC GAA GGG TTG TTT TTT TTT TTT
1585  TAA ATA AAA TTT TAA AAA AAG GAA AAA AAA AAA
```

FIG. 13B

```
  1  GTG GAA AAT AGC AAC TGT GTT TCT CAA GGA TCC AAT
 37  CCC AAC CTA AGG TGG CAG CGC ACA ATG AAG AAT CAA
                                     met lys asn gln 73  GAC AAA AAG AAC GGG GCT GCC AAA CAG CCC AAC CCC
     asp lys lys asn gly ala ala lys gln pro asn pro 109  AAA AGC AGC CCG GGA CAG CCG GAA GCA GGA GCG GAG
     lys ser ser pro gly gln pro glu ala gly ala glu 145  GGA GCC CAG GGG CGG CCC GGC CGG CCG GCC CCC GCC
     gly ala gln gly arg pro gly arg pro ala pro ala 181  CGA GAA GCC GAA GGT GCC AGC AGC CAG GCT CCC GGG
     arg glu ala glu gly ala ser ser gln ala pro gly 217  AGG CCG GAG GGG GCT CAA GCC AAA ACT GCT CAG CCT
     arg pro glu gly ala gln ala lys thr ala gln pro 253  GGG GCG CTC TGT GAT GTC TCT GAG GAG CTG AGC CGC
     gly ala leu cys asp val ser glu glu leu ser arg 289  CAG TTG GAA GAC ATA CTC AGT ACA TAC TGT GTG GAC
     gln leu glu asp ile leu ser thr tyr cys val asp 325  AAC AAC CAG GGG GCC CCG GGT GAG GAT GGG GTC CAG
     asn asn gln gly ala pro gly glu asp gly val gln 361  GGT GAG CCC CCT GAA CCT GAA GAT GCA GAG AAG TCT
     gly glu pro pro glu pro glu asp ala glu lys ser 397  CGC GCC TAT GTG GCA AGG AAT GGG GAG CCG GAG CCG
     arg ala tyr val ala arg asn gly glu pro glu pro 433  GGC ACC CCA GTA GTC AAT GGC GAG AAG GAG ACC TCC
     gly thr pro val val asn gly glu lys glu thr ser 469  AAG GCA GAG CCG GGC ACG GAA GAG ATC CGG ACG AGC
     lys ala glu pro gly thr glu glu ile arg thr ser 505  GAT GAG GTC GGA GAC CGA GAC CAC CGG AGG CCA CAG
     asp glu val gly asp arg asp his arg arg pro gln
```

FIG. 14A

```
541   GAA AAG AAG AAG GCC AAG GGT CTG GGA AAG GAG ATC
      glu lys lys lys ala lys gly leu gly lys glu ile 577   ACG CTG CTG ATG CAG ACA CTG AAC ACG CTG AGC ACC
      thr leu leu met gln thr leu asn thr leu ser thr 613   CCA GAG GAG AAG CTG GCG GCT CTG TGC AAG AAG TAT
      pro glu glu lys leu ala ala leu cys lys lys tyr 649   GCG GAA CTG CTC GAG GAG CAC CGG AAC TCG CAG AAG
      ala glu leu leu glu glu his arg asn ser gln lys 685   CAG ATG AAG CTG CTG CAG AAG AAG CAG AGC CAG CTG
      gln met lys leu leu gln lys lys gln ser gln leu 721   GTG CAG GAG AAG GAC CAC CTG CGT GGC GAG CAC AGC
      val gln glu lys asp his leu arg gly glu his ser 757   AAG GCC ATC CTG GCC CGC AGC AAG CTC GAG AGC CTG
      lys ala ile leu ala arg ser lys leu glu ser leu 793   TGC CGG GAG CTG CAG CGG CAC AAC CGC TCG CTC AAG
      cys arg glu leu gln arg his asn arg ser leu lys 829   GAA GAA GGT GTG CAG CGA GCC CGA GAG GAG GAG GAG
      glu glu gly val gln arg ala arg glu glu glu glu 865   AAG CGC AAG GAG GTG ACG TCA CAC TTC CAG ATG ACG
      lys arg lys glu val thr ser his phe gln met thr 901   CTC AAC GAC ATT CAG CTG CAG ATG GAG CAG CAC AAC
      leu asn asp ile gln leu gln met glu gln his asn 937   GAG CGC AAC TCC AAG CTG CGC CAG GAG AAC ATG GAG
      glu arg asn ser lys leu arg gln glu asn met glu 973   CTG GCC GAG CGG CTC AAG AAG CTG ATT GAG CAG TAC
      leu ala glu arg leu lys lys leu ile glu gln tyr 1009  GAG CTG CGA GAA GAG CAC ATC GAC AAA GTC TTC AAA
      glu leu arg glu glu his ile asp lys val phe lys
```

FIG. 14B

```
1045  CAC AAG GAT CTG CAG CAG CAG CTG GTG GAC GCC AAG
      his lys asp leu gln gln gln leu val asp ala lys 1081  CTC CAG CAG GCC CAG GAG ATG CTG AAG GAG GCA GAG
      leu gln gln ala gln glu met leu lys glu ala glu 1117  GAG CGG CAC CAG CGG GAG AAG GAC TTT CTC CTG AAG
      glu arg his gln arg glu lys asp phe leu leu lys 1153  GAG GCC GTG GAG TCC CAG AGG ATG TGC GAG CTG ATG
      glu ala val glu ser gln arg met cys glu leu met 1189  AAG CAA CAG GAG ACC CAC CTG AAG CAG CAG CTT GCC
      lys gln gln glu thr his leu lys gln gln leu ala 1225  CTA TAC ACA GAG AAG TTT GAG GAG TTC CAG AAC ACT
      leu tyr thr glu lys phe glu glu phe gln asn thr 1261  CTT TCC AAA AGC AGC GAG GTG TTC ACC ACA TTC AAA
      leu ser lys ser ser glu val phe thr thr phe lys 1297  CAG GAA ATG GAA AAG ATG ACA AAG AAG ATC AAG AAG
      gln glu met glu lys met thr lys lys ile lys lys 1333  CTG GAG AAA GAG ACC ACC ATG TAC CGT TCC CGG TGG
      leu glu lys glu thr thr met tyr arg ser arg trp 1369  GAG AGC AGC AAC AAG GCC CTG CTT GAG ATG GCT GAG
      glu ser ser asn lys ala leu leu glu met ala glu 1405  GAG AAA ACA CTC CGG GAC AAA GAG CTG GAA GGC CTG
      glu lys thr leu arg asp lys glu leu glu gly leu 1441  CAG GTG AAA ATC CAG CGG CTG GAG AAG CTG TGC CGG
      gln val lys ile gln arg leu glu lys leu cys arg 1477  GCA CTG CAG ACA GAG CGC AAT GAC CTG AAC AAG AGG
      ala leu gln thr glu arg asn asp leu asn lys arg 1513  GTG CAG GAC CTG AGT GCC GGT GGC CAG GGC CCC GTC
      val gln asp leu ser ala gly gly gln gly pro val
```

FIG. 14C

```
1549  TCC GAC AGC GGT CCT GAG CGG AGG CCA GAG CCC GCC
      ser asp ser gly pro glu arg arg pro glu pro ala 1585  ACC ACC TCC AAG GAG CAG GGT GTC GAG GGC CCC GGG
      thr thr ser lys glu gln gly val glu gly pro gly 1621  GCT CAA GTA CCC AAC TCT CCA AGG GCC ACA GAC GCT
      ala gln val pro asn ser pro arg ala thr asp ala 1657  TCC TGC TGC GCA GGT GCA CCC AGC ACA GAG GCA TCA
      ser cys cys ala gly ala pro ser thr glu ala ser 1693  GGC CAG ACA GGG CCC CAG GAG CCC ACC ACT GCC ACT
      gly gln thr gly pro gln glu pro thr thr ala thr 1729  GCC TAG AGA GCT TGG TGC TGG GGT GTG CCA GGA AGG
      ala 1765  GAG CAG GCA GCC CAG CCA GGC CTG GCC CAG CCC AGG
1801  CTC CCA TGC TAA GCA GTC CGG TGC TGA GGC CAG GAT
1837  GTT CTG ACC TGG CTG GCA CCT GAC CCT CTG CAG TCT
1873  TGG ATT TTG TGG GTC AGT TTT ACA TGC ATA TGG CAC
1909  ACA TGC AAG GCC TCA CAC ATT TGT GTC TCT AAG TGT
1945  ACT GTG GGC TTG CAT CGG GGG TGA CGA TGG ACA GAT
1981  GAA GCC AGC GGC TCC CTT GTG AGC TGA AGT CTT ACG
2017  GAG GAG ACG GCG TCT GCA CTG CCA TCG CAG TGA CCT
2053  GCA GGA CGA GTT CCT TGA GCT TTC CCT GCC TGC TTT
2089  GAG GCT GAG ACC CCT CCC GGC CCT TCA GAG CTC CTG
2125  ACA GGT GAT ACA CAC CCA GCC TTG ACC GCA CTT CTC
2161  TTG GGT AGC TGG GCT CTC CTA GCC TCC CCC AGA GGC
2197  GCC ATT GCT TCT CTT GAC TTG GAG AGG GGA TGC CCA
2233  GGC GTG GCC TTG GCA GGC ACT GGG AGC TAG TGA TTG
2269  GGC TGC TCT CCT GCC TCG AGC AGG GCA GGA GTT GTT
2305  TCT GGT GGG ATG ATG CGC TCG CTG GTC AGG AGC CCC
2341  GTG GGC GCT GCT TCC CCC GCC CTC TGG TGA TGC CAG
2377  GAC CAG GCC AGT GAT GCT TCT CAG TAG CCT TAC CAT
2413  TCA CAG GTG CCT CTC CAG CCC GCA CAG TGA GTG ACA
2449  AGA TCA TCC AAA GGA TTC CTT CTG AAG GTG TTC GTT
2485  TCG TTT TGT TTT GTT GCA CGT GAC GGT TTG TAT TGA
2521  GGA CCC TCT GAG GAA GAG GGG TGC TGT AGC AGT GGT
2557  CCC TGC GTG CCT GGC TCC AGT GTC CTG CCC TCC CCC
2593  CCC TCG CCA TGG CTC CTC GGC CGC CTT GGT GCT GAG
2629  GTT TCT GTT TGG TGA GAT CAG GTT GTC TGT TCA GAG
```

FIG. 14D

```
2665  AGA AGA GGC GTC TGA TGG CTT TGC CGC CAG CTT GCC
2701  TGC GGG CCT CAA TCC CGG GAG GCC GCC CGG TTC CCG
2737  TCA CTG TTG TCC CCG TGC AGT GCG TTG CTG GTC CCC
2773  AGG ACC AGC TGC TCG TTT GCT GTA TGG GTC AGT TTC
2809  TGC TTC CTG CCC CCC ACT CCA CCT AAC TGC AAT CCT
2845  TGG GGT TTC CCT GGT TCT CGT CCC TGG TAC CTC TGT
2881  GCC CAA GAA GTA GCC TTC TTT GGG ATT CTT GTT CTG
2917  CCC ATG CGG GAG CTG CTG CTG TCT GAC AGG TGA GGC
2953  CTG AGA CTC AGC GGC TGA CAG AGC TGC AGA GCT CTG
2989  CAC GGT GGC TCC CGG GGC GGC CTC TGT GTG CTG CAC
3025  ACC GCT GCT CTG CTG GCA CTG GCC AGT CTG TGC AGA
3061  GCA TTT GAG TAC TGG CTC AGG AGG GAG GGC TCT GCT
3097  GGC CTC GAG GGA CAG CGC CAC GTC TCC AGC TGG GCT
3133  CAG GGA GAG CCC CAG ACT GGC TGC GTA GGG TGC TTG
3169  GGG TTT GCT TCT TGC AGT ATT TCT TGG AAG CTG TTT
3205  TGT TGT CCT GCT ATT CCT TCA TCT TCC ACA GTC CAC
3241  GCT CAG CCT TTA ACT TGG ATC CCT CAC ATA ACA GGG
3277  TTC ATG AGA CCC GCA AGT ACG CCC AAG CTA CGT ATG
3313  GCT GAG GCC AGC TGG CAG GTG AAT GGC ACG CCA TTG
3349  CTG CTG CTA ATC CCT GGC ATA TCT TTA GTT CAC CTC
3385  GAA ATG CCC CCG CCA CAG TGC AAG CAG TGA GTC CAC
3421  GTG CCA CCC TGG GCT GAA TCC CAC CCC CTG TGA GTG
3457  TTG CCC GAG ATT GTG TCT CTT CTG AAT GCC TTC ACT
3493  GGG AAT GGC CTC TGC CGC CTC CTG CTC AGG GAG GCT
3529  TTC CCC TTC CCT CAG CCC CTG TGC CAG ACT GAG GTA
3565  CAA GAA CCG CCA AGC CCA TGC AAG GTG TGG CTA GGC
3601  GCC AGG GTG CAG GAA GGA GGC AGG TAG CTG CCT GCA
3637  CCC TTG AAA GCC AAG AGG CCT ACG GTG GCC TCC ATC
3673  CTG GCT TGC CTC ACT TCA GCT ACC TCG CAT AGC CCA
3709  GGG GTG GGG CTA TTG GAT TCC AGG GTG GGG GGA TGG
3745  GAA GCT GCA GGG GGC AGG TGG CTC TCA CTA GGC TTC
3781  CCA GCT CAG GAA TGT GGG CCT CAG GTA GGG GAG AGC
3817  CTT TGC TCC ACT CCA CCC ATT TGC AGG CAT CTA GGC
3853  CAG TCT AGA TGG CGA CCC CTT CTC TTC CTC TCC ATT
3889  GAC CAA ATC GTA CCT GTC TCT CCA GCT GCT CGC TTG
3925  CTC TGC TTT CCA AAG TCA GCC CAG GTA CCC AGG TGC
3961  CGC CCA CAT TGG CCT GGA ACC TGG ACC AGA GGC AAG
3997  GGA GGT GGC CTA TCC TTG AGT GAT AGC AGT GCC TT
4033  CCT CAC CCG GTG GCT TCC ATG CCT GTG ACC TCA GAT
4069  TTA GGA CCA AGA GCT GTG TTG GTT TCT TAC GTT GTG
4105  AGC TTT CCC TCC AGG GGA CCA CAG CAG GTG AGG CTC
4141  GGA GCC CAG AGC CCT TGG CGC CGC CAG CAG TAA CTT
4177  GTG TCC GGA CCT TGT CCA GCT GAG CGC TTC GTG TAT
```

FIG. 14E

```
4213  GAC TCA GCT TCG TGT GTG AGT CCA GCG GAG TGC GTC
4249  ACG TGA CCT AGA CTC AGC GGT GTC AGC CGC ACT TTG
4285  ATT TGT TTG TTT TCC ATG AGG TTT TTG GAC CAT GGG
4321  CTT AGC TCA GGC AAC TTT TCT GTA AGG AGA ATG TTA
4357  ACT TTC TGT AAA GAT GCT TAT TTA ACT AAC GCC TGC
4393  TTC CCC CAC TCC CAA CCA GGT GGC CAC CGA GAG CTC
4429  ACC AGG AGG CCA ATA GAG CTG CTC CAG CTC TCC CAT
4465  CTT GCA CCG CAC AAA GGT GGC CGC CCC AGG GAC AGC
4501  CAG GCA CCT GCC TGG GGG AGG GGC TTC TCT TCC TTA
4537  TGG CCT GGC CAT CTA GAT TGT TTA AAG TTG TGC TGA
4573  CAG CTT TTT TTG GTT TTT TGG TTT TTG TTT TTG TTT
4609  TTG TTT TTG TTT TTG TCT ACT TTT GGT ATT CAC AAC
4645  AGC CAG GGA CTT GAT TTT GAT GTA TTT TAA GCC ACA
4681  TTA AAT AAA GAG TCT GTT GCC TTA AAA AAA AAA AAA
4717  AAA AAA
```

FIG. 14F

```
  1  GAC GCC TCA GAG CGG AAC AGG GAA GTG AAT CAG GCG
 37  CCG GGT AGT GGG TTG CTG GGC TGG GCT TGC TGA GGT
 73  AGA GGC AGC GCC AAG AAG AGG CCT TTG CCG CTG GTC
109  GGG ATT GGG ATG TCG AAG AAC ACA GTG TCG TCG GCC
                     met ser lys asn thr val ser ser ala 145  CGC TTC CGG AAG GTG GAC GTG GAT GAA TAT GAC GAG
     arg phe arg lys val asp val asp glu tyr asp glu 181  AAC AAG TTC GTG GAC GAA GAA GAT GGG GGC GAC GGC
     asn lys phe val asp glu glu asp gly gly asp gly 217  CAG GCC GGG CCC GAC GAG GGC GAG GTG GAC TCC TGC
     gln ala gly pro asp glu gly glu val asp ser cys 253  CTG CGG CAA GGA AAC ATG ACA GCT GCC CTA CAG GCA
     leu arg gln gly asn met thr ala ala leu gln ala 289  GCT CTG AAG AAC CCC CCT ATC AAC ACC AAG AGT CAG
     ala leu lys asn pro pro ile asn thr lys ser gln 325  GCA GTG AAG GAC CGG GCA GGC AGC ATT GTC TTG AAG
     ala val lys asp arg ala gly ser ile val leu lys 361  GTG CTC ATC TCT TTT AAA GCT AAT GAT ATA GAA AAG
     val leu ile ser phe lys ala asn asp ile glu lys 397  GCA GTT CAA TCT CTG GAC AAG AAT GGT GTG GAT CTC
     ala val gln ser leu asp lys asn gly val asp leu 433  CTA ATG AAG TAT ATT TAT AAA GGA TTT GAG AGC CCG
     leu met lys tyr ile tyr lys gly phe glu ser pro 469  TCT GAC AAT AGC AGT GCT ATG TTA CTG CAA TGG CAT
     ser asp asn ser ser ala met leu leu gln trp his 505  GAA AAG GCA CTT GCT GCT GGA GGA GTA GGG TCC ATT
     glu lys ala leu ala ala gly gly val gly ser ile 541  GTT CGT GTC TTG ACT GCA AGA AAA ACT GTG TAG TCT
     val arg val leu thr ala arg lys thr val
```

FIG. 15A

```
577   GGC AGG AAG TGG ATT ATC TGC CTC GGG AGT GGG AAT
613   TGC TGG TAC AAA GAC CAA AAC AAC CAA ATG CCA CCG
649   CTG CCC TGT GGG TAG CAT CTG TTT CTC TCA GCT TTG
685   CCT TCT TGC TTT TTC ATA TCT GTA AAG AAA AAA ATT
721   ACA TAT CAG TTG TCC CTT TAA TGA AAA TTG GGA TAA
757   TAT AGA AGA AAT TGT GTT AAA ATA GAA GTG TTT CAT
793   CCT TTC AAA ACC ATT TCA GTG ATG TTT ATA CCA ATC
829   TGT ATA TAG TAT AAT TTA CAT TCA AGT TTT AAT TGT
865   GCA ACT TTT AAC CCT GTT GGC TGG TTT TTG GTT CTG
901   TTT GGT TTT GTA TTA TTT TTA ACT AAT ACT GAA AAA
937   TTT GGT CAG AAT TTG AGG CCA GTT TCC TAG CTC ATT
973   GCT AGT CAG GAA ATG ATA TTT ATA AAA AAT ATG AGA
1009  GAC TGG CAG CTA TTA ACA TTG CAA AAC TGG ACC ATA
1045  TTT CCC TTA TTT AAT AAG CAA AAT ATG TTT TTG GAA
1081  TAA GTG GTG GGT GAA TAC CAC TGC TAA GTT ATA GCT
1117  TTG TTT TTG CTT GCC TCC TCA TTA TCT GTA CTG TGG
1153  GTT TAA GTA TGC TAC TTT CTC TCA GCA TCC AAT AAT
1189  CAT GGC CCC TCA ATT TAT TTG TGG TCA CGC AGG GTT
1225  CAG AGC AAG AAG TCT TGC TTT ATA CAA ATG TAT CCA
1261  TAA AAT ATC AGA GCT TGT TGG GCA TGA ACA TCA AAC
1297  TTT TGT TCC ACT AAT ATG GCT CTG TTT GGA AAA AAC
1333  TGC AAA TCA GAA AGA ATG ATT TGC AGA AAG AAA GAA
1369  AAA CTA TGG TGT AAT TTA AAC TCT GGG CAG CCT CTG
1405  AAT GAA ATG CTA CTT TCT TTA GAA ATA TAA TAG CTG
1441  CCT TAG ACA TTA TGA GGT ATA CAA CTA GTA TTT AAG
1477  ATA CCA TTT AAT ATG CCC GGT AAA TGT CTT CAG TGT
1513  TCT TCA GGG TAG TTG GGA TCT CAA AAG ATT TGG TTC
1549  AGA TCC AAA CAA ATA CAC ATT CTG TGT TTT AGC TCA
1585  GTG TTT TCT AAA AAA AGA AAC TGC CAC ACA GCA AAA
1621  AAT TGT TTA CTT TGT TGG ACA AAC CAA ATC AGT TCT
1657  CAA AAA ATG ACC GGT GCT TAT AAA AAG TTA TAA ATA
1693  TCG AGT AGC TCT AAA ACA AAC CAC CTG ACC AAG AGG
1729  GAA GTG AGC TTG TGC TTA GTA TTT ACA TTG GAT GCC
1765  AGT TTT GTA ATC ACT GAC TTA TGT GCA AAC TGG TGC
1801  AGA AAT TCT ATA AAC TCT TTG CTG TTT TTG ATA CCT
1837  GCT TTT TGT TTC ATT TTG TTT TGT TTT GTA AAA ATG
1873  ATA AAA CTT CAG AAA ATA AAA TGT CAG TGT TGA ATA
1909  ATT AAA AAA AAA AAA AA
```

FIG. 15B

```
  1  GAA GAG CGA GTA CTT GAG AAA GAA GAG GAA GAA GAT
     glu glu arg val leu glu lys glu glu glu glu asp 37  GAT GAT GAA GAT GAA GAT GAA GAA GAT GAT GTG TCA
     asp asp glu asp glu asp glu glu asp asp val ser 73  GAG GGC TCT GAA GTG CCC GAG AGT GAC CGT CCT GCA
     glu gly ser glu val pro glu ser asp arg pro ala 109  GGT GCC CAG CAC CAC CAG CTT AAC GGC GAG CGG GGA
     gly ala gln his his gln leu asn gly glu arg gly 145  CCT CAG AGT GCC AAG GAG AGG GTC AAG GAG TGG ACC
     pro gln ser ala lys glu arg val lys glu trp thr 181  CCC TGC GGA CCG CAC CAG GGC CAG GAT GAA GGG CGG
     pro cys gly pro his gln gly gln asp glu gly arg 217  GGG CCA GCC CCG GGC AGC GGC ACC CGC CAG GTG TTC
     gly pro ala pro gly ser gly thr arg gln val phe 253  TCC ATG GCA GCC ATG AAC AAG GAA GGG GGA ACA GCT
     ser met ala ala met asn lys glu gly gly thr ala 289  TCT GTT GCC ACC GGG CCA GAC TCC CCG TCC CCC GTG
     ser val ala thr gly pro asp ser pro ser pro val 325  CCT TTG CCC CCA GGC AAA CCA GCC CTA CCT GGG GCC
     pro leu pro pro gly lys pro ala leu pro gly ala 361  GAC GGG ACC CCC TTT GGC TGT CCT CCC GGG CGC AAA
     asp gly thr pro phe gly cys pro pro gly arg lys 397  GAG AAG CCA TCT GAT CCC GTC GAG TGG ACC GTG ATG
     glu lys pro ser asp pro val glu trp thr val met 433  GAT GTC GTC GAA TAT TTT ACT GAG GCT GGA TTC CCG
     asp val val glu tyr phe thr glu ala gly phe pro 469  GAG CAG GCG ACA GCT TTC CAA GAG CAG GAA ATT GAT
     glu gln ala thr ala phe gln glu gln glu ile asp
```

FIG. 16A

```
505  GGC AAA TCT TTG CTG CTC ATG CAG CGC ACA GAT GTG
     gly lys ser leu leu leu met gln arg thr asp val 541  CTC ACC GGC CTG TCC ATC CGC CTC GGG CCA GCC CTG
     leu thr gly leu ser ile arg leu gly pro ala leu 577  AAA ATC TAC GAG CAC CAC ATC AAG GTG CTT CAG CAA
     lys ile tyr glu his his ile lys val leu gln gln 613  GGC CAC TTT GAG GAT GAT GAC CCC GAT GGC TTC TTA
     gly his phe glu asp asp asp pro asp gly phe leu 649  GGC TGA GCG CCC AGC CTC ACC CCT GCC CCA GCC CAT
     gly 685  TCC GGC CCC CAT CTC ACC CAA GAT CCC CCA GAG TCC
721  AGG AGC TGG ACG GGG ACA CCC TCA GCC CTC ATA ACA
757  GAT CCA AAG GAG AGG GCA CCC TCT TGT CCT TAT CTT
793  TGC CCC TTG TNT CTG TCT CAC ACA CAT CTG CTC CTC
829  AGC ACG TCG GTG TGG GGA GGG GAT TGC TCC TTA AAC
865  CCC AGG TGG CTG ACC CTC CCC ACC CAG TCC AGG ACA
901  TTT TAG GAA AAA AAA AAT GAA ATG TGG GGG GCT TCT
937  CAT CTC CCC AAG ATC CTC TTC CGT TCA GCC AGA TGT
973  TTC CTG TAT AAA TGT TTG GAT CTG CCT GTT TAT TTT
1009 GGT GGG TGG TCT TTC CTC CCT CCC CTA CCA CCC ATG
1045 CCC CCC TTC TCA GTC TGC CCC TGG CCT CCA GCC CCT
1081 AGG GGA CTA GCT GGG TTG GGG TTC CTC GGG CCT TTT
1117 CTC TCC TCC CTC TTT TCT TTC TGT TGA TTG TCG CTC
1153 CAG CTG GCT GTA TTG CTT TTT AAT ATT GCA CCG AAG
1189 GTT TTT TAA ATA AAA TTT TA
```

FIG. 16B

```
  1   CA AAA AGC AGC CCA GGA CAA CCG GAA GCA GGA CCC GAG GGA GCC
         lys ser ser pro gly gln pro glu ala gly pro glu gly ala 45   CAG GAG CGG CCC AGC CAG GCG GCT CCT GCA GTA GAA GCA GAA GGT
      gln glu arg pro ser gln ala ala pro ala val glu ala glu gly 90   CCC GGC AGC AGC CAG GCT CCT CGG AAG CCG GAG GGG GCT CAA GCC
      pro gly ser ser gln ala pro arg lys pro glu gly ala gln ala 135   AGA ACG GCT CAG TCT GGG GCC CTT CGT GAT GTC TCT GAG GAG CTG
      arg thr ala gln ser gly ala leu arg asp val ser glu glu leu 180   AGC CGC CAA CTG GAA GAC ATA CTG AGC ACA TAC TGT GTG GAC AAT
      ser arg gln leu glu asp ile leu ser thr tyr cys val asp asn 225   AAC CAG GGG GGC CCC GGC GAG GAT GGG GCA CAG GGT GAG CCG GCT
      asn gln gly gly pro gly glu asp gly ala gln gly glu pro ala 270   GAA CCC GAA GAT GCA GAG AAG TCC CGG ACC TAT GTG GCA AGG AAT
      glu pro glu asp ala glu lys ser arg thr tyr val ala arg asn 315   GGG GAG CCT GAA CCA ACT CCA GTA GTC TAT GGA GAG AAG GAA CCC
      gly glu pro glu pro thr pro val val tyr gly glu lys glu pro 360   TCC AAG GGG GAT CCA AAC ACA GAA GAG ATC CGG CAG AGT GAC GAG
      ser lys gly asp pro asn thr glu glu ile arg gln ser asp glu 405   GTC GGA GAC CGA GAC CAT CGA AGG CCA CAG GAG AAG AAA AAA GCC
      val gly asp arg asp his arg arg pro gln glu lys lys lys ala 450   AAG GGT TTG GGG AAG GAG ATC ACG TTG CTG ATG CAG ACA TTG AAT
      lys gly leu gly lys glu ile thr leu leu met gln thr leu asn 495   ACT CTG AGT ACC CCA GAG GAG AAG CTG GCT GCT CTG TGC AAG AAG
      thr leu ser thr pro glu glu lys leu ala ala leu cys lys lys 540   TAT GCT GAA CTG CTG GAG GAG CAC CGG AAT TCA CAG AAG CAG ATG
      tyr ala glu leu leu glu glu his arg asn ser gln lys gln met 585   AAG CTC CTA CAG AAA AAG CAG AGC CAG CTG GTG CAA GAG AAG GAC
      lys leu leu gln lys lys gln ser gln leu val gln glu lys asp 630   CAC CTG CGC GGT GAG CAC AGC AAG GCC GTC CTG GCC CGC AGC AAG
      his leu arg gly glu his ser lys ala val leu ala arg ser lys 675   CTT GAG AGC CTA TGC CGT GAG CTG CAG CGG CAC AAC CGC TCC CTC
      leu glu ser leu cys arg glu leu gln arg his asn arg ser leu
```

FIG. 17A

```
720   AAG GAA GAA GGT GTG CAG CGG GCC CGG GAG GAG GAG GAG AAG CGC
      lys glu glu gly val gln arg ala arg glu glu glu glu lys arg 765   AAG GAG GTG ACC TCG CAC TTC CAG GTG ACA CTG AAT GAC ATT CAG
      lys glu val thr ser his phe gln val thr leu asn asp ile gln 810   CTG CAG ATG GAA CAG CAC AAT GAG CGC AAC TCC AAG CTG CGC CAA
      leu gln met glu gln his asn glu arg asn ser lys leu arg gln 855   GAG AAC ATG GAG CTG GCT GAG AGG CTC AAG AAG CTG ATT GAG CAG
      glu asn met glu leu ala glu arg leu lys lys leu ile glu gln 900   TAT GAG CTG CGC GAG GAG CAT ATC GAC AAA GTC TTC AAA CAC AAG
      tyr glu leu arg glu glu his ile asp lys val phe lys his lys 945   GAC CTA CAA CAG CAG CTG GTG GAT GCC AAG CTC CAG CAG GCC CAG
      asp leu gln gln gln leu val asp ala lys leu gln gln ala gln 990   GAG ATG CTA AAG GAG GCA GAA GAG CGG CAC CAG CGG GAG AAG GAT
      glu met leu lys glu ala glu glu arg his gln arg glu lys asp 1035  TTT CTC CTG AAA GAG GCA GTA GAG TCC CAG AGG ATG TGT GAG CTG
      phe leu leu lys glu ala val glu ser gln arg met cys glu leu 1080  ATG AAG CAG CAA GAG ACC CAC CTG AAG CAA CAG CTT GCC CTA TAC
      met lys gln gln glu thr his leu lys gln gln leu ala leu tyr 1125  ACA GAG AAG TTT GAG GAG TTC CAG AAC ACA CTT TCC AAA AGC AGC
      thr glu lys phe glu glu phe gln asn thr leu ser lys ser ser 1170  GAG GTA TTC ACC ACA TTC AAG CAG GAG ATG GAA AAG ATG ACT AAG
      glu val phe thr thr phe lys gln glu met glu lys met thr lys 1215  AAG ATC AAG AAG CTG GAG AAA GAA ACC ACC ATG TAC CGG TCC CGG
      lys ile lys lys leu glu lys glu thr thr met tyr arg ser arg 1260  TGG GAG AGC AGC AAC AAG GCC CTG CTT GAG ATG GCT GAG GAG AAA
      trp glu ser ser asn lys ala leu leu glu met ala glu glu lys 1305  ACA GTC CGG GAT AAA GAA CTG GAG GGC CTG CAG GTA AAA ATC CAA
      thr val arg asp lys glu leu glu gly leu gln val lys ile gln 1350  CGG CTG GAG AAG CTG TGC CGG GCA CTG CAG ACA GAG CGC AAT GAC
      arg leu glu lys leu cys arg ala leu gln thr glu arg asn asp 1395  CTG AAC AAG AGG GTA CAG GAC CTG AGT GCT GGT GGC CAG GGC TCC
      leu asn lys arg val gln asp leu ser ala gly gly gln gly ser 1440  CTC ACT GAC AGT GGC CCT GAG AGG AGG CCA GAG GGG CCT GGG GCT
      leu thr asp ser gly pro glu arg arg pro glu gly pro gly ala
```

FIG. 17B

```
1485  CAA GCA CCC AGC TCC CCC AGG GTC ACA GAA GCG CCT TGC TAC CCA
      gln ala pro ser ser pro arg val thr glu ala pro cys tyr pro 1530  GGA GCA CCG AGC ACA GAA GCA TCA GGC CAG ACT GGG CCT CAA GAG
      gly ala pro ser thr glu ala ser gly gln thr gly pro gln glu 1575  CCC ACC TCC GCC AGG GCC TAG AGA GCC TGG TGT TGG GTC ATG CTG
      pro thr ser ala arg ala ***

1620  GGA AGG GAG CGG CAG CCC AGC CAG GCC TGG CCC ATA AAA GGC TCC
1665  CAT GCT GAG CAG CCC ATT GCT GAA GCC AGG ATG TTC TTG ACC TGG
1710  CTG GCA TCT GGC ACT TGC AAT TTT GGA TTT TGT GGG TCA GTT TTA
1755  CGT ACA TAG GGC ATT TTG CAA GGC CTT GCA AAT GCA TTT ATA CCT
1800  GTA AGT GTA CAG TGG GCT TGC ATT GGG GAT GGG GGT GTG TAC AGA
1845  TGA AGT CAG TGG CTT GTC TGT GAG CTG AAG AGT CTT GAG AGG GGC
1890  TGT CAT CTG TAG CTG CCA TCA CAG TGA GTT GGC AGA AGT GAC TTG
1935  AGC ATT TCT CTG TCT GAT TTG AGG CTC AGA CCC CTC CCT GCC CTT
1980  TCA GAG CTC AAA ACA AGT AAT ACA CCA AGG TCT TGA CTG CAT TTG
2025  TCT TGT GAG CAG GGC TTG CTT GGT CAG CTC AGG CCC TCC TAG CTG
2070  CTT GGA GGC TCC TTT GAT TCT CTA GAC CTG GAA AAG GTG TCC CTA
2115  GGC AGA GCC CTG GCA GGG CGC TCA GAG CTG GGA TTT CCT GCC TGG
2160  AAC AAG GGA CCT GGA GAA TGT TTT TGC GTG GGA TGA TGT GCT GGT
2205  CAG GAG CCC CTT GGG CAT CGC TTC CCC TGC CCT TTG GTA GTG CCA
2250  GGA CCA GGC AAA TGA TGC TTC TCA GTA GCC TTA TCA TTC ACA GGT
2295  GCC TCT CTA GCC TGC ACA AAT GAT TGA CAA GAG ATC ACC CAA AGG
2340  ATT ATT TCT GAA GGT GTT TTT TTC TTT ATT TCT TTT TCT TTT TTT
2385  TTT TTT CTT TTT CTT TTT TTT TTG CAC ATG ACA GTG TTT GTA TTG
2430  AGG ACC TTC CAA GGA AAA GGG ATG CTG TAC CAG TGG TGC CTG GGT
2475  GCC TGG CCT CCA GTG TCC CAC CTC CTT CAC CAC CCC ACT TGG CTC
2520  CTT TGC CAT CTT GAT GCT GAG GTT CCT GTT TGT GTG AGA TCA GGT
2565  TGT TTG TGG TAA AAG AAA GGA AAG GGC TTC TGA TGG CTT TGC CAC
2610  AAG CTT ACC TGT GGG TTT CAG TCC TGA GAG GCC ACC ACC AGT TCC
2655  CAT CAG CAC TGT CTC CAT GCA GCA GTT GCT GGG TCC CAT GTC CAG
2700  CTG CCT CTT TGG CTT CAT GGG TTT TTC TGC TTC CTG CCC CCA CCC
2745  CCA CAT GTG CAA TCC TCA AGA TTT GTC CTG ATT CTA TTT CCT GGC
2790  ACC TCC CTG CCT GTC CTT GGG GAT TCT ACT TCT CCT GTG TGG GG
2835  CCC ATA GCT GTT GTC TAA CAG GTA AGA AAT GAA ATT GAA CTA TTG
2880  ACT GGG CCC CAG AAA TCC ATA AAA TGG CTG CAG ACA GTT GTT TCT
2925  GTG TCC TGT TCT ACC CCC ACT CCA GTA CAT AAC TAC TAT GTA CTG
2970  TGT AGA GCC ATT CTA TAT GCT GAA TGT TCT GCT GTT GCA AAC TTG
3015  CCA GGG TAT TAG CCA GTG TTT GTG CCA AGC AGT TTT CGG GGA CAA
3060  CAG AAT GAC TCA GAC CAA GAT GGA TAG GAT GGT TAG GGC TTT GCT
3105  TCT TGC TGT TTT TCT TTG AAC TAG TCA TTG TCC TGC AGG. TCC CTT
3150  CAT CTT CCA TAC CTA GCC CAC TCT TTT AGC CCT TAC CTT AAA TCT
3195  CTC AGA TAA GTT GGT TCA CAA AGA ATG TTA AGT ACT GAA TCA TGT
3240  GTG ACT GAG ACC AGA GAT GGC AAA TGA ATG CAC ACA TTC TCC
3285  TTC TCC TGC CCC AGG GCA GGT ACC ACT GAT CTG CAT CAG AGT TGC
3330  CTG CTA TTC TCT GGT GTA CCT TCA CAT CTT AGG TGC CCT CAA GCA
3375  GCT GTG TGA GTG TTG AGA TCT CTG CCA TCT CTG GCT GAG ATA CTG
3420  CTG TCC TGT GAA GTG TTT CCC ATG ACC TTT TTC TTC CCC TTT GAA
3465  TCC CTC TTG TCT GGA GTA GTC CTT GCC TTC TTC TTG CTC CAG TAG
```

FIG. 17C

```
3510  GCC TTT TCC TTA CCC CAG CCC TTG TGC CAG GCT AAG CTG GTA CAA
3555  GAG CTG CCA ACT CAC AGA GTT TTG CTA GGC GAG AGA GGT GCA GGG
3600  AAG AGG CAG AGG TAT GCA CCT TCC CCC TTG AAG AGA GGG GAA AGG
3645  CCT ACA GTG GCC CAC ATA ATT GCC TGA CTC ACA CTT CAG CTA CCT
3690  CTT AAT GCC TGT GGA GGG ACT GGA GCT GCT GGA TCC CAG TGT GGT
3735  GGT GTA GGA GGC CAC AGT GAG CAG GTG GCC CCA GCT GGG TTT CCC
3780  AGG TCA GGA ATG TGG GCC CCA GGC AAG GTG CAG CCT TTG CTC ACA
3825  GCT CCA TCC ATG TCT AGA CCT TCA GGC AGT CT GCA GAT GAG GTT
3870  CCC TAC CTT TTT CTT CTC TTC ATT GAC CAA ATC AAC CAA TCA CTA
3915  CAG CTG CTC TGC TTC TGC TTT CCA AAG TAG CCC AGG TCC TGG GCC
3960  AGA TGC AGG GGA GGT GCC TAT CCA TGA GTG AAG GCC AGT GTC TTC
4005  CTC ACC TGG GTG GTC CCA CAC TTG TGA CCC TCA GTT TTA GGA CCC
4050  AAG ATC TGT GTT GGT TTC TTA GAT GCT AG CTT TTC CTC CAG GGG
4095  ACC ACA GCA GGT GAA GCT CAA GAG CGC ATG GCT CTG CTA ATA GTA
4140  AAT TGT TTT CAG GGC CTT GTC CAG CTG AGA GCT TCA TGT CCA CCA
4185  GAT TCT GAG AGG TGT CAG CAG CAC TTT TTT TTT TTA TTT GTT GTT
4230  TGT TTT CCA TGA GGT TAT CGG ACC ATG GGC TGA GCT CAG GCA CTT
4275  TCT GTA GGA GAC TGT TAT TTC TGT AAA GAT GGT TAT TTA ACC CTC
4320  CTC CAC CCC ATC ACG TGG CCT GAG GCT GAC CCG GAG GCC AGT
4365  GGA GCT GCC TGG TGT CCA CGG GGG AGG GCC AAG GCC TGC TGA GCT
4410  GAT TCT CCA GCT GCT GCC CCA GCC TTT CCG CCT TGC ACA GCA CAG
4455  AGG TGG TCA CCC CAG GGA CAG CCA GGC ACC TGC TCC TCT TGC CCT
4500  TCC TGG GGG AAA GGA GCT GCC TTC TGT CCC TGT AAC TGC TTT CCT
4545  TAT GGC CCA ACC CGG CCA CTC AGA CTT GTT TGA AGC TGC ACT GGC
4590  AGC TTT TTT GTC TCC TTT GGG TAT TCA CAA CAG CCA GGG ACT TGA
4635  TTT TGA TGT ATT TTA AAC CAC ATT AAA TAA AGA GTC TGT TGC CTT
4680  AAA AAA AAA AAA AAA AAA
```

FIG. 17D

```
GTG GAC GTG GAT GAG TAC GAC GAG AAC AAG TTC GTG
val asp val asp glu tyr asp glu asn lys phe val GAC GAG GAA GAC GGC GGC GAC GGC
asp glu glu asp gly gly asp gly
```

FIG. 18

```
        1                                                           50
Rabbit  MSKNTVSSAR FRKVDVDEYD ENKFVDEEDG GDGQAGPDEG EVDSCLRQGN
Human   .......... .......... .......... .......... ..........

51                                                          100
Rabbit  MTAALQAALK NPPINTRSQA VKDRAGSIVL KVLISFKAGD IEKAVQSLDR
Human   .......... ......K... .......... ........N. .........K 101                                                         150
Rabbit  NGVDLLMKYI YKGFESPSDN SSAVLLQWHE KALAAGGVGS IVRVLTARKT
Human   .......... .......... ...M...... .......... ..........

151
Rabbit  V
Human
```

FIG. 19

|         | 1          |            |            |            | 50         |
|---------|------------|------------|------------|------------|------------|
| Rabbit  | EERVLEKEEE | EEEEEDDEDD | DDDVVSEGSE | VPESDRPAGA | QHHQLNGGER |
| Human   | .......... | .DDD..EDEE | ..--...... | .......... | .......-... |

|         | 51         |            |            |            | 100        |
|---------|------------|------------|------------|------------|------------|
| Rabbit  | GPQTAKERAK | EWSLCGPHPG | QEEGRGPAAG | SGTRQVFSMA | ALSKEGGSAS |
| Human   | ...S....V. | ..TP....Q. | .D......P. | .......... | .MN....T.. |

|         | 101        |            |            |            | 150        |
|---------|------------|------------|------------|------------|------------|
| Rabbit  | STTGPDSPSP | VPLPPGKPAL | PGADGTPFGC | PAGRKEKPAD | PVEWTVMDVV |
| Human   | VA........ | .......... | .......... | .P......S. | .......... |

|         | 151        |            |            |            | 200        |
|---------|------------|------------|------------|------------|------------|
| Rabbit  | EYFTEAGFPE | QATAFQEQEI | DGKSLLLMQR | TDVLTGLSIR | LGPALKIYEH |
| Human   | .......... | .......... | .......... | .......... | .......... |

|         | 201        | 220        |
|---------|------------|------------|
| Rabbit  | HIKVLQQGHF | EDDDPEGFLG |
| Human   | .......... | .....D.... |

FIG. 20

|  | 1 |  |  |  | 50 |
|---|---|---|---|---|---|
| Rabbit | MKNQDKKNGA | AKQPNPKSSP | GQPEAGAEGA | QGRPGRPAPA | REAEG-ASSQ |
| Human | ---------- | ------.... | ......P... | .E..SQA... | V....PG... |

|  | 51 |  |  |  | 100 |
|---|---|---|---|---|---|
| Rabbit | APGRPEGAQA | KTAQPGALCD | VSEELSRQLE | DILSTYCVDN | NQGAPGEDGV |
| Human | ..RK...... | R...S...R. | .......... | .......... | ...G.....A |

|  | 101 |  |  |  | 150 |
|---|---|---|---|---|---|
| Rabbit | QGEPPEPEDA | EKSRAYVARN | GEPEPGTPVV | NGEKETSKAE | PGTEEIRTSD |
| Human | ....A..... | ....T..... | ......-... | Y....P..GD | .N.....Q.. |

|  | 151 |  |  |  | 200 |
|---|---|---|---|---|---|
| Rabbit | EVGDRDHRRP | QEKKKAKGLG | KEITLLMQTL | NTLSTPEEKL | AALCKKYAEL |
| Human | .......... | .......... | .......... | .......... | .......... |

|  | 201 |  |  |  | 250 |
|---|---|---|---|---|---|
| Rabbit | LEEHRNSQKQ | MKLLQKKQSQ | LVQEKDHLRG | EHSKAILARS | KLESLCRELQ |
| Human | .......... | .......... | .......... | .....V.... | .......... |

|  | 251 |  |  |  | 300 |
|---|---|---|---|---|---|
| Rabbit | RHNRSLKEEG | VQRAREEEEK | RKEVTSHFQM | TLNDIQLQME | QHNERNSKLR |
| Human | .......... | .......... | ........V | .......... | .......... |

|  | 301 |  |  |  | 350 |
|---|---|---|---|---|---|
| Rabbit | QENMELAERL | KKLIEQYELR | EEHIDKVFKH | KDLQQQLVDA | KLQQAQEMLK |
| Human | .......... | .......... | .......... | .......... | .......... |

|  | 351 |  |  |  | 400 |
|---|---|---|---|---|---|
| Rabbit | EAEERHQREK | DFLLKEAVES | QRMCELMKQQ | ETHLKQQLAL | YTEKFEEFQN |
| Human | .......... | .......... | .......... | .......... | .......... |

|  | 401 |  |  |  | 450 |
|---|---|---|---|---|---|
| Rabbit | TLSKSSEVFT | TFKQEMEKMT | KKIKKLEKET | TMYRSRWESS | NKALLEMAEE |
| Human | .......... | .......... | .......... | .......... | .......... |

|  | 451 |  |  |  | 500 |
|---|---|---|---|---|---|
| Rabbit | KTLRDKELEG | LQVKIQRLEK | LCRALQTERN | DLNKRVQDLS | AGGQGPVSDS |
| Human | ..V....... | .......... | .......... | .......... | .....SLT.. |

|  | 501 |  |  |  | 550 |
|---|---|---|---|---|---|
| Rabbit | GPERRPEPAT | TSKEQGVEGP | GAQVPNSPRA | TDASCCAGAP | STEASGQTGP |
| Human | .....----- | -------... | ...A.S...V | .E.P.YP... | .......... |

|  | 551 |
|---|---|
| Rabbit | QEPTTATA |
| Human | ....S.R. |

FIG. 21

|  |  |  |
|---|---|---|
| 1 | AAGCTTTATAAAGATTTAACTACCTAATAAGGTAGAGAAGTAATTTATGTGCCCACTAAA | 60 |
| 61 | AAATACTCAATTTCTGAATGTTCGTCCAAAATTAACTTGTCAGATCATTAAATCATTGAC | 120 |
| 121 | TAGAAACACGTTGAGTACCTATTATGTACTAGGCACTTAGATCATTGTGAGACAATAAAA | 180 |
| 181 | AATACTGCATTAGAAAAGGACATTTTTCACATCTTAAATGCAATAAGCATTATTTGGCTG | 240 |
| 241 | GCAGTTAATTACATTTAACACATTAAACATATAGAGCAAAATTCTGAGCAATCAAAATAA | 300 |
| 301 | TTATACCCTTGAGCAATCGATTATTTAAATTTCTTTCACTATTCCCTTAAGCTGATTTCT | 360 |
| 361 | ACTCTGGGATTCTTTCATAGTTCTCAAATAAGAAAATAAAAAATTTCCTAAATAAGGCAA | 420 |
| 421 | TACAAAAGAATAGAAATGTAAGAGAAGAGATATATTAGCTCTTGAATCCCTGTTTCCATT | 480 |
| 481 | TGCTGTCAATAGTGCCTCTAATGTTCGATTTTCTCTTCAAAGAAAAATCTTGATTTAAAA | 540 |
| 541 | GGAAGAAAAAGTACAATCACCTTTAACAGCTAAAGTATACTGATTAGCATCTACTAAAGT | 600 |
| 601 | TAGCAAAGACTGAAACTGAAAAAAAATTGTAAAATCTTTATTCTAAGTTATATAACGCCA | 660 |
| 661 | TTCACCATAGTAATGATTTATACTTTGGTATATGGCTTTTTAAAATAAATATTGCCAAC | 720 |
| 721 | AGGTAAAAATTTTTCCTTTGCTGTCTTAAGGCATTCCTAAGAGAATTTTTACCAGTGTGT | 780 |
| 781 | GTTCATAACTTGAATGTTAATTTAAACAATGTTACTTCTATCACCTAAATGATATACTTA | 840 |
| 841 | TAGAAGAGTGGTTTAATTGGGAACAGAAAAACACCACATTGCTTCTTCCCAAGAAAAAGG | 900 |
| 901 | GATGTATTCCATTCTCGAGGTCTCTCTCCCACTCTCTATTTATATATAATATACTGCATA | 960 |
| 961 | GATAAATATACACACATTATATATGTATTTTTTGAACTTAAAGAAGACTGGACATATGT | 1020 |
| 1021 | ATTTACATGTATATATCCAACAAATATTTAATTTTGAGATCTCTCTCCCTCTTCTGATTT | 1080 |
| 1081 | ATTATTCTCAGTATGAATTCTCAAACTGTACGGTCTTTCACATTTCATTCATTCATCAAG | 1140 |
| 1141 | CATGTATCGAGTCCCTTCTGCATGCTTAGCTTTTTGTCATATGGAAGGAAGATACAAAAG | 1200 |
| 1201 | AAAAACTGTTTCTGCCCTTCAGAATCTTTCCATCTCTTCTAGGAAGGAGATAAAACACCA | 1260 |
| 1261 | TATATCATTAAGAAATTTATAAGACTAGTCCCAAAACCAATGGTACAAGCAACATGCATT | 1320 |
| 1321 | TTACATTTATGTAGAATTTTAGAGCTTGGAAACACTTTCGTGTATATAATCCTAAGAAC | 1380 |
| 1381 | AATCTTGTAAAGTGCACATTATTAGCTCCATTTCAGTGATGAGGAATCTGAGACAGAATT | 1440 |
| 1441 | TTAAGTGACATGTCTCGTTCAAACATTATGAGTGGAAGAGTCAACACTTAAGCCTGAGTT | 1500 |
| 1501 | TTCTGATTCTAAGCCTAGTGCTCTTTTCAACACAGCACTGGAAACCAAAGATTGTGGTAC | 1560 |
| 1561 | ACAACAAGGCAACAGCCAGTCTTCTTGCTCGAGGTCCAACTAAACTGGACCCATACCGAG | 1620 |
| 1621 | CAGTGTCCAGCCAAATGTCCAAATTAATTTTATCCTGCAAATATTTGTTCTTCAGTGTAA | 1680 |
| 1681 | TACACACAGCACAACTACCATTTCCTTCGTCTTAGTGCCTTTATCTCCTACATTCCAGAA | 1740 |
| 1741 | ATGGGGATGTCAAATATTTTTTAAATCTGGCCTAGATGGAATCATATAAATCTCAAATC | 1800 |
| 1801 | ATAATATAAATCTTAAAGGTCTGGTTTCCACCAATCCTTCCACATTTTGTTTTCCCCCAG | 1860 |
| 1861 | CACTAGAGAGCCTAACCTACCCTCACCCCTTTCGAGCATTCTTGCTCCAAACGACCACCT | 1920 |
| 1921 | ATTTTAAGATGTCAATGACCCTTTCCCAAATTCTACAAATTCACCCCAGTTTTGCCACCC | 1980 |
| 1981 | GACCCCAGCGCCTGCCCGGACACGTTCCCTCCCTCCCAATAGATTTGATACCGAGTTCA | 2040 |
| 2041 | GGTTCTGCAGATCCCGTTGCGATGCTGTCACACAGCACTGACAGATAAGATTTGACCTTT | 2100 |
| 2101 | CGACTCCGTCCTTGGGGACTTCCCGCTGGCCAAGAAGGGTAGTTCCAATCCCAGGAAACG | 2160 |
| 2161 | GGCTTCCTGCTCAGGAACGCAGCCTCTAGCAGCGCACAGTCTGAGGCAATGTCTCCGGCA | 2220 |
| 2221 | ATTAGAACGATGCTGGGCGCCCGGGTGTGCATCACTCTGCCTCATACTCCTACCAACTGC | 2280 |
| 2281 | AGGGCACTCGGTCCGGCAGCCAGTCCATCCCACCCACACCCAAGTCCCAGCCAGCCGGAC | 2340 |
| 2341 | CTTACGCAGGACCCCGATGATAGGTCGTTGACGGCTGCAGCAAAAGCCAAGGCCACCTGC | 2400 |
| 2401 | CGCTGCTGCCCATCCCCGCCAATCTGAGACCCCCTAGACTGGACCGCAGAAAAGCGTTTC | 2460 |
| 2461 | TATGGGAACCCCCCCACCGAGAATCACGTGACGCAATCGGACGACCAATCGCTTCTTACC | 2520 |
| 2521 | TCTGCCCGCGGTCCAGCTTTTGGCCCTCCCTCTCGCCCCGCCTCCTTCGCCCAGCCCCG | 2580 |
| 2581 | CCCCTTGCCTGCGGAGAGCCCGCGCCTGCGCGCTGTGTCCTGCGCGCTCCTTCCCTCGCG | 2640 |
| 2641 | CGCGCTCTCCGTGGAAGAGCAGGGGCAGCGTGGGAGGCGCCAAGGGAGCGCGAACCTGAG | 2700 |
| 2701 | GAGGAAGAAACGGGGCTAGCGCGCAGGCCCAGAACGGTCCGAGCCGCGGCAGTCGGCGAC | 2760 |
| 2761 | GCCTCAGAGCGGAAGAGGGAAGTGAATCAGGCGCCGGGTAGTGGGTTGCTGGGCTGGGCT | 2820 |
| 2821 | TGCTGAGGTAGAGGCAGCGCCAAGAAGAGGCCTTTGCCGCTGGTCGGGATTGGGATGTCG | 2880 |
|  |                                                                     M  S |  |
| 2881 | AAGAACACAGTGTCGTCGGCCCGCTTCCGGAAGGTGGACGTGGATGAATATGACGAGAAC | 2940 |
|  |  K   N   T   V   S   S   A   R   F   R   K   V   D   V   D   E   Y   D   E   N |  |

FIG. 22A

```
2941  AAGTTCGTGGACGAAGAAGATGGGGGCGACGGCCAGGCCGGGCCCGACGAGGGCGAGGTG  3000
       K   F   V   D   E   E   D   G   G   D   G   Q   A   G   P   D   E   G   E   V

3001  GACTCCTGCCTGCGGCAATATCCTTGCATTCACCGCCCTCCCCACCCCAGCCCAGCCCAG  3060
       D   S   C   L   R   Q

3061  CCCGCCCTTCTCCTGGGACCCGGGAGCCTGCAGGATCCGCGGGGCACCGGCGCGGAGCTG  3120
3121  CCTCTCAACCTGCGGCTTAACCTGTCTCTTTGGGATCGCCCGCTCTGAGAGGGCAAGGGG  3180
3181  GAAGCCCCCGTTTCCTACCCAGTCGGCAGGAGACGCGAGGGTCCCACTCTTGGAAGCCTG  3240
3241  CCCTACCCCGCGCGCCTTCCACGCCCCCAGATTCCTCAGGTTGCACCCGAGTGCCTGCCT  3300
3301  GCCTCGGGAACTGGTCCCGCCGCCCGCGCCCTCGCGGCGCTGGGGAAGGCGGCCCCGGCT  3360
3361  GGTGGGGAAGGCTGGTGCCGACCGCCTTAGTTTTTCTTCCTAGAACTCTGATTTCCTGGG  3420
3421  GTCACATTAGCTCCAGAAATTTCTGATTGTGGGGAACCTGCATCTTTCCTTAGTGGTTTT  3480
3481  GTTTTTTGGTTGTGTTTTTGTTATTGGTAGCGTTAAGGTAGTTTATTGCTTACCGGGGGG  3540
3541  CCGGGGGAGATGGGACTGTTCGAAAATTGAGGGTCCCTGTGCTTTCAGCCCATTGGCCTT  3600
3601  TTTAAAAAAAAAAAAAAAGAAGAAGAAGAAGGGGATTTGGCAAAATATACATTGTACAG  3660
3661  AATTTGTTAACTGGGGGAGGGGAATGAATACAAAAAATACAAAACTCCTAGAAGGAAGCT  3720
3721  TGGAGCCTTTTACCTGCTAAGAAAAGGACAATAGAAAAAACAACGGGGAATGCGTGTGGA  3780
3781  GAATCCTTGGAAATATTTAAAATAAACCCCAATGAATAAGATAGAAGATGAGTCATTCGT  3840
3841  ATAAAGCAGAATCATTTTTGTAATCCTAAAATTGTTTCCATTTTAGTTAAAATATGGCAG  3900
3901  TCAGTTCCCGGTTTCTGTTTTTGCATATTTGAATATTCATAACTTTGGCTTCGCATTTGC  3960
3961  ATTACATCTTTTTTAGAAAAATGTAAATGTTGCAAAAAAACCGAAGCTGTAGTTTTAGAA  4020
4021  AATCTCAGACACTGAATTTGTATGCATTTCTAATTCTTGGGTGTATTCATAAGGAAGACT  4080
4081  CTCAACAATGTCCTGTTATAGTGGGGAAATATGAGAGTGAAAATATTTAATGGCAACAAT  4140
4141  ATCCTTTTTTAAAGGCACCTAAATAGAGCATTAGACATTTATCAATATATAGATAGTGCT  4200
4201  TTGCCCAACTTTCACAATTAATTAGCTGTTGCTCTTTTGCATTATTTAAATACTTAAGTG  4260
4261  CTTGGAGTTATAAAAAATGAGCTAATCTACATCAGGCATGCTTCTCTAGAAATCCCTGCA  4320
4321  GCCTTGAAAATAACAGCTTGTCAACCAGGATTTTGTGTAAGAACTTTTTCTTTAGAAAA  4380
4381  TAAATGGTGAACATGCTTCCTAAAAACATTATTTGTGATGGGATAAGATGGTGTTTTATG  4440
4441  AAACCCCAGTGTATTTTAGGTAATTTGTGGTGACTTTTAAAAGGTACTGCTGTATCCATA  4500
4501  TCAGTGGATCTGCTTTTTGATCAGTTCATCTTAAAATATAAAGATACTGTCTCTTCTTAC  4560
4561  CGTTACATACAGCCAGGAAAGACAGCCCTAGTGGTGGGGTACTAGAGTTGGAGGAACAAG  4620
4621  TGAACTCTGTGGTTTTCCTTTTAGGGGAATGTTTGTACATTCTGACAGTCTGATTGGCCT  4680
4681  TCTGTTTCTCATGCTTGCTAACTCACTAGTGCTTTCAAAGAGAGCCTGAATTTAATAGGT  4740
4741  ATGGTCTAACACAGTTTGAATAACCTTTGTGAAATATGAGAGAAAATATCTAAAGCAAAA  4800
4801  AATTAAGCTGCCACCTAAGGGACATATGAATTATTACATCTTCTGTGATGCCTCTTTTCA  4860
4861  TCAATATTGAGAGATTGCTAATGTGTATCATTCAGATTGCTAATCTGCCAGCATGTTCTA  4920
4921  CCAGCATTTCAGATAATACAGAATATGGTTCTAGCAAAAGTTTGGTCTTTATTTTTTCAA  4980
4981  TTAGAATCACAGGAAAAGACATATTTTGGTTGATAATAGGTTATTTCATTTGGGGGACTA  5040
5041  ATAATTCTGATATATATTTTAGGATTTCTTTAACACCACTCTAGGTAATGTTTGCATATG  5100
5101  TATCTCACTGGGAAATGAAAGACTATCAAGGTGTTCACTTGATAGTTAGAACCAAGGGTG  5160
5161  AAACAGTCTTTGCTTTATTAAAAAAAAGTCTAATGTTCTATTTTGCTTTTGATATTTTGC  5220
5221  CTTTGATTAACATCCTGGAAACCAACACATTGAATTTCAGTATTGAACATAGTGACCAA  5280
5281  AGTAATTTTCTTTTATATGTAAATCAAGTCATAAAGAACCAGTGGTTATAATGCTTTCT  5340

5341  GGGGGCCATCCTTTGCTGTTACACCCTTAACTTCCATCACAGGAAACATGACAGCTGCCC  5400
                                                       G   N   M   T   A   A   L

5401  TACAGGCAGCTCTGAAGAACCCCCCTATCAACACCAAGAGTCAGGCAGTGAAGGTGAGTC  5460
       Q   A   A   L   K   N   P   P   I   N   T   K   S   Q   A   V   K
```

FIG. 22B

| | | |
|---|---|---|
| 5461 | GCAGACTACAACACAGTGATCTCTGCTGATATCTTATTCTTAGTAAAATCCTTGCAGTGC | 5520 |
| 5521 | AAAAAAAATCAATATTTTAACTGTTTGCTATCTTTGACAAGAAGAGTTTATAATGTAGT | 5580 |
| 5581 | TTGATAGGTAAAAATTTCACGTGAAAAAATAGCCCTATAATGTAGTTATGATAATGCTGC | 5640 |
| 5641 | ATGGTAAGATACAGTAAGTTCAAACGATAGTGAAATCATTTGTGTGTGTTTTTAGAGGAG | 5700 |
| 5701 | ACCACTCAGGCTGAATTTGAGCAAAGGTTTGAAAAATAAGTTAAACCTTTACAAAAATAA | 5760 |
| 5761 | ACAGATTGTAATTGCTTTTTAAAGATTTTTTAAAACCATACAAATACTAAATACTTATTA | 5820 |
| 5821 | TAGAAAGCTCAGACATATGAGAAGGTTAAAAAGATAGTGGTTTGTGGTCCCAGCACCCAG | 5880 |
| 5881 | AGATAACAGTTACTACTTTGGGGCCTTGCTGTATTGTTACAGAGTTCCCTTTTGTTTTTT | 5940 |
| 5941 | TAAGAATGAATTTTTAAAACGGGCTTTTTCAGCTATATGCAATGGTACATGAGCTTTCCT | 6000 |
| 6001 | TCCCCAATAAGTTAATAGCCTTTTTTAACACTTGTATATGGATAAGCTCCAGTGTATACA | 6060 |
| 6061 | TAACTAATCTTTTGTTTATATTTAGACTGACTTTTTTTTTCCTATTGTAAACCACTGAAA | 6120 |
| 6121 | TCAATATTTTTGGTAAATTTTTAATTGTTCTCTTTGAGTAAATTGCTAGCAGTGAATTA | 6180 |
| 6181 | CTGGATCAAAGAATGCACTTTTTTTTAAGGCTTTTGGTATGCAGTATTGCCAAATTGCCC | 6240 |
| 6241 | TTCAGAACAGTTGTGCAACTTACATTCTCTGCAGTCTTTTACTAATTCTTAACCTATTTA | 6300 |
| 6301 | CGTATTTATTTAAAATGATGCCCATAGCATCAACCCCGTTGTCCATAGCTATTCATACAT | 6360 |
| 6361 | CCTAGGAGCTTCAAGAATCTCAATTGAATAGTAGTAAGTAATAACTTAGGTAAATGCATA | 6420 |
| 6421 | ATAATTATCTAGGTAACATAATTTTTATTGGGGAAAATTTCTTTGGTTTTTACAAGTTG | 6480 |
| 6481 | TAAAGATTGTCGTTGAAATTTCATTTTTACCGTGGATGCAAAGATATTTTTCTAAATCTG | 6540 |
| 6541 | GTAATTGCAGTCTTTAAACCAAAGATAACAGTAGGTGGTAGAAACATTCTGTGAAATCCT | 6600 |
| 6601 | GACCAGTAGGAATGCTGGAGGTATCACTTTGTGTTGAATGGAAGGAGAAACGAATTGTTG | 6660 |
| 6661 | AAAAGGTCAGTTAAGTGTTTCCTTTGCTTGGCCGGATGGGTAAGAAAATAACTGCTTTTG | 6720 |
| 6721 | AAGCAGGCTTTTGCCAAAGAAAAAGATCATTATTAATGAACATCACTATATTTCATATC | 6780 |
| 6781 | TACAGTCAATTCATATAAATTACAGTCAATTTTCTTTTAAGACAGCTTGGTTTATTAAAA | 6840 |
| 6841 | TTTTTAAATAAAAAGTTTTTAAGAAAAAATTACTTCTGAAGGATAATTCAAGGTGAAAC | 6900 |
| 6901 | TGCAAATCTGCCTCCTTGTTTTGTTGGGAATTTTTTTTTTTTTTTTTTTTTGAGACG | 6960 |
| 6961 | GAGTCTCACTCTATCACCCAGGTTGGAGTGCAGTGGTGCAATCTCAACTCACTGCACCCT | 7020 |
| 7021 | CCGCCTCCCGGGTTAAGCAATCCTCCTGCTTCAGCCTCCCGAGTAGCTGGGATCACAGG | 7080 |
| 7081 | CACACACCACCATGCCTGGATAATTTCTGTATTTTTAGAAGAAAACAGGGTTTTACCATT | 7140 |
| 7141 | TTGGCCAGGCTGGTCTCGAACTCCTGACCTCAGGTGATCTGCCCATCTCGGCCTCCCAAA | 7200 |
| 7201 | GTGCTGGGATTACAGCTGTGGGCCACCACACCCGGCCGTTTGTTGGGATTTTTTTTTTT | 7260 |
| 7261 | TAAGATCAAGACATAAATTTAAATGTTGTTTTAATAAATTGTTAAATTATCACATTGATC | 7320 |
| 7321 | TGTTAGCAAATCCTCTCAGCTCTGCCTTCAATTATGTTAATAGTCTGTCAAGTTTCTTAC | 7380 |
| 7381 | CACCTCCACTGCTACTATGCTTACCACATCCAGCCTGTATTATTGCAATTGCCTCCTAAT | 7440 |
| 7441 | TGCTCTCCCTGCTTCTACCTTATCCCCTACTCCCACAGCTTATTTCTGTAACATAGATG | 7500 |
| 7501 | CCAAAGCAATCCTGTTAAAATGTGAGTCAGATTATGGCACTGCTCTTAAAACCTTCCAAT | 7560 |
| 7561 | GTCTTCTCATTTCTCTCAGTAAAAGCCAAACTCCTTACAATGCCTGTAGGCCTTACACGA | 7620 |
| 7621 | TCTGTCCTCCCATAACCTCTGACTTACTCACGTGCTTTTCTCCCACCAATCCACTCCAAC | 7680 |
| 7681 | CACATTGGGTTTTTTCTGTTCCTGGAACACACTGAACACACACTAATAGCACTGTTCTT | 7740 |
| 7741 | TCCTCTGTCTGAAACACTTTCCTCAGTTATCCCAAGCCTTCTTTCACGTCCTTCAGGTCC | 7800 |
| 7801 | TTACTCAAATGTCACATTCATAGTGTAGACTTTCTGAAATTCTAAACCCTCCTCATACAG | 7860 |

| 7861 | ATATGTCTAAATGTTCTGTTATTTATTGACCCACCAGGACCGGGCAGGCAGCATTGTCTT | 7920 |
|---|---|---|
| |                                                    D  R  A  G  S  I  V  L | |

| 7921 | GAAGGTGCTCATCTCTTTTAAAGCTAATGATATAGAAAAGGCAGTTCAATCTCTGGACAA | 7980 |
|---|---|---|
| |   K  V  L  I  S  F  K  A  N  D  I  E  K  A  V  Q  S  L  D  K | |

| 7981 | GAATGGTGTGGATCTCCTAATGAAGTATATTTATAAAGGATTTGAGAGCCCGTCTGACAA | 8040 |
|---|---|---|
| |   N  G  V  D  L  L  M  K  Y  I  Y  K  G  F  E  S  P  S  D  N | |

| 8041 | TAGCAGTGCTATGTTACTGCAATGGCATGAAAAGGTAAGTTATGAATTATAAATCTATAT | 8100 |
|---|---|---|
| |   S  S  A  M  L  L  Q  W  H  E  K | |

FIG. 22C

| | | |
|---|---|---|
| 8101 | GACTGGTTCTTTTACAATAGGGAATGACAATGACAACCTCTCTCACCTAAATAACCATTT | 8160 |
| 8161 | TGATTTGTTGTACATTTTTGTTATTACAAATAAAATGCATGAAAAGGATAGTTCATATTT | 8220 |
| 8221 | ATGTTTACTAGCCTTGGTCTTAAGAGATTCTGATTCCAACACTTGTGTTTATTCAACAAT | 8280 |
| 8281 | GATTATTAGTAATTAAACATAATCTTGAACTCTGAATTAAATCAAAACTTTGTAAAAGAA | 8340 |
| 8341 | AATAAGCAATACAAATCAAGAATTCTTTCACAGTGACCAAAAGGTGAAAACAACACAAGG | 8400 |
| 8401 | ATCGAATATGATTCAACCA | 8419 |
| 8420 | TTAAAAGGAATGACATTCTGACACATGCTATAACATTAATAAACCTTGAAAACATACCAA | 8479 |
| 8480 | GTGAAATGAGCCAAACACAAAAGAACTAATATTTTATAATTTTACTTATATGAAATAATC | 8539 |
| 8540 | TAGGATAGGCAAACACAAAGGGACAGAAAGTCCTTAGAGGTTACTAGGAAGTAGGGAAAG | 8599 |
| 8600 | CAAGGAATAGGGAGTTAGTGCTTAATAGGTACAGAGTTCCTCCTTGGAGTGGTAAAAAAG | 8659 |
| 8660 | TTTTGGAAACAGATAGTGGTGATGGCTACAGTACATTGTAATATAATTAATGCCAATGG | 8719 |
| 8720 | ATTTTACACTTAAAGATGGTTAAAATGGCAAATTTTGTGTTAGATATTTACAACTTTTT | 8779 |
| 8780 | TAAAGAATTAGGAGTTTGGAGGATCAAGAATTCTTAAATCATGTTTTCTATTTTCATGT | 8839 |
| 8840 | GTATATTTTGCAATGTAAGTAGATGCTGGTACATCATCTGTCAAAGAGTATAAGTGATT | 8899 |
| 8900 | TTGAGCTTTGGGTAAAAAACTGGATAACATGTAAATAGAACCAGTCATAAAAATATTGAG | 8959 |
| 8960 | TGTTTGAAGTGTATCTGAGTGAAAACACAAACATAAGAAAAAGCACATAGTAAAACAAT | 9019 |
| 9020 | AGTTCCCCTTTTACTCTAAAATGCACCAATTTGGGTAGTAATTTATATGGCACCCTATT | 9079 |
| 9080 | CATGGAACACTTTCTGTTGCCAGGTACCATACTATTAATGTTTTATTTAACCTTTACAAC | 9139 |
| 9140 | AACCCTGTGGAAGTATATAAATATCTTTATCATCCTCAATTTACAGATGAAAAGCTAGCT | 9199 |
| 9200 | TTAAAACCCAAGCCAGCGTAGTTCTAGCATAGCCTCAAGATTGCAGTGAACATTGATTAC | 9259 |
| 9260 | TTATTATATTCCACATATTCTTCAAAGGACTTTATAAATATTAACTCATTTAATCCTCAT | 9319 |
| 9320 | AAAAATGGAGGGAAATGCTTGCTATTATTCCTCTTTTGTCACTGAGGAAACTGAGGCATG | 9379 |
| 9380 | TGTGAAGTCTTCATTTCTTCCAAATGTCAGTCACCAGTTTTTACCAATCTTCGAAGTATT | 9439 |
| 9440 | TCTGAAATCTATCTGTTCAAGCGTATCTAATGCAGCTGTTCACAGCATCTCTCCCAGTCT | 9499 |
| 9500 | GTTGCCATAGCTTCCTGACTGGTTTCCCAGTTAACAGTTTTGCCTCCTTCAAATCTGTTC | 9559 |
| 9560 | TCCACCCAGCCATCAAAATGATATCTTTAAAATCAAAATTGCCCTTGTCAGTCACCTGCA | 9619 |
| 9620 | GGGATAAAGTCAAAGTTCCCAAGTCTAGCTTCATCTTCCATGTCATTCTTCCCCTCAGGC | 9679 |
| 9680 | TATAGCAATGCCAGCCTTTTTCCTGAATGCACCATATTGTTTCACACCTCCATACATTTG | 9739 |
| 9740 | CTCATGATTTTCTGGTGTTAGCCTGTCACCTACTCATTCTTTTAATGTGTCATTTCCTCC | 9799 |
| 9800 | ATGAAGCCTTAGCTGAAACATTCCTCTATACTGTTAATCTGGGTATAAGCCTCTCCCTGG | 9859 |
| 9860 | TGCTTTAATAGCACCTGCAGCACAACTCTCATTTCATACATTAGATTAAAATTACCTGTT | 9919 |
| 9920 | TATATGTCTGTCTCCTCATGCTAGACCAGAAAATGCTGTATTTGTTCACTTTTGTATCCC | 9979 |
| 9980 | CAGCATCTAGCACAGTACTCAGTATACAAAGGTATTCCATAAATATTTTTGAACAGAAA | 10039 |
| 10040 | GAAACCAGAGCTCAGATTCCTAATACTTGATCATTACTCTCTATTTTTCAAATTAGAGTC | 10099 |
| 10100 | AGAGTTAAAGTTTCTAAGTTCTTAGCTATTAAACAATACCTTCTTTCTTTGGGAGAAAAA | 10159 |
| 10160 | AAATCTGACAAAGGCTGACTAATCGAAGTGGAAGTTGGGATGGTTGATCCCAGTTTGAAT | 10219 |
| 10220 | TTTCTTCTGACTATGTGGTGAGAATGAGAAATGCAGAATGTCCACCTGTTTTGAGCAGGA | 10279 |
| 10280 | ACACTATGCTGCAGATTTTTTTTTTTTTTTTTTTTTTTTGAGACGGAGTCTTGC | 10339 |
| 10340 | TCTGTCGCCCAGGCTGGAGTGCAGTGGCGCAATCTCGGCTCACTGCAAGCTCCGCCTCCT | 10399 |
| 10400 | GGGTTCACACCATTGTCCTGCCTCAGCCTCCCGAGTAGCTGGGACTACAGGCACCCGCCA | 10459 |
| 10460 | CCACGCCCGGCTAATTTTTTGTATTTTTAGTAGAGACGGGGTTTCACCATGTTAGCCAGG | 10519 |
| 10520 | ATGGTCTTGATCTCCTGACCTCGTGATCCGCCGGCCTCGGCCTCCCAAAGTGCTGGGATT | 10579 |
| 10580 | ACAGGCGTGAGCCACCGCGCCCGGCCTATGCTGCAGATTTTTAAAACATTATTTAGAAT | 10639 |
| 10640 | TAATGTACTAAAATGTAAACTAGTATCTCACTAGAATGTAACTTCATGAGGGCAGGGACT | 10699 |
| 10700 | TCAAGGTTTTGTTTATTACTGTAACCTCAGTGCCAAGAACAGTACCTGGTGCATAATTG | 10759 |
| 10760 | GTGCTCAAGAATTTATTATTTGTTAACTAATAAATTCAGGGTCTATAGCAGTGCCCATTC | 10819 |
| 10820 | CTTCTTTAAGAAAAATGTTTTACCAAATATGAGAATTGACCTTTTATTATTCTGTCAACA | 10879 |

| | | |
|---|---|---|
| 10880 | TTTACATCCTGGTTTGTTTTTAGGCACTTGCTGCTGGAGGAGTAGGGTCCATTGTTCGTG<br>                                     A  L  A  A  G   V   G   S   I   V   R   V | 10939 |
| 10940 | TCTTGACTGCAAGAAAAACTGTGTAGTCTGGCAGGAAGTGGATTATCTGCCTCGGGAGTG<br>    L   T   A   R   K   T   V   * | 10999 |

FIG. 22D

| | | |
|---|---|---|
| 11000 | GGAATTGCTGGTACAAAGACCAAAACAACCAAATGCCACCGCTGCCCTGTGGGTAGCATC | 11059 |
| 11060 | TGTTTCTCTCAGCTTTGCCTTCTTGCTTTTTCATATCTGTAAAGAAAAAAATTACATATC | 11119 |
| 11120 | AGTTGTCCTTTAATGAAAATTGGGATAATATAGAAGAAATTGTGTTAAAATAGAAGTGTT | 11179 |
| 11180 | TCATCCTTTCAAAACCATTTCAGTGATGTTTATACCAATCTGTATATAGTATAATTTACA | 11239 |
| 11240 | TTCAAGTTTAATTGTGCAACTTTTAACCCCTGTTGGCTGGTTTTTTGTTCTGTTTTGTTT | 11299 |
| 11300 | TGTATTATTTTAACTAATACTGAGAGATTTGGTCAGAATTTGAGGCCAGTTTCCTAGCT | 11359 |
| 11360 | CATTGCTAGTCAGGGAAATGATATTTATAAAAAATATGAGAGACTGGCAGCTATTAACAT | 11419 |
| 11420 | TGCAAAACTGGACCATATTTCCCTTATTAATAAGCAAAATATGTTTTTGGAATAAGTGG | 11479 |
| 11480 | TGGGTGAATACCACTGCTAAGTTATAGCTTTGTTTTGCTTGCCTCCTGATTATCTGTAC | 11539 |
| 11540 | TGTGGGTTTAAGTATGCTACTTTCTCTCAGCATCCAATAATCATGGCCCCTCAATTTATT | 11599 |
| 11600 | TGTGGTCACCCAGGGTTCAGAGCAAGAAGTCTTGCTTTATACAAATGTATCCATAAAATA | 11659 |
| 11660 | TCAGAGCTTGTTGGGCATGAACATCAAACTTTTGTTCCACTAATATGGCTCTGTTGGAA | 11719 |
| 11720 | AAAACTGCAAATCAGAAAGAATGATTTGCAGAAAGAAAGAAAAACTATGGTGTAATTTAA | 11779 |
| 11780 | ACTCTGGGCAGCCTCTGAATGAAATGCTACTTTCTTTAGAAATATAATAGCTGCCTTAGA | 11839 |
| 11840 | CATTATGAGGTATACAACTAGTATTTAAGATACCATTTAATATGCCCCGTAAATGTCTTC | 11899 |
| 11900 | AGTGTTCTTCAGGGTAGTTGGGATCTCAAAAGATTTGGTTCAGATCCAAACAAATACACA | 11959 |
| 11960 | TTCTGTGTTTTAGCTCAGTGTTTTCTAAAAAAAGAAACTGCCACACAGCAAAAAATTGTT | 12019 |
| 12020 | TACTTTGTTGGACAAACCAAATCAGTTCTCAAAAAATGACCGGTGCTTATAAAAAGTTAT | 12079 |
| 12080 | AAATATCGAGTAGCTCTAAAACAAACCACCTGACCAAGAGGGAAGTGAGCTTGTGCTTAG | 12139 |
| 12140 | TATTTACATTGGATGCCAGTTTGTAATCACTGACTTATGTGCAAACTGGTGCAGAAATT | 12199 |
| 12200 | CTATAAACTCTTTGCTGTTTTTGATACCTGCTTTTTGTTTCATTTGTTTTGTTTGTAA | 12259 |
| 12260 | AAATGATAAAACTTCAGAAAATAAAATGTCAGTGTTGAATAATTTATTTTTCTCTGACAC | 12319 |
| 12320 | TTTAACAATTATGAATGTATGGTTAATTAAGAGGAAAGGTTTTCTGCTTCTACCACCAAG | 12379 |
| 12380 | TACTGTACTCTTAACAAGAACAGTTTGGTAGGGTTTTTATAAGACTATATAGATATAAGA | 12439 |
| 12440 | TGATAGAGAAGAGAGTCATGAATGATGTCAGAGCACTACTGAAGCCTTTGGAGTGATTCC | 12499 |
| 12500 | ATAGCCTTCTGGATGGCAGCTGAATACCTATATGTAGTATCACTGCCCAAAGACCTAGAC | 12559 |
| 12560 | TAGAAAGTGCAAAGTAGCTTAGCAGCTGCAGTCATTCACTCCCAGCCTCCAAAATTCTCT | 12619 |

FIG. 22E

```
   1 -                                                      GATCCCTCTCCAGGTGGAAG -   60    /|\
  61 - CTCCCTTCATACCAAAGTTTAAAGGCCCTGGGGATACGAGTAACTTTGACGACTATGAGG -  120     |
 121 - AAGAAGAAATCCGGGTCTCCATCAATGAGAAGTGTGGCAAGGAGTTTTCTGAGTTTTAGG -  180     |
 181 - GGCATGCCTGTGCCCCATGGGTTTTCTTTTTTCTTTTTTCTTTTTTTGGTCGGGGGGG   -  240     |
 241 - TGGGAGGGTTGGATTGAACAGCCAGAGGGCCCCAGAGTTCCTTGCATCTAATTTCACCCC -  300     |
 301 - CACCCCACCCTCCAGGGTTAGGGGGAGCAGGAAGCCCAGATAATCAGAGGGACAGAAACA -  360     |
 361 - CCAGCTGCTCCCCCTCATCCCCTTCACCCTCCTGCCCCCTCTCCCACTTTTCCCTTCCTC -  420     |
 421 - TTTCCCCACAGCCCCCCAGCCCCTCAGCCCTCCCAGCCCACTTCTGCCTGTTTTAAACGA -  480     |
 481 - GTTTCTCAACTCCAGTCAGACCAGGTCTTGCTGGTGTATCCAGGGACAGGGTATGGAAAG -  540     |
 541 - AGGGGCTCACGCTTAACTCCAGCCCCCACCCACACCCCATCCCACCCAACCACAGGCCC  -  600     |
                                                Human cAMP-dependent protein kinase
                                                catalytic subunit alpha
                                                Accession number X07767 (until *)
                                              - follow arrow until line that
                                                begins 1561 -
 601 - CACTTGCTAAGGGCAAATGAACGAAGCGCCAACCTTCCTTTCGGAGTAATCCTGCCTGGG -  660     |
 661 - AAGGAGAGATTTTTAGTGACATGTTCAGTGGGTTGCTTGCTAGAATTTTTTTAAAAAAAC -  720     |
 721 - AACAATTTAAAATCTTATTTAAGTTCCACCAGTGCCTCCCTCCCTCCTTCCTCTACTCCC -  780     |
 781 - ACCCCTCCCATGTCCCCCCATTCCTCAAATCCATTTTAAAGAGAAGCAGACTGACTTTGG -  840     |
 841 - AAAGGGAGGCGCTGGGGTTTGAACCTCCCCGCTGCTAATCTCCCCTGGGCCCCTCCCCGG -  900     |
 901 - GGAATCCTCTCTGCCAATCCTGCGAGGGTCTAGGCCCCTTTAGGAAGCCTCCGCTCTCTT -  960     |
 961 - TTTCCCCAACAGACCTGTCTTCACCCTTGGGCTTTGAAAGCCAGACAAAGCAGCTGCCCC - 1020     |
1021 - TCTCCCTGCCAAAGAGGAGTCATCCCCAAAAAGACAGAGGGGGGAGCCCCAAGCCCAAGT - 1080     |
1081 - CTTTCCTCCCAGCAGCGTTTCCCCCCAACTCCTTAATTTTATTCTCCGCTAGATTTTAAC - 1140     |
1141 - GTCCAGCCTTCCCTCAGCTGAGTGGGGAGGGCATCCCTGCAAAAGGGAACAGAAGAGGCC - 1200     |
1201 - AAGTCCCCCCAAGCCACGGCCCGGGTTCAAGGCTAGAGCTGCTGGGGAGGGGCTGCCTG  - 1260     |
1261 - TTTTACTCACCCACCAGCTTCCGCCTCCCCCATCCTGGGCGCCCCTCCTCCAGCTTAGCT - 1320     |
1321 - GTCAGCTGTCCATCACCTCTCCCCCACTTTCTCATTTGTGCTTTTTTCTCTCGTAATAGA - 1380     |
1381 - AAAGTGGGGAGCCGCTGGGGAGCCACCCCATTCATCCCCGTATTTCCCCCTCTCATAACT - 1440     |
1441 - TCTCCCCATCCCAGGAGGAGTTCTCAGGCCTGGGGTGGGGCCCCGGGTGGGTGCGGGGGC - 1500     |
1501 - GATTCAACCTGTGTGCTGCGAAGGACGAGACTTCCTCTTGAACAGTGTGCTGTTGTAAAC - 1560     |
1561 - ATATTTGAAAACTATTACCAATAAAGTTTTGTT*TAAAAAAAAAGTGTCGCTGGTGTTCTC - 1620    |
1621 - GACTTCGATCACCCACCCACACACCCCCAGGGGGTTGGAAAGGGAATTTCGGACCCCAGC - 1680
1681 - GTGCAGGCCGATCAGGTCCTGGCTTGAAGTCCTTGTAACCAGGGTTTAGCTGAAATTCCG - 1740
1741 - GCACTCCTTCGGCCCCGCAGGAGAAACGAGCGTCAAACTGCCCTTTGACCCCAGATTCGG - 1800
1801 - GGTCCCCAAATCTGCGGCGCGCCCCCTCGGCGTCCAGCCCGGGACCGAGAGGGCGCTCTA - 1860
1861 - GGGAGGCGCTGGGGCTGGCGCGCCAGGAGGCCGAGCGGCGGCGGGGGCGGCCCTGGCAGG - 1920
1921 - GGGAGTAGAAGGGGGAGAGGGTGCGCGCCCCCCTTCCCGCATCCTCAGCGCCGGGCCAGG - 1980
1981 - CGCGCCTGAGGGACGCGGGGGCGGCGGCAGCAGGAGGGTCCCCGCAGCACCCTGCGAGCG - 2040
2041 - CGGCAGCCCCGGCCCGCGGGCGGCGAGTTCCCGGTAAGTGCGGTCCCGAGAGCGGAGCGC - 2100
2101 - GCTGGAGAGGCGTGGAGAGGGGGCTGGGCGCCGGGACGTCTGGGTCCCGCGCCCAATG   - 2160
2161 - GCTGGAGGGCGGCCGAGCGCCGCCCGCCCGCCCTGCCCGCCCCCTCTCCCCTCCCCCCGG - 2220
2221 - CACTCCCCTCCCCCTCCCCCGCCCGCCGCCTTTCCCCCGCCCCCGCCCCGGCGCCAACTCC - 2280
2281 - GCGGCGCCTCCCCTTAAAAAGCGCGCGGGAGTTGTAAGGGCGGCCGGAGCGAGCCGGAGTG - 2340
2341 - AGCGAGAGCGCAGGGTAAAGGGGCGGGCGGGGGGCCCGGGCTCCACCTTAAAAGCGGGC  - 2400
2401 - GCGTGGGGGTGGGAGGGAGGAAGGCGGGCGGCGGGGAGGAGGGAGGGAAGGAAGGG     - 2460
2461 - GGGCGGAGTGTCCCGGGCGCAGGGCGCGCGTGCGGCGGCGGCGGCGGGGAGGGGCC     - 2520
2521 - GGCCGCGCCGCGCTCCCCTCCTCCCCCTCGCATCCCCGGCCCCGCGCGCGCCCAGCAGAA - 2580
2581 - GCGGGTCTGTGTGTGCGTGCGTGCGAGTGAGTGAGTGTGTGCATATTTTTTTCTCTCTTT - 2640
2641 - TCTTTCTCTCTCACTGTTTTTTCCTCTCTCTCTCTCCCTCTCTCTCTCTTTTTTTTTT   - 2700
2701 - TTTTTTTTTGCAAAGAAACAGCAGCGCCGCCGCCGCTCCGCCGAGGCGCTGCGCCCCCC   - 2760
2761 - GGGGGGGAGGCGGAGGAGGCGGGCAGCGGCGGAGGGAGGGGAGCCGGGGAGGGGGCGC    - 2820
```

FIG. 23A

2821 - CGCGCTGGGAGGGAGGCAGCGCGCACGGTGCAGCCGGGCCGGGCGGGAGGCATGGCGGGG - 2880
                                                              M  A  G

2881 - CCCCCGGCCCTACCCCCGCCGGAGACGGCGGCGGCCGCCACCACGGCGGCCGCCGCCTCG - 2940
      - P  P  A  L  P  P  P  E  T  A  A  A  A  T  T  A  A  A  A  S

2941 - TCGTCCGCCGCTTCCCCGCACTACCAAGAGTGGATCCTGGACACCATCGACTCGCTGCGC - 3000
      - S  S  A  A  S  P  H  Y  Q  E  W  I  L  D  T  I  D  S  L  R

3001 - TCGCGCAAGGCGCGGCCGGACCTGGAGCGCATCTGCCGGATGGTGCGGCGGCGGCACGGC - 3060
      - S  R  K  A  R  P  D  L  E  R  I  C  R  M  V  R  R  R  H  G

3061 - CCGGAGCCGGAGCGCACGCGCGCCGAGCTCGAGAAACTGATCCAGCAGCGCGCCGTGCTC - 3120
      - P  E  P  E  R  T  R  A  E  L  E  K  L  I  Q  Q  R  A  V  L

3121 - CGGGTCAGCTACAAGGGGAGCATCTCGTACCGCAACGCGGCGCGCGTCCAGCCGCCCCGG - 3180
      - R  V  S  Y  K  G  S  I  S  Y  R  N  A  A  R  V  Q  P  P  R

3181 - CGCGGAGCCACCCCGCCGGCCCCGCCGCGCGCCCCCGCGGGGCCCCGCCGCCGCCGCC - 3240
      - R  G  A  T  P  P  A  P  P  R  A  P  R  G  A  P  A  A  A  A

3241 - GCCGCCGCCGCCGCCCACGCCCGCCCCGCCGCCACCGCCCGCGCCCGTCGCCGCCGCC - 3300
      - A  A  A  P  P  P  T  P  A  P  P  P  P  P  A  P  V  A  A  A

3301 - GCCCCGGCCCGGGCGCCCCGCGCGGCCGCCGCCGCCGCCACAGCGCCCCCCTCGCCTGGC - 3360
      - A  P  A  R  A  P  R  A  A  A  A  A  T  A  P  P  S  P  G

3361 - CCCGCGCAGCCGGGCCCCGCGCGCAGCGGGCCGCGCCCCTGGCCGCGCCGCCGCCCGCG - 3420
      - P  A  Q  P  G  P  R  A  Q  R  A  A  P  L  A  A  P  P  A

3421 - CCAGCCGCTCCCCCGGCGGTGGCGCCCCCGGCCGGCCCGCGCCGCGCCCCCCCGCCCGCC - 3480
      - P  A  A  P  P  A  V  A  P  P  A  G  P  R  R  A  P  P  P  A

3481 - GTCGCCGCCCGGGAGCCGCCGCTGCCGCCGCCGCCACAGCCGCCGGCGCCGCCACAGCAG - 3540
      - V  A  A  R  E  P  P  L  P  P  P  P  Q  P  P  A  P  P  Q  Q

3541 - CAGCAGCCGCCGCCGCCGCAGCCACAGCCGCCGCCGGAGGGGGGCGCGGTGCGGGCCGGC - 3600
      - Q  Q  P  P  P  P  Q  P  Q  P  P  P  E  G  G  A  V  R  A  G

3601 - GGCGCGGCGCGGCCCGTGAGCCTGCGGGAAGTCGTGCGCTACCTCGGGGGCAGCGGCGGC - 3660
      - G  A  A  R  P  V  S  L  R  E  V  V  R  Y  L  G  G  S  G  G

3661 - GCCGGCGGTCGCCTAACCCGCGGCCGCGTGCAGGGGCTGCTGGAGGAGGAGGCGGCGGCT - 3720
      - A  G  G  R  L  T  R  G  R  V  Q  G  L  L  E  E  E  A  A  A

3721 - CGAGGCCGTCTGGAGCGCACCCGTCTCGGAGCGCTTGCGCTGCCCCGCGGGGACAGGCCC - 3780
      - R  G  R  L  E  R  T  R  L  G  A  L  A  L  P  R  G  D  R  P

3781 - GGACGGGCGCCGCCGGCCGCCAGCGCCCGCCCGTCTCGCAGCAAGGTGAGCGCGCCGGGG - 3840
      - G  R  A  P  P  A  A  S  A  R  P  S  R  S  K

3841 - AGCGGGGGCGCCGCGCGGTGGGCAGGTGCGGGCGAAGTTGGTGGCGGGGGCGCGAGTCCC - 3900
3901 - GGGAGGAACTGGGTGGCGGGTGGCTGGGCTTTGCGCGCGTTTCCTGCGGGCTCGGTGCG - 3960

FIG. 23B

```
3961 - TGGTGACCTTGGCAAGTGATTGAATCTCCCGGAGCCTCAGTTTCCTCCGCTGTAAACGCG - 4020
4021 - GTTTAATAACAGTAGCGACCCCTTGGGGTTGTTGAGCGAGTTTAGTAAGATTTGGTTGTC - 4080
4081 - GAGGGCTTTAGTTAACACAGAGCCTGGCACGGAGTGAATGCGTAAAAGTTAGTCCGTATT - 4140
4141 - GTTCTTAAAGGTGGAATCGGTTCCTCCTCCCCACCGCCCGGACGCCACAGTCAGGGTCTG - 4200

4201 - GGATTAGAACAGCTACTAATTTTGCATGCTTCTCTCCTCGGCTCCAGAGAGGTGGAGAAG - 4260
      -                                              R  G  G  E  E

4261 - AGCGAGTACTTGAGAAAGAAGAGGAAGAAGATGATGATGAAGATGAAGATGAAGAAGATG - 4320
      -  R  V  L  E  K  E  E  E  D  D  D  E  D  E  D  E  E  D  D

4321 - ATGTGTCAGAGGGCTCTGAAGTGCCCGAGAGTGACCGTCCTGCAGGTGCCCAGCACCACC - 4380
      -  V  S  E  G  S  E  V  P  E  S  D  R  P  A  G  A  Q  H  H  Q

4381 - AGCTTAACGGCGAGCGGGGACCTCAGAGTGCCAAGGAGAGGGTCAAGGAGTGGACCCCCT - 4440
      -  L  N  G  E  R  G  P  Q  S  A  K  E  R  V  K  E  W  T  P  C

4441 - GCGGACCGCACCAGGGCCAGGATGAAGGGCGGGGGCCAGCCCCGGGCAGCGGCACCCGCC - 4500
      -  G  P  H  Q  G  Q  D  E  G  R  G  P  A  P  G  S  G  T  R  Q

1 - AGGTGTTCTCCATGGCAGCCATGAACAAGGAAGGGGGAACAGGTAAGGATCCCTCTGGGT - 60
      -  V  F  S  M  A  A  M  N  K  E  G  G  T

61 - GGGGAAGAGTGCTAGGTGGAGAGGAACTCAGCCCGAAGACAAAGCCAAAGACAGGTGTTT - 120

121 - TTTTCCTTCCCAGCTTCTGTTGCCACCGGGCCAGACTCCCCGTCCCCGTGCCTTTGCCC - 180
      -                   A  S  V  A  T  G  P  D  S  P  S  P  V  P  L  P

181 - CCAGGCAAACCAGCCCTACCTGGGGCCGACGGGACCCCCTTTGGCTGTCCGTAAGTTGGG - 240
      -  P  G  K  P  A  L  P  G  A  D  G  T  P  F  G  C  P

241 - GTATTGGAGACATGGGGGTGCTGCTCAGGTGTGTGGTACAGCCAGAGAGACATCCGTGTT - 300

301 - CACTGGTGTCTGTTTGTTTTGATGCAGTCCCGGGCGCAAAGAGAAGCCATCTGATCCCGT - 360
      -                        P  G  R  K  E  K  P  S  D  P  V

361 - CGAGTGGACCGTGATGGATGTCGTCGAATATTTTACTGAGGCTGGATTCCCGGAGCAGGC - 420
      -  E  W  T  V  M  D  V  V  E  Y  F  T  E  A  G  F  P  E  Q  A

421 - GACAGCTTTCCAAGAGCAGGTGAGTTTCCAGCCCAGGACTACACACTGACAGACACAGAG - 480
      -  T  A  F  Q  E  Q

481 - GGCCTCCCTGGGATGTGCCCTGATCCCGGCTTTCTCTGTTCCTGTCCCACCCAGGAAATT - 540
      -                                                          E  I

541 - GATGGCAAATCTTTGCTGCTCATGCAGCGCACAGATGTGCTCACCGGCCTGTCCATCCGC - 600
      -  D  G  K  S  L  L  L  M  Q  R  T  D  V  L  T  G  L  S  I  R

601 - CTCGGGCCAGCCCTGAAAATCTACGAGCACCACATCAAGGTGCTTCAGCAAGGCCACTTT - 660
      -  L  G  P  A  L  K  I  Y  E  H  H  I  K  V  L  Q  Q  G  H  F
```

FIG. 23C

661 - GAGGATGATGACCCCGATGGCTTCTTAGGCTGAGCGCCCAGCCTCACCCCTGCCCCAGCC - 720
    -  E   D   D   D   P   D   G   F   L   G   *

721 - CATTCCGGCCCCCATCTCACCCAAGATCCCCCAGAGTCCAGGAGCTGGACGGGGACACCC - 780
781 - TCAGCCCTCATAACAGATTCCAAGGAGAGGGCACCCTCTTGTCCTTATCTTTGCCCCTTG - 840
841 - TGTCTGTCTCACACACATCTGCTCCTCAGCACGTCGGTGTGGGGAGGGGATTGCTCCTTA - 900
901 - AACCCCAGGTGGCTGACCCTCCCCACCCAGTCCAGGACATTTTAGGAAAAAAAAAATGAA - 960
961 - ATGTGGGGGGCTTCTCATCTCCCCAAGATCCTCTTCCGTTCAGCCAGATGTTTCCTGTAT - 1020
1021 - AAATGTTTGGATCTGCCTGTTTATTTTGGTGGGTGGTCTTTCCTCCCTCCCCTACCACCC - 1080
1081 - ATGCCCCCCTTCTCAGTCTGCCCCTGGCCTCCAGCCCTAGGGGACTAGCTGGGTTGGGG - 1140
1141 - TTCCTCGGGCCTTTTCTCTCCTCCCTTTTCTTTCTGTTGATTGTCGCTCCAGCTGGCTG - 1200
1201 - TATTGCTTTTTAATATTGCACCGAAGGTTTTTTAAATAAAATTTTAAAAAAAGAAAAAGG - 1260
1261 - GAAAAAAAAGCCACGGAGTCCATTTATGAATGGGGTGGGGAGAGGGCACTAAAGAGCCT - 1320
1321 - CCTAAGAGAGCCTCAGGTTAGGACAGAATTGTTTGGGGAGGGAGAAAAACAGAAACAATG - 1380
1381 - AATTATAGCTGCCTCACAGCCATGTATAACAATAATTGCTCCAGGAAGGTGGGAATATTT - 1440
1441 - GCTTTTTTTCTTCTGTAATCTCACCGTGTCCGTGTCCAGAACAGAGCTAGGCACACAGC - 1500
1501 - AGGTGCTCAATTTTTGTTTTTCGTTTAGACAGGTTTCATTCTTTCACCCAGGCTGGAGTG - 1560
1561 - CAGTGGTGCTATCATAGCTCATTGTAGCCTCAAACTCCTGGGCTGAAGTGATCCTCCCAC - 1620
1621 - CTCAGCCTCCTGAGTAGCTGGGACTACAGGTGCACTCTGCCATGCCGGGCTAACTTTTAA - 1680
1681 - AAATTTTTGTCCGGGCACAGTGGCTCATGCCTGTAATCCCAGCACTTTGGGAGGCCGAGG - 1740
1741 - TGGGTGGATCATGAGGTCAGGAGTTCAAGATCAGCCTGGCCAAGATGATGAAACCCTGTC - 1800
1801 - TCTACTAAAAATATAAAAAAAAATTAGCTGGGCGTGGTGGTGGGTGCCTGTAATCCTAGC - 1860
1861 - TATTCAGGAGGCTGAGGCAGAGGATTGCTTACACCTGGGAGGCGGAGGGTGCAGTGAGCC - 1920
1921 - AAGATCGTGCCACTGCACTCCAGCCTGGGTGACAAAGTGAGACTCTGTCTCAAAAAAAAA - 1980
1981 - TCTTTGTGTGTGTGGAGATGAGGGTATGCACTTGTTGGCCAGGTTGGCCTCGAACTC - 2040
2041 - CCAGCCAAGCAATTCTGCCTGGGATTACAAGCGTGAGCCACCATGCCTGGCCTCAAATAT - 2100
2101 - TGTTGAATGGCTAGCAGTTAAGTCCTTGGGTTTATAAGCATTTCCTCAACTGTCCTCCCA - 2160
2161 - AGTCCCCATAAGACAAAAAACTCATAAAATCCCACCTTACAGAAGAGGCAGCTGGCCCGG - 2220
2221 - CACAGAGATGCTGTCTGCCCCGGGTCACACAGGGTGGCATCTGACACCCTGTCTGAGTTC - 2280
2281 - TTCACTCAGAGTCTTTAAATATAATTAGCGTATTTGACATAATGTACATTAAAAACTATA - 2340
2341 - AACCTGTCAGCCTTTGTCTACTGCAAAGAATCCACTACAAATATTGGGGCAGGGATCTGT - 2400
2401 - TCTTGGACCATAGTAGTGTCTCCAGACCTCATGGTCCTCTTCATTAAAACAACAGAAAAT - 2460
2461 - TCCTTCTGGGCCATCAGATGAGACCATGAGATAGAAGATTTCCAAGTGAAGATTTTGTTT - 2520
2521 - CAAGACAGAGTCTTGCTCTGTCACTCAGGCTAGAGTGTACTGGTGCAATCATAACTGTGG - 2580
2581 - TGACAGCCTCGAACTTTTGGGTACAAGTGATTCTCATGCCTCAGACAACACCCAACTAAT - 2640
2641 - ATTTTGGTTTTTGTATAGACAGGGTCTTGCTATGTGGCTTAGGCTGGTCTTGAACTCCTG - 2700
2701 - GCCTCAAGCAGTCCTCCCGCTTCAGCCTCCTAAAGTGTCAGGATTACAGACATGAGCCAC - 2760
2761 - CAAGTCCAGCCTGAAGATTTTTAAAAATTATTGTTAGTAGTAGTCGCCAGAGTTACTACA - 2820
2821 - TCCAAAGTCCCTACTAAGTTCTAAGTAGTCCCTACTAAGTTCTAAGGCAGTTTCTCAACT - 2880
2881 - CATTAGAGTTGTTTTTGTTTTAAAGAAAAAAAGAGGCTGGGCACTTTAGGAGACCGAC - 2940
2941 - ACGGGAGGATCGCTTGAGTCCAGGAGTTTGAGACCAACCTGGGCAACATGGGCCCCATC - 3000
3001 - TCTAAAAATTTTAAATTAAAAAAATGTTTTAACAACAAAAAGCGTTCTGGGAGTGAGGGG - 3060
3061 - CTGGGGCCTGGGCGGCCTCATTCCATATACCTGTGCCGGGTTGAGGGGTTGGAGACACGT - 3120
3121 - TTAGAGACCCCTCCACTCTAGGAATCCACCTCGAGAGATAAAGGTCCCGGCCCTAGCCAC - 3180
3181 - ACCCCCAGGACACGGCCAGAGGCCACCTCCCTAGGCGGGTCCCTCCCCACCGCCAGGTTC - 3240
3241 - CTGGAGCGCGTGCGGCGCGTGTGCAGGGGTAGGGGCCGCAGGCGCGCGGACTGGAGAGG - 3300
3301 - CGCGCCCCTCCCGCGTGTTGAAATTCAAAAGAGGCGAACGGCCCCGGCGCGGCGGCGCG - 3360
3361 - GCTCCGGTGGAGAGGTCAAGGCAGGGGCCAGTCGGAGGCTCCGGGGCGGGTCGAACCC - 3420
3421 - GCGGCCAACCTGAGCAGCAGCGGAAGCTTAAAGAGCTCAGGTTCCCGCCCCCCGGCCCTA - 3480
3481 - CCATGGCTACAGAGCAGTGGTTCGAGGGGTCGCTCCCCTGGACCCTGGAGAAACACCGC - 3540
3541 - CTCCAGACGCCTTGGAACCTGGGACGCCGCCCTGCGGAGACCCCTCCAGGTCGACGCCCC - 3600
3601 - CTGGCAGGCCTGGGAACCCATCTGAGCCGGATCCTGAAGATGCCGAGGGGCGGCTGGCTG - 3660
3661 - AGGCCCGGGCCTCCACGTCTTCCCCCAAACCTCTGGTCCCCCGGCCTGGGCCAGCACCTC - 3720

FIG. 23D

```
3721 - CCCGCCTATCCCTGGACACTTTGTTCAGCCCCATCACCCAACAGCTGCGCTACCTACTGA - 3780
3781 - AGAAGGCAGATGATTTCCAGAGCTACTTGCTCTACAGGTGATGCTGGACAGGGTCCCAGG - 3840
3841 - TCCCCATGGGTAAGGAGACTTGGAGGGGAGGCGACAGGATGGGTGACACACACCAGGGTC - 3900
3901 - GCAAAATTACAAGCGCTAGGAGCCAGAGGGAGACAGTGGAAGAAGCTAGCATATTAGAAT - 3960
3961 - CCAGTTTAAGAGAATGAGGAAGACTGTAGAATTGCGGGTAGGGGATGGCTGCTATTACTG - 4020
4021 - TCGTGGCAGGGTGGGCCTGGGGTTGTCAAGTCTCTAGGACTTTTTCTCCCAGTTTTTAAG - 4080
4081 - TGCTGTCTTACATTTTGAGCCCTGTGCTGGCTAAACAAGACCCACCTGAGCCAAACTTGG - 4140
4141 - CCTGCAGGACATCAGTTTGAGACTCCAAAGGATAATGTGATTCCCAGACCAGGTTTCCCT - 4200
4201 - GTGACTCTCAATTTCAGTGTCCATTGGAATTTCCTAGGAGGCTGGGTTGGGTTTGTTTGC - 4260
4261 - GTGTTTGTTTTTGAGATGGAGTCTCACTCTGTCGCCCAGGCTGGAGTGCAGTGGTGCAAT - 4320
4321 - CTCAGCTCACTGCAACCTCCGCCTCCGGATTGAAGCAATTCTCTGCCTCAGCCTCCCGA - 4380
4381 - GTAGCTGGGATTACAGGCGCCCACCAACATGTGTTGCCCGGCTAATTTTTTCTTTTCTT - 4440
4441 - AGTAGAGACAGAGTTTCACCATCTTGGCCAGACTGGTCTTGAGCTCCTGACCTCATGATC - 4500
4501 - CACCCGCCTTGGCCTCCCAAAGTGCTGGAATTACAGACGTGAGCCACCGCGCCTACCCGA - 4560
4561 - GGCTGGGTTTTTTGTTTGTTTTGTTGTTATGTGTTTTTTTGAAATGGAGTCTTGCTCT - 4620
4621 - GTCACCTAGGCTGGAGTGCAGTGGGGCGAACTCAGCTCACTGCAACCTCCGCCTCCCAGG - 4680
4681 - TTCGAGGGATTCTCATGAGGCTGTTTTTTTTTTTAATGAGACAGGGTCTCGCTCTGTC - 4740
4741 - ACCCAAGCTGGAGTGCAAGTGGGGCAGTCATAGCTCACTGCACCCTCGAACTCCTGGTCT - 4800
4801 - CAAGCAATCTTCCACCTCCCCTCCTGGGTAACTGGGACTACAGGTGCCACCATGCCCAGC - 4860
4861 - TAATTATTTTTGTGTAGAGATGGGTTCTTGCTATGTTGCCTAGGCTTGTCTGGAACTCCT - 4920
4921 - GGCCTCAAGCAATCCTCCAGCCTCAGCCTCCCAAAACTCTAGGATTGCAGGCGTGAGCCA - 4980
4981 - CTGTGCCCAGACCCTGCAGGAAGCTCTGGGTCCTAAGTGTTGTGACACTCAGGTGTCAGC - 5040
5041 - ACTTTAACAAGTGTTCCAAATGGGTTTGATGCAGGTAAACCAGAAAGATGTTCAGAAAAG - 5100
5101 - ACCTGAAACTGGGGGCTTTTCTAATGGGTCAAAGCCAGGGATACAGGTTGGGATTGAGTA - 5160
5161 - GAATGGGGAAAACTGCGGGGTGGGAGGGGTTGTGAGGGATTCCAGGCAAAGGCCCCCTT - 5220
5221 - CTTCCTTCAGCAGAGACCAAGTACAGAAGGAGCAGCTGGCCAAGGCCATGCCCACCTTCT - 5280
5281 - TACAGATGTGTGAGCCCTACTTCCTGTACCTGGAGGCAGCCGCGAGAAGCATACCCCCA - 5340
5341 - TCTATGGACCCCTGCAGGAGCTGGTCCGAAAGGGGTGTGTGGAGGTTTCTTAGACCCCA - 5400
5401 - CGCCCCTTTCTTCTCGCAGCTCTGAGCCTGTGGGGATGGTGGAGGGGGAGGCCCACTCCT - 5460
5461 - CGCAGGCCAGCTGATCTCACTGTACCCCCTCTTGTATGCAGCTGTTAGAGATCTCCCAA - 5520
5521 - CAGCTGACCCTGCGCCTGGAACAGCTGGTCCTCATGTACGCTTCCTTTGGGTTCGTGGAC - 5580
5581 - CTGGAGGAGATGAACCCCCTTAGGTAAAATGGTAGGAGACTCAGATGGGGGGATGAAGGA - 5640
5641 - GTCCAAGGCCCAGCCTCACCCCTCCATTCTCTCATGTCTCGCCAGCATCTCCTGTTTCTT - 5700
5701 - TTGCGGGAGGTTCTCCATCAGCCTGTCCCATGAGGTCTCCATCTTCAGATACTGTGCCCC - 5760
5761 - AACCGCCTACACTGCCAGCCGCTTCCCCGCTACCTCTATAAGAAGATGCGCTGGCACCT - 5820
5821 - GGAAGCCACCCCAGAGGCCCCTGGTCGGGGACAAGATTCCCTTGTGGATTAGTAAGTCCT - 5880
5881 - CTTACCCAAATCAAAGTCCTCCCCTTTCTATGATGAATGCCAATATGACCCTCCAAACCG - 5940
5941 - TCACCAGCAAAGTGAAAAGTGAGCCAGGGCCCGAGGCAGTGGCTCACGCCTGTAATCCCA - 6000
6001 - ACACTTTGGGAGGCCGAGGCAGGAGGATCACTTGAGCTCAAGAGTTTGAGATCAGCCTGG - 6060
6061 - GCAAGATGGCAAGACCCTGTCTCAACAACAAAGAAATTCGCCAGGCGTGATGGCTGGCAC - 6120
6121 - CTGTAGTCCCAGCTACTTGGGAGGCTTAGGCAGGAGGAGCACTTGAGCCCAGGAATCAAG - 6180
6181 - GCTACGGTGAGCTGTGATTGTGCCACTGCACTCCACCCTGAGTGGAAGCAATAATCTGTC - 6240
6241 - TCTTAAAAAAAAAAAAAAGTGAACCAGGAAACTAAAGGCTTTTGAAAGGCTACCTCTATT - 6300
6301 - TTCTTAAAACCCACCCTCCCACCAAAATAAAAGTTCTCATCTTAAAAGTAGGCTGGCAGG - 6360
6361 - GAGAAAAGGCCTTGGAGTCACATTCCTACCTGAGAACTTCAGGGCAACTTCTGATGAGTT - 6420
6421 - CCCACCTCAACTCCAAAATTAAAGCCCTCAACAGAAGTAGCTAGGAAGCTGATCACTTCT - 6480
6481 - AATTACAGCTCCCTCCCCTCCTAGCTACTTTCTGTGCTATCGAGATACTTGGGAAGACAC - 6540
6541 - AGGCCAGAGTCCAGCCAATTCGTGCCCACAGATCCAGAAGCTGTGGTCCATCGGCCGATG - 6600
6601 - GGTGCCCCTAGGACCAGCCGAGGATGACCTTTATTCATGGTAGGAGCTAGGGCAATAGCA - 6660
6661 - ACGTGGGCCTGGGAGCTGGAGGGGAGGCAGAACCCCACCAAAGACAATCCACCTTCCCA - 6720
6721 - AACACTTTGCTTCCCTTAGTAGTGATAGCATTTTATTGTGCCCTGAAAAGCACTTCATGC - 6780
6781 - AGACCCCAGTAACAACCCATGGAGATCTATGCTATTGGCCCCATTTAACAAAGAAAACAG - 6840
6841 - GGTGCTCAGAGAAGTTGTTACCTGCCCAAGGACACACAGCTAGCAGAGCGAATGGACAGG - 6900
6901 - TCAGGACCAGTTATTCAGCCTCTAGGAGCCATTACTAAGTCTCTGATCAACAAGGAAACA - 6960
6961 - AGTTTCCCCCGGGGGTTTTTCCCACCCGCAGCTGAAACAAAGCCTCTTTCACCTGAGCCT - 7020
```

FIG. 23E

```
7021 - CTCACTCAAAGGGAGGGACTCCCGAGGGGCAGGGGGCACTCAAGTCCAGGCCTGTCTATC - 7080
7081 - CCTGGCCCCCCCACCCCAGGATTTTGTGCCCGCACCGCTTGGGGACTACCAGCAGCTGCT - 7140
7141 - GACCATCGGCTTCGAGGAGCCCACGCCCACGCTGGCCACCGACCTGCTGGTGCAGATCCT - 7200
7201 - CACGGGCCAGGCAGGCCAGGCCCGGCCTCCGAGCGCAGCCGGGCCTGCGGGGTGGGCAGC - 7260
7261 - GCAGGGGTCTTGAACCTGGGGAAGAGGGTAGGAGCTGGAACTTGACAGTTCCAAACTCCA - 7320
7321 - GAATAGGGGGCAGGGGAGGGGCTCACTCGTTCTCGCAGTGCAGCCGGGCCTCGCCTTCCA - 7380
7381 - AAGGGCCAGGCCGAGCTGACCTGTCTGCACCGAGTCCGGCTTGGCCGTGGGGCCCTGAAT - 7440
7441 - GCGGACACGTCAGTTTTGTGTTAAATAAAAGAAAGAAAGAGGTCACAGGCTCAGCGTCCG - 7500
7501 - CTGCGAATGCCGCGCCCCTCCCCCGGGGGATTGCCCCACCCACTCGCGTGGCCTTCTGGG - 7560
7561 - AAATGTAGTCTTTTGAAAGAAGCCTGGAATTCGCCAATAGGCGGACGAGAGTTTGGCGCA - 7620
7621 - TGCGCATAGGCGCACATGAAGCAAAAAGGGAAGTGGTGCCCGTCAACACCGGAACCCAGA - 7680
7681 - AAACTGCAAGTTTAGGGTACCGGGGAAATTCAACGTCCACTGGAGGAAGAGACTTAAGGC - 7740
7741 - TACGCCCACTCCCATATTTTGACCCGGAAGTTATTTATTTTAGCGTAGAAGACTACTTTT - 7800
7801 - CCCGACGCGCCCCAGGAAAGTGCCCTCGATCAGTTTCCTAAGGGCCCGAGTTAGACTTTT - 7860
7861 - TTTTTCTCTTCCAGCTTTTGGGACTTGGGGGCCGGACAGGTCGTCGTCTTTCTTGGGGTA - 7920
7921 - TCCGGGGTGCGGACAAGGTGGGAGAGCCCTACGGTATCCAAGCTT - 7965
```

FIG. 23F

```
   1 - CAACATGCTTGGGACCAGAAGTGTTTCCAATTTGGGATTTTCTCAAATTTTACCGGTTGA -   60
  61 - GCTTCCCCAATCTGAAAATCTGAAATCCAACATGCACGGCTCTGAAGTCTTTCACTGAGC -  120
 121 - CTTTGGGGGAAATATTTAACATCCTAACAGCCCTAAACCAACGCTCAATTAGCACAACAG -  180
 181 - TTTACAATCTTCTCTACCCACAGCCTGATGCGAGGCTCTGGGACTAGACTATTTAGCCAA -  240
 241 - CAGTTCTTGCAAAATTAACTGACTTATAAGTAAATAGTAATTTCAACACCTCACTGCTAA -  300
 301 - TGCTGTAACAACTCTGCAGACCTAGGGAGCAAGTACGGTTTGCAGAGCACTGGGAAGGCT -  360
 361 - CTGAAGTGACCTTTGAACTGGGCCTCAAAAAATTTTGGGTTTGGCAAAAGTCAAATCTCT -  420
 421 - TAGGCTTCAAATTCCAGGCACAAGGATTGTTGGGTTTGATTTCATTATCCAGAAGCAATG -  480
 481 - GGGATACAGAATTGTGATCTCATGTGTAGGGAACTGTGGGGGTTTTTTCTACTTTAACCC -  540
 541 - CAGTGAGACTTTGTAGAGTGTGGGGTAGAGAAAAGGCTCATGAATATGCCTGAAGCCTAA -  600
 601 - CTCAGCACCTTTCTGAGGAACTGACTGCCAAAATGGTAATGGAGAGGGGAAAATATGACC -  660
 661 - TACTTTCACAAGTTACCTTGACTGCCTCAGGGAAACCTGCTGTGGTAGTGTTTCTTCTGG -  720
 721 - GTGAAAGACCAGGTAATTACCTGGGTGCTGGTCTCAGACTTACCAGTTTTGAATCCCTGT -  780
 781 - TTTAACCACTCACTATCGATATGACCTTGGATAAGTTACCTAACCTTTCTCTTACTGTCC -  840
 841 - TTTTCCGTAAAATGGGGATAACAGATAGTAGTTATTTCTATGAGTGGTTATGAGAACCAA -  900
 901 - GCTATTAGATAGCGGGAAAGCACACAGTAAGCGTTCAAGGAACTGCTATTGTTATTAAAA -  960
 961 - GCCTCCTTTGGAAGAAGGACATTGAGGCCCAGAGAGAGAACAGAACGTCCAGCCACACAG - 1020
1021 - CAAATCCGTGATGAAGTTGGGACTGGAGTATGGGTCTCCTGAGTCTCAGCCCAGGACTCT - 1080
1081 - ATCCCTCTTCCCGAGTCCTCGGAGTTCCCGGATGGAGTCACATTTGTTCACGGCCAGGGA - 1140
1141 - GGAAGGTTTGATGGAGGCCTGCAGGAAACAACAGCCAGGCGCAAGGCTTTGGGAGTTGAA - 1200
1201 - GCATAGCTTCTGCAGATAGAAACAAGGTTGACATGGGCACTCGTGCAGAATGACGGGCT - 1260
1261 - CCTTTTGGACTCCCAGGACTACAGTCCCTTATGCACCTTGGGATCTGCGGCTAGCCCCTG - 1320
1321 - CGTAAAGAGGGACGCGTAGTCTTTTCCCTGCCCCGCCCTGCCGGGGCGCCCGCCTCCGAG - 1380
1381 - GCCGCCCTCGCTTCGTCCTTCCCAGCAAGCTCCGCGCCGGCGCCGGCTATTGATTGGCTG - 1440
1441 - AGGCGGGAGCAGGCGGCTGGCCGGCAGCAGTTACTCGGGGTTTCCGGTGCGAGGCCAGAG - 1500
1501 - GTGGGAAGCCATCGGACGTCGGCGGTGAGGTACGTGCAGCGGCGGCCGGTGGGCGAGAC - 1560
1561 - TATTTGAGAGTGTGCGGGCCGGGATGTTCTCGGCCTGTGGGGAAATCACGCCAACTCCCC - 1620
1621 - GCGTGGGCCGGGGGCTGTCTGGGGATATGCGGCATGCGCGGGCGTGCCTCGCCGGCTTGAGG - 1680
1681 - GCGCGCGGGGCGTGGGTGGCTGCGCGCGCGGGGGGCGCACGTGCGGCTCGAGGGGCGGGG - 1740
1741 - GCGGTGCCGGGAGTCCCGCCACGTCAGTCTCCGGCCCTGAGCCAATCCCGCGCCCGGCCT - 1800
1801 - GCCGCGAGGGGCCGGTTGTGCCGGGAAGTGGCTCCAGGGAGAAGAGGCCTCTTCCCTCA - 1860
1861 - CCCGCTGTGGGAGCTGCGCCCCGAAAGCCTGCCCCGGCACGTCGGGCTCTCCTGACCCGC - 1920
1921 - CAAGACCAGAGAGCCGTTGGCGCCCTCCGCCCGGGCCTGCCGGTCCGTTTATTTTAAGAA - 1980
1981 - GCTTTGTGCGCCTGCTGTGGGGATTTCTGATCCAGGCTGCGAAGAATTTCGAAGTCTGGA - 2040

2041 - AAATAGCAACTGTGTTTGTTTCTAAAGGATCTTCTCCTGACCCAGCATCGCTCATCACAA - 2100
     -                                                            M

2101 - TGAAGAACCAAGACAAAAAGAACGGGGCTGCCAAACAATCCAATCCAAAAAGCAGCCCAG - 2160
     -   K  N  Q  D  K  K  N  G  A  A  K  Q  S  N  P  K  S  S  P  G

2161 - GACAACCGGAAGCAGGACCCGAGGGAGCCCAGGAGCGGCCCAGCCAGGCGGCTCCTGCAG - 2220
     -   Q  P  E  A  G  P  E  G  A  Q  E  R  P  S  Q  A  A  P  A  V

2221 - TAGAAGCAGAAGGTCCCGGCAGCAGCCAGGCTCCTCGGAAGCCGGAGGGTGTGTGCCAGC - 2280
     -   E  A  E  G  P  G  S  S  Q  A  P  R  K  P  E  G

2281 - TCTGCGTTGCCAGCGGGCAGGGGGAGGAGCTGTGGGGTCGGCCTCGCTTCTGGACTTACA - 2340
2341 - GGCCGAGGCCAGGTTGTCCGGGAGGAGGAGATGTAGAATGAGAGGACAGTGCTGGGGGCC - 2400
2401 - GCGGTCCCCCTGCGCTCTGGCGAGTTGGCGGAGCTGCCCCCTCTAAGCACAGGAACAGA - 2460
2461 - GTTCTGGAGAGAAGCTCCGACGGGATTAAGTCAGGTGGCAGCCAAACGAGGCACCCAGTC - 2520
```

FIG. 24A

```
2521 - AGGAAATCCAGGTCCCGTTAGAAACACCTCAGCCACCAGCAGCTAACTGCCCTTCCTGTT - 2580
2581 - TGAGGCATTTCTAGAATGATCTGAATGGCAAGAAATGGGTTTTGTGGGGGGGAAGGAGAT - 2640
2641 - GGACTAGAAGTTGCTCCGTGCCATCCCTGTGTGCTGATGCTTTACATACTTTTATGATCT - 2700
2701 - AACAAATATGTTCGGGTGGTAGTGAGAAATAGTTGTGTCATTTTACAAGTAAACAGACTT - 2760
2761 - AAAGAAGTTAGGCAACGATTACTATAATTTCTTGATTTAAAAGATGTTTCGAATCTAAAT - 2820
2821 - TCTGACAGGAACTAGATTTGCTGAATGATACTCCATTCTTGCTTCTCAGTTTCCATAAAA - 2880
2881 - AAAAAAGTTAGGCAACATTTAACTCAAACTGATGAGTTTGGCTGGGCCTGAAAAATCCCA - 2940

2941 - ACCAGTGGTATAATCGTCTTCTTTCTCACTCTACCCCTCATCCTCTCCTGCTGTAGGGGC - 3000
     -                                                            A

3001 - TCAAGCCAGAACGGCTCAGTCTGGGGCCCTTCGTGATGTCTCTGAGGAGCTGAGCCGCCA - 3060
     -  Q  A  R  T  A  Q  S  G  A  L  R  D  V  S  E  E  L  S  R  Q

3061 - ACTGGAAGACATACTGAGCACATACTGTGTGGACAATAACCAGGGGGGCCCCGGCGAGGA - 3120
     -  L  E  D  I  L  S  T  Y  C  V  D  N  N  Q  G  G  P  G  E  D

3121 - TGGGGCACAGGGTGAGCCGGCTGAACCCGAAGATGCAGAGAAGTCCCGGACCTATGTGGC - 3180
     -  G  A  Q  G  E  P  A  E  P  E  D  A  E  K  S  R  T  Y  V  A

3181 - AAGGAATGGGGAGCCTGAACCAACTCCAGTAGTCAATGGAGAGAAGGAACCCTCCAAGGG - 3240
     -  R  N  G  E  P  E  P  T  P  V  V  N  G  E  K  E  P  S  K  G

3241 - GGATCCAAACACAGAAGAGATCCGGCAGAGTGACGAGGTCGGAGACCGAGACCATCGAAG - 3300
     -  D  P  N  T  E  E  I  R  Q  S  D  E  V  G  D  R  D  H  R  R

3301 - GCCACAGGAGAAGAAAAAGCCAAGGGTTTGGGTGAGCAGAGGGCGGCTCTTTGTGAAGC - 3360
     -  P  Q  E  K  K  K  A  K  G  L  G

3361 - TGGTGAGGAGAGGGAGTTTGGACTTGACGTTCTCTGGGCCAGTCTGTTCTGCCAGGATTC - 3420
3421 - AAAGGAAAACGGTACTTCTCAGAGCAGCAAGTCACTCTAGTCTAATCAAAGCCAGGGATG - 3480
3481 - TGGGGGCCACGGCATAGAGAGATGCAGGAGTTACCACAAAGCCTTCTGGGTTTTGGA - 3540
3541 - GCAACTGGAGCTTGGCATGGGACCTGTTCTCTCTTTGAGAAAATGGAGACGGGAGGCTAG - 3600
3601 - GGTAGGCTCCTGTGCCAGCCAGTACTACCTGCTGTGTGACCTTGGGTGTGTCCCTTCTCC - 3660
3661 - TCTCTGGGTCTTAGTTTATATTTCTCTTTACAGTAAGAAAATTAGACTAGGCCAGAGTTG - 3720
3721 - AAAACCCAAATATCTGCATAAGCTGGGCTTGGCCATGGGGCCACCTGAAGATGGAGGCTT - 3780
3781 - TACTGCTTCCCTGATTAGTTGCTCTCACTAGCCAACTGAGAGCAGGCAAAACTACAGGCT - 3840
3841 - GGGTGCAGTCAGGCTTTTTTTTTTTTTTTTTAAATAAAGAAAAGCCAGAAATCT - 3900
3901 - AGAGTTATGTGAGAACTCTAGATTTTTCATAGTTAGCAGCTAAAATGGTAAGAGCCAAA - 3960
3961 - CAAAACCCATCCGTGGGTTGGATTTGGCACACATGCCTGCGAATTGCAGTCTCCATGCTG - 4020
4021 - ATCTCTTGGGCCCTTCTGGGGAGGCAGAGGGAAGGCTCCCTGACTCAGTCACAGGCAATG - 4080
4081 - GGGAATAGGCAGTGACAGTCATTTTACAGCAGGGTATGTATGTTTAAGAGTCTAGGCCGG - 4140
4141 - GGTGTGGTGGCTCACGCCTGTAATTGCAGCACTTTGGGAGGCCGAGGCGGGTGGATCACC - 4200
4201 - TGAGGGTCAGGAGTTCGAGAACAGCCTGGCCAACATGATGAAATCCCGTCTCTACTAAAA - 4260
4261 - ATACAAAAATTAGCTGGACATGCTGGCACACGCCTGTAATCCCAGCTACTTGGGAGGCTG - 4320
4321 - AGGCAGGAGAATGGCTTGAACCCGGGAGGCAGAGGTTGCAGTGAACTGAGATTGTGCCAC - 4380
4381 - TACATCCAGCCTGGGTGACAAGAGTGAAACTCTGTCTCAAAAAAAAAAAAAAGAATCTA - 4440
4441 - GAATCTAAGTCGAGTGTCATTATATCCATGTTTTATTCCTATTCCCTTTTCCCCTTATGT - 4500
4501 - ATCCTCTTACTTTAAAGAGGAACTTTAAAAAATCTTAGGGACGACTAGGCAGAGTGGCTC - 4560
4561 - ACACCTGTAACTCCAGCACTTTGGGAGGCCAAGGCAGGCAGATTATGAGGTCAGGAGTTC - 4620
4621 - GAGACCAGCCTGGCCAACATGGTGAAACCCCAGTTCTACTAAAGATACAAAAAATCAGCC - 4680
4681 - GGGCGTGGTGGCACGTGCCTATAATCCCAGCAGATACTCGGGAGGCTGAGGCAGGAGAATCAC - 4740
4741 - TTGAACCCGTGAGGCAAAGTTTTCAGTGAGCTGAGATCATGCCATTGCACTCCACCTGGG - 4800
```

FIG. 24B

```
4801 - TGACAGGGTGAGACTCCATCTCAAAAAAAGAAAAAGGAAAAAATCTTAACGTCACATACA - 4860
4861 - TGGAAAGATCATCTTTTTCACCCCCCACCCCCAACTGAGATGGAGTTTTGCTCTTGTCAC - 4920
4921 - CCAAGCTGGAGTGCACTGGCGCGATCTAGCTCCCTGCAAGCTCCGCCTCCCGGGTTCACA - 4980
4981 - CCATTCTCCCTGCCTCAGCCTCCCGAGTAGCTGGGACTACAGGCTCCTGCTACCATGCCC - 5040
5041 - GGCTAATTTTTTGTATTTTTTTAGTAGAGACGGGGTTTCATCTGTGTTAGCCAGGATG - 5100
5101 - GTTTTGATCTCCTGACCTCGTGATCCGCCCGCCTCAGCCTCCCAAAGTGCTGGGATTACA - 5160
5161 - GGCGTAAGCCACTGCACCCCGCCTTTTTTTTTAATTAATTAATTTTTTTAGACAGAGTC - 5220
5221 - TCGCTCTGTCCCAAGCTGGAGTGCAGTGGCGCGATCTGGGCTCACTGCAACCTCCGCCTC - 5280
5281 - CTGGGTTCACGGCGATTCTCCTGCCTCAGCCTCCCGAGTAGCTGGGACTACAGGCTCCTG - 5340
5341 - CTACCATGCCCGGCTAATTTTTTGTATTTTTTTAGTAGAGACGGGGTTTCACTGTGTT - 5400
5401 - AGCCAGGATGGTTTTGATCTCCTGACCTCGTGATCCGCCCGCCTCAGCCTCCCAAAGTCC - 5460
5461 - GCCTCAGCCTCCCAAAGTGCTGGGATTACAGGCGTAAGCCACTGTACCCTGCCTTTTTTT - 5520
5521 - TTTAATTAATTAATTTTTTTAGACAGAGTCTCGCTCTGTCACCAAGCTGGAGTGCAGTGG - 5580
5581 - CGCGATTTGGGCTCACTGCAACCTCCGCTTCTTGGGTTCAAGCGATTTTCCTACCTCAGC - 5640
5641 - CTCCGGAGTAACTGGGACTACAGGCGCGTGCCACCACACCAAGCTAATTTTTTGTGTAT - 5700
5701 - GTCTTTAGTAGAGATGGGGTTTCACCATGTTAGGATGGTCTCGATCTCTTGACCTCGTGA - 5760
5761 - TCCGCCTGCCTCGGCCTCCCAAAGTGCTGGGATTACAGGCATGAGCCACCTTGCCTGGCC - 5820
5821 - GAAAGTATCTTCATTTTAAAGTTCACTGTTTGGCTACTCTGTTGACAAGAGTTTAGTATT - 5880
5881 - TCTCAAGGAGGCTAAGATACCCTATTCCTTTTTGGATCCTACCTCTATCAGGAGGGTGGGC - 5940
5941 - CTTCCTTGCATTGAAACAGTATGAAAACAGTAGCCCTGAATTCATAAGTGGGACACCTTT - 6000
6001 - CTTCTATTGGTAGAGCAGGCAGTTTTTTTCTCCTGCCAATGGTGCCTACTAAGGAGATTT - 6060
6061 - CACTAGGGTACAGTCGTTCATTTGATAAGCATTTGTTGAGCATATCCTCTGTGATGGTAC - 6120
6121 - TATGGACAGTACTGGGGCTATAGTGAGGGCAGGATTGAGTTGGTCCTTATGGCAAGGAAG - 6180
6181 - GCAGCTAATCAACAAGCAAAATATAAAGTATGATGGGGAGGGCTGTCTTCAGCACTCATG - 6240
6241 - AGTGTGAGCCCAGGCCTGGAGGGGACACCTGGAGAAGAGGGTGCATGTCTTTGCTCCTGT - 6300

6301 - GCTTTTCAGGGAAGGAGATCACGTTGCTGATGCAGACATTGAATACTCTGAGTACCCCAG - 6360
       -         K  E  I  T  L  L  M  Q  T  L  N  T  L  S  T  P  E

6361 - AGGAGAAGCTGGCTGCTCTGTGCAAGAAGTATGCTGAACTGGTCAGTTCCCCCCTCCGCG - 6420
       -   E  K  L  A  A  L  C  K  K  Y  A  E  L

6421 - GGCACCTTCCCTGCGTTGGGAAAATCAGCATGCCACCTGGTGTAAGGTTGGGGGTGCAGA - 6480
6481 - GTCAAGTAGGTGGCTTAATTCCTGTTCAGCTTTTCTCTGAACTATCTGTTAAATGGGGAA - 6540
6541 - TCACTTCCAGCCAGCCTCTTCAGGGCTGTGCAGCAAGAGGAGAAACTGCATATTCCTTGA - 6600
6601 - AAGAAATTTCTCAAAGAATGATTCCAAGGTGGTAGAGCCCTTGTTCCTGGCCTGAGTCCA - 6660
6661 - AGACACCTTGTGATCTTGATGCTTCTTCCTCAAATACAGATGCATAGAGCCATTATCACA - 6720
6721 - GTTAATAAAACTAACACTAGTCACTTGATACTTTTCCTTTTACTCCAGAGCAGTCTTCT - 6780
6781 - TGTCACTGCCTCCTCATATTCCCCATGACATTGACTTTTAACAGAAACTAGACTAGCTGT - 6840
6841 - CTTGTAGGATGCCCCCTTCTAGCTTTGTCATCTCTGTGGTATCATTTTACTTCTTTACCT - 6900
6901 - CCTGGTACATGTAAGTGAAGTAGAAGTTAGCTCTAAAGCTTGATCCAATTCAGCTTCAAC - 6960
6961 - TTTTTGACAAGAATTCTTCATAAGTACTTCATGTTCCATCACAATAAATGCAAAGCATGC - 7020
7021 - TCTTCCCACTTTGTTGTAACATTGTTCAGTGGGTTGGGGGTGGGGCAGCCAGATTCTTCC - 7080
7081 - ATCATCAGGTCCCTTGTCAGAATTTGAACTAACAGATTTATCCATTGATGGTCACAGCCT - 7140
7141 - GTGTATGTATGTATGTATGTATGTATGTATGTATGTATTTATTTATTTATTTTTGAGAC - 7200
7201 - GGGGTCTTGCTCTGTCGCCCAGGCTGGGGTGCAGTGGCACGATCTCGGCTCGCTGCAAGC - 7260
7261 - TCCGCCTTCTGGGTTCATGCCATTCTCCTGCCTCAGCCTCCCGAGTAGCTGGGTCTACAG - 7320
7321 - GCGCCCGCCACCATGCTAGGCTATTTTTTTTTTTTTTTTTTTAGTAGAGACGGGGT - 7380
7381 - TTCACCGTGTTAGCCAGGATGGTCTCGATCTCTTGACCTCGTGATCCGCCCGCCTCGGCC - 7440
7441 - TCCCAAAGTGCTGGGATTACAGGCTGAGCCACCGCCTGGCCTATTTATTTATTTATT - 7500
7501 - CAGAGTCAGAGTCTCGCTCTGTCACCAGGCTGGAGTGCAGTGGCGCGATCTCGGCTCATT - 7560
7561 - GCAACCTCCACCTCCCAGGTTCAAGCGAGTCTCCTGCCTCAGCCTCCCGAGTAGCTGGGA - 7620
7621 - TTACAGGTGCATGTCACCATGCCTGGCTAAATTTGTATGTTTTAGTAGAGACAGAGTTT - 7680
```

FIG. 24C

```
7681 - CAGTATGTTGGCCAGGATGGTCTTGATCTCTTGGCCTCGTGATCCGCCCGTCTCAGCCTC - 7740
7741 - CCAAAGTGCTGGGATTACAGGTGTGAGCCACTGTGCCTGGCCTCTAAGTATTTATTTTAA - 7800
7801 - AATTAATTCATTCCACACACATTTATTAATATTTTCCTGTAAGGAACTTTACTCATCTTT - 7860
7861 - AAAATGGGGAATGTCATACCTGCCTAATGACATTCTTGTAAGGATTAAATAAAAGGTATA - 7920
7921 - AGGAAGATAAGCACCCTTTTGGAGTGATCCAGCCAGGGGAAAATTGCTGATGCAAGAGAG - 7980
7981 - GAAATGAGTTGCTAGAGTGGTGTTGTGAGTAGAGGAGGGGAGCTGAGGCCTGCCCAAGAA - 8040
8041 - GGGGGCTTGGCTGTGGTAACCACATGGCTAGGTCTGTGTGACTGGAGGAGAGGACGGGGC - 8100
8101 - AGGTGGACTGGTAGATGTGCAGCTTGTGCCCCTGATTCTCTAGTTTCTTCTGTGTTTTGA - 8160
8161 - GATTTGATGAGAACGATGAAATAGTTGTCTGGAAGGAGAGGAGTGTGAATAGCATATGCA - 8220
8221 - TTGTATTGGGATTGCTGGTCTTCCTGAAATTGGTGGCCATGAATTTAAAGTGAGACTCTT - 8280
8281 - CAAGTAGGGTTGTTATAGTACTGGTGTAAAGCAGGAAGGTGCTTTACTAGGGTTGCAGTA - 8340
8341 - CTACTGGGGAAGGGCCAAGAGAGTTGAGGGTGTAAGAAATCCAAGCCAGGTAATGTAGTT - 8400
8401 - ATTTTAAAGGAGAGTGGAAGGATGGTTGAGTCAATGGATTGGAGGTCCTATAGGGTAAGA - 8460
8461 - GACTTTCTGAGGATCACAGATACTGATTGGAATGAGCTAAAAAGATAGGTGATGGTAGTC - 8520
8521 - CTGGACTGGGATGCTGGAAATTGAGATAGTGGGTGTGCTCTCTGGTAGTGACAAATCTAG - 8580
8581 - ATCTGCGCTGTCCAAGATAAATTCGTCTCTAGCTAATTGACATGTGGCCAGTTTGAATTT - 8640
8641 - GAACATGCTATAAATGTAAGATACACATCAGCTTTTGAAGACTTAAGCAAAAACAAAGAA - 8700
8701 - TATAAAACATCTTTTTGTGAGAGAGTGTCTCAGTCACCCAGGCTGGAGTGCAGTGGCGTG - 8760
8761 - ATGTCCTGCTTCCAGGTTCAAACGATTCTCCTGCCTCACAGCCTCCTGGAGTAACTGAGA - 8820
8821 - TTACAGGCGCATGCCACCAAACTGGCTACTTTTTGTATTTTTTTTAGTAGAAACGGT - 8880
8881 - TTCACCATGTTGGCCAGGCTGGTCTTGAACTCCTGACCTCAAGTGATCTGCCTGCCTCAG - 8940
8941 - CCTCCCAAAGTGCTGGGATTACAGGCATGAGCCACCACTCCCGGCCTCACTTTTTTACAT - 9000
9001 - TGATTCCGTGTTGAAATTGTAATGTTTTGGATATTAGGTTAAATACATATATTACTAAAA - 9060
9061 - TTAATTTCACCTGTTTTTTACTTTTTTAGTGCGGCCAGTAGAATATTTTAATTACTTAT - 9120
9121 - GTGGTTTGCATTATATTTCTGTTGTACAGGCCTGGATAGGGTCATGGGAGGGGGACTGAG - 9180
9181 - CTGGGGAAAGGAGTGGGTTTGTGGAAGAGGTGATGGACTGTGAGGCCAGGGAGTTAGAAG - 9240
9241 - GATTATCTGTTGATACTGAAGTGGCCACAAATGAGAAAAGTAATTGTGTTGGGGAGAGCG - 9300
9301 - CTGATGAACGCAGCGCTAACGTTTTGAAGGAATGCGAGGGAGCGATGGGGGTCTGTCTGT - 9360
9361 - TAATAGGCACAAGGTACGGTAGCAGGTGGTCTCATCCTCGGGCATGAGTGTCCAGCAAGT - 9420
9421 - TGGGGAAATGCAACAGCTTGAAGTGGCTCTAGTGGCCCAGAGTCAGAGCTGGAATAGGAA - 9480
9481 - TTGGCATCTGCTGGCTGTGTGGCCCCTGCTTGCCCTAGTGAGTTACCATTTCTCTGTCCC - 9540
9541 - TACGGTGGAGCCTTTGGGGTTATTGTGAGTTCATGGGAGGAGCGTGTAAGCACCGGCACA - 9600
9601 - GCATCAGCCCATGAGAGTGCTCCTGGCCTGAGAGGGTAAGGGTCAGGGCAGCTCAGGAGA - 9660
9661 - CCCTAGACCTGCATAGTGATCCCCCCACCAGGAAGGCCCCACAAGATGCTCACCTGCCCT - 9720

9721 - CCCTATCCCTGTCCCCAGCTGGAGGAGCACCGGAATTCACAGAAGCAGATGAAGCTCCTA - 9780
       -                   L  E  E  H  R  N  S  Q  K  Q  M  K  L  L

9781 - CAGAAAAAGCAGAGCCAGCTGGTGCAAGAGAAGGACCACCTGCGCGGTGAGCACAGCAAG - 9840
       - Q  K  K  Q  S  Q  L  V  Q  E  K  D  H  L  R  G  E  H  S  K

9841 - GCCGTCCTGGCCCGCAGCAAGCTTGAGAGCCTATGCCGTGAGCTGCAGCGGCACAACCGC - 9900
       - A  V  L  A  R  S  K  L  E  S  L  C  R  E  L  Q  R  H  N  R

9901 - TCCCTCAAGGTAGGCCTGGGCCCCCTGGAACAGGTGACTCTGGTTTCCTTGACTTCCACT - 9960
       - S  L  K

9961  - TAATGTTTCTTTCATGGGCTTTCCTCTTAAAAAGTAGTGCAGGCTAGGGCCAGGCGCAGT  - 10020
10021 - GGCACACATAAGTGATTAAAAATCTTCTGGCCACTAAAAAACAGAAATTAATTTTAGTAA  - 10080
10081 - TATACTTAACCCAATATCCAAAACATTACAATTTCAACATGAAATCAGTGTAAAAAAGCA  - 10140
10141 - AGGCTGGGTGTGGTGGCTCACACCTGTAATCCCAACACTTTGGGAGGCTGAGGTGGATGG  - 10200
10201 - ATCACTTGAGGCCAGGAGTTTGAGACCAACCTGGTCAACGCAGTGAAACCCCATTCTACT  - 10260
10261 - AAAAATACAAAAATTAGCCGAGTGTGCTGGCAAATGCCTATAATCCCAGCTACTCAGGTG  - 10320
```

FIG. 24D

```
10321 - GCTCAGGCATGAGAATTGCTTGCACCTGGGAGGCTGAGGTTGCAGTGAGCCGAGATTGCA - 10380
10381 - TCACTGCATTACAGCCTGGGCAACAGAGTGAGACTCAGTGTCCAAAAAAAAAAAAAAGTA - 10440
10441 - GTGCAGGCTTGTGGCATAGAAATACACTTTCTCAATAATGCCTTACGTTAAGAGAGTACT - 10500
10501 - GCTTGTAATCATTTGACATGTATTAGATAAGGTGAAGGATAAAGTACTAAGAGAATCCAT - 10560
10561 - AATGCACTGGCGTTAGTATTTCTCAATGAAATGACAGTCCCCTGGTAAGCGGAGGCCTGG - 10620
10621 - CTCTGACAAGCAGCTCTTGTCCCAGACGTTGGTCAGTCAGGAACCTGGGTCCTTCCCATG - 10680
10681 - TTCTGCTTCTATGGTGAGGTCAGTCTGTGGTTACACCAAGTTTAAATACAGCCTTTT - 10740
10741 - AACTTTCTTTTTTATATGTAAAATCTTACATGTAGTTTTTAGAATGAAATTATTATACAT - 10800
10801 - GTACCATTTCATATCCTGTGCCTTTTTTCACTTTACATAACATTTTTCCCTATCAGTAT - 10860
10861 - GTGTAGGGCTATCTTCTCATTATATGGATATATTATATCAGTGCCCTAGTTAAAGCATTT - 10920
10921 - TGGGGGTTGTTTACAATTTTTCATTATTACATATAGAACTATAGTGAAAATTCTTGTTAT - 10980
10981 - ATTTATCACTGGTCAGTTATATAGAACTTATCTGTAGGATAAGTCATGGAATTGAAATGG - 11040
11041 - CTAGGTCACAGTATATGCAGATTTTTCATTTAATAGATTTTGCTGGATTGCCTTCCAGT - 11100
11101 - GAGGGGGCAGTGTGCCTTCCCCATCAAAAGTGTTGAGTGCCTAATTCTGCACAACTTTGC - 11160
11161 - AAACCCTGGGTGTTACTAAATTTTAACAGCTTGGTCTCTGGGGGTACAGAGGGGACAAAT - 11220
11221 - GCACATTAATCTGAAATCTGGAAGAATAGGCCTTAGGAGATCCGACTTGCTTCAGAATGG - 11280
11281 - CACTTAGCACTTACATGTGTGCATGTGTGCCTGCATTTTTCTTCCTTTTTTTTTTTG - 11340
11341 - GGGACGGAGTCTTGCTCTGTGGCCCATCGCCCAGGCTGGAGTGCAGTGGCGCGATCATAG - 11400
11401 - CTCACCACAACCTCCGCCTCCCAGGTTCAAATGACTCCTCTGCCTCAGCCTCCCAAGCAG - 11460
11461 - CTGGGACCACAGGTGCACACCATCACGCCGGCTAATTTTGTATTTTAGTAGAAACGGGG - 11520
11521 - TTTCACCATATTGGCCAGGCTGGTCTCAAACTCCTGACCTCGTGATCCGCCCACCTCAGC - 11580
11581 - CTCCCAAAGTGCTGGGATTACAGGCGTGAGCCACCGCGCCTGCCATGTGCCTGCATTTTT - 11640
11641 - CTAGGGGAGAATCTCACTTGATGTCACCTGATATACAGAGGGGCCCATTGGAACCCGCA - 11700
11701 - TTGCACAACATCCTGGAGTCTGGCTACTCCACGCTTTGGGAGCAGGGAGGGCTGTTGGCA - 11760
11761 - GAGACCATCTGTGGACTAGCTGGGGACCCTTGTGAGGTAGCAGTGGATGATGGCTCTCG - 11820

11821 - GGCTGACTTCTTTGCCCAGGAAGAAGGTGTGCAGCGGGCCCGGGAGGAGGAGGAGAAGCG - 11880
                  E  E  G  V  Q  R  A  R  E  E  E  E  K  R

11881 - CAAGGAGGTGACCTCGCACTTCCAGGTGACACTGAATGACATTCAGCTGCAGATGGAACA - 11940
        K  E  V  T  S  H  F  Q  V  T  L  N  D  I  Q  L  Q  M  E  Q

11941 - GCACAATGAGCGCAACTCCAAGCTGCGCCAAGAGAACATGGAGCTGGCTGAGAGGCTCAA - 12000
        H  N  E  R  N  S  K  L  R  Q  E  N  M  E  L  A  E  R  L  K

12001 - GAAGCTGATTGAGCAGTATGAGCTGCGCGAGGAGGTAAGGGTATCACGGACAGCAGTCAT - 12060
        K  L  I  E  Q  Y  E  L  R  E  E

12061 - GGCCCAGAAATTGTGAGGTTTTGAGTGTGTGCTAGGCACTGGGACAGTACCTTTTCAGGC - 12120
12121 - TTCATCCCATTCTCCCTTTCTTCCTCCTCCTCCTTGGGAGGAGAGTAATGTTATTCC - 12180
12181 - TCATAGATAAAAACAGGTGTGGAGAAGAGACTCACTTACAGCCACACAGCCCCAGGTCC - 12240
12241 - ACAGTGCCTTGTCCCAAATGACTGGGCCAGGCATCTTTTGGAATTAGAACTATCCACATT - 12300
12301 - TTAGAATGGAGGTACATGTATGGACTGTGTTATATAGCACCCTCAGCAGGGCCTTGGG - 12360
12361 - GAAGCCAGACACATTAATGTATTTATGCAGTAGAACTTCCAAATACTCACCTACATTATG - 12420
12421 - GGCTTACAATGATGCAGGTCAAGTCTGGCTGCCAGCTTATGACAATTTCCATTTTCAGAA - 12480
12481 - CTTTGTAGAATTTGGAATTGCAGGGGAGGGTGTACCTGTGATCAGTGATGGACTCCAGA - 12540
12541 - GACTGTGTCCACTGATTCCTTGCTGCTCCTGCCACTCAAAAGGCAGAATTTATCAGGCTG - 12600
12601 - GGCGTGGTGGCTCATGCCTGTAATCCCAACACTTTGGGAGGCCAAAGCGGGCGGATCACC - 12660
12661 - TGAGGTCAGGAGTTCAAGACCAGCCTGGCCAACATGGTGAAACCCTGTCTCTACTAAAAA - 12720
12721 - TACAAAAAATTAGCCAGGTGTGGTGGTGCACGGCTGTAGTCCCAGCTACTCAGGAGGCTG - 12780
12781 - AGGCAGGAGAATTGCTTGAACCCAGGAGGCAGAGGTTGCAATGAGCCAAGATTGTGCTAC - 12840
12841 - TGCACTCTAGCCTGGGTGATATACCGAGACTCCATCTCAAAAAAAAAAAAAAAAAAAGC - 12900
12901 - AGGATGTCACTCCCTTTGTCACTGCGTTGGCTGCCACCCCAGGCACTTGAATCTTTGGAT - 12960
```

FIG. 24E

```
12961 - CTTCCCTGCCAGTCACCTGGCTGTTCTGGGCGCGTTCTCATCATGAGAAGGGAGACCTGC - 13020
13021 - AGCCCCCTTACAGGGCTGGCAGAGGACCTGCTCTGGATTAGGCCCTTTCCTAGCCCCTGG - 13080
13081 - GGTGTGGCAGTGGGTGAGACCGGGAAGATCTGCCCTCTTAGGTTCATAGGCCAAAGTGAT - 13140
13141 - GATCGTGTGTGCAGGACCTAGAGGGCGCTCCCCTGACCCACCCCTTTCCTTGCCATACTT - 13200
13201 - CATCCTCTGGGAACAAAGCTGCTTGTTTGGTTTGAGGGGAGTTGGTTTGGTTCTTATCCC - 13260
13261 - TCAGCGCTGAGACATAGAGGCTTCCTGGGCCACTACAGTGAGACACGAACTTCAAGAATC - 13320
13321 - TGAATACCCCCGTTTTCTCTCCCCGCCAAGGCAAAAAAGGACTTAGTACTACCTGTGGAG - 13380
13381 - AAGGAGGTGCAGGACTACCAGGCCCTGCTGCTTTGCATTTACAGCCCTCCCCAGACAGAC - 13440
13441 - ACAGGCACCCTCATCATACCCAAACTGGACTTACCTGCTAGGCACCTTCCCTTCCCCATC - 13500
13501 - CAAAAAATGGAGTTATTTTCCCTTATTTCAGCAAGTCCAGTTGATTTTACCTTTGAAGT - 13560
13561 - AGCACCTGAGTCCTTCACCTTCTCTCCATCCCTTCTCTCTCACCTGACACAGGTCTGCAG - 13620
13621 - CGCTCCTCTAGTAGGCAGGACAGCCATTCCTTGGGGATGCACATGTCTAGTCTTTGCCTA - 13680
13681 - GATATGGCAAGTCTTTGCCAACTGAGCTAGGCTGTTATGTTCTTAGAGGCATTGTTTTTG - 13740
13741 - CCCATTCTTCCCATTTACAAGAGAATCAGGGACACAGAAGTGAGGGCTTCCAGCCCCATA - 13800
13801 - GGTGATCAATCCTGGGGTCAGAGATTTGAGTGTGTTTATTGCTTGCCTTCTTGGGAGCAG - 13860
13861 - ATTCCATCCATAAACCATGTGCTTACCAAGGTCTGACTCACTGGGAGAGAAACGACGTGA - 13920
13921 - GGTTGGAAAGCTGACCTTCCAGAGACTTGGGGCCCATGTTGTGTGGTACACATGGGAGTC - 13980
13981 - CATCATATCAGATTGAGATGGGGGCTGGGCAAAGTGCCCTGGTCTGTGGCTGTGGGGCT - 14040

14041 - ACCCTGAGAAAGGGAGCGCCTGACAAGCCGACTGCTCCCACCATCTTTGTTGCAGCATAT - 14100
       -                                                       H  I
14101 - CGACAAAGTCTTCAAACACAAGGACCTACAACAGCAGCTGGTGGATGCCAAGCTCCAGCA - 14160
       -  D  K  V  F  K  H  K  D  L  Q  Q  Q  L  V  D  A  K  L  Q  Q

14161 - GGCCCAGGAGATGCTAAAGGAGGCAGAAGAGCGGCACCAGCGGGAGAAGGATTTTGTGAG - 14220
       -  A  Q  E  M  L  K  E  A  E  E  R  H  Q  R  E  K  D  F

14221 - GCTCAGGCCCCAGGGTTGGGGTGGGGGTGTGGGAGGAGACAGGCTGGGCTCTGGCTCAGC - 14280
14281 - TCATAGCCGGGTTATATGGGAGAAGTCTGGCCAGACCAGGCACAGATTCCTTGAGTACCA - 14340
14341 - GTCTGAGAGCAGGAAGCCTCAGTGGGTCTGGTGCTTGTGGCTAAAAACCAAACATAGCCC - 14400

14401 - CTGGGGGCTTCTGACAGGATCTGGGGTTCTGTCTTGGAAATAGCTCCTGAAAGAGGCAGT - 14460
       -                                             L  L  K  E  A  V

14461 - AGAGTCCCAGAGGATGTGTGAGCTGATGAAGCAGCAAGAGACCCACCTGAAGCAACAGGT - 14520
       -  E  S  Q  R  M  C  E  L  M  K  Q  Q  E  T  H  L  K  Q  Q

14521 - GAGAGCATATAACCTGACCCTGTGCCTTCAAGTTTCCCTCACTGGGCCCCATCCTGGGGG - 14580
14581 - TAGTGAAATGGGACCCTCATTCTAGGACTGGCTGTGTCCTGGCTGCTATGACGCCTTGGT - 14640
14641 - TGAGCTTAGGTGGGCTCAGAGGACTTCATTTGTAGCTCAGAAATGTATTGCTTTTGAGGA - 14700
14701 - GGTAGGAACAGAAGAGTTTGAAAATCAACATAAAGGCAAAATAAAAGTCACCCTAAGTCT - 14760
14761 - CCTACTTTCCAGGCTTAGCATTTTGGATTATATCCTTCCAAATATATAGCTTTGCTTTGT - 14820
14821 - TTAAGGAAAAATAGTATCTCAATAGAATTACTGGTCAGAGAGTCAAGGACGGGTCTGAG - 14880
14881 - TGTGTTGACCAGAGTGCCTCCCAGAGAAACCCAGTCTTATCTGTGGGCTGCTTTCTCCCC - 14940

14941 - ACAGCTTGCCCTATACACAGAGAAGTTTGAGGAGTTCCAGAACACACTTTCCAAAAGCAG - 15000
       -    L  A  L  Y  T  E  K  F  E  E  F  Q  N  T  L  S  K  S  S
```

FIG. 24F

```
15001 - CGAGGTATTCACCACATTCAAGCAGGAGATGGAAAAGGTAACTGTGGTCCAGGCCAGGCA - 15060
      -  E  V  F  T  T  F  K  Q  E  M  E  K

15061 - TGGCTGCTGGGGCATAAGCTGCTTCATTCAAAATTGTTGGGCCTGCCTTCAGGAAGCTCC - 15120
15121 - CATCTGGGGTGTCTCAAGGGCAGGGCTGTTAGGAAGGTTCACAGCCTTTCCCCTCTTGAG - 15180
15181 - GCAGTATCAGTGGTATGTATACACTCCAGGTTGTCCCAGGGAATGGGGCAGTCTTTTCTG - 15240
15241 - TTTGTTTGGTTTTTTTGGGGGGTTTGTTGTTGTTGTTGTTGTTGTTGTTTGAGA - 15300
15301 - TGGAGACTCACCTATTGCCCAGGCTGGAGTGCAGTGGCATGATCTCAGCTCATTGCAGCC - 15360
15361 - TTTGCCCCCCGGGTTCAAGTGATTCTCCTGCCTCAGCCTCCTGACTAGCTGGAATTACAG - 15420
15421 - GCGCGTGCCACCATGCCTGGCTAATTTTTTCTTTCTTTTTTTTTGTATTTTTAGTAGAG - 15480
15481 - ACGGGGTTTCACCATGTTGGCCAGGCTGGTCTCGAACTCTTGGCCTCAAGTGATCTGCCC - 15540
15541 - GCCTTGGCCTCCCAAAGTGCTGGGATTATAGGCGTGAGCCACCATGCCTGGCCCCTTACC - 15600
15601 - ATTCCTTGTTATTGGTGGTGGACACCTCTGACTTCCTGGTGGTGAGGTGGCACAGAGGGC - 15660
15661 - ATTGACTGCATCCTGTAATGCCTTGCGCCTTGGGATCAATCATTCCCCACCTTGGAGACA - 15720
15721 - CAGGTGCAGTCCCCACCTTGGAGACACAGACCTTGGAGAGGCCAGCTCTGACCATTTCCT - 15780

15781 - TCTGTCTGTCACATAACCTAGATGACTAAGAAGATCAAGAAGCTGGAGAAAGAAACCACC - 15840
      -                                M  T  K  K  I  K  K  L  E  K  E  T  T

15841 - ATGTACCGGTCCCGGTGGGAGAGCAGCAACAAGGCCCTGCTTGAGATGGCTGAGGAGGTGG - 15901
      - M  Y  R  S  R  W  E  S  S  N  K  A  L  L  E  M  A  E  E

15902 - GCTGTCTGTGATCTGCAGCCAGGGTGGGGGTGTGCACTTAGCGCATATCAGGCCCTTTCC - 15961
15962 - TGTATGTTCTACCCATCAGTGACACAGCTAGCATGAGGTAGAGGTGAGATTTGCACACAA - 16021
16022 - TGTCCAAGTCCAAAGTTAATGCTGTTCTCTCCCATGGGAGGTGGTGAGCCCAGTGGTAG - 16081
16082 - GTCTCCAGTGGGAGTGAAGGGAGCAAATGGAAGAAAGGAATAAAAGAGCAGAAAAAAACG - 16141
16142 - GGTGCCAGTGATGTGCCTGGTTTACATGTAAAGCAGCCCAGGTAGTTTGTGATTTCACAG - 16201
16202 - CTTGTAATGTAGAAGAAAGGAACTAACGATGGAGCAGCAACTGCAAGCCAGACCTTGCTG - 16261
16262 - AAAGTTTTTGGGTTTTTTTTGTCTTTTTTGCTGCTGAATGTTTTAGGTACGTTGTTCAT - 16321
16322 - TGAACCTTCTCTTGAGCTCTGAGGATGGTATTAGTAGTCCTGTTTTATAGATGAGACAGG - 16381
16382 - CTCAAAAGTCAAGTCCTTTGCCAAGGTCACGTGGTAGATAAATGGAGGAATACGTTATCT - 16441
16442 - CCAAGCCGTGCCCCTTTTCTGCACCATGCTGCCCCACCTGACAGCCTAGTCATGGCTTCA - 16501
16502 - ACTAGGACTGTTTCCTAAAGGGGGCCAGCTTTGGACTCGGTCTGCTCTCAGCCTTGTTAA - 16561
16562 - AGTGTTTGCCGCCAAGTGGTGATGGTAAGTGGGAGGTTGATGGGGCACGGCACTGAAGGT - 16621

16622 - CTCATTTCTTTCCCTAGAAAACAGTCCGGGATAAAGAACTGGAGGGCCTGCAGGTAAAAA - 16681
      -                  K  T  V  R  D  K  E  L  E  G  L  Q  V  K  I

16682 - TCCAACGGCTGGAGAAGCTGTGCCGGGCACTGCAGACAGAGCGCAATGACCTGAACAAGA - 16741
      -  Q  R  L  E  K  L  C  R  A  L  Q  T  E  R  N  D  L  N  K  R

16742 - GGGTACAGGACCTGAGTGCTGGTGGCCAGGGCTCCCTCACTGACAGTGGCCCTGAGAGGA - 16801
      -  V  Q  D  L  S  A  G  G  Q  G  S  L  T  D  S  G  P  E  R  R

16802 - GGCCAGAGGGGCCTGGGGCTCAAGCACCCAGCTCCCCAGGGTCACAGAAGCGCCTTGCT - 16861
      -  P  E  G  P  G  A  Q  A  P  S  S  P  R  V  T  E  A  P  C  Y

16862 - ACCCAGGAGCACCGAGCACAGAAGCATCAGGCCAGACTGGGCCTCAAGAGCCCACCTCCG - 16921
      -  P  G  A  P  S  T  E  A  S  G  Q  T  G  P  Q  E  P  T  S  A

16922 - CCAGGGCCTAGAGAGCCTGGTGTTGGGTCATGCTGGGAAGGGAGCGGCAGCCCAGCCAGG - 16981
      -  R  A  *
```

FIG. 24G

```
16982 - CCTGGCCCATAAAAGGCTCCCATGCTGAGCAGCCCATTGCTGAAGCCAGGATGTTCTGAC - 17041
17042 - CTGGCTGGCATCTGGCACTTGCAATTTTGGATTTTGTGGGTCAGTTTTACGTACATAGGG - 17101
17102 - CATTTTGCAAGGCCTTGCAAATGCATTTATACCTGTAAGTGTACAGTGGGCTTGCATTGG - 17161
17162 - GGATGGGGGTGTGTACAGATGAAGTCAGTGGCTTGTCTGTGAGCTGAAGAGTCTTGAGAG - 17221
17222 - GGGCTGTCATCTGTAGCTGCCATCACAGTGAGTTGGCAGAAGTGACTTGAGCATTTCTCT - 17281
17282 - GTCTGATTTGAGGCTCAGACCCCTCCCTGCCCTTCAGAGCTCAAGACAAGTAATACACCC - 17341
17342 - AGGTCTTGACTGCATTTGTCTTGTGAGCAGGGCTTGCTTGGTCAGCTCAGGCCCTCCTAG - 17401
17402 - CTGCTCTGGAGGCTCCTTTGATTCTCTAGACCTGGAAAAGGTGTCCCTAGGCAGAGCCCT - 17461
17462 - GGCAGGGCGCTCAGAGCTGGGGATTTGCTGCCTGGAACAAGGGACCTGGAGAATGTTTTT - 17521
17522 - GCGTGGGATGATGTGCTGGTCAGGAGCCCCTTGGGCATCGCTTCCCTGCCCTTTGGTAG - 17581
17582 - TGCCAGGACCAGGCCAATGATGCTTCTCAGTAGCCTTATCATTCACAGGTGCCTCTCTAG - 17641
17642 - CCTGCACAAATGATTGACAAGAGATCACCCAAAGGATTATTTCTGAAGGTGTTTTTTTCT - 17701
17702 - TTATTTCTTTTTCTTTTTTTTTTTTCTTTTTCTTTTTTTTTGCACATGACAGTGTT - 17761
17762 - TGTATTGAGGACCTTCCAAGGAAGAGGGATGCTGTAGCAGTGGTGCCTGGGTGCCTGGCC - 17821
17822 - TCCAGTGTCCCACCTCCTTCACCACCCCACTTGGCTCCTTTGCCATCTTGATGCTGAGGT - 17881
17882 - TTCCTGTTTGGTGAGATCAGGTTGTTTGTGGTAAAAGAAAGGAAAGGGCTTCTGATGGCT - 17941
17942 - TTGCCACAAGCTTACCTGTGGGTTTCAGTCCTGAGAGGCCACCACCAGTTCCCATCAGCA - 18001
18002 - CTGTCTCCATGCAGCAGTTGCTGGGTCCCATGTCCAGCTGCCTCTTTGGCTTCATGGGTT - 18061
18062 - TTTCTGCTTCCTGCCCCCACCCCACATGTGCAATCCTCAAGATTTGTCCTGATTCTATT - 18121
18122 - TCCTGGCACCTCCCTGCCTGTCCTTGGGGATTCTACTTCTTCCTGTGTGGGAGCCCATAG - 18181
18182 - CTGTTGTCTAACAGGTAAGAAATGAAATTGAACTATTGACTGGGCCCCAGAAATCCATAA - 18241
18242 - AATGGCTGCAGACAGTTGTTTCTGTGTCCTGTTCTACCCCCACTCCAGTACATAACTACT - 18301
18302 - ATGTACTGTGTAGAGCCATTCTATATGCTGAATGTTCTGCTGTTGCAAACTTGCCAGGGT - 18361
18362 - ATTAGCCAGTGTTTGTGCCAAGCAGTTTTCTGGGACAACAGAATGACTCAGACCAAGATG - 18421
18422 - GATAGGATGGTTAGGGCTTTGCTTCTTGCTGTTTTTCTTTGAAGCTAGTTCATTGTCCTG - 18481
18482 - CAGGTCCCTTCATCTTCCATACCTAGCCCACTCTTTTAGCCCTTACCTTAAATCTCTCAG - 18541
18542 - ATAAGTTGGTTCACAAAGAATGTTAAGTACTGAATCATGTGTGACTGAGACCAGAGATGG - 18601
18602 - CAAATGAATGGCACACCATTTCTCCTTCTCCTGCCCCAGGGCAGGTACCACTGATCTGCA - 18661
18662 - TCAGAGTTGCCTGCTATTCTCTGGTGTATCCTTCACATCTAGGTGCCCTCAAGCAGCTGT - 18721
18722 - GTGAGTGTTGAGATCTCTGCCATCTCTGGCTGAGATACTGCTGTCCTGTGAAGTGTTTCC - 18781
18782 - CATGACCTTTTTCTTCCCCTTTGAATCCCTCTGTCTGGAGTAGTCCTTGCCTCTTCCTGC - 18841
18842 - TCCAGTAGGGCCTTTTCCCTACCCCAGCCCCTGTGCCAGGCTAAGCTGGTACAAGAGCTG - 18901
18902 - CCAACCTCACAGAGTGTTTGCTAGGCGAGAGAGGTGCAGGGAAGAGGCAGAGGTATGCAC - 18961
18962 - CTTCCCCCTTGAAGAGAGGGGAAAGGCCTACAGTGGCCCACATAATTGCCTGACTCACAC - 19021
19022 - TTCAGCTACCTCTTAATGCCTGTGGAGGGACTGGAGCTGCTGGATCCCAGTGTGGTGGTG - 19081
19082 - TAGGAGGCCACAGTGAGCAGGTGGCCCCAGCTGGGTTTCCCAGGTCAGGAATGTGGGCCC - 19141
19142 - CAGGCAAGGTGCAGCCTTTGCTCACAGCTCCATCCATGTCTAGACCTTCAGGCCAGTCTG - 19201
19202 - CAGATGAGGTTCCCTACCTTTTTCTTCTCATTGACCAAATCAACCAATCACTACAGC - 19261
19262 - TGCTCTGCTTCTGCTTTCCAAAGTAGCCCAGGTCCTGGGCCAGATGCAGGGGAGGTGCCT - 19321
19322 - ATCCATGAGTGAAGGCCAGTGTCTTCCTCACCTGGGTGGGTCCCACACTTGTGACCTCAG - 19381
19382 - TTTTAGGACCAAGATCTGTGTTGGTTTCTTAGATTGCTAGCTTTTCCTCCAGGGGACCAC - 19441
19442 - AGCAGGTGAAGCTCAAGAGCGCATGGCTCTGCTAATAGTAAATTGTTTTCAGGGCCTTGT - 19501
19502 - CCAGCTGAGAGCTTCATGTCCACCAGATTCTGAGAGGTGTCAGCAGCACTTTTTTTTTTT - 19561
19562 - ATTTGTTGTTTGTTTTCCATGAGGTTATCGGACCATGGGCTGAGCTCAGGCACTTTCTGT - 19621
19622 - AGGAGACTGTTATTTCTGTAAAGATGGTTATTTAACCCTTCTCACCCCATCACGGTGGCC - 19681
19682 - CTGAGGGCTGACCCGGAGGCCAGTGGAGCTGCCTGGTGTCCACGGGGGAGGGCCAAGGCC - 19741
19742 - TGCTGAGCTGATTCTCCAGCTGCTGCCCCAGCCTTTCCGCCTTGCACAGCACAGAGGTGG - 19801
19802 - TCACCCCAGGGACAGCCAGGCACCTGCTCCTCTTGCCCTTCCTGGGGAAGGGAGCTGCC - 19861
19862 - TTCTGTCCCTGTAACTGCTTTCCTTATGGCCCAGCCCGGCCACTCAGACTTGTTTGAAGC - 19921
19922 - TGCACTGGCAGCTTTTTGTCTCCTTTGGGTATTCACAACAGCCAGGGACTTGATTTTGA - 19981
19982 - TGTATTTTAAACCACATTAAATAAAGAGTCTGTTGCCTTACTTGTTTCTCTCCTGACCTG - 20041
20042 - TGTATTCCTTTGTTTCTGGATCTGATCCATTCAGCCCCTTCCATCATCACTGACTTGTTC - 20101
20102 - AGGTCTGCTGCAGAGCGCCCATGGTGGTTCCCTGGTATCTTACATATTCCACAGTGTCTT - 20161
20162 - TGAGCAGTCGCCACAGCCTCAGGATGCTGGCATATTCACTTGAGCTGCCTGAGTGGAGCC - 20221
20222 - CTTGGCAAAGTTGGCAAGACCCTTGCCTCAGAGAGGATCACACACACACAAAAAAGTTTT - 20281
```

FIG. 24H

```
20282 - CCCTGACCTGGGGGCTCACAGGCTAGTGAAGGGAAAAGGTACTTTTAGCTATAGACAGGT - 20341
20342 - CAATGGTGCTGAGAGCAGAGAGGAGGCCCCTGCCCCCTTCAGCAAGGTGAGGGGTGATA - 20401
20402 - CCTGGAATGGCCTTCTGAACCACAGGGCAGGTAGAAGATGAACGTCATTTAGTGATTAAA - 20461
20462 - TGGTACAGCTGGGAAGCAGGTCCATGGGACTGGGAGAGGGGTGAGGCTGGGCCCAGAGT - 20521
20522 - CTGGGTACCAGGTTAAGGAATGTGGGCTAGATCCAGAGGGCAGGGGGGGCAACTGAAGGT - 20581
20582 - GTTTCAATAGGAAATTGATAGGCTCCAGCAGTAAGGCAAAAGGCATGGAGCCAGGCATAG - 20641
20642 - GCCATTTGAGGCCCAGGTTAAGAGGGGTGGACACTCATCACTGCTATTTGGGTCTGAGCT - 20701
20702 - GTGGGTAGGCTCCTATAGCCCTGGCCTGCCCAAGGGAATTCACAGGGGCCTCTAATTGTA - 20761
20762 - TGCATTCCTTAAGGAGAGCACATTCTCTGTTCAGTTTTTACACCCCCCATTTACCCACCT - 20821
20822 - CAAGCATGGGACTCCTATATGGGAGACATGCTGCTGGTGGCCTCACCCAGCACCCTGTTC - 20881
20882 - TCTCTGGGTCCTGGGTTGGTCAGGCACAAAGGATGATATGTGCTGAATGCCCAGGAAATG - 20941
20942 - GCAGAGACAACCCACCTGCCCTTCCCTCCAGGCCTCCACAAATAGATGTGCCCACAATGA - 21001
21002 - CTGTGACAGTCCCAGCAGAGCCTCTGACCCTTCTAGCTGGGTCCTGATACATGTTTTCCA - 21061
21062 - TGCTGGCCATGTTATTTCTAGTCGCAGATCCTCTGGAGGGTGTGGGGGGGGTGCCGCCCC - 21121
21122 - AACTCTTGGAGATTCCAAGCAAAGCAGCTCTGAGAATAATGAGGTTTCTGACCCCCCAGT - 21181
21182 - GAAGCAGCTGAGGATGGGAACCACAGGGGTGCTCCCTCTGTCAGCAGCATTACCACTGTC - 21241
21242 - TACTCTAGCAGCTCCGGTGGGGAAGGAGAGGGATTTCTGTTGTCCCCAGTCTGGGCCCCT - 21301
21302 - GGTTATTGAAAAAGTTCGGAATTACTCTTTACCCTTGTGGAGTGTTCTGAGTGTTGGAAG - 21361
21362 - TACCCAGGAAGAAGCCCTGAGCAGGTGCCCTCAGGAGCAGTGCCCATGGCTCCCCACATC - 21421
21422 - AGCCAAGAGGCCCAACCCCAGGAAGCCACTCCTGCCCGGGGATGGGGAAGGTGGGCTGGG - 21481
21482 - TGGCTGTGTGCACTGCCCTGGGCCAGCTCACTTGAGCCTGCTGAGCCGCCTGGCCAAACA - 21541
21542 - TGAGCCTCTCTCCTGTTGTATCAGATGCTGTTCTGGGGACCTGCGCCAGGAGCCTCTGCC - 21601
21602 - AGGGCTTTAAATAGCTGCCCCCATTGATCTGGCTGCAGGCAGCAGCAGTCACACTGGGTC - 21661
21662 - AGCCTCCATCAGGTGCTCAGGTTTCCCTGAGGACTGGAGTCAGGTGCCAGGGAATCGCGT - 21721
21722 - GGTCTACCTTATGACCTGGTGCTCCCCACACCTGTCTCCTAGGCCTGGGGGGTGGGGAGG - 21781
21782 - ACTCCTGTCACTTCATCTGCGGCAAAATACAGCCCCCACCACTTACCAGAGAAAACTGTC - 21841
21842 - TGGCATTGTAGAGAGAGGGGTTTTGCCCTCAAAAGACTGTTGCTTACTTTCAGTAGAATG - 21901
21902 - GGGAATGACACTGGTATCTTCCTTAAGGGTTGTTATGGGGATGAAATGTATGTAAAGTGC - 21961
21962 - TCAATAGGGCACTGGACTCACTCCATTGATGGCTGTCTTTGCTCGAAGTGTCTTCCTGAT - 22021
22022 - GCTGCTGCTGTTGCTGCTTGTGCTTCTTCTGTGCTTACATTCTCTCTCTCACTCACTC - 22081
22082 - ACTCTGTCTCTCCTCTCCCCGCCCCACCCCCTTTCTGACAAAGCCACCACCATTTGTA - 22141
22142 - AGGAACTGTAGCTTCTCTCTGAAACTGCCGGGAAAGGGAAAATCTTTTTAAAATAGACAT - 22201
22202 - CACACAACCAACAGGGTCCCCTAGGTTCAGGCGGGGAGGTGAGGTCGAGTGAGA - 22255
```

FIG. 24!

SEQUENCE LISTING

<160> NUMBER OF SEQ ID NOS: 53

<210> SEQ ID NO 1
<211> LENGTH: 151
<212> TYPE: PRT
<213> ORGANISM: Oryctolagus cuniculus

<400> SEQUENCE: 1

Met Ser Lys Asn Thr Val Ser Ser Ala Arg Phe Arg Lys Val Asp Val
1               5                   10                  15

Asp Glu Tyr Asp Glu Asn Lys Phe Val Asp Glu Glu Asp Gly Gly Asp
            20                  25                  30

```
Gly Gln Ala Gly Pro Asp Glu Gly Val Asp Ser Cys Leu Arg Gln
         35                  40                  45

Gly Asn Met Thr Ala Ala Leu Gln Ala Ala Leu Lys Asn Pro Pro Ile
 50                  55                  60

Asn Thr Arg Ser Gln Ala Val Lys Asp Arg Ala Gly Ser Ile Val Leu
 65                  70                  75                  80

Lys Val Leu Ile Ser Phe Lys Ala Gly Asp Ile Glu Lys Ala Val Gln
                 85                  90                  95

Ser Leu Asp Arg Asn Gly Val Asp Leu Leu Met Lys Tyr Ile Tyr Lys
             100                 105                 110

Gly Phe Glu Ser Pro Ser Asp Asn Ser Ser Ala Val Leu Leu Gln Trp
         115                 120                 125

His Glu Lys Ala Leu Ala Ala Gly Gly Val Gly Ser Ile Val Arg Val
 130                 135                 140

Leu Thr Ala Arg Lys Thr Val
145                 150

<210> SEQ ID NO 2
<211> LENGTH: 317
<212> TYPE: PRT
<213> ORGANISM: Oryctolagus cuniculus
<220> FEATURE:
<221> NAME/KEY: VARIANT
<222> LOCATION: (1)...(317)
<223> OTHER INFORMATION: Xaa = Any Amino Acid

<400> SEQUENCE: 2

Asp Cys Arg Ser Ser Asn Asn Arg Xaa Pro Lys Gly Gly Ala Ala
 1               5                  10                  15

Arg Ala Gly Gly Pro Ala Arg Pro Val Ser Leu Arg Glu Val Val Arg
                 20                  25                  30

Tyr Leu Gly Gly Ser Ser Gly Ala Gly Gly Arg Leu Thr Arg Gly Arg
             35                  40                  45

Val Gln Gly Leu Leu Glu Glu Ala Ala Ala Arg Gly Arg Leu Glu
 50                  55                  60

Arg Thr Arg Leu Gly Ala Leu Ala Leu Pro Arg Gly Asp Arg Pro Gly
 65                  70                  75                  80

Arg Ala Pro Pro Ala Ala Ser Arg Ala Ala Arg Asn Lys Arg Ala
                 85                  90                  95

Gly Glu Glu Arg Val Leu Glu Lys Glu Glu Glu Glu Glu Glu
             100                 105                 110

Asp Asp Glu Asp Asp Asp Asp Val Val Ser Glu Gly Ser Glu Val
         115                 120                 125

Pro Glu Ser Asp Arg Pro Ala Gly Ala Gln His His Gln Leu Asn Gly
 130                 135                 140

Gly Glu Arg Gly Pro Gln Thr Ala Lys Glu Arg Ala Lys Glu Trp Ser
145                 150                 155                 160

Leu Cys Gly Pro His Pro Gly Gln Glu Glu Gly Arg Gly Pro Ala Ala
                 165                 170                 175

Gly Ser Gly Thr Arg Gln Val Phe Ser Met Ala Ala Leu Ser Lys Glu
             180                 185                 190

Gly Gly Ser Ala Ser Ser Thr Thr Gly Pro Asp Ser Pro Ser Pro Val
         195                 200                 205

Pro Leu Pro Pro Gly Lys Pro Ala Leu Pro Gly Ala Asp Gly Thr Pro
 210                 215                 220
```

```
Phe Gly Cys Pro Ala Gly Arg Lys Glu Lys Pro Ala Asp Pro Val Glu
225                 230                 235                 240

Trp Thr Val Met Asp Val Val Glu Tyr Phe Thr Glu Ala Gly Phe Pro
            245                 250                 255

Glu Gln Ala Thr Ala Phe Gln Glu Gln Glu Ile Asp Gly Lys Ser Leu
        260                 265                 270

Leu Leu Met Gln Arg Thr Asp Val Leu Thr Gly Leu Ser Ile Arg Leu
    275                 280                 285

Gly Pro Ala Leu Lys Ile Tyr Glu His His Ile Lys Val Leu Gln Gln
290                 295                 300

Gly His Phe Glu Asp Asp Pro Glu Gly Phe Leu Gly
305                 310                 315

<210> SEQ ID NO 3
<211> LENGTH: 232
<212> TYPE: PRT
<213> ORGANISM: Oryctolagus cuniculus

<400> SEQUENCE: 3

Ala Ser Ala Arg Ala Ala Arg Asn Lys Arg Ala Gly Glu Glu Arg Val
1               5                   10                  15

Leu Glu Lys Glu Glu Glu Glu Glu Glu Asp Glu Asp Asp
            20                  25                  30

Asp Asp Asp Val Val Ser Glu Gly Ser Glu Val Pro Glu Ser Asp Arg
        35                  40                  45

Pro Ala Gly Ala Gln His His Gln Leu Asn Gly Gly Arg Gly Pro
    50                  55                  60

Gln Thr Ala Lys Glu Arg Ala Lys Glu Trp Ser Leu Cys Gly Pro His
65                  70                  75                  80

Pro Gly Gln Glu Glu Gly Arg Gly Pro Ala Ala Gly Ser Gly Thr Arg
                85                  90                  95

Gln Val Phe Ser Met Ala Ala Leu Ser Lys Glu Gly Gly Ser Ala Ser
            100                 105                 110

Ser Thr Thr Gly Pro Asp Ser Pro Ser Pro Val Pro Leu Pro Pro Gly
        115                 120                 125

Lys Pro Ala Leu Pro Gly Ala Asp Gly Thr Pro Phe Gly Cys Pro Ala
130                 135                 140

Gly Arg Lys Glu Lys Pro Ala Asp Pro Val Glu Trp Thr Val Met Asp
145                 150                 155                 160

Val Val Glu Tyr Phe Thr Glu Ala Gly Phe Pro Glu Gln Ala Thr Ala
                165                 170                 175

Phe Gln Glu Gln Glu Ile Asp Gly Lys Ser Leu Leu Leu Met Gln Arg
            180                 185                 190

Thr Asp Val Leu Thr Gly Leu Ser Ile Arg Leu Gly Pro Ala Leu Lys
        195                 200                 205

Ile Tyr Glu His His Ile Lys Val Leu Gln Gln Gly His Phe Glu Asp
210                 215                 220

Asp Asp Pro Glu Gly Phe Leu Gly
225                 230

<210> SEQ ID NO 4
<211> LENGTH: 252
<212> TYPE: PRT
<213> ORGANISM: Oryctolagus cuniculus

<400> SEQUENCE: 4
```

```
Thr Arg Leu Gly Ala Leu Ala Leu Pro Arg Gly Asp Arg Pro Gly Arg
1               5                   10                  15

Ala Pro Pro Ala Ala Ser Ala Arg Ala Arg Asn Lys Arg Ala Gly
            20                  25                  30

Glu Glu Arg Val Leu Glu Lys Glu Glu Glu Glu Glu Glu Glu Asp
        35                  40                  45

Asp Glu Asp Asp Asp Asp Val Val Ser Gly Ser Glu Val Pro
50                  55                  60

Glu Ser Asp Arg Pro Ala Gly Ala Gln His His Gln Leu Asn Gly Gly
65              70                  75                  80

Glu Arg Gly Pro Gln Thr Ala Lys Glu Arg Ala Lys Glu Trp Ser Leu
                85                  90                  95

Cys Gly Pro His Pro Gly Gln Glu Glu Gly Arg Gly Pro Ala Ala Gly
                100                 105                 110

Ser Gly Thr Arg Gln Val Phe Ser Met Ala Ala Leu Ser Lys Glu Gly
            115                 120                 125

Gly Ser Ala Ser Ser Thr Thr Gly Pro Asp Ser Pro Ser Pro Val Pro
130                 135                 140

Leu Pro Pro Gly Lys Pro Ala Leu Pro Gly Ala Asp Gly Thr Pro Phe
145                 150                 155                 160

Gly Cys Pro Ala Gly Arg Lys Glu Lys Pro Ala Asp Pro Val Glu Trp
                165                 170                 175

Thr Val Met Asp Val Val Glu Tyr Phe Thr Glu Ala Gly Phe Pro Glu
            180                 185                 190

Gln Ala Thr Ala Phe Gln Glu Gln Glu Ile Asp Gly Lys Ser Leu Leu
        195                 200                 205

Leu Met Gln Arg Thr Asp Val Leu Thr Gly Leu Ser Ile Arg Leu Gly
210                 215                 220

Pro Ala Leu Lys Ile Tyr Glu His His Ile Lys Val Leu Gln Gln Gly
225                 230                 235                 240

His Phe Glu Asp Asp Asp Pro Glu Gly Phe Leu Gly
                245                 250

<210> SEQ ID NO 5
<211> LENGTH: 557
<212> TYPE: PRT
<213> ORGANISM: Oryctolagus cuniculus

<400> SEQUENCE: 5

Met Lys Asn Gln Asp Lys Lys Asn Gly Ala Ala Lys Gln Pro Asn Pro
1               5                   10                  15

Lys Ser Ser Pro Gly Gln Pro Glu Ala Gly Ala Glu Gly Ala Gln Gly
            20                  25                  30

Arg Pro Gly Arg Pro Ala Pro Ala Arg Glu Ala Glu Gly Ala Ser Ser
        35                  40                  45

Gln Ala Pro Gly Arg Pro Glu Gly Ala Gln Ala Lys Thr Ala Gln Pro
50                  55                  60

Gly Ala Leu Cys Asp Val Ser Glu Glu Leu Ser Arg Gln Leu Glu Asp
65                  70                  75                  80

Ile Leu Ser Thr Tyr Cys Val Asp Asn Asn Gln Gly Ala Pro Gly Glu
                85                  90                  95

Asp Gly Val Gln Gly Glu Pro Pro Glu Pro Glu Asp Ala Glu Lys Ser
            100                 105                 110

Arg Ala Tyr Val Ala Arg Asn Gly Glu Pro Glu Pro Gly Thr Pro Val
        115                 120                 125
```

```
Val Asn Gly Glu Lys Glu Thr Ser Lys Ala Glu Pro Gly Thr Glu Glu
    130                 135                 140

Ile Arg Thr Ser Asp Glu Val Gly Asp Arg Asp His Arg Arg Pro Gln
145                 150                 155                 160

Glu Lys Lys Lys Ala Lys Gly Leu Gly Lys Glu Ile Thr Leu Leu Met
                165                 170                 175

Gln Thr Leu Asn Thr Leu Ser Thr Pro Glu Glu Lys Leu Ala Ala Leu
                180                 185                 190

Cys Lys Lys Tyr Ala Glu Leu Leu Glu Glu His Arg Asn Ser Gln Lys
            195                 200                 205

Gln Met Lys Leu Leu Gln Lys Lys Gln Ser Gln Leu Val Gln Glu Lys
        210                 215                 220

Asp His Leu Arg Gly Glu His Ser Lys Ala Ile Leu Ala Arg Ser Lys
225                 230                 235                 240

Leu Glu Ser Leu Cys Arg Glu Leu Gln Arg His Asn Arg Ser Leu Lys
                245                 250                 255

Glu Glu Gly Val Gln Arg Ala Arg Glu Glu Glu Lys Arg Lys Glu
                260                 265                 270

Val Thr Ser His Phe Gln Met Thr Leu Asn Asp Ile Gln Leu Gln Met
            275                 280                 285

Glu Gln His Asn Glu Arg Asn Ser Lys Leu Arg Gln Glu Asn Met Glu
        290                 295                 300

Leu Ala Glu Arg Leu Lys Lys Leu Ile Glu Gln Tyr Glu Leu Arg Glu
305                 310                 315                 320

Glu His Ile Asp Lys Val Phe Lys His Lys Asp Leu Gln Gln Gln Leu
                325                 330                 335

Val Asp Ala Lys Leu Gln Gln Ala Gln Glu Met Leu Lys Glu Ala Glu
                340                 345                 350

Glu Arg His Gln Arg Glu Lys Asp Phe Leu Leu Lys Glu Ala Val Glu
            355                 360                 365

Ser Gln Arg Met Cys Glu Leu Met Lys Gln Gln Glu Thr His Leu Lys
        370                 375                 380

Gln Gln Leu Ala Leu Tyr Thr Glu Lys Phe Glu Glu Phe Gln Asn Thr
385                 390                 395                 400

Leu Ser Lys Ser Ser Glu Val Phe Thr Thr Phe Lys Gln Glu Met Glu
                405                 410                 415

Lys Met Thr Lys Lys Ile Lys Lys Leu Glu Lys Glu Thr Thr Met Tyr
                420                 425                 430

Arg Ser Arg Trp Glu Ser Ser Asn Lys Ala Leu Leu Glu Met Ala Glu
            435                 440                 445

Glu Lys Thr Leu Arg Asp Lys Glu Leu Glu Gly Leu Gln Val Lys Ile
        450                 455                 460

Gln Arg Leu Glu Lys Leu Cys Arg Ala Leu Gln Thr Glu Arg Asn Asp
465                 470                 475                 480

Leu Asn Lys Arg Val Gln Asp Leu Ser Ala Gly Gly Gln Gly Pro Val
                485                 490                 495

Ser Asp Ser Gly Pro Glu Arg Arg Pro Glu Pro Ala Thr Thr Ser Lys
                500                 505                 510

Glu Gln Gly Val Glu Gly Pro Gly Ala Gln Val Pro Asn Ser Pro Arg
            515                 520                 525

Ala Thr Asp Ala Ser Cys Cys Ala Gly Ala Pro Ser Thr Glu Ala Ser
530                 535                 540
```

```
Gly Gln Thr Gly Pro Gln Glu Pro Thr Thr Ala Thr Ala
545                 550                 555
```

<210> SEQ ID NO 6
<211> LENGTH: 151
<212> TYPE: PRT
<213> ORGANISM: Homo sapiens

<400> SEQUENCE: 6

```
Met Ser Lys Asn Thr Val Ser Ser Ala Arg Phe Arg Lys Val Asp Val
1               5                   10                  15

Asp Glu Tyr Asp Glu Asn Lys Phe Val Asp Glu Glu Asp Gly Gly Asp
            20                  25                  30

Gly Gln Ala Gly Pro Asp Glu Gly Glu Val Asp Ser Cys Leu Arg Gln
        35                  40                  45

Gly Asn Met Thr Ala Ala Leu Gln Ala Leu Lys Asn Pro Pro Ile
    50                  55                  60

Asn Thr Lys Ser Gln Ala Val Lys Asp Arg Ala Gly Ser Ile Val Leu
65                  70                  75                  80

Lys Val Leu Ile Ser Phe Lys Ala Asn Asp Ile Glu Lys Ala Val Gln
                85                  90                  95

Ser Leu Asp Lys Asn Gly Val Asp Leu Leu Met Lys Tyr Ile Tyr Lys
            100                 105                 110

Gly Phe Glu Ser Pro Ser Asp Asn Ser Ser Ala Met Leu Leu Gln Trp
        115                 120                 125

His Glu Lys Ala Leu Ala Ala Gly Gly Val Gly Ser Ile Val Arg Val
    130                 135                 140

Leu Thr Ala Arg Lys Thr Val
145                 150
```

<210> SEQ ID NO 7
<211> LENGTH: 217
<212> TYPE: PRT
<213> ORGANISM: Homo sapiens

<400> SEQUENCE: 7

```
Glu Glu Arg Val Leu Glu Lys Glu Glu Glu Asp Asp Asp Glu Asp
1               5                   10                  15

Glu Asp Glu Glu Asp Asp Val Ser Glu Gly Ser Glu Val Pro Glu Ser
            20                  25                  30

Asp Arg Pro Ala Gly Ala Gln His His Gln Leu Asn Gly Glu Arg Gly
        35                  40                  45

Pro Gln Ser Ala Lys Glu Arg Val Lys Glu Trp Thr Pro Cys Gly Pro
    50                  55                  60

His Gln Gly Gln Asp Glu Gly Arg Gly Pro Ala Pro Gly Ser Gly Thr
65                  70                  75                  80

Arg Gln Val Phe Ser Met Ala Ala Met Asn Lys Glu Gly Gly Thr Ala
                85                  90                  95

Ser Val Ala Thr Gly Pro Asp Ser Pro Ser Pro Val Pro Leu Pro Pro
            100                 105                 110

Gly Lys Pro Ala Leu Pro Gly Ala Asp Gly Thr Pro Phe Gly Cys Pro
        115                 120                 125

Pro Gly Arg Lys Glu Lys Pro Ser Asp Pro Val Glu Trp Thr Val Met
    130                 135                 140

Asp Val Val Glu Tyr Phe Thr Glu Ala Gly Phe Pro Glu Gln Ala Thr
145                 150                 155                 160
```

```
Ala Phe Gln Glu Gln Glu Ile Asp Gly Lys Ser Leu Leu Met Gln
                165                 170                 175

Arg Thr Asp Val Leu Thr Gly Leu Ser Ile Arg Leu Gly Pro Ala Leu
            180                 185                 190

Lys Ile Tyr Glu His His Ile Lys Val Leu Gln Gln Gly His Phe Glu
        195                 200                 205

Asp Asp Asp Pro Asp Gly Phe Leu Gly
    210                 215

<210> SEQ ID NO 8
<211> LENGTH: 530
<212> TYPE: PRT
<213> ORGANISM: Homo sapiens

<400> SEQUENCE: 8

Lys Ser Ser Pro Gly Gln Pro Glu Ala Gly Pro Gly Ala Gln Glu
1               5                   10                  15

Arg Pro Ser Gln Ala Ala Pro Ala Val Glu Ala Glu Pro Gly Ser
            20                  25                  30

Ser Gln Ala Pro Arg Lys Pro Glu Gly Ala Gln Ala Arg Thr Ala Gln
            35                  40                  45

Ser Gly Ala Leu Arg Asp Val Ser Glu Glu Leu Ser Arg Gln Leu Glu
    50                  55                  60

Asp Ile Leu Ser Thr Tyr Cys Val Asp Asn Asn Gly Gly Pro Gly
65              70                  75                  80

Glu Asp Gly Ala Gln Gly Glu Pro Ala Glu Pro Glu Asp Ala Glu Lys
                85                  90                  95

Ser Arg Thr Tyr Val Ala Arg Asn Gly Glu Pro Glu Pro Thr Pro Val
            100                 105                 110

Val Tyr Gly Glu Lys Glu Pro Ser Lys Gly Asp Pro Asn Thr Glu Glu
        115                 120                 125

Ile Arg Gln Ser Asp Glu Val Gly Asp Arg Asp His Arg Arg Pro Gln
    130                 135                 140

Glu Lys Lys Lys Ala Lys Gly Leu Gly Lys Glu Ile Thr Leu Leu Met
145                 150                 155                 160

Gln Thr Leu Asn Thr Leu Ser Thr Pro Glu Glu Lys Leu Ala Ala Leu
                165                 170                 175

Cys Lys Lys Tyr Ala Glu Leu Leu Glu Glu His Arg Asn Ser Gln Lys
            180                 185                 190

Gln Met Lys Leu Leu Gln Lys Lys Gln Ser Gln Leu Val Gln Glu Lys
        195                 200                 205

Asp His Leu Arg Gly Glu His Ser Lys Ala Val Leu Ala Arg Ser Lys
    210                 215                 220

Leu Glu Ser Leu Cys Arg Glu Leu Gln Arg His Asn Arg Ser Leu Lys
225                 230                 235                 240

Glu Glu Gly Val Gln Arg Ala Arg Glu Glu Glu Lys Arg Lys Glu
                245                 250                 255

Val Thr Ser His Phe Gln Val Thr Leu Asn Asp Ile Gln Leu Gln Met
            260                 265                 270

Glu Gln His Asn Glu Arg Asn Ser Lys Leu Arg Gln Glu Asn Met Glu
        275                 280                 285

Leu Ala Glu Arg Leu Lys Lys Leu Ile Glu Gln Tyr Glu Leu Arg Glu
    290                 295                 300

Glu His Ile Asp Lys Val Phe Lys His Lys Asp Leu Gln Gln Gln Leu
305                 310                 315                 320
```

Val Asp Ala Lys Leu Gln Gln Ala Gln Glu Met Leu Lys Glu Ala Glu
            325                 330                 335

Glu Arg His Gln Arg Glu Lys Asp Phe Leu Leu Lys Glu Ala Val Glu
        340                 345                 350

Ser Gln Arg Met Cys Glu Leu Met Lys Gln Gln Glu Thr His Leu Lys
    355                 360                 365

Gln Gln Leu Ala Leu Tyr Thr Glu Lys Phe Glu Phe Gln Asn Thr
    370                 375                 380

Leu Ser Lys Ser Ser Glu Val Phe Thr Thr Phe Lys Gln Glu Met Glu
385                 390                 395                 400

Lys Met Thr Lys Lys Ile Lys Lys Leu Glu Lys Glu Thr Thr Met Tyr
                405                 410                 415

Arg Ser Arg Trp Glu Ser Ser Asn Lys Ala Leu Leu Glu Met Ala Glu
            420                 425                 430

Glu Lys Thr Val Arg Asp Lys Glu Leu Glu Gly Leu Gln Val Lys Ile
        435                 440                 445

Gln Arg Leu Glu Lys Leu Cys Arg Ala Leu Gln Thr Glu Arg Asn Asp
    450                 455                 460

Leu Asn Lys Arg Val Gln Asp Leu Ser Ala Gly Gly Gln Gly Ser Leu
465                 470                 475                 480

Thr Asp Ser Gly Pro Glu Arg Arg Pro Glu Gly Pro Ala Gln Ala
                485                 490                 495

Pro Ser Ser Pro Arg Val Thr Ala Pro Cys Tyr Pro Gly Ala Pro
            500                 505                 510

Ser Thr Glu Ala Ser Gly Gln Thr Gly Pro Gln Glu Pro Thr Ser Ala
        515                 520                 525

Arg Ala
    530

<210> SEQ ID NO 9
<211> LENGTH: 20
<212> TYPE: PRT
<213> ORGANISM: Homo sapiens

<400> SEQUENCE: 9

Val Asp Val Asp Glu Tyr Asp Glu Asn Lys Phe Val Asp Glu Glu Asp
1               5                   10                  15

Gly Gly Asp Gly
            20

<210> SEQ ID NO 10
<211> LENGTH: 1404
<212> TYPE: DNA
<213> ORGANISM: Oryctolagus cuniculus
<220> FEATURE:
<221> NAME/KEY: CDS
<222> LOCATION: (58)...(510)

<400> SEQUENCE: 10
aagcctcgca gcggtcgggg cggcgccgcg gaggctcgag ggcggcgggc ggcggcg atg      60
                                                                Met
                                                                1 tcg aag aac acg gtg tcg tcg gcg cgg ttc cgg aag gtg gac gtg gat     108
Ser Lys Asn Thr Val Ser Ser Ala Arg Phe Arg Lys Val Asp Val Asp
        5                   10                  15 gag tac gac gag aac aag ttc gtg gac gag gaa gac ggc ggc gac ggc     156
Glu Tyr Asp Glu Asn Lys Phe Val Asp Glu Glu Asp Gly Gly Asp Gly
    20                  25                  30

```
cag gcg ggg ccg gac gag ggc gag gtg gac tcg tgc ctg cgg caa ggg      204
Gln Ala Gly Pro Asp Glu Gly Glu Val Asp Ser Cys Leu Arg Gln Gly
         35                  40                  45 aac atg aca gcc gcc ctg cag gcg gcg ctg aag aac cct ccc atc aac      252
Asn Met Thr Ala Ala Leu Gln Ala Ala Leu Lys Asn Pro Pro Ile Asn
 50                  55                  60                  65 acc agg agc cag gcg gtg aag gac cgg gca ggc agc atc gtg ctg aag      300
Thr Arg Ser Gln Ala Val Lys Asp Arg Ala Gly Ser Ile Val Leu Lys
                 70                  75                  80 gtg ctc atc tcc ttc aag gcc ggc gac ata gaa aag gcc gtg cag tcc      348
Val Leu Ile Ser Phe Lys Ala Gly Asp Ile Glu Lys Ala Val Gln Ser
             85                  90                  95 ctg gac agg aac ggc gtg gac ctc ctc atg aag tac atc tac aag ggc      396
Leu Asp Arg Asn Gly Val Asp Leu Leu Met Lys Tyr Ile Tyr Lys Gly
        100                 105                 110 ttc gag agc ccc tcc gac aac agc agc gcc gtg ctc ctg cag tgg cac      444
Phe Glu Ser Pro Ser Asp Asn Ser Ser Ala Val Leu Leu Gln Trp His
    115                 120                 125 gag aag gcg ctg gct gca gga gga gtg ggc tcc atc gtc cgt gtc ctg      492
Glu Lys Ala Leu Ala Ala Gly Gly Val Gly Ser Ile Val Arg Val Leu
130                 135                 140                 145 act gca agg aaa acc gtg tagcctggca ggaacgggtg cctgccgggg             540
Thr Ala Arg Lys Thr Val
                150 agcgggagct gccggtacaa agaccaaaac gcccagatgc cgccgctgcc ctgtgggcgg    600 cgtctgttcc cagcttcgct ttttcccttt cccgtgtctg tcaggattac ataaggtttc    660 ccttcgtgag aatcggagtg gcgcagaggg tcctgttcat acgcgccgtg cgtccggctg    720 tgtaagaccc ctgccttcag tgtccttgag caacggtagc gtgtcgccgg ctgggtttgg    780 ttttgtcgtg gagggatctg gtcagaattt gaggccagtt tcctaactca ttgctggtca    840 ggaaatgatc ttcatttaaa aaaaaaaaaa agactggcag ctattatgca aaactggacc    900 ctcttcccctt atttaagcag agtgagtttc tggaaccagt ggtgccccccc ccccgcccc   960 ggccgccgtc ctgctcaagg gaagcctccc tgcagagcag cagagcccct gggcaggagc   1020 gccgcgtccc gctcccagga gacagcatgc gcggtcacgc ggcacttcct gtgcctccca   1080 gccccagtgc cccggagttc ttcagggcga caggacctc agaagactgg atccgatcca   1140 gacagacgcc cattcttggt tcagctcagt gttttcaaaa ggaacgtgct accgtgggta   1200 gagcacactg gttctcagaa cacggccggc gcttgacggt tgtcacagct ccagaacaaa   1260 tcctgggaga caggcgagcg cgagtcgccg ggcaggaatt ccacacactc gtgctgtttt   1320 tgatacctgc tttttgtttt gttttgtaaa aatgatgcac ttgagaaaat aaaacgtcag   1380 tgttgacaaa aaaaaaaaaa aaaa                                         1404

<210> SEQ ID NO 11
<211> LENGTH: 1617
<212> TYPE: DNA
<213> ORGANISM: Oryctolagus cuniculus
<220> FEATURE:
<221> NAME/KEY: CDS
<222> LOCATION: (1)...(951)

<400> SEQUENCE: 11 gac tgc cgc agc agc agc aac aac cgc tag ccg aag ggt ggc gcg gcg       48
Asp Cys Arg Ser Ser Ser Asn Asn Arg  *  Pro Lys Gly Gly Ala Ala
  1               5                  10                  15 cgg gcc ggc ggc ccg gcg cgg ccc gtg agc ctg cgg gaa gtc gtg cgc       96
```

```
                                         -continued

Arg Ala Gly Gly Pro Ala Arg Pro Val Ser Leu Arg Glu Val Val Arg
            20                  25                  30 tac ctc ggg ggt agc agc ggc gct ggc ggc cgc ctg acc cgc ggc cgc        144
Tyr Leu Gly Gly Ser Ser Gly Ala Gly Gly Arg Leu Thr Arg Gly Arg
                35                  40                  45 gtg cag ggt ctg ctg gaa gag gag gcg gcg gcg cgg ggc cgc ctg gag        192
Val Gln Gly Leu Leu Glu Glu Glu Ala Ala Ala Arg Gly Arg Leu Glu
            50                  55                  60 cgc acc cgt ctc gga gcg ctt gcg ctg ccc cgc ggg gac agg ccc gga        240
Arg Thr Arg Leu Gly Ala Leu Ala Leu Pro Arg Gly Asp Arg Pro Gly
65                  70                  75                  80 cgg gcg cca ccg gcc gcc agc gcc cgc gcg gcg cgg aac aag aga gct        288
Arg Ala Pro Pro Ala Ala Ser Ala Arg Ala Ala Arg Asn Lys Arg Ala
                85                  90                  95 ggc gag gag cga gtg ctt gaa aag gag gag gag gag gag gag gag gaa        336
Gly Glu Glu Arg Val Leu Glu Lys Glu Glu Glu Glu Glu Glu Glu Glu
            100                 105                 110 gac gag gac gac gac gac gac gtc gtg tcc gag ggc tcg gag gtg            384
Asp Glu Asp Asp Asp Asp Asp Val Val Ser Glu Gly Ser Glu Val
        115                 120                 125 ccc gag agc gat cgt ccc gcg ggt gcg cag cat cac cag ctg aat ggc        432
Pro Glu Ser Asp Arg Pro Ala Gly Ala Gln His His Gln Leu Asn Gly
            130                 135                 140 ggc gag cgc ggc ccg cag acc gcc aag gag cgg gcc aag gag tgg tcg        480
Gly Glu Arg Gly Pro Gln Thr Ala Lys Glu Arg Ala Lys Glu Trp Ser
145                 150                 155 ctg tgt ggc ccc cac cct ggc cag gag gaa ggg cgg ggg ccg gcc gcg        528
Leu Cys Gly Pro His Pro Gly Gln Glu Glu Gly Arg Gly Pro Ala Ala
160                 165                 170                 175 ggc agt ggc acc cgc cag gtg ttc tcc atg gcg gcc ttg agt aag gag        576
Gly Ser Gly Thr Arg Gln Val Phe Ser Met Ala Ala Leu Ser Lys Glu
                180                 185                 190 ggg gga tca gcc tct tcg acc acc ggg cct gac tcc ccg tcc ccg gtg        624
Gly Gly Ser Ala Ser Ser Thr Thr Gly Pro Asp Ser Pro Ser Pro Val
            195                 200                 205 cct ttg ccc ccc ggg aag cca gcc ctc cca gga gcc gat ggg acc ccc        672
Pro Leu Pro Pro Gly Lys Pro Ala Leu Pro Gly Ala Asp Gly Thr Pro
            210                 215                 220 ttt ggc tgc cct gcc ggg cgc aaa gag aag ccg gca gac ccc gtg gag        720
Phe Gly Cys Pro Ala Gly Arg Lys Glu Lys Pro Ala Asp Pro Val Glu
225                 230                 235 tgg aca gtc atg gac gtc gtg gag tac ttc acc gag gcg ggc ttc cct        768
Trp Thr Val Met Asp Val Val Glu Tyr Phe Thr Glu Ala Gly Phe Pro
240                 245                 250                 255 gag caa gcc acg gct ttc cag gag cag gag atc gac ggc aag tcc ctg        816
Glu Gln Ala Thr Ala Phe Gln Glu Gln Glu Ile Asp Gly Lys Ser Leu
                260                 265                 270 ctg ctc atg cag cgc acc gat gtc ctc acc ggc ctg tcc atc cgc ctg        864
Leu Leu Met Gln Arg Thr Asp Val Leu Thr Gly Leu Ser Ile Arg Leu
            275                 280                 285 ggg cca gcg ttg aaa atc tat gag cac cat atc aag gtg ctg cag cag        912
Gly Pro Ala Leu Lys Ile Tyr Glu His His Ile Lys Val Leu Gln Gln
            290                 295                 300 ggt cac ttc gag gac gat gac ccg gaa ggc ttc ctg gga tgagcacaga        961
Gly His Phe Glu Asp Asp Asp Pro Glu Gly Phe Leu Gly
305                 310                 315 gccgccgcgc ccttgtccc caccccacc ccgcctggac ccattcctgc ctccatgtca       1021
cccaaggtgt cccagaggcc aggagctgga ctgggcaggc gaggggtgcg gacctaccct    1081
```

-continued

```
gattctggta gggggcgggg ccttgctgtg ctcattgcta cccccccacc ccgtgtgtgt   1141
ctctgcacct gcccccagca cacccctccc ggagcctgga tgtcgcctgg gactctggcc   1201
tgctcatttt gccccagat cagccccctc cctccctcct gtcccaggac atttttaaa   1261 agaaaaaaag gaaaaaaaaa aattggggag gggctggga aggtgcccca agatcctcct   1321
cggcccaacc aggtgtttat tcctatatat atatatatat gttttgttct gcctgttttt   1381
cgttttttgg tgcgtggcct ttcttcctc ccaccaccac tcatgccccc agccctgctc   1441
gccctgtcgg cgggagcagc tgggaatggg aggagggtgg gaccttgggt ctgtctccca   1501
ccctctctcc cgttggttct gttgtcgctc cagctggctg tattgctttt taatattgca   1561
ccgaagggtt gttttttttt ttttaaataa aattttaaaa aaggaaaaa aaaaaa       1617
```

```
<210> SEQ ID NO 12
<211> LENGTH: 1362
<212> TYPE: DNA
<213> ORGANISM: Oryctolagus cuniculus
<220> FEATURE:
<221> NAME/KEY: CDS
<222> LOCATION: (1)...(696)

<400> SEQUENCE: 12
```

| | | | | | | | | | | | | | | | | |
|---|---|---|---|---|---|---|---|---|---|---|---|---|---|---|---|---|
| gcc | agc | gcc | cgc | gcg | gcg | cgg | aac | aag | aga | gct | ggc | gag | gag | cga | gtg | 48 |
| Ala | Ser | Ala | Arg | Ala | Ala | Arg | Asn | Lys | Arg | Ala | Gly | Glu | Glu | Arg | Val | |
| 1 | | | 5 | | | | | 10 | | | | | 15 | | | |

| ctt | gaa | aag | gag | gag | gag | gag | gag | gag | gaa | gac | gac | gag | gac | gac | | 96 |
|---|---|---|---|---|---|---|---|---|---|---|---|---|---|---|---|---|
| Leu | Glu | Lys | Glu | Glu | Glu | Glu | Glu | Glu | Glu | Asp | Asp | Glu | Asp | Asp | | |
| | | 20 | | | | | 25 | | | | | 30 | | | | |

| gac | gac | gac | gtc | gtg | tcc | gag | ggc | tcg | gag | gtg | ccc | gag | agc | gat | cgt | 144 |
|---|---|---|---|---|---|---|---|---|---|---|---|---|---|---|---|---|
| Asp | Asp | Asp | Val | Val | Ser | Glu | Gly | Ser | Glu | Val | Pro | Glu | Ser | Asp | Arg | |
| | 35 | | | | | 40 | | | | | 45 | | | | | |

| ccc | gcg | ggt | gcg | cag | cat | cac | cag | ctg | aat | ggc | ggc | gag | cgc | ggc | ccg | 192 |
|---|---|---|---|---|---|---|---|---|---|---|---|---|---|---|---|---|
| Pro | Ala | Gly | Ala | Gln | His | His | Gln | Leu | Asn | Gly | Gly | Glu | Arg | Gly | Pro | |
| 50 | | | | | 55 | | | | | 60 | | | | | | |

| cag | acc | gcc | aag | gag | cgg | gcc | aag | gag | tgg | tcg | ctg | tgt | ggc | ccc | cac | 240 |
|---|---|---|---|---|---|---|---|---|---|---|---|---|---|---|---|---|
| Gln | Thr | Ala | Lys | Glu | Arg | Ala | Lys | Glu | Trp | Ser | Leu | Cys | Gly | Pro | His | |
| 65 | | | | 70 | | | | | 75 | | | | | 80 | | |

| cct | ggc | cag | gag | gaa | ggg | cgg | ggg | ccg | gcc | gcg | ggc | agt | ggc | acc | cgc | 288 |
|---|---|---|---|---|---|---|---|---|---|---|---|---|---|---|---|---|
| Pro | Gly | Gln | Glu | Glu | Gly | Arg | Gly | Pro | Ala | Ala | Gly | Ser | Gly | Thr | Arg | |
| | | | | 85 | | | | | 90 | | | | | 95 | | |

| cag | gtg | ttc | tcc | atg | gcg | gcc | ttg | agt | aag | gag | ggg | gga | tca | gcc | tct | 336 |
|---|---|---|---|---|---|---|---|---|---|---|---|---|---|---|---|---|
| Gln | Val | Phe | Ser | Met | Ala | Ala | Leu | Ser | Lys | Glu | Gly | Gly | Ser | Ala | Ser | |
| | | | 100 | | | | | 105 | | | | | 110 | | | |

| tcg | acc | acc | ggg | cct | gac | tcc | ccg | tcc | ccg | gtg | cct | ttg | ccc | ccc | ggg | 384 |
|---|---|---|---|---|---|---|---|---|---|---|---|---|---|---|---|---|
| Ser | Thr | Thr | Gly | Pro | Asp | Ser | Pro | Ser | Pro | Val | Pro | Leu | Pro | Pro | Gly | |
| | | 115 | | | | | 120 | | | | | 125 | | | | |

| aag | cca | gcc | ctc | cca | gga | gcc | gat | ggg | acc | ccc | ttt | ggc | tgc | cct | gcc | 432 |
|---|---|---|---|---|---|---|---|---|---|---|---|---|---|---|---|---|
| Lys | Pro | Ala | Leu | Pro | Gly | Ala | Asp | Gly | Thr | Pro | Phe | Gly | Cys | Pro | Ala | |
| | 130 | | | | | 135 | | | | | 140 | | | | | |

| ggg | cgc | aaa | gag | aag | ccg | gca | gac | ccc | gtg | gag | tgg | aca | gtc | atg | gac | 480 |
|---|---|---|---|---|---|---|---|---|---|---|---|---|---|---|---|---|
| Gly | Arg | Lys | Glu | Lys | Pro | Ala | Asp | Pro | Val | Glu | Trp | Thr | Val | Met | Asp | |
| 145 | | | | | 150 | | | | | 155 | | | | | 160 | |

| gtc | gtg | gag | tac | ttc | acc | gag | gcg | ggc | ttc | cct | gag | caa | gcc | acg | gct | 528 |
|---|---|---|---|---|---|---|---|---|---|---|---|---|---|---|---|---|
| Val | Val | Glu | Tyr | Phe | Thr | Glu | Ala | Gly | Phe | Pro | Glu | Gln | Ala | Thr | Ala | |
| | | | | 165 | | | | | 170 | | | | | 175 | | |

| ttc | cag | gag | cag | gag | atc | gac | ggc | aag | tcc | ctg | ctc | atg | cag | cgc | | 576 |
|---|---|---|---|---|---|---|---|---|---|---|---|---|---|---|---|---|
| Phe | Gln | Glu | Gln | Glu | Ile | Asp | Gly | Lys | Ser | Leu | Leu | Met | Gln | Arg | | |
| | | | 180 | | | | | 185 | | | | | 190 | | | |

| acc | gat | gtc | ctc | acc | ggc | ctg | tcc | atc | cgc | ctg | ggg | cca | gcg | ttg | aaa | 624 |
|---|---|---|---|---|---|---|---|---|---|---|---|---|---|---|---|---|
| Thr | Asp | Val | Leu | Thr | Gly | Leu | Ser | Ile | Arg | Leu | Gly | Pro | Ala | Leu | Lys | |

-continued

```
             195                 200                 205
atc tat gag cac cat atc aag gtg ctg cag cag ggt cac ttc gag gac        672
Ile Tyr Glu His His Ile Lys Val Leu Gln Gln Gly His Phe Glu Asp
210                 215                 220 gat gac ccg gaa ggc ttc ctg gga tgagcacaga gccgccgcgc ccttgtccc        726
Asp Asp Pro Glu Gly Phe Leu Gly
225                 230 cacccccacc ccgcctggac ccattcctgc ctccatgtca cccaaggtgt cccagaggcc       786
aggagctgga ctgggcaggc gaggggtgcg gacctaccct gattctggta ggggcgggg        846 ccttgctgtg ctcattgcta ccccccaccc cgtgtgtgt tctgcacct gccccagca         906 cacccctccc ggagcctgga tgtcgcctgg gactctggcc tgctcatttt gcccccagat      966
cagccccctc cctccctcct gtcccaggac attttttaaa agaaaaaaag gaaaaaaaaa     1026
aattggggag ggggctggga aggtgcccca agatcctcct cggcccaacc aggtgtttat     1086
tcctatatat atatatatat gttttgttct gcctgttttt cgtttttttgg tgcgtggcct    1146 ttcttccctc ccaccaccac tcatggcccc agccctgctc gccctgtcgg cgggagcagc    1206
tgggaatggg aggagggtgg gaccttgggt ctgtctccca ccctctctcc cgttggttct    1266
gttgtcgctc cagctggctg tattgctttt taatattgca ccgaagggtt gtttttttttt   1326 ttttaaataa aatttttaaaa aaaggaaaaa aaaaaa                             1362

<210> SEQ ID NO 13
<211> LENGTH: 1422
<212> TYPE: DNA
<213> ORGANISM: Oryctolagus cuniculus
<220> FEATURE:
<221> NAME/KEY: CDS
<222> LOCATION: (1)...(756)

<400> SEQUENCE: 13 acc cgt ctc gga gcg ctt gcg ctg ccc cgc ggg gac agg ccc gga cgg         48
Thr Arg Leu Gly Ala Leu Ala Leu Pro Arg Gly Asp Arg Pro Gly Arg
1               5                   10                  15 gcg cca ccg gcc gcc agc gcc cgc gcg gcg cgg aac aag aga gct ggc         96
Ala Pro Pro Ala Ala Ser Ala Arg Ala Ala Arg Asn Lys Arg Ala Gly
                20                  25                  30 gag gag cga gtg ctt gaa aag gag gag gag gag gag gag gag gaa gac        144
Glu Glu Arg Val Leu Glu Lys Glu Glu Glu Glu Glu Glu Glu Glu Asp
            35                  40                  45 gac gag gac gac gac gac gac gtc gtg tcc gag ggc tcg gag gtg ccc        192
Asp Glu Asp Asp Asp Asp Asp Val Val Ser Glu Gly Ser Glu Val Pro
50                  55                  60 gag agc gat cgt ccc gcg ggt gcg cag cat cac cag ctg aat ggc ggc        240
Glu Ser Asp Arg Pro Ala Gly Ala Gln His His Gln Leu Asn Gly Gly
65                  70                  75                  80 gag cgc ggc ccg cag acc gcc aag gag cgg gcc aag gag tgg tcg ctg        288
Glu Arg Gly Pro Gln Thr Ala Lys Glu Arg Ala Lys Glu Trp Ser Leu
                85                  90                  95 tgt ggc ccc cac cct ggc cag gag gaa ggg cgg ggg ccg gcc gcg ggc        336
Cys Gly Pro His Pro Gly Gln Glu Glu Gly Arg Gly Pro Ala Ala Gly
                100                 105                 110 agt ggc acc cgc cag gtg ttc tcc atg gcg gcc ttg agt aag gag ggg        384
Ser Gly Thr Arg Gln Val Phe Ser Met Ala Ala Leu Ser Lys Glu Gly
            115                 120                 125 gga tca gcc tct tcg acc acc ggg cct gac tcc ccg tcc ccg gtg cct        432
Gly Ser Ala Ser Ser Thr Thr Gly Pro Asp Ser Pro Ser Pro Val Pro
130                 135                 140
```

```
ttg ccc ccc ggg aag cca gcc ctc cca gga gcc gat ggg acc ccc ttt        480
Leu Pro Pro Gly Lys Pro Ala Leu Pro Gly Ala Asp Gly Thr Pro Phe
145                 150                 155                 160 ggc tgc cct gcc ggg cgc aaa gag aag ccg gca gac ccc gtg gag tgg        528
Gly Cys Pro Ala Gly Arg Lys Glu Lys Pro Ala Asp Pro Val Glu Trp
                165                 170                 175 aca gtc atg gac gtc gtg gag tac ttc acc gag gcg ggc ttc cct gag        576
Thr Val Met Asp Val Val Glu Tyr Phe Thr Glu Ala Gly Phe Pro Glu
            180                 185                 190 caa gcc acg gct ttc cag gag cag gag atc gac ggc aag tcc ctg ctg        624
Gln Ala Thr Ala Phe Gln Glu Gln Glu Ile Asp Gly Lys Ser Leu Leu
        195                 200                 205 ctc atg cag cgc acc gat gtc ctc acc ggc ctg tcc atc cgc ctg ggg        672
Leu Met Gln Arg Thr Asp Val Leu Thr Gly Leu Ser Ile Arg Leu Gly
    210                 215                 220 cca gcg ttg aaa atc tat gag cac cat atc aag gtg ctg cag cag ggt        720
Pro Ala Leu Lys Ile Tyr Glu His His Ile Lys Val Leu Gln Gln Gly
225                 230                 235                 240 cac ttc gag gac gat gac ccg gaa ggc ttc ctg gga tgagcacaga            766
His Phe Glu Asp Asp Asp Pro Glu Gly Phe Leu Gly
                245                 250 gccgccgcgc cccttgtccc cacccccacc ccgcctggac ccattcctgc ctccatgtca     826
cccaaggtgt cccagaggcc aggagctgga ctgggcaggc gaggggtgcg gacctaccct     886
gattctggta gggggcgggg ccttgctgtg ctcattgcta ccccccccacc ccgtgtgtgt     946 ctctgcacct gcccccagca caccccctccc ggagcctgga tgtcgcctgg gactctggcc   1006
tgctcatttt gcccccagat cagccccctc cctccctcct gtcccaggac atttttttaaa   1066 agaaaaaaag gaaaaaaaaa aattggggag ggggctggga aggtgcccca agatcctcct   1126
cggcccaacc aggtgtttat tcctatatat atatatatat gttttgttct gcctgttttt   1186
cgttttttgg tgcgtggcct ttcttccctc ccaccaccac tcatggcccc agccctgctc   1246
gccctgtcgg cgggagcagc tgggaatggg aggagggtgg gaccttgggt ctgtctccca   1306
ccctctctcc cgttggttct gttgtcgctc cagctggctg tattgctttt taatattgca   1366
ccgaagggtt gttttttttt ttttaaataa aattttaaaa aaaggaaaaa aaaaaa        1422
```

<210> SEQ ID NO 14
<211> LENGTH: 4722
<212> TYPE: DNA
<213> ORGANISM: Oryctolagus cuniculus
<220> FEATURE:
<221> NAME/KEY: CDS
<222> LOCATION: (61)...(1731)

<400> SEQUENCE: 14

```
gtggaaaata gcaactgtgt ttctcaagga tccaatccca acctaaggtg gcagcgcaca       60 atg aag aat caa gac aaa aag aac ggg gct gcc aaa cag ccc aac ccc        108
Met Lys Asn Gln Asp Lys Lys Asn Gly Ala Ala Lys Gln Pro Asn Pro
1               5                  10                  15 aaa agc agc ccg gga cag ccg gaa gca gga gcg gag gga gcc cag ggg        156
Lys Ser Ser Pro Gly Gln Pro Glu Ala Gly Ala Glu Gly Ala Gln Gly
            20                  25                  30 cgg ccc ggc cgg ccg gcc ccc gcc cga gaa gcc gaa ggt gcc agc agc        204
Arg Pro Gly Arg Pro Ala Pro Ala Arg Glu Ala Glu Gly Ala Ser Ser
        35                  40                  45 cag gct ccc ggg agg ccg gag ggg gct caa gcc aaa act gct cag cct        252
Gln Ala Pro Gly Arg Pro Glu Gly Ala Gln Ala Lys Thr Ala Gln Pro
    50                  55                  60
```

-continued

| | |
|---|---|
| ggg gcg ctc tgt gat gtc tct gag gag ctg agc cgc cag ttg gaa gac<br>Gly Ala Leu Cys Asp Val Ser Glu Glu Leu Ser Arg Gln Leu Glu Asp<br>65                    70                   75                 80 | 300 |
| ata ctc agt aca tac tgt gtg gac aac aac cag ggg gcc ccg ggt gag<br>Ile Leu Ser Thr Tyr Cys Val Asp Asn Asn Gln Gly Ala Pro Gly Glu<br>                   85                   90                 95 | 348 |
| gat ggg gtc cag ggt gag ccc cct gaa cct gaa gat gca gag aag tct<br>Asp Gly Val Gln Gly Glu Pro Pro Glu Pro Glu Asp Ala Glu Lys Ser<br>    100                   105               110 | 396 |
| cgc gcc tat gtg gca agg aat ggg gag ccg gag ccg ggc acc cca gta<br>Arg Ala Tyr Val Ala Arg Asn Gly Glu Pro Glu Pro Gly Thr Pro Val<br>       115                 120               125 | 444 |
| gtc aat ggc gag aag gag acc tcc aag gca gag ccg ggc acg gaa gag<br>Val Asn Gly Glu Lys Glu Thr Ser Lys Ala Glu Pro Gly Thr Glu Glu<br>130                   135               140 | 492 |
| atc cgg acg agc gat gag gtc gga gac cga gac cac cgg agg cca cag<br>Ile Arg Thr Ser Asp Glu Val Gly Asp Arg Asp His Arg Arg Pro Gln<br>145                   150               155               160 | 540 |
| gaa aag aag aag gcc aag ggt ctg gga aag gag atc acg ctg ctg atg<br>Glu Lys Lys Lys Ala Lys Gly Leu Gly Lys Glu Ile Thr Leu Leu Met<br>                  165               170               175 | 588 |
| cag aca ctg aac acg ctg agc acc cca gag gag aag ctg gcg gct ctg<br>Gln Thr Leu Asn Thr Leu Ser Thr Pro Glu Glu Lys Leu Ala Ala Leu<br>       180                 185               190 | 636 |
| tgc aag aag tat gcg gaa ctc ctc gag gag cac cgg aac tcg cag aag<br>Cys Lys Lys Tyr Ala Glu Leu Leu Glu Glu His Arg Asn Ser Gln Lys<br>195                   200               205 | 684 |
| cag atg aag ctg ctg cag aag aag cag agc cag ctg gtg cag gag aag<br>Gln Met Lys Leu Leu Gln Lys Lys Gln Ser Gln Leu Val Gln Glu Lys<br>    210                   215               220 | 732 |
| gac cac ctg cgt ggc gag cac agc aag gcc atc ctg gcc cgc agc aag<br>Asp His Leu Arg Gly Glu His Ser Lys Ala Ile Leu Ala Arg Ser Lys<br>225                   230               235               240 | 780 |
| ctc gag agc ctg tgc cgg gag ctg cag cgg cac aac cgc tcg ctc aag<br>Leu Glu Ser Leu Cys Arg Glu Leu Gln Arg His Asn Arg Ser Leu Lys<br>                  245               250               255 | 828 |
| gaa gaa ggt gtg cag cga gcc cga gag gag gag aag cgc aag gag<br>Glu Glu Gly Val Gln Arg Ala Arg Glu Glu Glu Lys Arg Lys Glu<br>       260                 265               270 | 876 |
| gtg acg tca cac ttc cag atg acg ctc aac gac att cag ctg cag atg<br>Val Thr Ser His Phe Gln Met Thr Leu Asn Asp Ile Gln Leu Gln Met<br>               275               280               285 | 924 |
| gag cag cac aac gag cgc aac tcc aag ctg cgc cag gag aac atg gag<br>Glu Gln His Asn Glu Arg Asn Ser Lys Leu Arg Gln Glu Asn Met Glu<br>    290                 295               300 | 972 |
| ctg gcc gag cgg ctc aag aag ctg att gag cag tac gag ctg cga gaa<br>Leu Ala Glu Arg Leu Lys Lys Leu Ile Glu Gln Tyr Glu Leu Arg Glu<br>305                   310               315               320 | 1020 |
| gag cac atc gac aaa gtc ttc aaa cac aag gat ctg cag cag cag ctg<br>Glu His Ile Asp Lys Val Phe Lys His Lys Asp Leu Gln Gln Gln Leu<br>                  325               330               335 | 1068 |
| gtg gac gcc aag ctc cag cag gcc cag gag atg ctg aag gag gca gag<br>Val Asp Ala Lys Leu Gln Gln Ala Gln Glu Met Leu Lys Glu Ala Glu<br>       340                 345               350 | 1116 |
| gag cgg cac cag cgg gag aag gac ttt ctc ctg aag gag gcc gtg gag<br>Glu Arg His Gln Arg Glu Lys Asp Phe Leu Leu Lys Glu Ala Val Glu<br>355                   360               365 | 1164 |
| tcc cag agg atg tgc gag ctg atg aag caa cag gag acc cac ctg aag<br>Ser Gln Arg Met Cys Glu Leu Met Lys Gln Gln Glu Thr His Leu Lys<br>    370                 375               380 | 1212 |

-continued

```
cag cag ctt gcc cta tac aca gag aag ttt gag gag ttc cag aac act      1260
Gln Gln Leu Ala Leu Tyr Thr Glu Lys Phe Glu Glu Phe Gln Asn Thr
385                 390                 395                 400 ctt tcc aaa agc agc gag gtg ttc acc aca ttc aaa cag gaa atg gaa      1308
Leu Ser Lys Ser Ser Glu Val Phe Thr Thr Phe Lys Gln Glu Met Glu
            405                 410                 415 aag atg aca aag aag atc aag aag ctg gag aaa gag acc acc atg tac      1356
Lys Met Thr Lys Lys Ile Lys Lys Leu Glu Lys Glu Thr Thr Met Tyr
        420                 425                 430 cgt tcc cgg tgg gag agc agc aac aag gcc ctg ctt gag atg gct gag      1404
Arg Ser Arg Trp Glu Ser Ser Asn Lys Ala Leu Leu Glu Met Ala Glu
    435                 440                 445 gag aaa aca ctc cgg gac aaa gag ctg gaa ggc ctg cag gtg aaa atc      1452
Glu Lys Thr Leu Arg Asp Lys Glu Leu Glu Gly Leu Gln Val Lys Ile
450                 455                 460 cag cgg ctg gag aag ctg tgc cgg gca ctg cag aca gag cgc aat gac      1500
Gln Arg Leu Glu Lys Leu Cys Arg Ala Leu Gln Thr Glu Arg Asn Asp
465                 470                 475                 480 ctg aac aag agg gtg cag gac ctg agt gcc ggt ggc cag ggc ccc gtc      1548
Leu Asn Lys Arg Val Gln Asp Leu Ser Ala Gly Gly Gln Gly Pro Val
            485                 490                 495 tcc gac agc ggt cct gag cgg agg cca gag ccc gcc acc acc tcc aag      1596
Ser Asp Ser Gly Pro Glu Arg Arg Pro Glu Pro Ala Thr Thr Ser Lys
        500                 505                 510 gag cag ggt gtc gag ggc ccc ggg gct caa gta ccc aac tct cca agg      1644
Glu Gln Gly Val Glu Gly Pro Gly Ala Gln Val Pro Asn Ser Pro Arg
    515                 520                 525 gcc aca gac gct tcc tgc tgc gca ggt gca ccc agc aca gag gca tca      1692
Ala Thr Asp Ala Ser Cys Cys Ala Gly Ala Pro Ser Thr Glu Ala Ser
530                 535                 540 ggc cag aca ggg ccc cag gag ccc acc act gcc act gcc tagagagctt      1741
Gly Gln Thr Gly Pro Gln Glu Pro Thr Thr Ala Thr Ala
545                 550                 555 ggtgctgggg tgtgccagga agggagcagg cagcccagcc aggcctggcc cagcccaggc   1801
tcccatgcta agcagtccgg tgctgaggcc aggatgttct gacctggctg cacctgacc    1861 ctctgcagtc ttggattttg tgggtcagtt ttacatgcat atggcacaca tgcaaggcct   1921
cacacatttg tgtctctaag tgtactgtgg gcttgcatcg ggggtgacga tggacagatg   1981
aagccagcgg ctcccttgtg agctgaagtc ttacggagga cggcgtct gcactgccat     2041 cgcagtgacc tgcaggacga gttccttgag ctttccctgc ctgctttgag gctgagaccc   2101
ctcccggccc ttcagagctc ctgacaggtg atacacaccc agccttgacc gcacttctct   2161
tgggtagctg ggctctccta gcctccccca gaggcgccat tgcttctctt gacttggaga   2221
ggggatgccc aggcgtggcc ttggcaggca ctgggagcta gtgattgggc tgctctcctg   2281
cctcgagcag gggcaggagt gtttctggtg ggatgatgcg ctcgctggtc aggagccccg   2341
tgggcgctgc ttcccccgcc ctctggtgat gccaggacca ggccagtgat gcttctcagt   2401
agccttacca ttcacaggtg cctctccagc ccgcacagtg agtgacaaga tcatccaaag   2461
gattccttct gaaggtgttc gtttcgtttt gttttgttgc acgtgacggt ttgtattgag   2521
gaccctctga ggaagagggg tgctgtagca gtggtccctg cgtgcctggc tccagtgtcc   2581
tgccctcccc ccctcgccca tggctcctcg gccgccttgg tgctgaggtt tctgtttggt   2641
gagatcaggt tgtctgttca gagagaagag gcgtctgatg gctttgccgc cagcttgcct   2701
gcgggcctca atcccgggag gccgcccggt tcccgtcact gttgtccccg tgcagtgcgt   2761
```

-continued

```
tgctggtccc caggaccagc tgctcgtttg ctgtatgggt cagtttctgc ttcctgcccc      2821
ccactccacc taactgcaat ccttgggggtt tccctggttc tcgtccctgg tacctctgtg     2881
cccaagaagt agccttcttt gggattcttg ttctgcccat gcgggagctg ctgctgtctg      2941
acaggtgagg cctgagactc agcggctgac agagctgcag agctctgcac ggtggctccc      3001
ggggcggcct ctgtgtgctg cacaccgctg ctctgctggc actggccagt ctgtgcagag      3061
catttgagta ctggctcagg agggagggct ctgctggcct cgaggacag cgccacgtct       3121 ccagctgggc tcagggagag ccccagactg gctgcgtagg gtgcttgggg tttgcttctt      3181
gcagtatttc ttggaagctg ttttgttgtc ctgctattcc ttcatcttcc acagtccacg      3241
ctcagccttt aacttggatc cctcacataa cagggttcat gagacccgca agtacgccca      3301
agctacgtat ggctgaggcc agctggcagg tgaatggcac gccattgctg ctgctaatcc      3361
ctggcatatc tttagttcac ctcgaaatgc ccccgccaca gtgcaagcag tgagtccacg      3421
tgccaccctg gctgaatcc caccccctgt gagtgttgcc cgagattgtg tctcttctga       3481
atgccttcac tgggaatggc ctctgccgcc tcctgctcag ggaggctttc ccctt cccctc    3541 agcccctgtg ccagactgag gtacaagaac cgccaagccc atgcaaggtg tggctaggcg      3601
ccagggtgca ggaaggaggc aggtagctgc ctgcacccct tgaaagccaag aggcctacgg     3661 tggcctccat cctggcttgc ctcacttcag ctacctcgca tagcccaggg gtggggctat      3721
tggattccag ggtgggggga tgggaagctg cagggggcag gtggctctca ctaggcttcc      3781
cagctcagga atgtgggcct caggtagggg agagcctttg ctccactcca cccatttgca      3841
ggcatctagg ccagtctaga tggcgacccc ttctcttcct ctccattgac caaatcgtac      3901
ctgtctctcc agctgctcgc ttgctctgct ttccaaagtc agcccaggta cccaggtgcc      3961
gcccacattg gcctggaacc tggaccagag gcaagggagg tggcctatcc ttgagtgata     4021
gccagtgcct tcctcacccg gtggcttcca tgcctgtgac ctcagattta ggaccaagag     4081
ctgtgttggt ttcttacgtt gtgagctttc cctccagggg accacagcag gtgaggctcg     4141
gagcccagag cccttggcgc cgccagcagt aacttgtgtc cggaccttgt ccagctgagc     4201
gcttcgtgta tgactcagct tcgtgtgtga gtccagcgga gtgcgtcacg tgacctagac     4261
tcagcggtgt cagccgcact ttgatttgtt tgttttccat gaggttttg gaccatgggc      4321 ttagctcagg caacttttct gtaaggagaa tgttaacttt ctgtaaagat gcttatttaa      4381
ctaacgcctg cttcccccac tcccaaccag gtggccaccg agagctcacc aggaggccaa     4441
tagagctgct ccagctctcc catcttgcac cgcacaaagg tggccgcccc agggacagcc     4501
aggcacctgc ctgggggagg ggcttctctt ccttatggcc tggccatcta gattgtttaa     4561
agttgtgctg acagcttttt ttggtttttt ggttttgtt tttgttttg ttttgtttt        4621 tgtctacttt tggtattcac aacagccagg gacttgattt tgatgtattt taagccacat    4681 taaataaga gtctgttgcc ttaaaaaaaa aaaaaaaaa a                            4722
```

<210> SEQ ID NO 15
<211> LENGTH: 1925
<212> TYPE: DNA
<213> ORGANISM: Homo sapiens
<220> FEATURE:
<221> NAME/KEY: CDS
<222> LOCATION: (118)...(570)

<400> SEQUENCE: 15

```
gacgcctcag agcggaacag ggaagtgaat caggcgccgg gtagtgggtt gctgggctgg       60
```

-continued

```
gcttgctgag gtagaggcag cgccaagaag aggcctttgc cgctggtcgg gattggg atg      120
                                                                Met
                                                                 1 tcg aag aac aca gtg tcg tcg gcc cgc ttc cgg aag gtg gac gtg gat         168
Ser Lys Asn Thr Val Ser Ser Ala Arg Phe Arg Lys Val Asp Val Asp
         5                  10                  15 gaa tat gac gag aac aag ttc gtg gac gaa gaa gat ggg ggc gac ggc         216
Glu Tyr Asp Glu Asn Lys Phe Val Asp Glu Glu Asp Gly Gly Asp Gly
             20                  25                  30 cag gcc ggg ccc gac gag ggc gag gtg gac tcc tgc ctg cgg caa gga         264
Gln Ala Gly Pro Asp Glu Gly Glu Val Asp Ser Cys Leu Arg Gln Gly
 35                  40                  45 aac atg aca gct gcc cta cag gca gct ctg aag aac ccc cct atc aac         312
Asn Met Thr Ala Ala Leu Gln Ala Ala Leu Lys Asn Pro Pro Ile Asn
 50                  55                  60                  65 acc aag agt cag gca gtg aag gac cgg gca ggc agc att gtc ttg aag         360
Thr Lys Ser Gln Ala Val Lys Asp Arg Ala Gly Ser Ile Val Leu Lys
                 70                  75                  80 gtg ctc atc tct ttt aaa gct aat gat ata gaa aag gca gtt caa tct         408
Val Leu Ile Ser Phe Lys Ala Asn Asp Ile Glu Lys Ala Val Gln Ser
                 85                  90                  95 ctg gac aag aat ggt gtg gat ctc cta atg aag tat att tat aaa gga         456
Leu Asp Lys Asn Gly Val Asp Leu Leu Met Lys Tyr Ile Tyr Lys Gly
            100                 105                 110 ttt gag agc ccg tct gac aat agc agt gct atg tta ctg caa tgg cat         504
Phe Glu Ser Pro Ser Asp Asn Ser Ser Ala Met Leu Leu Gln Trp His
        115                 120                 125 gaa aag gca ctt gct gct gga gga gta ggg tcc att gtt cgt gtc ttg         552
Glu Lys Ala Leu Ala Ala Gly Gly Val Gly Ser Ile Val Arg Val Leu
130                 135                 140                 145 act gca aga aaa act gtg tagtctggca ggaagtggat tatctgcctc                600
Thr Ala Arg Lys Thr Val
                150 gggagtggga attgctggta caaagaccaa acaaccaaa tgccaccgct gccctgtggg        660
tagcatctgt ttctctcagc tttgccttct gcttttttca tatctgtaaa gaaaaaatt        720
acatatcagt tgtcccttta atgaaaattg ggataatata gaagaaattg tgttaaaata      780
gaagtgtttc atcctttcaa aaccatttca gtgatgttta taccaatctg tatatagtat      840
aatttacatt caagttttaa ttgtgcaact tttaaccctg ttggctggtt tttggttctg      900
tttggttttg tattattttt aactaatact gaaaaatttg gtcagaattt gaggccagtt      960
tcctagctca ttgctagtca ggaaatgata tttataaaaa atatgagaga ctggcagcta    1020
ttaacattgc aaaactggac catatttccc ttatttaata agcaaatat gtttttggaa      1080
taagtggtgg gtgaatacca ctgctaagtt atagctttgt ttttgcttgc ctcctcatta    1140
tctgtactgt gggtttaagt atgctacttt ctctcagcat ccaataatca tggcccctca    1200
atttatttgt ggtcacgcag ggttcagagc aagaagtctt gctttataca aatgtatcca    1260
taaaatatca gagcttgttg ggcatgaaca tcaaactttt gttccactaa tatggctctg    1320
tttgaaaaaa actgcaaatc agaagaatg atttgcagaa agaaagaaaa actatggtgt    1380
aatttaaact ctgggcagcc tctgaatgaa atgctacttt ctttagaaat ataatagctg    1440
ccttagacat tatgaggtat acaactagta tttaagatac catttaatat gccccgtaaa    1500
tgtcttcagt gttcttcagg gtagttggga tctcaaaaga tttggttcag atccaaacaa    1560
atacacattc tgtgttttag ctcagtgttt tctaaaaaaa gaaactgcca cacagcaaaa    1620
aattgtttac tttgttggac aaaccaaatc agttctcaaa aaatgaccgg tgcttataaa    1680
```

-continued

```
aagttataaa tatcgagtag ctctaaaaca aaccacctga ccaagaggga agtgagcttg   1740
tgcttagtat ttacattgga tgccagtttt gtaatcactg acttatgtgc aaactggtgc   1800
agaaattcta taaactcttt gctgttttg atacctgctt tttgtttcat tttgttttgt    1860
tttgtaaaaa tgataaaact tcagaaaata aaatgtcagt gttgaataat taaaaaaaaa   1920
aaaaa                                                                1925

<210> SEQ ID NO 16
<211> LENGTH: 1208
<212> TYPE: DNA
<213> ORGANISM: Homo sapiens
<220> FEATURE:
<221> NAME/KEY: CDS
<222> LOCATION: (1)...(651)

<400> SEQUENCE: 16 gaa gag cga gta ctt gag aaa gaa gag gaa gaa gat gat gat gaa gat     48
Glu Glu Arg Val Leu Glu Lys Glu Glu Glu Glu Asp Asp Asp Glu Asp
1               5                   10                  15 gaa gat gaa gaa gat gat gtg tca gag ggc tct gaa gtg ccc gag agt     96
Glu Asp Glu Glu Asp Asp Val Ser Glu Gly Ser Glu Val Pro Glu Ser
                20                  25                  30 gac cgt cct gca ggt gcc cag cac cac cag ctt aac ggc gag cgg gga    144
Asp Arg Pro Ala Gly Ala Gln His His Gln Leu Asn Gly Glu Arg Gly
            35                  40                  45 cct cag agt gcc aag gag agg gtc aag gag tgg acc ccc tgc gga ccg    192
Pro Gln Ser Ala Lys Glu Arg Val Lys Glu Trp Thr Pro Cys Gly Pro
        50                  55                  60 cac cag ggc cag gat gaa ggg cgg ggg cca gcc ccg ggc agc ggc acc    240
His Gln Gly Gln Asp Glu Gly Arg Gly Pro Ala Pro Gly Ser Gly Thr
65                  70                  75                  80 cgc cag gtg ttc tcc atg gca gcc atg aac aag gaa ggg gga aca gct    288
Arg Gln Val Phe Ser Met Ala Ala Met Asn Lys Glu Gly Gly Thr Ala
                85                  90                  95 tct gtt gcc acc ggg cca gac tcc ccg tcc ccc gtg cct ttg ccc cca    336
Ser Val Ala Thr Gly Pro Asp Ser Pro Ser Pro Val Pro Leu Pro Pro
            100                 105                 110 ggc aaa cca gcc cta cct ggg gcc gac ggg acc ccc ttt ggc tgt cct    384
Gly Lys Pro Ala Leu Pro Gly Ala Asp Gly Thr Pro Phe Gly Cys Pro
        115                 120                 125 ccc ggg cgc aaa gag aag cca tct gat ccc gtc gag tgg acc gtg atg    432
Pro Gly Arg Lys Glu Lys Pro Ser Asp Pro Val Glu Trp Thr Val Met
130                 135                 140 gat gtc gtc gaa tat ttt act gag gct gga ttc ccg gag cag gcg aca    480
Asp Val Val Glu Tyr Phe Thr Glu Ala Gly Phe Pro Glu Gln Ala Thr
145                 150                 155                 160 gct ttc caa gag cag gaa att gat ggc aaa tct ttg ctg ctc atg cag    528
Ala Phe Gln Glu Gln Glu Ile Asp Gly Lys Ser Leu Leu Leu Met Gln
                165                 170                 175 cgc aca gat gtg ctc acc ggc ctg tcc atc cgc ctc ggg cca gcc ctg    576
Arg Thr Asp Val Leu Thr Gly Leu Ser Ile Arg Leu Gly Pro Ala Leu
            180                 185                 190 aaa atc tac gag cac cac atc aag gtg ctt cag caa ggc cac ttt gag    624
Lys Ile Tyr Glu His His Ile Lys Val Leu Gln Gln Gly His Phe Glu
        195                 200                 205 gat gat gac ccc gat ggc ttc tta ggc tgagcgccca gcctcacccc          671
Asp Asp Asp Pro Asp Gly Phe Leu Gly
210                 215 tgccccagcc cattccggcc cccatctcac ccaagatccc ccagagtcca ggagctggac   731
```

-continued

```
ggggacaccc tcagccctca taacagattc caaggagagg gcaccctctt gtccttatct      791
ttgccccttg tgtctgtctc acacacatct gctcctcagc acgtcggtgt ggggaggga       851 ttgctcctta aacccaggt ggctgaccct ccccacccag tccaggacat tttaggaaaa       911
aaaaaatgaa atgtgggggg cttctcatct ccccaagatc ctcttccgtt cagccagatg      971
tttcctgtat aaatgtttgg atctgcctgt ttattttggt gggtggtctt tcctccctcc     1031
cctaccaccc atgccccct tctcagtctg ccctggcct ccagcccta ggggactagc        1091 tgggttgggg ttcctcgggc cttttctctc ctccctcttt tctttctgtt gattgtcgct     1151
ccagctggct gtattgcttt ttaatattgc accgaaggtt ttttaaataa aatttta        1208

<210> SEQ ID NO 17
<211> LENGTH: 4697
<212> TYPE: DNA
<213> ORGANISM: Homo sapiens
<220> FEATURE:
<221> NAME/KEY: CDS
<222> LOCATION: (3)...(1592)

<400> SEQUENCE: 17 ca aaa agc agc cca gga caa ccg gaa gca gga ccc gag gga gcc cag         47
   Lys Ser Ser Pro Gly Gln Pro Glu Ala Gly Pro Glu Gly Ala Gln
   1               5                  10                 15 gag cgg ccc agc cag gcg gct cct gca gta gaa gca gaa ggt ccc ggc        95
Glu Arg Pro Ser Gln Ala Ala Pro Ala Val Glu Ala Glu Gly Pro Gly
                20                  25                  30 agc agc cag gct cct cgg aag ccg gag ggg gct caa gcc aga acg gct       143
Ser Ser Gln Ala Pro Arg Lys Pro Glu Gly Ala Gln Ala Arg Thr Ala
            35                  40                  45 cag tct ggg gcc ctt cgt gat gtc tct gag gag ctg agc cgc caa ctg       191
Gln Ser Gly Ala Leu Arg Asp Val Ser Glu Glu Leu Ser Arg Gln Leu
        50                  55                  60 gaa gac ata ctg agc aca tac tgt gtg gac aat aac cag ggg ggc ccc       239
Glu Asp Ile Leu Ser Thr Tyr Cys Val Asp Asn Asn Gln Gly Gly Pro
    65                  70                  75 ggc gag gat ggg gca cag ggt gag ccg gct gaa ccc gaa gat gca gag       287
Gly Glu Asp Gly Ala Gln Gly Glu Pro Ala Glu Pro Glu Asp Ala Glu
80                  85                  90                  95 aag tcc cgg acc tat gtg gca agg aat ggg gag cct gaa cca act cca       335
Lys Ser Arg Thr Tyr Val Ala Arg Asn Gly Glu Pro Glu Pro Thr Pro
                100                 105                 110 gta gtc tat gga gag aag gaa ccc tcc aag ggg gat cca aac aca gaa       383
Val Val Tyr Gly Glu Lys Glu Pro Ser Lys Gly Asp Pro Asn Thr Glu
            115                 120                 125 gag atc cgg cag agt gac gag gtc gga gac cga gac cat cga agg cca       431
Glu Ile Arg Gln Ser Asp Glu Val Gly Asp Arg Asp His Arg Arg Pro
        130                 135                 140 cag gag aag aaa aaa gcc aag ggt ttg ggg aag gag atc acg ttg ctg       479
Gln Glu Lys Lys Lys Ala Lys Gly Leu Gly Lys Glu Ile Thr Leu Leu
    145                 150                 155 atg cag aca ttg aat act ctg agt acc cca gag gag aag ctg gct gct       527
Met Gln Thr Leu Asn Thr Leu Ser Thr Pro Glu Glu Lys Leu Ala Ala
160                 165                 170                 175 ctg tgc aag aag tat gct gaa ctg ctg gag gag cac cgg aat tca cag       575
Leu Cys Lys Lys Tyr Ala Glu Leu Leu Glu Glu His Arg Asn Ser Gln
                180                 185                 190 aag cag atg aag ctc cta cag aaa aag cag agc cag ctg gtg caa gag       623
Lys Gln Met Lys Leu Leu Gln Lys Lys Gln Ser Gln Leu Val Gln Glu
            195                 200                 205
```

```
aag gac cac ctg cgc ggt gag cac agc aag gcc gtc ctg gcc cgc agc      671
Lys Asp His Leu Arg Gly Glu His Ser Lys Ala Val Leu Ala Arg Ser
        210                 215                 220 aag ctt gag agc cta tgc cgt gag ctg cag cgg cac aac cgc tcc ctc      719
Lys Leu Glu Ser Leu Cys Arg Glu Leu Gln Arg His Asn Arg Ser Leu
225                 230                 235 aag gaa gaa ggt gtg cag cgg gcc cgg gag gag gag aag cgc aag          767
Lys Glu Glu Gly Val Gln Arg Ala Arg Glu Glu Glu Lys Arg Lys
240                 245                 250                 255 gag gtg acc tcg cac ttc cag gtg aca ctg aat gac att cag ctg cag      815
Glu Val Thr Ser His Phe Gln Val Thr Leu Asn Asp Ile Gln Leu Gln
                260                 265                 270 atg gaa cag cac aat gag cgc aac tcc aag ctg cgc caa gag aac atg      863
Met Glu Gln His Asn Glu Arg Asn Ser Lys Leu Arg Gln Glu Asn Met
            275                 280                 285 gag ctg gct gag agg ctc aag aag ctg att gag cag tat gag ctg cgc      911
Glu Leu Ala Glu Arg Leu Lys Lys Leu Ile Glu Gln Tyr Glu Leu Arg
        290                 295                 300 gag gag cat atc gac aaa gtc ttc aaa cac aag gac cta caa cag cag      959
Glu Glu His Ile Asp Lys Val Phe Lys His Lys Asp Leu Gln Gln Gln
    305                 310                 315 ctg gtg gat gcc aag ctc cag cag gcc cag gag atg cta aag gag gca     1007
Leu Val Asp Ala Lys Leu Gln Gln Ala Gln Glu Met Leu Lys Glu Ala
320                 325                 330                 335 gaa gag cgg cac cag cgg gag aag gat ttt ctc ctg aaa gag gca gta     1055
Glu Glu Arg His Gln Arg Glu Lys Asp Phe Leu Leu Lys Glu Ala Val
                340                 345                 350 gag tcc cag agg atg tgt gag ctg atg aag cag caa gag acc cac ctg     1103
Glu Ser Gln Arg Met Cys Glu Leu Met Lys Gln Gln Glu Thr His Leu
            355                 360                 365 aag caa cag ctt gcc cta tac aca gag aag ttt gag gag ttc cag aac     1151
Lys Gln Gln Leu Ala Leu Tyr Thr Glu Lys Phe Glu Glu Phe Gln Asn
        370                 375                 380 aca ctt tcc aaa agc agc gag gta ttc acc aca ttc aag cag gag atg     1199
Thr Leu Ser Lys Ser Ser Glu Val Phe Thr Thr Phe Lys Gln Glu Met
    385                 390                 395 gaa aag atg act aag aag atc aag aag ctg gag aaa gaa acc acc atg     1247
Glu Lys Met Thr Lys Lys Ile Lys Lys Leu Glu Lys Glu Thr Thr Met
400                 405                 410                 415 tac cgg tcc cgg tgg gag agc agc aac aag gcc ctg ctt gag atg gct     1295
Tyr Arg Ser Arg Trp Glu Ser Ser Asn Lys Ala Leu Leu Glu Met Ala
                420                 425                 430 gag gag aaa aca gtc cgg gat aaa gaa ctg gag ggc ctg cag gta aaa     1343
Glu Glu Lys Thr Val Arg Asp Lys Glu Leu Glu Gly Leu Gln Val Lys
            435                 440                 445 atc caa cgg ctg gag aag ctg tgc cgg gca ctg cag aca gag cgc aat     1391
Ile Gln Arg Leu Glu Lys Leu Cys Arg Ala Leu Gln Thr Glu Arg Asn
        450                 455                 460 gac ctg aac aag agg gta cag gac ctg agt gct ggt ggc cag ggc tcc     1439
Asp Leu Asn Lys Arg Val Gln Asp Leu Ser Ala Gly Gly Gln Gly Ser
    465                 470                 475 ctc act gac agt ggc cct gag agg agg cca gag ggg cct ggg gct caa     1487
Leu Thr Asp Ser Gly Pro Glu Arg Arg Pro Glu Gly Pro Gly Ala Gln
480                 485                 490                 495 gca ccc agc tcc ccc agg gtc aca gaa gcg cct tgc tac cca gga gca     1535
Ala Pro Ser Ser Pro Arg Val Thr Glu Ala Pro Cys Tyr Pro Gly Ala
                500                 505                 510 ccg agc aca gaa gca tca ggc cag act ggg cct caa gag ccc acc tcc     1583
Pro Ser Thr Glu Ala Ser Gly Gln Thr Gly Pro Gln Glu Pro Thr Ser
```

-continued

```
         515                 520                 525
gcc agg gcc tagagagcct ggtgttgggt catgctggga agggagcggc         1632
Ala Arg Ala
        530 agcccagcca ggcctggccc ataaaaggct cccatgctga gcagcccatt gctgaagcca   1692 ggatgttctt gacctggctg gcatctggca cttgcaattt tggattttgt gggtcagttt   1752 tacgtacata gggcattttg caaggccttg caaatgcatt tatacctgta agtgtacagt   1812 gggcttgcat tggggatggg ggtgtgtaca gatgaagtca gtggcttgtc tgtgagctga   1872 agagtcttga gaggggctgt catctgtagc tgccatcaca gtgagttggc agaagtgact   1932 tgagcatttc tctgtctgat ttgaggctca gaccccctccc tgccctttca gagctcaaaa   1992 caagtaatac accaaggtct tgactgcatt tgtcttgtga gcagggcttg cttggtcagc   2052 tcaggccctc ctagctgctt ggaggctcct ttgattctct agacctggaa aaggtgtccc   2112 taggcagagc cctggcaggg cgctcagagc tgggatttcc tgcctggaac aagggacctg   2172 gagaatgttt ttgcgtggga tgatgtgctg gtcaggagcc ccttgggcat cgcttcccct   2232 gccctttggt agtgccagga ccaggccaat gatgcttctc agtagcctta tcattcacag   2292 gtgcctctct agcctgcaca aatgattgac aagagatcac ccaaaggatt atttctgaag   2352 gtgttttttt ctttatttct ttttctttt tttttttct ttttctttt tttttgcaca   2412 tgacagtgtt tgtattgagg accttccaag gaaaagggat gctgtaccag tggtgcctgg   2472 gtgcctggcc tccagtgtcc cacctccttc accaccccac ttggctcctt tgccatcttg   2532 atgctgaggt ttcctgtttg gtgagatcag gttgtttgtg gtaaagaaa ggaaagggct   2592 tctgatggct ttgccacaag cttacctgtg ggtttcagtc ctgagaggcc accaccagtt   2652 cccatcagca ctgtctccat gcagcagttg ctgggtccca tgtccagctg cctctttggc   2712 ttcatgggtt tttctgcttc ctgccccac ccccacatgt gcaatcctca agatttgtcc   2772 tgattctatt tcctggcacc tccctgcctg tccttgggga ttctacttct tcctgtgtgg   2832 ggcccatagc tgttgtctaa caggtaagaa atgaaattga actattgact gggcccaga   2892 aatccataaa atggctgcag acagttgttt ctgtgtcctg ttctacccc actccagtac   2952 ataactacta tgtactgtgt agagccattc tatatgctga atgttctgct gttgcaaact   3012 tgccagggta ttagccagtg tttgtgccaa gcagttttcg gggacaacag aatgactcag   3072 accaagatgg ataggatggt tagggctttg cttcttgctg ttttttcttg aactagtcat   3132 tgtcctgcag gtcccttcat cttccatacc tagcccactc ttttagccct taccttaaat   3192 ctctcagata agttggttca caaagaatgt taagtactga atcatgtgtg actgagacca   3252 gagatggcaa atgaatggca caccatttct ccttctcctg cccagggca ggtaccactg   3312 atctgcatca gagttgcctg ctattctctg gtgtatcctt cacatctagg tgccctcaag   3372 cagctgtgtg agtgttgaga tctctgccat ctctggctga gatactgctg tcctgtgaag   3432 tgtttcccat gacctttttc ttcccctttg aatccctctt gtctggagta gtccttgcct   3492 tcttcttgct ccagtaggcc ttttccttac cccagccctt gtgccaggct aagctggtac   3552 aagagctgcc aactcacaga gttttgctag gcgagagagg tgcagggaag aggcagaggt   3612 atgcaccttc cccctttgaag agaggggaaa ggcctacagt ggcccacata attgcctgac   3672 tcacacttca gctacctctt aatgcctgtg gagggactgg agctgctgga tcccagtgtg   3732 gtggtgtagg aggccacagt gagcaggtgg ccccagctgg gtttcccagg tcaggaatgt   3792 gggccccagg caaggtgcag ccttttgctca cagctccatc catgtctaga ccttcaggcc   3852
```

-continued

```
agtctgcaga tgaggttccc tacctttttc ttctcttcat tgaccaaatc aaccaatcac      3912
tacagctgct ctgcttctgc tttccaaagt agcccaggtc ctgggccaga tgcaggggag      3972
gtgcctatcc atgagtgaag ccagtgtct cctcacctg gtggtccca cacttgtgac         4032 cctcagtttt aggacccaag atctgtgttg gtttcttaga ttgctagctt ttcctccagg      4092
ggaccacagc aggtgaagct caagagcgca tggctctgct aatagtaaat tgttttcagg      4152
gccttgtcca gctgagagct tcatgtccac cagattctga gaggtgtcag cagcactttt      4212 ttttttatt tgttgtttgt tttccatgag gttatcggac catgggctga gctcaggcac       4272
tttctgtagg agactgttat ttctgtaaag atggttattt aaccctcctc cacccatca       4332 cggtggccct gagggctgac ccggaggcca gtgggagctgc ctggtgtcca cgggggaggg     4392
ccaaggcctg ctgagctgat tctccagctg ctgcccagc ctttccgcct tgcacagcac       4452
agaggtggtc accccaggga cagccaggca cctgctcctc ttgcccttcc tgggggaaag     4512
gagctgcctt ctgtccctgt aactgctttc cttatggccc aacccggcca ctcagacttg     4572
tttgaagctg cactggcagc ttttttgtct cctttgggta ttcacaacag ccagggactt     4632
gattttgatg tattttaaac cacattaaat aagagtctg ttgccttaaa aaaaaaaaa      4692 aaaaa                                                                   4697
```

<210> SEQ ID NO 18
<211> LENGTH: 60
<212> TYPE: DNA
<213> ORGANISM: Homo sapiens
<220> FEATURE:
<221> NAME/KEY: CDS
<222> LOCATION: (1)...(60)

<400> SEQUENCE: 18

```
gtg gac gtg gat gag tac gac gag aac aag ttc gtg gac gag gaa gac        48
Val Asp Val Asp Glu Tyr Asp Glu Asn Lys Phe Val Asp Glu Glu Asp
1               5                   10                  15 ggc ggc gac ggc                                                          60
Gly Gly Asp Gly
            20
```

<210> SEQ ID NO 19
<211> LENGTH: 15
<212> TYPE: PRT
<213> ORGANISM: Homo sapiens

<400> SEQUENCE: 19

```
Glu Glu Glu Glu Asp Asp Asp Glu Asp Glu Asp Glu Glu Asp Asp
1               5                   10                  15
```

<210> SEQ ID NO 20
<211> LENGTH: 26
<212> TYPE: PRT
<213> ORGANISM: Homo sapiens

<400> SEQUENCE: 20

```
Glu Glu Glu Glu Asp Asp Asp Glu Asp Glu Glu Asp Asp Val
1               5                   10                  15

Ser Glu Gly Ser Glu Val Pro Glu Ser Asp
            20                  25
```

<210> SEQ ID NO 21
<211> LENGTH: 11
<212> TYPE: PRT

<213> ORGANISM: Homo sapiens

<400> SEQUENCE: 21

Val Ser Glu Gly Ser Glu Val Pro Glu Ser Asp
1               5                   10

<210> SEQ ID NO 22
<211> LENGTH: 10
<212> TYPE: PRT
<213> ORGANISM: Homo sapiens

<400> SEQUENCE: 22

Glu Asp Asp Asp Pro Asp Gly Phe Leu Gly
1               5                   10

<210> SEQ ID NO 23
<211> LENGTH: 30
<212> TYPE: PRT
<213> ORGANISM: Oryctolagus cuniculus

<400> SEQUENCE: 23

Val Asp Val Asp Glu Tyr Asp Glu Asn Lys Phe Val Asp Glu Asp
1               5                   10                  15
Gly Gly Asp Gly Gln Ala Gly Pro Asp Glu Gly Glu Val Asp
            20                  25                  30

<210> SEQ ID NO 24
<211> LENGTH: 6
<212> TYPE: PRT
<213> ORGANISM: Oryctolagus cuniculus

<400> SEQUENCE: 24

Asp Glu Gly Glu Val Asp
1               5

<210> SEQ ID NO 25
<211> LENGTH: 16
<212> TYPE: PRT
<213> ORGANISM: Oryctolagus cuniculus

<400> SEQUENCE: 25

Glu Glu Glu Glu Glu Glu Glu Asp Glu Asp Asp Asp Asp
1               5                   10                  15

<210> SEQ ID NO 26
<211> LENGTH: 28
<212> TYPE: PRT
<213> ORGANISM: Oryctolagus cuniculus

<400> SEQUENCE: 26

Glu Glu Glu Glu Glu Glu Glu Asp Glu Asp Asp Asp Asp
1               5                   10                  15
Val Val Ser Glu Gly Ser Glu Val Pro Glu Ser Asp
            20                  25

<210> SEQ ID NO 27
<211> LENGTH: 12
<212> TYPE: PRT
<213> ORGANISM: Oryctolagus cuniculus

<400> SEQUENCE: 27

Val Val Ser Glu Gly Ser Glu Val Pro Glu Ser Asp
1               5                   10

<210> SEQ ID NO 28
<211> LENGTH: 10
<212> TYPE: PRT
<213> ORGANISM: Oryctolagus cuniculus

<400> SEQUENCE: 28

Pro Pro Gly Lys Pro Ala Leu Pro Gly Ala
1               5                   10

<210> SEQ ID NO 29
<211> LENGTH: 15
<212> TYPE: PRT
<213> ORGANISM: Oryctolagus cuniculus

<400> SEQUENCE: 29

Glu Asp Gly Val Gln Gly Glu Pro Pro Glu Pro Glu Asp Ala Glu
1               5                   10                  15

<210> SEQ ID NO 30
<211> LENGTH: 45
<212> TYPE: DNA
<213> ORGANISM: Homo sapiens

<400> SEQUENCE: 30
gaagaggaag aagatgatga tgaagatgaa gatgaagaag atgat            45

<210> SEQ ID NO 31
<211> LENGTH: 78
<212> TYPE: DNA
<213> ORGANISM: Homo sapiens

<400> SEQUENCE: 31
gaagaggaag aagatgatga tgaagatgaa gatgaagaag atgatgtgtc agagggctct   60
gaagtgcccg agagtgac                                                78

<210> SEQ ID NO 32
<211> LENGTH: 33
<212> TYPE: DNA
<213> ORGANISM: Homo sapiens

<400> SEQUENCE: 32
gtgtcagagg gctctgaagt gcccgagagt gac                         33

<210> SEQ ID NO 33
<211> LENGTH: 30
<212> TYPE: DNA
<213> ORGANISM: Homo sapiens

<400> SEQUENCE: 33
gaggatgatg accccgatgg cttcttaggc                             30

<210> SEQ ID NO 34
<211> LENGTH: 90
<212> TYPE: DNA
<213> ORGANISM: Homo sapiens

<400> SEQUENCE: 34
gtggacgtgg atgaatatga cgagaacaag ttcgtggacg aagaagatgg gggcgacggc   60
caggccgggc ccgacgaggg cgaggtggac                                   90

<210> SEQ ID NO 35
<211> LENGTH: 18

<212> TYPE: DNA
<213> ORGANISM: Homo sapiens

<400> SEQUENCE: 35
gacgagggcg aggtggac                                                          18

<210> SEQ ID NO 36
<211> LENGTH: 48
<212> TYPE: DNA
<213> ORGANISM: Homo sapiens

<400> SEQUENCE: 36
gaggaggagg aggaggagga ggaagacgac gaggacgacg acgacgac                          48

<210> SEQ ID NO 37
<211> LENGTH: 84
<212> TYPE: DNA
<213> ORGANISM: Homo sapiens

<400> SEQUENCE: 37
gaggaggagg aggaggagga ggaagacgac gaggacgacg acgacgacgt cgtgtccgag            60
ggctcggagg tgcccgagag cgat                                                   84

<210> SEQ ID NO 38
<211> LENGTH: 36
<212> TYPE: DNA
<213> ORGANISM: Homo sapiens

<400> SEQUENCE: 38
gtcgtgtccg agggctcgga ggtgcccgag agcgat                                      36

<210> SEQ ID NO 39
<211> LENGTH: 30
<212> TYPE: DNA
<213> ORGANISM: Homo sapiens

<400> SEQUENCE: 39 cccccccggga agccagccct cccaggagcc                                            30

<210> SEQ ID NO 40
<211> LENGTH: 45
<212> TYPE: DNA
<213> ORGANISM: Homo sapiens

<400> SEQUENCE: 40
gaggatgggg tccagggtga gccccctgaa cctgaagatg cagag                            45

<210> SEQ ID NO 41
<211> LENGTH: 7
<212> TYPE: PRT
<213> ORGANISM: Homo sapiens

<400> SEQUENCE: 41

Arg Asp Val Ser Glu Glu Leu
1               5

<210> SEQ ID NO 42
<211> LENGTH: 21
<212> TYPE: DNA
<213> ORGANISM: Homo sapiens

<400> SEQUENCE: 42
cgtgatgtct ctgaggagct g                                                      21

<210> SEQ ID NO 43
<211> LENGTH: 538
<212> TYPE: PRT
<213> ORGANISM: Homo sapiens

<400> SEQUENCE: 43

```
Met Ala Gly Pro Pro Ala Leu Pro Pro Glu Thr Ala Ala Ala
1               5                  10                  15

Thr Thr Ala Ala Ala Ala Ser Ser Ala Ala Ser Pro His Tyr Gln
            20                  25                  30

Glu Trp Ile Leu Asp Thr Ile Asp Ser Leu Arg Ser Arg Lys Ala Arg
            35                  40                  45

Pro Asp Leu Glu Arg Ile Cys Arg Met Val Arg Arg His Gly Pro
    50                  55                  60

Glu Pro Glu Arg Thr Arg Ala Glu Leu Glu Lys Leu Ile Gln Gln Arg
65                  70                  75                  80

Ala Val Leu Arg Val Ser Tyr Lys Gly Ser Ile Ser Tyr Arg Asn Ala
                85                  90                  95

Ala Arg Val Gln Pro Pro Arg Arg Gly Ala Thr Pro Pro Ala Pro Pro
            100                 105                 110

Arg Ala Pro Arg Gly Ala Pro Ala Ala Ala Ala Ala Ala Pro Pro
        115                 120                 125

Pro Thr Pro Ala Pro Pro Pro Pro Ala Pro Val Ala Ala Ala Ala
    130                 135                 140

Pro Ala Arg Ala Pro Arg Ala Ala Ala Ala Ala Thr Ala Pro Pro
145                 150                 155                 160

Ser Pro Gly Pro Ala Gln Pro Gly Pro Arg Ala Gln Arg Ala Ala Pro
                165                 170                 175

Leu Ala Ala Pro Pro Ala Pro Ala Ala Pro Ala Val Ala Pro
            180                 185                 190

Pro Ala Gly Pro Arg Arg Ala Pro Pro Ala Val Ala Ala Arg Glu
        195                 200                 205

Pro Pro Leu Pro Pro Pro Gln Pro Ala Pro Pro Gln Gln Gln
    210                 215                 220

Gln Pro Pro Pro Gln Pro Gln Pro Pro Glu Gly Gly Ala Val
225                 230                 235                 240

Arg Ala Gly Gly Ala Ala Arg Pro Val Ser Leu Arg Glu Val Val Arg
                245                 250                 255

Tyr Leu Gly Gly Ser Gly Gly Ala Gly Gly Arg Leu Thr Arg Gly Arg
            260                 265                 270

Val Gln Gly Leu Leu Glu Glu Ala Ala Arg Gly Arg Leu Glu
        275                 280                 285

Arg Thr Arg Leu Gly Ala Leu Ala Leu Pro Arg Gly Asp Arg Pro Gly
    290                 295                 300

Arg Ala Pro Pro Ala Ala Ser Ala Arg Pro Ser Arg Ser Lys Arg Gly
305                 310                 315                 320

Gly Glu Glu Arg Val Leu Glu Lys Glu Glu Glu Asp Asp Glu
                325                 330                 335

Asp Glu Asp Glu Glu Asp Asp Val Ser Glu Gly Ser Glu Val Pro Glu
            340                 345                 350

Ser Asp Arg Pro Ala Gly Ala Gln His His Gln Leu Asn Gly Glu Arg
        355                 360                 365

Gly Pro Gln Ser Ala Lys Glu Arg Val Lys Glu Trp Thr Pro Cys Gly
```

```
                370             375             380
Pro His Gln Gly Gln Asp Glu Gly Arg Gly Pro Ala Pro Gly Ser Gly
385                 390                 395                 400

Thr Arg Gln Val Phe Ser Met Ala Ala Met Asn Lys Glu Gly Gly Thr
            405                 410                 415

Ala Ser Val Ala Thr Gly Pro Asp Ser Pro Ser Pro Val Pro Leu Pro
                420                 425                 430

Pro Gly Lys Pro Ala Leu Pro Gly Ala Asp Gly Thr Pro Phe Gly Cys
            435                 440                 445

Pro Pro Gly Arg Lys Glu Lys Pro Ser Asp Pro Val Glu Trp Thr Val
450                 455                 460

Met Asp Val Val Glu Tyr Phe Thr Glu Ala Gly Phe Pro Glu Gln Ala
465                 470                 475                 480

Thr Ala Phe Gln Glu Gln Glu Ile Asp Gly Lys Ser Leu Leu Leu Met
                485                 490                 495

Gln Arg Thr Asp Val Leu Thr Gly Leu Ser Ile Arg Leu Gly Pro Ala
            500                 505                 510

Leu Lys Ile Tyr Glu His His Ile Lys Val Leu Gln Gln Gly His Phe
            515                 520                 525

Glu Asp Asp Asp Pro Asp Gly Phe Leu Gly
            530                 535

<210> SEQ ID NO 44
<211> LENGTH: 546
<212> TYPE: PRT
<213> ORGANISM: Homo sapiens

<400> SEQUENCE: 44

Met Lys Asn Gln Asp Lys Lys Asn Gly Ala Ala Lys Gln Ser Asn Pro
1               5                   10                  15

Lys Ser Ser Pro Gly Gln Pro Glu Ala Gly Pro Glu Gly Ala Gln Glu
            20                  25                  30

Arg Pro Ser Gln Ala Ala Pro Ala Val Glu Ala Glu Gly Pro Gly Ser
        35                  40                  45

Ser Gln Ala Pro Arg Lys Pro Glu Gly Ala Gln Ala Arg Thr Ala Gln
50                  55                  60

Ser Gly Ala Leu Arg Asp Val Ser Glu Glu Leu Ser Arg Gln Leu Glu
65                  70                  75                  80

Asp Ile Leu Ser Thr Tyr Cys Val Asp Asn Asn Gln Gly Gly Pro Gly
                85                  90                  95

Glu Asp Gly Ala Gln Gly Glu Pro Ala Glu Pro Glu Asp Ala Glu Lys
            100                 105                 110

Ser Arg Thr Tyr Val Ala Arg Asn Gly Glu Pro Glu Pro Thr Pro Val
        115                 120                 125

Val Asn Gly Glu Lys Glu Pro Ser Lys Gly Asp Pro Asn Thr Glu Glu
130                 135                 140

Ile Arg Gln Ser Asp Glu Val Gly Asp Arg Asp His Arg Arg Pro Gln
145                 150                 155                 160

Glu Lys Lys Lys Ala Lys Gly Leu Gly Lys Glu Ile Thr Leu Leu Met
                165                 170                 175

Gln Thr Leu Asn Thr Leu Ser Thr Pro Glu Glu Lys Leu Ala Ala Leu
            180                 185                 190

Cys Lys Lys Tyr Ala Glu Leu Leu Glu Glu His Arg Asn Ser Gln Lys
        195                 200                 205
```

```
Gln Met Lys Leu Leu Gln Lys Lys Gln Ser Gln Leu Val Gln Glu Lys
    210                 215                 220

Asp His Leu Arg Gly Glu His Ser Lys Ala Val Leu Ala Arg Ser Lys
225                 230                 235                 240

Leu Glu Ser Leu Cys Arg Glu Leu Gln Arg His Asn Arg Ser Leu Lys
                245                 250                 255

Glu Glu Gly Val Gln Arg Ala Arg Glu Glu Glu Lys Arg Lys Glu
            260                 265                 270

Val Thr Ser His Phe Gln Val Thr Leu Asn Asp Ile Gln Leu Gln Met
                275                 280                 285

Glu Gln His Asn Glu Arg Asn Ser Lys Leu Arg Gln Glu Asn Met Glu
    290                 295                 300

Leu Ala Glu Arg Leu Lys Lys Leu Ile Glu Gln Tyr Glu Leu Arg Glu
305                 310                 315                 320

Glu His Ile Asp Lys Val Phe Lys His Lys Asp Leu Gln Gln Gln Leu
                325                 330                 335

Val Asp Ala Lys Leu Gln Gln Ala Gln Glu Met Leu Lys Glu Ala Glu
                340                 345                 350

Glu Arg His Gln Arg Glu Lys Asp Phe Leu Leu Lys Glu Ala Val Glu
    355                 360                 365

Ser Gln Arg Met Cys Glu Leu Met Lys Gln Gln Glu Thr His Leu Lys
370                 375                 380

Gln Gln Leu Ala Leu Tyr Thr Glu Lys Phe Glu Glu Phe Gln Asn Thr
385                 390                 395                 400

Leu Ser Lys Ser Ser Glu Val Phe Thr Thr Phe Lys Gln Glu Met Glu
                405                 410                 415

Lys Met Thr Lys Lys Ile Lys Lys Leu Glu Lys Glu Thr Thr Met Tyr
                420                 425                 430

Arg Ser Arg Trp Glu Ser Ser Asn Lys Ala Leu Leu Glu Met Ala Glu
            435                 440                 445

Glu Lys Thr Val Arg Asp Lys Glu Leu Glu Gly Leu Gln Val Lys Ile
    450                 455                 460

Gln Arg Leu Glu Lys Leu Cys Arg Ala Leu Gln Thr Glu Arg Asn Asp
465                 470                 475                 480

Leu Asn Lys Arg Val Gln Asp Leu Ser Ala Gly Gly Gln Gly Ser Leu
                485                 490                 495

Thr Asp Ser Gly Pro Glu Arg Arg Pro Glu Gly Pro Gly Ala Gln Ala
            500                 505                 510

Pro Ser Ser Pro Arg Val Thr Glu Ala Pro Cys Tyr Pro Gly Ala Pro
    515                 520                 525

Ser Thr Glu Ala Ser Gly Gln Thr Gly Pro Gln Glu Pro Thr Ser Ala
    530                 535                 540

Arg Ala
545

<210> SEQ ID NO 45
<211> LENGTH: 1614
<212> TYPE: DNA
<213> ORGANISM: Homo sapiens
<220> FEATURE:
<221> NAME/KEY: CDS
<222> LOCATION: (1)...(1614)

<400> SEQUENCE: 45 atg gcg ggg ccc ccg gcc cta ccc ccg ccg gag acg gcg gcg gcc gcc    48
Met Ala Gly Pro Pro Ala Leu Pro Pro Pro Glu Thr Ala Ala Ala Ala
```

```
1               5                   10                  15
acc acg gcg gcc gcc gcc tcg tcg tcc gcc gct tcc ccg cac tac caa    96
Thr Thr Ala Ala Ala Ala Ser Ser Ser Ala Ala Ser Pro His Tyr Gln
                20                  25                  30 gag tgg atc ctg gac acc atc gac tcg ctg cgc tcg cgc aag gcg cgg   144
Glu Trp Ile Leu Asp Thr Ile Asp Ser Leu Arg Ser Arg Lys Ala Arg
        35                  40                  45 ccg gac ctg gag cgc atc tgc cgg atg gtg cgg cgg cgg cac ggc ccg   192
Pro Asp Leu Glu Arg Ile Cys Arg Met Val Arg Arg Arg His Gly Pro
    50                  55                  60 gag ccg gag cgc acg cgc gcc gag ctc gag aaa ctg atc cag cag cgc   240
Glu Pro Glu Arg Thr Arg Ala Glu Leu Glu Lys Leu Ile Gln Gln Arg
65                  70                  75                  80 gcc gtg ctc cgg gtc agc tac aag ggg agc atc tcg tac cgc aac gcg   288
Ala Val Leu Arg Val Ser Tyr Lys Gly Ser Ile Ser Tyr Arg Asn Ala
                85                  90                  95 gcg cgc gtc cag ccg ccc cgg cgc gga gcc acc ccg ccc gcc ccg ccg   336
Ala Arg Val Gln Pro Pro Arg Arg Gly Ala Thr Pro Pro Ala Pro Pro
                100                 105                 110 cgc gcc ccc cgc ggg gcc ccc gcc gcc gcc gcc gcc gcc gcg ccg ccg   384
Arg Ala Pro Arg Gly Ala Pro Ala Ala Ala Ala Ala Ala Ala Pro Pro
            115                 120                 125 ccc acg ccc gcc ccg ccg cca ccg ccc gcg ccc gtc gcc gcc gcc gcc   432
Pro Thr Pro Ala Pro Pro Pro Pro Ala Pro Val Ala Ala Ala Ala
        130                 135                 140 ccg gcc cgg gcg ccc cgc gcg gcc gcc gcc gcc gcc aca gcg ccc ccc   480
Pro Ala Arg Ala Pro Arg Ala Ala Ala Ala Ala Thr Ala Pro Pro
145                 150                 155                 160 tcg cct ggc ccc gcg cag ccg ggc ccc cgc gcg cag cgg gcc gcg ccc   528
Ser Pro Gly Pro Ala Gln Pro Gly Pro Arg Ala Gln Arg Ala Ala Pro
                165                 170                 175 ctg gcc gcg ccg ccg ccc gcg cca gcc gct ccc ccg gcg gtg gcg ccc   576
Leu Ala Ala Pro Pro Pro Ala Pro Ala Ala Pro Ala Val Ala Pro
                180                 185                 190 ccg gcc ggc ccg cgc cgc gcc ccc ccg ccc gcc gtc gcc gcc cgg gag   624
Pro Ala Gly Pro Arg Arg Ala Pro Pro Pro Ala Val Ala Ala Arg Glu
            195                 200                 205 ccg ccg ctg ccg ccg ccg cca cag ccg ccg gcg ccg cca cag cag cag   672
Pro Pro Leu Pro Pro Pro Pro Gln Pro Pro Ala Pro Pro Gln Gln Gln
        210                 215                 220 cag ccg ccg ccg ccg cag cca cag ccg ccg ccg gag ggg ggc gcg gtg   720
Gln Pro Pro Pro Pro Gln Pro Gln Pro Pro Glu Gly Gly Ala Val
225                 230                 235                 240 cgg gcc ggc ggc gcg gcg cgg ccc gtg agc ctg cgg gaa gtc gtg cgc   768
Arg Ala Gly Gly Ala Ala Arg Pro Val Ser Leu Arg Glu Val Val Arg
                245                 250                 255 tac ctc ggg ggc agc ggc ggc gcc ggc ggt cgc cta acc cgc ggc cgc   816
Tyr Leu Gly Gly Ser Gly Gly Ala Gly Gly Arg Leu Thr Arg Gly Arg
            260                 265                 270 gtg cag ggg ctg ctg gag gag gag gcg gcg gct cga ggc cgt ctg gag   864
Val Gln Gly Leu Leu Glu Glu Glu Ala Ala Ala Arg Gly Arg Leu Glu
        275                 280                 285 cgc acc cgt ctc gga gcg ctt gcg ctg ccc cgc ggg gac agg ccc gga   912
Arg Thr Arg Leu Gly Ala Leu Ala Leu Pro Arg Gly Asp Arg Pro Gly
    290                 295                 300 cgg gcg ccg ccg gcc gcc agc gcc cgc ccg tct cgc agc aag aga ggt   960
Arg Ala Pro Pro Ala Ala Ser Ala Arg Pro Ser Arg Ser Lys Arg Gly
305                 310                 315                 320 gga gaa gag cga gta ctt gag aaa gaa gag gaa gaa gat gat gat gaa  1008
```

```
Gly Glu Glu Arg Val Leu Glu Lys Glu Glu Glu Asp Asp Glu
                325                 330                 335 gat gaa gat gaa gaa gat gat gtg tca gag ggc tct gaa gtg ccc gag      1056
Asp Glu Asp Glu Glu Asp Asp Val Ser Glu Gly Ser Glu Val Pro Glu
            340                 345                 350 agt gac cgt cct gca ggt gcc cag cac cac cag ctt aac ggc gag cgg      1104
Ser Asp Arg Pro Ala Gly Ala Gln His His Gln Leu Asn Gly Glu Arg
        355                 360                 365 gga cct cag agt gcc aag gag agg gtc aag gag tgg acc ccc tgc gga      1152
Gly Pro Gln Ser Ala Lys Glu Arg Val Lys Glu Trp Thr Pro Cys Gly
    370                 375                 380 ccg cac cag ggc cag gat gaa ggg cgg ggg cca gcc ccg ggc agc ggc      1200
Pro His Gln Gly Gln Asp Glu Gly Arg Gly Pro Ala Pro Gly Ser Gly
385                 390                 395                 400 acc cgc cag gtg ttc tcc atg gca gcc atg aac aag gaa ggg gga aca      1248
Thr Arg Gln Val Phe Ser Met Ala Ala Met Asn Lys Glu Gly Gly Thr
                405                 410                 415 gct tct gtt gcc acc ggg cca gac tcc ccg tcc ccc gtg cct ttg ccc      1296
Ala Ser Val Ala Thr Gly Pro Asp Ser Pro Ser Pro Val Pro Leu Pro
            420                 425                 430 cca ggc aaa cca gcc cta cct ggg gcc gac ggg acc ccc ttt ggc tgt      1344
Pro Gly Lys Pro Ala Leu Pro Gly Ala Asp Gly Thr Pro Phe Gly Cys
        435                 440                 445 ccg ccc ggg cgc aaa gag aag cca tct gat ccc gtc gag tgg acc gtg      1392
Pro Pro Gly Arg Lys Glu Lys Pro Ser Asp Pro Val Glu Trp Thr Val
    450                 455                 460 atg gat gtc gtc gaa tat ttt act gag gct gga ttc ccg gag cag gcg      1440
Met Asp Val Val Glu Tyr Phe Thr Glu Ala Gly Phe Pro Glu Gln Ala
465                 470                 475                 480 aca gct ttc caa gag cag gaa att gat ggc aaa tct ttg ctg ctc atg      1488
Thr Ala Phe Gln Glu Gln Glu Ile Asp Gly Lys Ser Leu Leu Leu Met
                485                 490                 495 cag cgc aca gat gtg ctc acc ggc ctg tcc atc cgc ctc ggg cca gcc      1536
Gln Arg Thr Asp Val Leu Thr Gly Leu Ser Ile Arg Leu Gly Pro Ala
            500                 505                 510 ctg aaa atc tac gag cac cac atc aag gtg ctt cag caa ggc cac ttt      1584
Leu Lys Ile Tyr Glu His His Ile Lys Val Leu Gln Gln Gly His Phe
        515                 520                 525 gag gat gat gac ccc gat ggc ttc tta ggc                              1614
Glu Asp Asp Asp Pro Asp Gly Phe Leu Gly
    530                 535

<210> SEQ ID NO 46
<211> LENGTH: 1638
<212> TYPE: DNA
<213> ORGANISM: Homo sapiens
<220> FEATURE:
<221> NAME/KEY: CDS
<222> LOCATION: (1)...(1638)

<400> SEQUENCE: 46 atg aag aac caa gac aaa aag aac ggg gct gcc aaa caa tcc aat cca        48
Met Lys Asn Gln Asp Lys Lys Asn Gly Ala Ala Lys Gln Ser Asn Pro
1               5                   10                  15 aaa agc agc cca gga caa ccg gaa gca gga ccc gag gga gcc cag gag        96
Lys Ser Ser Pro Gly Gln Pro Glu Ala Gly Pro Glu Gly Ala Gln Glu
            20                  25                  30 cgg ccc agc cag gcg gct cct gca gta gaa gca gaa ggt ccc ggc agc       144
Arg Pro Ser Gln Ala Ala Pro Ala Val Glu Ala Glu Gly Pro Gly Ser
        35                  40                  45 agc cag gct cct cgg aag ccg gag ggt gct caa gcc aga acg gct cag       192
Ser Gln Ala Pro Arg Lys Pro Glu Gly Ala Gln Ala Arg Thr Ala Gln
```

```
Ser Gln Ala Pro Arg Lys Pro Glu Gly Ala Gln Ala Arg Thr Ala Gln
 50              55                  60 tct ggg gcc ctt cgt gat gtc tct gag gag ctg agc cgc caa ctg gaa      240
Ser Gly Ala Leu Arg Asp Val Ser Glu Glu Leu Ser Arg Gln Leu Glu
 65              70                  75                  80 gac ata ctg agc aca tac tgt gtg gac aat aac cag ggg ggc ccc ggc      288
Asp Ile Leu Ser Thr Tyr Cys Val Asp Asn Asn Gln Gly Gly Pro Gly
                 85                  90                  95 gag gat ggg gca cag ggt gag ccg gct gaa ccc gaa gat gca gag aag      336
Glu Asp Gly Ala Gln Gly Glu Pro Ala Glu Pro Glu Asp Ala Glu Lys
            100                 105                 110 tcc cgg acc tat gtg gca agg aat ggg gag cct gaa cca act cca gta      384
Ser Arg Thr Tyr Val Ala Arg Asn Gly Glu Pro Glu Pro Thr Pro Val
        115                 120                 125 gtc aat gga gag aag gaa ccc tcc aag ggg gat cca aac aca gaa gag      432
Val Asn Gly Glu Lys Glu Pro Ser Lys Gly Asp Pro Asn Thr Glu Glu
    130                 135                 140 atc cgg cag agt gac gag gtc gga gac cga gac cat cga agg cca cag      480
Ile Arg Gln Ser Asp Glu Val Gly Asp Arg Asp His Arg Arg Pro Gln
145                 150                 155                 160 gag aag aaa aaa gcc aag ggt ttg ggt aag gag atc acg ttg ctg atg      528
Glu Lys Lys Lys Ala Lys Gly Leu Gly Lys Glu Ile Thr Leu Leu Met
                165                 170                 175 cag aca ttg aat act ctg agt acc cca gag gag aag ctg gct gct ctg      576
Gln Thr Leu Asn Thr Leu Ser Thr Pro Glu Glu Lys Leu Ala Ala Leu
            180                 185                 190 tgc aag aag tat gct gaa ctg ctg gag gag cac cgg aat tca cag aag      624
Cys Lys Lys Tyr Ala Glu Leu Leu Glu Glu His Arg Asn Ser Gln Lys
        195                 200                 205 cag atg aag ctc cta cag aaa aag cag agc cag ctg gtg caa gag aag      672
Gln Met Lys Leu Leu Gln Lys Lys Gln Ser Gln Leu Val Gln Glu Lys
    210                 215                 220 gac cac ctg cgc ggt gag cac agc aag gcc gtc ctg gcc cgc agc aag      720
Asp His Leu Arg Gly Glu His Ser Lys Ala Val Leu Ala Arg Ser Lys
225                 230                 235                 240 ctt gag agc cta tgc cgt gag ctg cag cgg cac aac cgc tcc ctc aag      768
Leu Glu Ser Leu Cys Arg Glu Leu Gln Arg His Asn Arg Ser Leu Lys
                245                 250                 255 gaa gaa ggt gtg cag cgg gcc cgg gag gag gag gag aag cgc aag gag      816
Glu Glu Gly Val Gln Arg Ala Arg Glu Glu Glu Glu Lys Arg Lys Glu
            260                 265                 270 gtg acc tcg cac ttc cag gtg aca ctg aat gac att cag ctg cag atg      864
Val Thr Ser His Phe Gln Val Thr Leu Asn Asp Ile Gln Leu Gln Met
        275                 280                 285 gaa cag cac aat gag cgc aac tcc aag ctg cgc caa gag aac atg gag      912
Glu Gln His Asn Glu Arg Asn Ser Lys Leu Arg Gln Glu Asn Met Glu
    290                 295                 300 ctg gct gag agg ctc aag aag ctg att gag cag tat gag ctg cgc gag      960
Leu Ala Glu Arg Leu Lys Lys Leu Ile Glu Gln Tyr Glu Leu Arg Glu
305                 310                 315                 320 gag cat atc gac aaa gtc ttc aaa cac aag gac cta caa cag cag ctg     1008
Glu His Ile Asp Lys Val Phe Lys His Lys Asp Leu Gln Gln Gln Leu
                325                 330                 335 gtg gat gcc aag ctc cag cag gcc cag gag atg cta aag gag gca gaa     1056
Val Asp Ala Lys Leu Gln Gln Ala Gln Glu Met Leu Lys Glu Ala Glu
            340                 345                 350 gag cgg cac cag cgg gag aag gat ttt ctc ctg aaa gag gca gta gag     1104
Glu Arg His Gln Arg Glu Lys Asp Phe Leu Leu Lys Glu Ala Val Glu
        355                 360                 365
```

```
tcc cag agg atg tgt gag ctg atg aag cag caa gag acc cac ctg aag    1152
Ser Gln Arg Met Cys Glu Leu Met Lys Gln Gln Glu Thr His Leu Lys
    370                 375                 380 caa cag ctt gcc cta tac aca gag aag ttt gag gag ttc cag aac aca    1200
Gln Gln Leu Ala Leu Tyr Thr Glu Lys Phe Glu Glu Phe Gln Asn Thr
385                 390                 395                 400 ctt tcc aaa agc agc gag gta ttc acc aca ttc aag cag gag atg gaa    1248
Leu Ser Lys Ser Ser Glu Val Phe Thr Thr Phe Lys Gln Glu Met Glu
                405                 410                 415 aag atg act aag aag atc aag aag ctg gag aaa gaa acc acc atg tac    1296
Lys Met Thr Lys Lys Ile Lys Lys Leu Glu Lys Glu Thr Thr Met Tyr
            420                 425                 430 cgg tcc cgg tgg gag agc agc aac aag gcc ctg ctt gag atg gct gag    1344
Arg Ser Arg Trp Glu Ser Ser Asn Lys Ala Leu Leu Glu Met Ala Glu
        435                 440                 445 gag aaa aca gtc cgg gat aaa gaa ctg gag ggc ctg cag gta aaa atc    1392
Glu Lys Thr Val Arg Asp Lys Glu Leu Glu Gly Leu Gln Val Lys Ile
450                 455                 460 caa cgg ctg gag aag ctg tgc cgg gca ctg cag aca gag cgc aat gac    1440
Gln Arg Leu Glu Lys Leu Cys Arg Ala Leu Gln Thr Glu Arg Asn Asp
465                 470                 475                 480 ctg aac aag agg gta cag gac ctg agt gct ggt ggc cag ggc tcc ctc    1488
Leu Asn Lys Arg Val Gln Asp Leu Ser Ala Gly Gly Gln Gly Ser Leu
                485                 490                 495 act gac agt ggc cct gag agg agg cca gag ggg cct ggg gct caa gca    1536
Thr Asp Ser Gly Pro Glu Arg Arg Pro Glu Gly Pro Gly Ala Gln Ala
            500                 505                 510 ccc agc tcc ccc agg gtc aca gaa gcg cct tgc tac cca gga gca ccg    1584
Pro Ser Ser Pro Arg Val Thr Glu Ala Pro Cys Tyr Pro Gly Ala Pro
        515                 520                 525 agc aca gaa gca tca ggc cag act ggg cct caa gag ccc acc tcc gcc    1632
Ser Thr Glu Ala Ser Gly Gln Thr Gly Pro Gln Glu Pro Thr Ser Ala
530                 535                 540 agg gcc                                                             1638
Arg Ala
545

<210> SEQ ID NO 47
<211> LENGTH: 550
<212> TYPE: PRT
<213> ORGANISM: Oryctolagus cuniculus

<400> SEQUENCE: 47

Met Ala Gly Pro Pro Ala Leu Pro Pro Pro Glu Thr Ala Ala Ala Ala
1               5                   10                  15

Thr Thr Ala Ala Ala Ala Ser Ser Ser Ala Ala Ser Pro His Tyr
            20                  25                  30

Gln Glu Trp Ile Leu Asp Thr Ile Asp Ser Leu Arg Ser Arg Lys Ala
        35                  40                  45

Arg Pro Asp Leu Glu Arg Ile Cys Arg Met Val Arg Arg His Gly
    50                  55                  60

Pro Glu Pro Glu Arg Thr Arg Ala Glu Leu Glu Lys Leu Ile Gln Gln
65                  70                  75                  80

Arg Ala Val Leu Arg Val Ser Tyr Lys Gly Ser Ile Ser Tyr Arg Asn
                85                  90                  95

Ala Ala Arg Val Gln Pro Pro Arg Arg Gly Ala Thr Pro Ala Pro
            100                 105                 110

Pro Arg Ala Pro Arg Gly Gly Pro Ala Ala Ala Ala Pro Pro Pro
        115                 120                 125
```

```
Thr Pro Ala Pro Pro Pro Pro Ala Pro Val Ala Ala Ala Ala
    130                 135                 140

Pro Ala Arg Ala Pro Arg Ala Ala Ala Ala Ala Ala Thr Ala
145                 150                 155                 160

Pro Pro Ser Pro Gly Pro Ala Gln Pro Gly Pro Arg Ala Gln Arg Ala
                165                 170                 175

Ala Pro Leu Ala Ala Pro Pro Ala Pro Ala Ala Pro Pro Ala Ala
        180                 185                 190

Ala Pro Pro Ala Gly Pro Arg Arg Ala Pro Pro Ala Ala Val
        195                 200                 205

Ala Ala Arg Glu Ser Pro Leu Pro Pro Pro Gln Pro Pro Ala Pro
    210                 215                 220

Pro Gln Gln Gln Gln Gln Pro Pro Pro Pro Pro Gln Gln Pro
225                 230                 235                 240

Gln Pro Pro Pro Glu Gly Gly Ala Ala Arg Ala Gly Gly Pro Ala Arg
                245                 250                 255

Pro Val Ser Leu Arg Glu Val Val Arg Tyr Leu Gly Gly Ser Ser Gly
        260                 265                 270

Ala Gly Gly Arg Leu Thr Arg Gly Arg Val Gln Gly Leu Leu Glu Glu
        275                 280                 285

Glu Ala Ala Ala Arg Gly Arg Leu Glu Arg Thr Arg Leu Gly Ala Leu
    290                 295                 300

Ala Leu Pro Arg Gly Asp Arg Pro Gly Arg Ala Pro Pro Ala Ala Ser
305                 310                 315                 320

Ala Arg Ala Ala Arg Asn Lys Arg Ala Gly Glu Glu Arg Val Leu Glu
                325                 330                 335

Lys Glu Glu Glu Glu Glu Glu Glu Asp Asp Glu Asp Asp Asp Asp
                340                 345                 350

Asp Val Val Ser Glu Gly Ser Glu Val Pro Glu Ser Asp Arg Pro Ala
        355                 360                 365

Gly Ala Gln His His Gln Leu Asn Gly Gly Glu Arg Gly Pro Gln Thr
    370                 375                 380

Ala Lys Glu Arg Ala Lys Glu Trp Ser Leu Cys Gly Pro His Pro Gly
385                 390                 395                 400

Gln Glu Glu Gly Arg Gly Pro Ala Ala Gly Ser Gly Thr Arg Gln Val
                405                 410                 415

Phe Ser Met Ala Ala Leu Ser Lys Glu Gly Gly Ser Ala Ser Ser Thr
        420                 425                 430

Thr Gly Pro Asp Ser Pro Ser Pro Val Pro Leu Pro Pro Gly Lys Pro
        435                 440                 445

Ala Leu Pro Gly Ala Asp Gly Thr Pro Phe Gly Cys Pro Ala Gly Arg
    450                 455                 460

Lys Glu Lys Pro Ala Asp Pro Val Glu Trp Thr Val Met Asp Val Val
465                 470                 475                 480

Glu Tyr Phe Thr Glu Ala Gly Phe Pro Glu Gln Ala Thr Ala Phe Gln
                485                 490                 495

Glu Gln Glu Ile Asp Gly Lys Ser Leu Leu Leu Met Gln Arg Thr Asp
                500                 505                 510

Val Leu Thr Gly Leu Ser Ile Arg Leu Gly Pro Ala Leu Lys Ile Tyr
        515                 520                 525

Glu His His Ile Lys Val Leu Gln Gln Gly His Phe Glu Asp Asp Asp
    530                 535                 540
```

```
Pro Glu Gly Phe Leu Gly
545             550

<210> SEQ ID NO 48
<211> LENGTH: 2561
<212> TYPE: DNA
<213> ORGANISM: Oryctolagus cuniculus
<220> FEATURE:
<221> NAME/KEY: CDS
<222> LOCATION: (246)...(1895)

<400> SEQUENCE: 48
ggtctgtgtg tgcgtgcgtg cgagtgagtg agtgtgtgca tatttttttt tctctttttct      60 ttctctctct ttttttttt tttgcaaaga aacagcagcg ccgccgccgc tccgccgagg       120
cgctgcgccc cccggggggg ggaggcggag gaggcgggca gcggcggagg gaggggagcc     180 ggggagggg gcgccgcgct gggagggagg cagcgcgcac ggtgcagccg ggccgggcgg      240 gaggc atg gcg ggg ccc ccg gcc cta ccc ccg ccg gag acg gcg gcg gcc    290
      Met Ala Gly Pro Pro Ala Leu Pro Pro Pro Glu Thr Ala Ala Ala
       1               5                  10                  15 gcc acc acg gcc gcg gcc gcc gcc tcg tcg tcc gcc gct tcc ccg cac      338
Ala Thr Thr Ala Ala Ala Ala Ala Ser Ser Ser Ala Ala Ser Pro His
             20                  25                  30 tac caa gag tgg att ctg gac acc atc gac tcg ctg cgc tcg cgc aag      386
Tyr Gln Glu Trp Ile Leu Asp Thr Ile Asp Ser Leu Arg Ser Arg Lys
         35                  40                  45 gcg cgg ccg gac ctg gag cgc atc tgc cgg atg gtg cgg cgg cac          434
Ala Arg Pro Asp Leu Glu Arg Ile Cys Arg Met Val Arg Arg His
     50                  55                  60 ggc ccg gag ccg gag cgc acg cgc gcc gag ctc gag aaa ctg atc cag      482
Gly Pro Glu Pro Glu Arg Thr Arg Ala Glu Leu Glu Lys Leu Ile Gln
 65                  70                  75 cag cgc gcc gtg ctc cgg gtc agc tac aag ggg agc atc tcg tac cgc      530
Gln Arg Ala Val Leu Arg Val Ser Tyr Lys Gly Ser Ile Ser Tyr Arg
 80                  85                  90                  95 aac gcg gcg cgc gtc cag ccg ccc cgg cgc gga gcc acc ccg ccg gcc      578
Asn Ala Ala Arg Val Gln Pro Pro Arg Arg Gly Ala Thr Pro Pro Ala
                100                 105                 110 ccg ccg cgc gcc ccc cgc ggg ggc ccc gcc gcc gcc gcg ccg ccg          626
Pro Pro Arg Ala Pro Arg Gly Gly Pro Ala Ala Ala Ala Pro Pro
            115                 120                 125 ccc acg ccc gcc ccg ccg ccg ccc gcg ccc gtc gcc gcc gcc gcc         674
Pro Thr Pro Ala Pro Pro Pro Pro Ala Pro Val Ala Ala Ala Ala
        130                 135                 140 gcc ccg gcc cgg gcg ccc cgc gcg gcc gcc gcc gcc gct gcc gcc aca     722
Ala Pro Ala Arg Ala Pro Arg Ala Ala Ala Ala Ala Ala Ala Thr
    145                 150                 155 gcg ccc ccc tcg ccc ggc ccc gcg cag ccg ggc ccc cgc gcg cag cgg     770
Ala Pro Pro Ser Pro Gly Pro Ala Gln Pro Gly Pro Arg Ala Gln Arg
160                 165                 170                 175 gcc gcg ccc ctg gcc gcg ccg ccg ccc gcg ccc gcc gct ccc ccg gcg     818
Ala Ala Pro Leu Ala Ala Pro Pro Pro Ala Pro Ala Ala Pro Pro Ala
                180                 185                 190 gcg gcg ccc ccg gcc ggc ccc cgc cgc gcc ccc ccg ccc gcc gcc gcc     866
Ala Ala Pro Pro Ala Gly Pro Arg Arg Ala Pro Pro Ala Ala Ala
            195                 200                 205 gtc gcc gcc cgg gag tcg ccc ctg ccg ccg cca cag ccg ccg gcg         914
Val Ala Ala Arg Glu Ser Pro Leu Pro Pro Pro Gln Pro Pro Ala
        210                 215                 220 ccg cca cag cag cag cag cag cag ccg ccg ccg cca ccg ccg cag cag     962
```

```
                Pro Pro Gln Gln Gln Gln Pro Pro Pro Pro Pro Pro Gln Gln
                    225                 230             235 cca cag ccg ccg gag ggg ggc gcg gcg cgg gcc ggc ggc ccg gcg        1010
Pro Gln Pro Pro Glu Gly Gly Ala Ala Arg Ala Gly Gly Pro Ala
240             245                 250                 255 cgg ccc gtg agc ctg cgg gaa gtc gtg cgc tac ctc ggg ggt agc agc    1058
Arg Pro Val Ser Leu Arg Glu Val Val Arg Tyr Leu Gly Gly Ser Ser
                260                 265                 270 ggc gct ggc ggc cgc ctg acc cgc ggc cgc gtg cag ggt ctg ctg gaa    1106
Gly Ala Gly Gly Arg Leu Thr Arg Gly Arg Val Gln Gly Leu Leu Glu
            275                 280                 285 gag gag gcg gcg gcg cgg ggc cgc ctg gag cgc acc cgt ctc gga gcg    1154
Glu Glu Ala Ala Ala Arg Gly Arg Leu Glu Arg Thr Arg Leu Gly Ala
        290                 295                 300 ctt gcg ctg ccc cgc ggg gac agg ccc gga cgg gcg cca ccg gcc gcc    1202
Leu Ala Leu Pro Arg Gly Asp Arg Pro Gly Arg Ala Pro Pro Ala Ala
    305                 310                 315 agc gcc cgc gcg gcg cgg aac aag aga gct ggc gag gag cga gtg ctt    1250
Ser Ala Arg Ala Ala Arg Asn Lys Arg Ala Gly Glu Glu Arg Val Leu
320                 325                 330                 335 gaa aag gag gag gag gag gag gag gaa gac gac gag gac gac gac        1298
Glu Lys Glu Glu Glu Glu Glu Glu Glu Asp Asp Glu Asp Asp Asp
                340                 345                 350 gac gac gtc gtg tcc gag ggc tcg gag gtg ccc gag agc gat cgt ccc    1346
Asp Asp Val Val Ser Glu Gly Ser Glu Val Pro Glu Ser Asp Arg Pro
            355                 360                 365 gcg ggt gcg cag cat cac cag ctg aat ggc ggc gag cgc ggc ccg cag    1394
Ala Gly Ala Gln His His Gln Leu Asn Gly Gly Glu Arg Gly Pro Gln
        370                 375                 380 acc gcc aag gag cgg gcc aag gag tgg tcg ctg tgt ggc ccc cac cct    1442
Thr Ala Lys Glu Arg Ala Lys Glu Trp Ser Leu Cys Gly Pro His Pro
    385                 390                 395 ggc cag gag gaa ggg cgg ggg ccg gcc gcg ggc agt ggc acc cgc cag    1490
Gly Gln Glu Glu Gly Arg Gly Pro Ala Ala Gly Ser Gly Thr Arg Gln
400                 405                 410                 415 gtg ttc tcc atg gcg gcc ttg agt aag gag ggg gga tca gcc tct tcg    1538
Val Phe Ser Met Ala Ala Leu Ser Lys Glu Gly Gly Ser Ala Ser Ser
                420                 425                 430 acc acc ggg cct gac tcc ccg tcc ccg gtg cct ttg ccc ccc ggg aag    1586
Thr Thr Gly Pro Asp Ser Pro Ser Pro Val Pro Leu Pro Pro Gly Lys
            435                 440                 445 cca gcc ctc cca gga gcc gat ggg acc ccc ttt ggc tgc cct gcc ggg    1634
Pro Ala Leu Pro Gly Ala Asp Gly Thr Pro Phe Gly Cys Pro Ala Gly
        450                 455                 460 cgc aaa gag aag ccg gca gac ccc gtg gag tgg aca gtc atg gac gtc    1682
Arg Lys Glu Lys Pro Ala Asp Pro Val Glu Trp Thr Val Met Asp Val
    465                 470                 475 gtg gag tac ttc acc gag gcg ggc ttc cct gag caa gcc acg gct ttc    1730
Val Glu Tyr Phe Thr Glu Ala Gly Phe Pro Glu Gln Ala Thr Ala Phe
480                 485                 490                 495 cag gag cag gag atc gac ggc aag tcc ctg ctg ctc atg cag cgc acc    1778
Gln Glu Gln Glu Ile Asp Gly Lys Ser Leu Leu Leu Met Gln Arg Thr
                500                 505                 510 gat gtc ctc acc ggc ctg tcc atc cgc ctg ggg cca gcg ttg aaa atc    1826
Asp Val Leu Thr Gly Leu Ser Ile Arg Leu Gly Pro Ala Leu Lys Ile
            515                 520                 525 tat gag cac cat atc aag gtg ctg cag cag ggt cac ttc gag gac gat    1874
Tyr Glu His His Ile Lys Val Leu Gln Gln Gly His Phe Glu Asp Asp
        530                 535                 540
```

-continued

| | |
|---|---|
| gac ccg gaa ggc ttc ctg gga tgagcacaga gccgccgcgc cccttgtccc<br>Asp Pro Glu Gly Phe Leu Gly<br>    545                    550 | 1925 |
| caccccacc ccgcctggac ccattcctgc ctccatgtca cccaaggtgt cccagaggcc | 1985 |
| aggagctgga ctgggcaggc gagggtgcg gacctaccct gattctggta ggggcgggg | 2045 |
| ccttgctgtg ctcattgcta ccccccacc ccgtgtgtgt ctctgcacct gcccccagca | 2105 |
| caccctccc ggagcctgga tgtcgcctgg gactctggcc tgctcatttt gccccagat | 2165 |
| cagcccctc cctccctcct gtcccaggac atttttaaa agaaaaaag gaaaaaaaa | 2225 |
| aattggggag gggctggga aggtgccca agatcctcct cggcccaacc aggtgtttat | 2285 |
| tcctatatat atatatat gttttgttct gcctgttttt cgttttttgg tgcgtggcct | 2345 |
| ttcttccctc ccaccaccac tcatggcccc agccctgctc gccctgtcgg cgggagcagc | 2405 |
| tgggaatggg aggagggtgg gaccttgggt ctgtctccca ccctctctcc cgttggttct | 2465 |
| gttgtcgctc cagctggctg tattgctttt taatattgca ccgaagggtt gtttttttt | 2525 |
| ttttaaataa aatttttaaaa aaggaaaaa aaaaaa | 2561 |

<210> SEQ ID NO 49
<211> LENGTH: 12619
<212> TYPE: DNA
<213> ORGANISM: Homo sapiens

<400> SEQUENCE: 49

| | |
|---|---|
| aagctttata aagatttaac tacctaataa ggtagagaag taatttatgt gcccactaaa | 60 |
| aaatactcaa tttctgaatg ttcgtccaaa attaacttgt cagatcatta aatcattgac | 120 |
| tagaaacacg ttgagtacct attatgtact aggcacttag atcattgtga gacaataaaa | 180 |
| aatactgcat tagaaaagga cattttttcac atcttaaatg caataagcat tatttggctg | 240 |
| gcagttaatt acatttaaca cattaaacat atagagcaaa attctgagca atcaaaataa | 300 |
| ttataccctt gagcaatcga ttatttaaat ttctttcact attcccttaa gctgatttct | 360 |
| actctgggat tctttcatag ttctcaaata agaaaataaa aaatttccta ataaggcaa | 420 |
| tacaaaagaa tagaaatgta agagaagaga tatattagct cttgaatccc tgtttccatt | 480 |
| tgctgtcaat agtgcctcta atgttcgatt ttctcttcaa agaaaaatct tgatttaaaa | 540 |
| ggaagaaaaa gtacaatcac ctttaacagc taaagtatac tgattagcat ctactaaagt | 600 |
| tagcaaagac tgaaactgaa aaaaaattgt aaaatcttta ttctaagtta tataacgcca | 660 |
| ttcaccatag taatgatttt atactttggt atatggcttt ttaaaataaa tattgccaac | 720 |
| aggtaaaaat ttttcctttg ctgtcttaag gcattcctaa gagaatttt accagtgtgt | 780 |
| gttcataact tgaatgttaa tttaaacaat gttacttcta tcacctaaat gatatactta | 840 |
| tagaagagtg gtttaattgg aacagaaaa acaccacatt gcttcttccc aagaaaagg | 900 |
| gatgtattcc attctcgagg tctctctccc actctctatt tatatataat atactgcata | 960 |
| gataaatata cacacattat atatgtattt ttttgaactt aaagaagact ggacatatgt | 1020 |
| atttacatgt atatatccaa caatatttta attttgagat ctctctccct cttctgattt | 1080 |
| attattctca gtatgaattc tcaaactgta cggtctttca catttcattc attcatcaag | 1140 |
| catgtatcga gtcccttctg catgcttagc ttttgtcat atggaaggaa gatacaaaag | 1200 |
| aaaaactgtt tctgcccttc agaatctttc catctcttct aggaaggaga taaaacacca | 1260 |
| tatatcatta agaaatttat aagactagtc ccaaaaccaa tggtacaagc aacatgcatt | 1320 |
| ttacatttat gtagaatttt agagcttgga aacactttcg tgatatataa tcctaagaac | 1380 |

```
aatcttgtaa agtgcacatt attagctcca tttcagtgat gaggaatctg agacagaatt    1440
ttaagtgaca tgtctcgttc aaacattatg agtggaagag tcaacactta agcctgagtt    1500
ttctgattct aagcctagtg ctcttttcaa cacagcactg gaaaccaaag attgtggtac    1560
acaacaaggc aacagccagt cttcttgctc gaggtccaac taaactggac ccataccgag    1620
cagtgtccag ccaaatgtcc aaattaattt tatcctgcaa atatttgttc ttcagtgtaa    1680
tacacacagc acaactacca tttccttcgt cttagtgcct ttatctccta cattccagaa    1740
atggggatgt caaatatttt tttaaatctg gcctagatgg aatcatataa atctcaaatc    1800
ataatataaa tcttaaaggt ctggtttcca ccaatccttc cacattttgt tttcccccag    1860
cactagagag cctaacctac cctcacccct ttcgagcatt cttgctccaa acgaccacct    1920
attttaagat gtcaatgacc cttccaaa ttctacaaat tcacccagt tttgccaccc    1980
gaccccagcg cctgcccgga cacgttcccc tccctcccaa tagatttgat accgagttca    2040
ggttctgcag atcccgttgc gatgctgtca cacagcactg acagataaga tttgacctt    2100
cgactccgtc cttggggact tcccgctggc caagaagggt agttccaatc ccaggaaacg    2160
ggcttcctgc tcaggaacgc agcctctagc agcgcacagt ctgaggcaat gtctccggca    2220
attagaacga tgctgggcgc ccgggtgtgc atcactctgc ctcatactcc taccaactgc    2280
agggcactcg gtccggcagc cagtccatcc cacccacacc caagtcccag ccagccggac    2340
cttacgcagg accccgatga taggtcgttg acggctgcag caaaagccaa ggccacctgc    2400
cgctgctgcc catccccgcc aatctgagac cccctagact ggaccgcaga aaagcgtttc    2460
tatgggaacc ccccaccga gaatcacgtg acgcaatcgg acgaccaatc gcttcttacc    2520
tctgcccgcg gtccagcttt tggccctccc tctcgccccc gcctccttcg cccagccccg    2580
cccttgcct gcggagagcc cgcgcctgcg cgctgtgtcc tgcgcgctcc ttccctcgcg    2640
cgcgctctcc gtggaagagc aggggcagcg tgggaggcgc caagggagcg cgaacctgag    2700
gaggaagaaa cggggctagc gcgcaggccc agaacggtcc gagccgcggc agtcggcgac    2760
gcctcagagc ggaagaggga agtgaatcag gcgccgggta gtgggttgct gggctgggct    2820
tgctgaggta gaggcagcgc caagaagagg cctttgccgc tggtcgggat tgggatgtcg    2880
aagaacacag tgtcgtcggc ccgcttccgg aaggtggacg tggatgaata tgacgagaac    2940
aagttcgtgg acgaagaaga tggggggcgac ggccaggccg ggcccgacga gggcgaggtg    3000
gactcctgcc tgcggcaata tccttgcatt caccgcctc ccacccag cccagcccag    3060
cccgccttc tcctgggacc cgggagcctg caggatccgc ggggcaccgg cgcggagctg    3120
cctctcaacc tgcggcttaa cctgtctctt tgggatcgcc cgctctgaga gggcaagggg    3180
gaagcccccg tttcctaccc agtcggcagg agacgcgagg gtcccactct ggaagcctg    3240
ccctaccccg cgcgccttcc acgccccag attcctcagg ttgcacccga gtgcctgcct    3300
gcctcgggaa ctggtcccgc cgcccgcgcc ctcgcggcgc tggggaaggc ggccccggct    3360
ggtgggaag gctggtgccg accgccttag ttttcttcc tagaactctg atttcctggg    3420
gtcacattag ctccagaaat ttctgattgt ggggaacctg catctttcct tagtggtttt    3480
gttttttggt tgtgttttg ttattggtag cgttaaggta gttattgct taccgggggg    3540
ccgggggaga tgggactgtt cgaaaattga gggtccctgt gctttcagcc cattggcctt    3600
tttaaaaaaa aaaaaaaaag aagaagaaga aggggatttg gcaaaatata cattgtacag    3660
aatttgttaa ctgggggagg ggaatgaata caaaaaatac aaaactccta gaaggaagct    3720
```

```
tggagccttt tacctgctaa gaaaaggaca atagaaaaaa caacggggaa tgcgtgtgga    3780
gaatccttgg aaatatttaa aataaacccc aatgaataag atagaagatg agtcattcgt    3840
ataaagcaga atcattttg taatcctaaa attgtttcca ttttagttaa aatatggcag     3900
tcagttcccg gtttctgttt ttgcatattt gaatattcat aactttggct tcgcatttgc    3960
attacatctt ttttagaaaa atgtaaatgt tgcaaaaaaa ccgaagctgt agttttagaa    4020
aatctcagac actgaatttg tatgcatttc taattcttgg gtgtattcat aaggaagact    4080
ctcaacaatg tcctgttata gtggggaaat atgagagtga aaatatttaa tggcaacaat    4140 atccttttt aaaggcacct aaatagagca ttagacattt atcaatatat agatagtgct     4200
ttgcccaact ttcacaatta attagctgtt gctcttttgc attatttaaa tacttaagtg    4260
cttggagtta taaaaaatga gctaatctac atcaggcatg cttctctaga aatccctgca    4320
gccttgaaaa taacagcttg tcaaccagag attttgtgta agaactttt ctttagaaaa     4380 taaatggtga acatgcttcc taaaaacatt atttgtgatg ggataagatg gtgttttatg    4440 aaacccagt gtattttagg taatttgtgg tgactttaa aaggtactgc tgtatccata      4500
tcagtggatc tgcttttga tcagttcatc ttaaaatata aagatactgt ctcttcttac     4560
cgttacatac agccaggaaa gacagcccta gtggtggggt actagagttg gaggaacaag    4620
tgaactctgt ggttttcctt ttaggggaat gtttgtacat tctgacagtc tgattggcct    4680
tctgtttctc atgcttgcta actcactagt gctttcaaag agagcctgaa tttaataggt    4740
atggtctaac acagtttgaa taaccttgt gaaatatgag agaaaatatc taaagcaaaa     4800
aattaagctg ccacctaagg gacatatgaa ttattacatc ttctgtgatg cctcttttca    4860
tcaatattga gagattgcta atgtgtatca ttcagattgc taatctgcca gcatgttcta    4920
ccagcatttc agataataca gaatatggtt ctagcaaaag tttggtcttt atttttcaa     4980 ttagaatcac aggaaaagac atattttggt tgataatagg ttatttcatt tgggggacta    5040
ataattctga tatatatttt aggatttctt taacaccact ctaggtaatg tttgcatatg    5100
tatctcactg ggaaatgaaa gactatcaag gtgttcactt gatagttaga accaagggtg    5160
aaacagtctt tgctttatta aaaaaaagtc taatgttcta ttttgctttt gatattttgc    5220
ctttgattaa catcctggaa accaacacat tgaatttcca gtattgaaca tagtgaccaa    5280 agtaatttc ttttatatg taaatcaagt cataaagaac cagtggttat aatgctttct      5340 ggggccatc ctttgctgtt acacccttaa cttccatcac aggaaacatg acagctgccc     5400
tacaggcagc tctgaagaac cccctatca acaccaagag tcaggcagtg aaggtgagtc     5460
gcagactaca acacagtgat ctctgctgat atcttattct tagtaaaatc cttgcagtgc    5520 aaaaaaaat caatattta actgtttgct atctttgaca agaagagttt ataatgtagt      5580
ttgataggta aaaatttcac gtgaaaaaat agccctataa tgtagttatg ataatgctgc    5640
atggtaagat acagtaagtt caaacgatag tgaaatcatt tgtgtgtgtt tttagaggag    5700
accactcagg ctgaatttga gcaaaggttt gaaaaataag ttaaaccttt acaaaaataa    5760
acagattgta attgcttttt aaagattttt taaaaccata caaatactaa atacttatta    5820
tagaaagctc agacatatga gaaggttaaa aagatagtgg tttgtggtcc cagcacccag    5880
agataacagt tactactttg gggccttgct gtattgttac agagttccct tttgtttttt    5940
taagaatgaa ttttaaaac gggcttttc agctatatgc aatggtacat gagctttcct      6000
tccccaataa gttaatagcc ttttttaaca cttgtatatg gataagctcc agtgtataca    6060
taactaatct tttgtttata tttagactga ctttttttt cctattgtaa accactgaaa     6120
```

```
tcaatatttt ttggtaaatt tttaattgtt ctctttgagt aaattgctag cagtgaatta    6180
ctggatcaaa gaatgcactt ttttttaagg cttttggtat gcagtattgc caaattgccc    6240
ttcagaacag ttgtgcaact tacattctct gcagtctttt actaattctt aacctattta    6300
cgtatttatt taaaatgatg cccatagcat caaccccgtt gtccatagct attcatacat    6360
cctaggagct tcaagaatct caattgaata gtagtaagta ataacttagg taaatgcata    6420
ataattatct aggtaacata atttttatt ggggaaaatt tctttggttt ttacaagttg     6480
taaagattgt cgttgaaatt tcattttac cgtggatgca aagatatttt tctaaatctg     6540
gtaattgcag tctttaaacc aaagataaca gtaggtggta gaaacattct gtgaaatcct    6600
gaccagtagg aatgctggag gtatcacttt gtgttgaatg gaaggagaaa cgaattgttg    6660
aaaaggtcag ttaagtgttt cctttgcttg gccggatggg taagaaaata actgcttttg    6720
aagcaggctt ttgccaaaga aaaaagatca ttattaatga acatcactat atttcatatc    6780
tacagtcaat tcatataaat tacagtcaat tttcttttaa gacagcttgg tttattaaaa    6840
tttttaaata aaaagttttt taagaaaaaa ttacttctga aggataattc aaggtgaaac    6900
tgcaaatctg cctccttgtt ttgttgggaa tttttttttt tttttttttt ttttgagacg    6960
gagtctcact ctatcaccca ggttggagtg cagtggtgca atctcaactc actgcaccct    7020
ccgcctcccg ggtttaagca atcctcctgc ttcagcctcc cgagtagctg ggatcacagg    7080
cacacaccac catgcctgga taatttctgt atttttagaa gaaaacaggg ttttaccatt    7140
ttggccaggc tggtctcgaa ctcctgacct caggtgatct gcccatctcg gcctcccaaa    7200
gtgctgggat tacagctgtg ggccaccaca cccggccgtt ttgttgggat tttttttttt    7260
taagatcaag acataaattt aaatgttgtt ttaataaatt gttaaattat cacattgatc    7320
tgttagcaaa tcctctcagc tctgccttca attatgttaa tagtctgtca agtttcttac    7380
cacctccact gctactatgc ttaccacatc cagcctgtat tattgcaatt gcctcctaat    7440
tgctctccct gcttctacct tatcccctac tcccacagct tattttctgt aacatagatg    7500
ccaaagcaat cctgttaaaa tgtgagtcag attatggcac tgctcttaaa accttccaat    7560
gtcttctcat ttctctcagt aaaagccaaa ctccttacaa tgcctgtagg ccttacacga    7620
tctgtcctcc cataacctct gacttactca cgtgcttttc tcccaccaat ccactccaac    7680
cacattgggt tttttctgt tcctggaaca cactgaacac acactaatag cactgttctt     7740
tcctctgtct gaaacacttt cctcagttat cccaagcctt cttcacgtc cttcaggtcc     7800 ttactcaaat gtcacattca tagtgtagac tttctgaaat tctaaaccct cctcatacag    7860
atatgtctaa atgttctgtt atttattgac ccaccaggac cgggcaggca gcattgtctt    7920
gaaggtgctc atctctttta aagctaatga tatagaaaag gcagttcaat ctctggacaa    7980
gaatggtgtg gatctcctaa tgaagtatat ttataaagga tttgagagcc cgtctgacaa    8040
tagcagtgct atgttactgc aatggcatga aaaggtaagt tatgaattat aaatctatat    8100
gactggttct tttacaatag ggaatgacaa tgacaacctc tctcacctaa ataaccatttt    8160 tgatttgttg tacattttg ttattacaaa taaaatgcat gaaaaggata gttcatattt     8220
atgtttacta gccttggtct taagagattc tgattccaac acttgtgttt attcaacaat    8280
gattattagt aattaaacat aatcttgaac tctgaattaa atcaaaactt tgtaaaagaa    8340
aataagcaat acaaatcaag aattctttca cagtgaccaa aaggtgaaaa caacacaagg    8400
atcgaatatg attcaaccat taaaaggaat gacattctga cacatgctat aacattaata    8460
```

```
aaccttgaaa acataccaag tgaaatgagc caaacacaaa agaactaata ttttataatt   8520
ttacttatat gaaataatct aggataggca aacacaaagg gacagaaagt ccttagaggt   8580
tactaggaag tagggaaagc aaggaatagg gagttagtgc ttaataggta cagagttcct   8640
ccttggagtg gtaaaaaagt tttggaaaca gatagtggtg atggctacag tacattgtga   8700
atataattaa tgccaatgga ttttacactt aaagatggtt aaaatggcaa attttgtgtt   8760
agatatttta caacttttt aaagaattag gagtttggag gatcaagaat tcttaaaatca  8820
tgttttcta ttttcatgtg tatattttgc aatgtaagta gatgctggta catcatctgt   8880
caaaagagta taagtgattt tgagcttttgg gtaaaaaact ggataacatg taaatagaac  8940
cagtcataaa aatattgagt gtttgaagtg tatctgagtg aaaacacaaa cataagaaaa  9000
aagcacatag taaacaata gttccccctt ttactctaaa atgcaccaat ttgggtagta   9060
atttatatgg cacctattc atggaacact ttctgttgcc aggtaccata ctattaatgt   9120
tttatttaac ctttacaaca accctgtgga agtatataaa tatctttatc atcctcaatt  9180
tacagatgaa aagctagctt taaaacccaa gccagcgtag ttctagcata gcctcaagat  9240
tgcagtgaac attgattact tattatattc cacatattct tcaaaggact ttataaaatat 9300
taactcattt aatcctcata aaaatggagg gaaatgcttg ctattattcc tcttttgtca  9360
ctgaggaaac tgaggcatgt gtgaagtctt catttcttcc aaatgtcagt caccagttt   9420
taccaatctt cgaagtattt ctgaaatcta tctgttcaag cgtatctaat gcagctgttc  9480
acagcatctc tcccagtctg ttgccatagc ttcctgactg gtttcccagt taacagtttt  9540
gcctccttca aatctgttct ccacccagcc atcaaaatga tatctttaaa atcaaaattg  9600
cccttgtcag tcacctgcag ggataaagtc aaagttccca agtctagctt catcttccat  9660
gtcattcttc ccctcaggct atagcaatgc cagccttttt cctgaatgca ccatattgtt  9720
tcacacctcc atacatttgc tcatgatttt ctggtgttag cctgtcacct actcattctt  9780
ttaatgtgtc atttcctcca tgaagcctta gctgaaacat tcctctatac tgttaatctg  9840
ggtataagcc tctccctggt gctttaatag cacctgcagc acaactctca tttcatacat  9900
tagattaaaa ttacctgttt atatgtctgt ctcctcatgc tagaccagaa aatgctgtat  9960
ttgttcactt ttgtatcccc agcatctagc acagtactca gtatacaaag gtattccata  10020
aatattttt gaacagaaag aaaccagagc tcagattcct aatacttgat cattactctc  10080
tattttcaa attagagtca gagttaaagt ttctaagttc ttagctatta aacaatacct  10140
tctttctttg ggagaaaaaa aatctgacaa aggctgacta atcgaagtgg aagttgggat  10200
ggttgatccc agtttgaatt ttcttctgac tatgtggtga gaatgagaaa tgcagaatgt  10260
ccacctgttt tgagcaggaa cactatgctg cagattttt ttttttttt tttttttttt   10320
ttttgagacg gagtcttgct ctgtcgccca ggctggagtg cagtggcgca atctcggctc  10380
actgcaagct ccgcctcctg ggttcacacc attgtcctgc ctcagcctcc cgagtagctg  10440
ggactacagg cacccgccac cacgcccggc taatttttttg tattttttagt agagacgggg  10500
tttcaccatg ttagccagga tggtcttgat ctcctgacct cgtgatccgc cggcctcggc  10560
ctcccaaagt gctgggatta caggcgtgag ccaccgcgcc cggcctatgc tgcagatttt  10620
ttaaaacatt atttagaatt aatgtactaa aatgtaaact agtatctcac tagaatgtaa  10680
cttcatgagg gcagggactt tcaaggtttt gtttattact gtaacctcag tgccaagaac  10740
agtacctggt gcataattgg tgctcaagaa tttattattt gttaactaat aaattccaggg 10800
tctatagcag tgcccattcc ttctttaaga aaaatgtttt accaaatatg agaattgacc  10860
```

-continued

```
ttttattatt ctgtcaacat ttacatcctg gtttgttttt aggcacttgc tgctggagga   10920
gtagggtcca ttgttcgtgt cttgactgca agaaaaactg tgtagtctgg caggaagtgg   10980
attatctgcc tcgggagtgg gaattgctgg tacaaagacc aaaacaacca aatgccaccg   11040
ctgccctgtg ggtagcatct gtttctctca gctttgcctt cttgcttttt catatctgta   11100
aagaaaaaaa ttacatatca gttgtccttt aatgaaaatt gggataatat agaagaaatt   11160
gtgttaaaat agaagtgttt catcctttca aaaccatttc agtgatgttt ataccaatct   11220
gtatatagta taatttacat tcaagtttaa ttgtgcaact tttaaccccct gttggctggt   11280 tttttgttct gttttgtttt gtattatttt taactaatac tgagagattt ggtcagaatt   11340
tgaggccagt ttcctagctc attgctagtc agggaaatga tatttataaa aaatatgaga   11400
gactggcagc tattaacatt gcaaaactgg accatatttc ccttatttaa taagcaaaat   11460 atgttttttgg aataagtggt gggtgaatac cactgctaag ttatagcttt gttttttgctt   11520 gcctcctgat tatctgtact gtgggtttaa gtatgctact ttctctcagc atccaataat   11580
catggcccct caatttattt gtggtcaccc agggttcaga gcaagaagtc ttgctttata   11640
caaatgtatc cataaaatat cagagcttgt tgggcatgaa catcaaactt ttgttccact   11700
aatatggctc tgtttggaaa aaactgcaaa tcagaaagaa tgatttgcag aaagaaagaa   11760
aaactatggt gtaatttaaa ctctgggcag cctctgaatg aaatgctact ttctttagaa   11820
atataatagc tgccttagac attatgaggt atacaactag tatttaagat accatttaat   11880
atgccccgta aatgtcttca gtgttcttca gggtagttgg gatctcaaaa gatttggttc   11940
agatccaaac aaatacacat tctgtgtttt agctcagtgt tttctaaaaa aagaaactgc   12000
cacacagcaa aaaattgttt actttgttgg acaaaccaaa tcagttctca aaaaatgacc   12060
ggtgcttata aaaagttata aatatcgagt agctctaaaa caaaccacct gaccaagagg   12120
gaagtgagct tgtgcttagt atttacattg gatgccagtt ttgtaatcac tgacttatgt   12180
gcaaactggt gcagaaattc tataaactct ttgctgtttt tgatacctgc ttttttgtttc   12240 atttttgtttt gttttgtaaa aatgataaaa cttcagaaaa taaaatgtca gtgttgaata   12300 attttatttttt ctctgacact ttaacaatta tgaatgtatg gttaattaag aggaaaggtt   12360
ttctgcttct accaccaagt actgtactct taacaagaac agtttggtag ggttttttata   12420 agactatata gatataagat gatagagaag agagtcatga atgatgtcag agcactactg   12480
aagcctttgg agtgattcca tagccttctg gatggcagct gaataccctat atgtagtatc   12540 actgcccaaa gacctagact agaaagtgca aagtagctta gcagctgcag tcattcactc   12600
ccagcctcca aaattctct                                                12619
```

<210> SEQ ID NO 50
<211> LENGTH: 12425
<212> TYPE: DNA
<213> ORGANISM: Homo sapiens

<400> SEQUENCE: 50

```
gatccctctc caggtggaag ctcccttcat accaaagttt aaaggccctg gggatacgag     60
taactttgac gactatgagg aagaagaaat ccgggtctcc atcaatgaga agtgtggcaa    120
ggagttttct gagttttagg ggcatgcctg tgccccatg ggttttcttt ttctttttt     180 ctttttttg gtcgggggggg tgggagggtt ggattgaaca gccagagggc cccagagttc    240
cttgcatcta atttcacccc cacccccaccc tccagggtta gggggagcag gaagcccaga    300
```

```
taatcagagg gacagaaaca ccagctgctc ccctcatcc ccttcaccct cctgccccct      360
ctcccacttt tcccttcctc tttccccaca gcccccagc ccctcagccc tcccagccca      420
cttctgcctg ttttaaacga gtttctcaac tccagtcaga ccaggtcttg ctggtgtatc     480
cagggacagg gtatggaaag aggggctcac gcttaactcc agccccacc cacacccca       540
tcccacccaa ccacaggccc cacttgctaa gggcaaatga acgaagcgcc aaccttcctt     600
tcggagtaat cctgcctggg aaggagagat ttttagtgac atgttcagtg ggttgcttgc     660
tagaattttt ttaaaaaaac aacaatttaa aatcttattt aagttccacc agtgcctccc     720
tccctccttc ctctactccc accctccca tgtccccca ttcctcaaat ccattttaaa       780
gagaagcaga ctgactttgg aaagggaggc gctggggttt gaacctcccc gctgctaatc     840
tcccctgggc ccctccccgg ggaatcctct ctgccaatcc tgcgagggtc taggccccct    900
taggaagcct ccgctctctt tttccccaac agacctgtct tcacccttgg gctttgaaag    960
ccagacaaag cagctgcccc tctccctgcc aaagaggagt catcccccaa aaagacagag   1020
ggggagcccc aagcccaagt cttcctcccc agcagcgttt ccccccaact ccttaatttt   1080
attctccgct agattttaac gtccagcctt ccctcagctg agtgggggagg catccctgc   1140
aaaagggaac agaagaggcc aagtccccc aagccacggc ccggggttca aggctagagc   1200
tgctggggag gggctgcctg ttttactcac ccaccagctt ccgcctcccc catcctgggc    1260
gcccctcctc cagcttagct gtcagctgtc catcacctct cccccacttt tcatttgtg    1320
cttttttctc tcgtaataga aaagtgggga gccgctgggg agccaccca ttcatccccg    1380
tatttccccc tctcataact tctccccatc ccaggaggag ttctcaggcc tggggtgggg   1440
ccccgggtgg gtgcggggc gattcaacct gtgtgctgcg aaggacgaga cttcctcttg    1500
aacagtgtgc tgttgtaaac atatttgaaa actattacca ataaagttt gtttaaaaaa    1560
aaagtgtcgc tggtgttctc gacttcgatc acccacccac acaccccag ggggttggaa    1620
agggaatttc ggaccccagc gtgcaggccg atcaggtcct ggcttgaagt ccttgtaacc   1680
agggtttagc tgaaattccg gcactccttc ggccccgcag gagaaacgag cgtcaaactg   1740
cccctttgacc ccagattcgg ggtccccaaa tctgcggcgc gccccctcgg cgtccagccc  1800
gggaccgaga gggcgctcta gggaggcgct ggggctggcg cgccaggagg ccgagcggcg   1860
gcgggggcgg ccctggcagg ggggagtagaa ggggggagagg gtgcgcgccc ccttcccgc   1920
atcctcagcg ccgggccagg cgcgcctgag ggacgcgggg gcggcggcag caggagggtc   1980
cccgcagcac cctgcgagcg cggcagcccc ggcccgcggg cggcgagttc ccggtaagtg   2040
cggtcccgag agcggagcgc gctggagagg cgtggagagg ggggctgggc gccggggacg   2100
tctgggtccc gcgcccaatg gctggagggc ggccgagcgc cgcccgcccg cctgcccgc    2160
cccctctccc ctcccccgg cactcccctc ccctccccc gccgccgct ttccccgcc       2220
cccgccccg cgccaactcc gcggcgcctc cttaaaagc gcgcggagt tgtaaggggg     2280
ggccggagcg agccggagtg agcgagagcg cagggtaaag ggggcgggcg ggggcccgg    2340
gctccacctt aaaagcgggc gcgtgggggt gggaggagg aaggcgggcg gcggggagga    2400
gggagggagg gaaggaaggg gggccggagt gtcccgggcg cagggcgcgc gtgcggcggc   2460
ggcggcggcg gggaggggcc ggccgcgccg cgctcccctc ctcccccctcg catccccggc  2520
cccgcgcgcg cccagcagaa gcgggtctgt gtgtgcgtgc gtgcgagtga gtgagtgtgt   2580
gcatattttt ttctctcttt tctttctctc tcactgtttt ttcctctctc tctctctccc   2640
tctctctctc tttttttttt tttttttttt gcaaagaaac agcagcgccg ccgccgctcc   2700
```

```
gccgaggcgc tgcgccccccc gggggggggag gcggaggagg cgggcagcgg cggagggagg    2760
ggagccgggg agggggggcgc cgcgctggga gggaggcagc gcgcacggtg cagccgggcc    2820
gggcgggagg catggcgggg cccccggccc taccccgcc ggagacgcg gcggccgcca    2880 ccacggcggc cgccgcctcg tcgtccgccg cttccccgca ctaccaagag tggatcctgg    2940
acaccatcga ctcgctgcgc tcgcgcaagg cgcggccgga cctggagcgc atctgccgga    3000
tggtgcggcg gcggcacggc ccggagccgg agcgcacgcg cgccgagctc gagaaactga    3060
tccagcagcg cgccgtgctc cgggtcagct acaaggggag catctcgtac cgcaacgcgg    3120
cgcgcgtcca gccgccccgg cgcggagcca ccccgccggc cccgccgcgc gccccccgcg    3180
gggcccccgc cgccgccgcc gccgccgcgc cgccgcccac gcccgccccg ccgcaccgc    3240 ccgcgcccgt cgccgccgcc gccccggccc gggcgccccg cgcggccgcc gccgccgcca    3300
cagcgccccc ctcgcctggc cccgcgcagc cgggcccccg cgcgcagcgg gccgcgcccc    3360
tggccgcgcc gccgcccgcg ccagccgctc ccccggcggt ggcgccccg gccggccgc    3420 gccgcgcccc ccgcccgcc gtcgccgccc gggagccgcc gctgccgccg ccgccacagc    3480
cgccggcgcc gccacagcag cagcagccgc cgccgccgca gccacagccg ccgccggagg    3540
ggggcgcggt gcgggccggc ggcgcggcgc ggcccgtgag cctgcgggaa gtcgtgcgct    3600
acctcggggg cagcggcggc gccggcggtc gcctaacccg cggccgcgtg caggggctgc    3660
tggaggagga ggcggcggct cgaggccgtc tggagcgcac ccgtctcgga gcgcttgcgc    3720
tgcccccgcg ggacaggccc ggacggggcgc cgccggccgc cagcgcccgc ccgtctcgca    3780
gcaaggtgag cgcgccgggg agcggggggcg ccgcgcggtg ggcaggtgcg ggcgaagttg    3840
gtggcggggg cgcgagtccc gggaggaact gggtggcggg tggctgggc tttgcgcgcg    3900 tttcctgcgg gctcggtgcg tggtgacctt ggcaagtgat tgaatctccc ggagcctcag    3960
tttcctccgc tgtaaacgcg gtttaataac agtagcgacc ccttgggtt gttgagcgag    4020 tttagtaaga tttggttgtc gagggcttta gttaacacag agcctggcac ggagtgaatg    4080
cgtaaaagtt agtccgtatt gttcttaaag gtggaatcgg ttcctcctcc ccaccgcccg    4140
gacgccacag tcagggtctg ggattagaac agctactaat tttgcatgct tctctcctcg    4200
gctccagaga ggtggagaag agcgagtact tgagaaagaa gaggaagaag atgatgatga    4260
agatgaagat gaagaagatg atgtgtcaga gggctctgaa gtgcccgaga gtgaccgtcc    4320
tgcaggtgcc cagcaccacc agcttaacgg cgagcgggga cctcagagtg ccaaggagag    4380
ggtcaaggag tggacccccct gcggaccgca ccagggccag gatgaagggc gggggccagc    4440
cccgggcagc ggcacccgcc aggtgttctc catggcagcc atgaacaagg aaggggggaac    4500 aggtaaggat ccctctgggt ggggaagagt gctaggtgga gaggaactca gcccgaagac    4560
aaagccaaag acaggtgttt ttttccttcc cagcttctgt tgccaccggg ccagactccc    4620
cgtcccccgt gcctttgccc ccaggcaaac cagccctacc tggggccgac gggaccccct    4680
ttggctgtcc gtaagttggg gtattggaga catgggggtg ctgctcaggt gtgtggtaca    4740
gccagagaga catccgtgtt cactggtgtc tgtttgtttt gatgcagtcc cgggcgcaaa    4800
gagaagccat ctgatcccgt cgagtggacc gtgatggatg tcgtcgaata ttttactgag    4860
gctggattcc cggagcaggc gacagctttc caagagcagg tgagttttcca gcccaggact    4920 acacactgac agacacagag ggcctccctg ggatgtgccc tgatcccggc tttctctgtt    4980
cctgtcccac ccaggaaatt gatggcaaat ctttgctgct catgcagcgc acagatgtgc    5040
```

-continued

```
tcaccggcct gtccatccgc ctcgggccag ccctgaaaat ctacgagcac cacatcaagg    5100
tgcttcagca aggccacttt gaggatgatg acccgatgg cttcttaggc tgagcgccca     5160
gcctcacccc tgcccagcc cattccggcc cccatctcac ccaagatccc ccagagtcca    5220
ggagctggac gggacacccc tcagccctca taacagattc caaggagagg gcaccctctt    5280
gtccttatct ttgccccttg tgtctgtctc acacacatct gctcctcagc acgtcggtgt    5340
ggggagggga ttgctcctta aaccccaggt ggctgaccct ccccacccag tccaggacat    5400
tttaggaaaa aaaaaatgaa atgtgggggg cttctcatct ccccaagatc ctcttccgtt    5460
cagccagatg tttcctgtat aaatgtttgg atctgcctgt ttattttggt gggtggtctt    5520
tcctccctcc cctaccaccc atgccccct tctcagtctg cccctggcct ccagccccta    5580
ggggactagc tggggttgggg ttcctcgggc cttttctctc ctcccttttt ctttctgttg    5640
attgtcgctc cagctggctg tattgctttt taatattgca ccgaaggttt tttaaataaa    5700
attttaaaaa aagaaaaagg gaaaaaaaag ccacggagtc cattttatga atgggtgg    5760
gagagggcac taaagagcct cctaagagag cctcaggtta ggacagaatt gtttggggag    5820
ggagaaaaac agaaacaatg aattatagct gcctcacagc catgtataac aataattgct    5880
ccaggaaggt gggaatattt gctttttttt cttctgtaat ctcaccgtgt ccgtgtccag    5940
aacagagcta ggcacacagc aggtgctcaa ttttttgtttt tcgtttagac aggtttcatt    6000
ctttcaccca ggctggagtg cagtggtgct atcatagctc attgtagcct caaactcctg    6060
ggctgaagtg atcctcccac ctcagcctcc tgagtagctg ggactacagg tgcactctgc    6120
catgccgggc taacttttaa aaattttttgt ccgggcacag tggctcatgc ctgtaatccc    6180
agcactttgg gaggccgagg tgggtggatc atgaggtcag gagttcaaga tcagcctggc    6240
caagatgatg aaaccctgtc tctactaaaa atataaaaaa aaattagctg gcgtggtgg    6300
tgggtgcctg taatcctagc tattcaggag gctgaggcag aggattgctt acacctggga    6360
ggcggagggt gcagtgagcc aagatcgtgc cactgcactc cagcctgggt gacaaagtga    6420
gactctgtct caaaaaaaaa tctttgtgtg tgtgtggaga tgagggtatg cactttgttg    6480
gccaggttgg cctcgaactc ccagccaagc aattctgcct gggattacaa gcgtgagcca    6540
ccatgcctgg cctcaaatat tgttgaatgg ctagcagtta agtccttggg tttataagca    6600
tttcctcaac tgtcctccca agtccccata agacaaaaaa ctcataaaat cccaccttac    6660
agaagaggca gctggcccgg cacagagatg ctgtctgccc cgggtcacac agggtggcat    6720
ctgacaccct gtctgagttc ttcactcaga gtctttaaat ataattagcg tatttgacat    6780
aatgtacatt aaaaactata aacctgtcag cctttgtcta ctgcaaagaa tccactacaa    6840
atattgggc agggatctgt tcttggacca tagtagtgtc tccagacctc atggtcctct    6900
tcattaaaac aacagaaaat tccttctggg ccatcagatg agaccatgag atagaagatt    6960
tccaagtgaa gattttgttt caagacagag tcttgctctg tcactcaggc tagagtgtac    7020
tggtgcaatc ataactgtgg tgacagcctc gaacttttgg gtacaagtga ttctcatgcc    7080
tcagacaaca cccaactaat attttggttt ttgtatagac agggtcttgc tatgtggctt    7140
aggctggtct tgaactcctg gcctcaagca gtcctcccgc ttcagcctcc taaagtgtca    7200
ggattacaga catgagccac caagtccagc ctgaagattt ttaaaaatta ttgttagtag    7260
tagtcgccag agttactaca tccaaagtcc ctactaagtt ctaagtagtc cctactaagt    7320
tctaaggcag tttctcaact cattagagtt gttttttgtt tttaaagaaa aaagaggct    7380
gggcacttta ggagaccgac acgggaggat cgcttgagtc caggagtttg agaccaacct    7440
```

```
gggcaacatg ggcccccatc tctaaaaatt ttaaattaaa aaaatgtttt aacaacaaaa   7500
agcgttctgg gagtgagggg ctggggcctg ggcggcctca ttccatatac ctgtgccggg   7560
ttgaggggtt ggagacacgt ttagagaccc ctccactcta ggaatccacc tcgagagata   7620
aaggtcccgg ccctagccac accccaggA cacggccaga ggccacctcc ctaggcgggt   7680
ccctccccac cgccaggttc ctggagcgcg tgccgcgcgt gtgcaggggt aggggccgc    7740 aggcgcgcgg actggagagg cgcgcccctc ccgcgtgttg aaattcaaaa gaggcgaacg   7800 gccccggcg cggcggcgcg gctccggtgg agaggtcaag gcaggggcca gtcggaggct    7860
cccggggcgg ggtcgaaccc gcggccaacc tgagcagcag cggaagctta aagagctcag   7920
gttcccgccc cccggcccta ccatggctac agagcagtgg ttcgaggggt cgctcccct    7980 ggaccctgga gaaacaccgc ctccagacgc cttggaacct gggacgccgc cctgcggaga   8040
cccctccagg tcgacgcccc ctggcaggcc tgggaaccca tctgagccgg atcctgaaga   8100
tgccgagggg cggctggctg aggcccgggc ctccacgtct tcccccaaac ctctggtccc   8160
ccggcctggg ccagcacctc cccgcctatc cctggacact tgttcagcc  ccatcaccca   8220 acagctgcgc tacctactga agaaggcaga tgatttccag agctacttgc tctacaggtg   8280
atgctggaca gggtcccagg tccccatggg taaggagact tggaggggag gcgacaggat   8340
gggtgacaca caccagggtc gcaaaattac aagcgctagg agccagaggg agacagtgga   8400
agaagctagc atattagaat ccagtttaag agaatgagga agactgtaga attgcgggta   8460
ggggatggct gctattactg tcgtggcagg gtgggcctgg ggttgtcaag tctctaggac   8520
tttttctccc agttttaag tgctgtctta cattttgagc cctgtgctgg ctaaacaaga    8580
cccacctgag ccaaacttgg cctgcaggac atcagtttga gactccaaag gataatgtga   8640
ttcccagacc aggtttccct gtgactctca atttcagtgt ccattggaat tcctaggag    8700 gctgggttgg gtttgtttgc gtgtttgttt ttgagatgga gtctcactct gtcgcccagg   8760
ctggagtgca gtggtgcaat ctcagctcac tgcaacctcc gcctcccgga ttgaagcaat   8820
tctctgcctc agcctcccga gtagctggga ttacaggcgc ccaccaacat gtgttgcccg   8880
gctaattttt ttcttttctt agtagagaca gagtttcacc atcttggcca gactggtctt   8940
gagctcctga cctcatgatc cacccgcctt ggcctcccaa agtgctggaa ttacagacgt   9000
gagccaccgc gcctacccga ggctgggttt ttttgttttg ttttgttgtt atgtgttttt   9060
ttgaaatgga gtcttgctct gtcacctagg ctggagtgca gtggggcgaa ctcagctcac   9120
tgcaacctcc gcctcccagg ttcgagggat tctcatgagg ctgtttttt  tttttttaatg  9180 agacagggtc tcgctctgtc acccaagctg gagtgcaagt ggggcagtca tagctcactg   9240
caccctcgaa ctcctggtct caagcaatct tccacctccc ctcctgggta actgggacta   9300
caggtgccac catgcccagc taattatttt tgtgtagaga tgggttcttg ctatgttgcc   9360
taggcttgtc tggaactcct ggcctcaagc aatcctccag cctcagcctc ccaaaactct   9420
aggattgcag gcgtgagcca ctgtgcccag accctgcagg aagctctggg tcctaagtgt   9480
tgtgacactc aggtgtcagc actttaacaa gtgttccaaa tgggtttgat gcaggtaaac   9540
cagaaagatg ttcagaaaag acctgaaact gggggctttt ctaatgggtc aaagccaggg   9600
atacaggttg ggattgagta gaatgggaa  aactgcgggg tggggagggg ttgtgaggga   9660
ttccaggcaa aggcccccctt cttccttcag cagagaccaa gtacagaagg agcagctggc  9720
caaggccatg cccaccttct tacagatgtg tgagccctac ttcctgtacc tggaggcagc   9780
```

```
cgcgagaagc ataccccca tctatggacc cctgcaggag ctggtccgaa aggggtgtg      9840 tggaggtttc ttagacccca cgcccctttc ttctcgcagc tctgagcctg tggggatggt    9900
ggagggggag gcccactcct cgcaggccag ctgatctcac tgtaccccc tcttgtatgc     9960 agctgttaga gatctcccaa cagctgaccc tgcgcctgga acagctggtc ctcatgtacg   10020
cttcctttgg gttcgtggac ctggaggaga tgaaccccct taggtaaaat ggtaggagac   10080
tcagatgggg ggatgaagga gtccaaggcc cagcctcacc cctccattct ctcatgtctc   10140
gccagcatct cctgtttctt ttgcgggagg ttctccatca gcctgtccca tgaggtctcc   10200
atcttcagat actgtgcccc aaccgcctac actgccagcc gcttccccg ctacctctat    10260 aagaagatgc gctggcacct ggaagccacc ccagaggccc ctggtcgggg acaagattcc   10320
cttgtggatt agtaagtcct cttacccaaa tcaaagtcct cccctttcta tgatgaatgc   10380
caatatgacc ctccaaaccg tcaccagcaa agtgaaaagt gagccagggc ccgaggcagt   10440
ggctcacgcc tgtaatccca cactttggg aggccgaggc aggaggatca cttgagctca    10500
agagtttgag atcagcctgg gcaagatggc aagaccctgt ctcaacaaca aagaaattcg   10560
ccaggcgtga tggctggcac ctgtagtccc agctacttgg gaggcttagg caggaggagc   10620
acttgagccc aggaatcaag gctacggtga gctgtgattg tgccactgca ctccaccctg   10680
agtggaagca ataatctgtc tcttaaaaaa aaaaaaaagt gaaccaggaa actaaaggct   10740
tttgaaaggc tacctctatt ttcttaaaac ccaccctccc accaaaataa aagttctcat   10800
cttaaaagta ggctggcagg gagaaaaggc cttggagtca cattcctacc tgagaacttc   10860
agggcaactt ctgatgagtt cccacctcaa ctccaaaatt aaagccctca acagaagtag   10920
ctaggaagct gatcacttct aattacagct ccctcccctc ctagctactt tctgtgctat   10980
cgagatactt gggaagacac aggccagagt ccagccaatt cgtgcccaca gatccagaag   11040
ctgtggtcca tcggccgatg ggtgcccta ggaccagccg aggatgacct ttattcatgg    11100
taggagctag ggcaatagca acgtgggcct gggagctgga gggggaggca gaaccccacc   11160
aaagacaatc caccttccca aacactttgc ttcccttagt agtgatagca ttttattgtg   11220
ccctgaaaag cacttcatgc agaccccagt aacaacccat ggagatctat gctattggcc   11280
ccatttaaca aagaaaacag ggtgctcaga gaagttgtta cctgcccaag gacacacagc   11340
tagcagagcg aatggacagg tcaggaccag ttattcagcc tctaggagcc attactaagt   11400
ctctgatcaa caaggaaaca agtttccccc gggggttttt cccacccgca gctgaaacaa   11460
agcctctttc acctgagcct ctcactcaaa gggagggact cccgaggggc aggggcact    11520 caagtccagg cctgtctatc cctggccccc ccaccccagg attttgtgcc cgcaccgctt   11580
ggggactacc agcagctgct gaccatcggc ttcgaggagc ccacgcccac gctggccacc   11640
gacctgctgg tgcagatcct cacgggccag gcaggccagg cccggcctcc gagcgcagcc   11700
gggcctgcgg ggtgggcagc gcaggggtct tgaacctggg gaagagggta ggagctggaa   11760
cttgacagtt ccaaactcca gaataggggg caggggaggg gctcactcgt tctcgcagtg   11820
cagccgggcc tcgccttcca aagggccagg ccgagctgac ctgtctgcac cgagtccggc   11880
ttggccgtgg ggccctgaat gcggacacgt cagttttgtg ttaaataaaa gaaagaaaga   11940
ggtcacaggc tcagcgtccg ctgcgaatgc gcgcccctc cccgggga ttgcccacc       12000 cactcgcgtg gccttctggg aaatgtagtc ttttgaaaga agcctggaat tcgccaatag   12060
gcggacgaga gtttgcgca tgcgcatagg cgcacatgaa gcaaaaggg aagtggtgcc    12120 cgtcaacacc ggaacccaga aaactgcaag tttagggtac cggggaaatt caacgtccac   12180
```

-continued

| | |
|---|---|
| tggaggaaga gacttaaggc tacgcccact cccatatttt gacccggaag ttatttattt | 12240 |
| tagcgtagaa gactactttt cccgacgcgc cccaggaaag tgccctcgat cagtttccta | 12300 |
| agggcccgag ttagactttt tttttctctt ccagcttttg ggacttgggg gccggacagg | 12360 |
| tcgtcgtctt tcttggggta tccggggtgc ggacaaggtg ggagagccct acggtatcca | 12420 |
| agctt | 12425 |

<210> SEQ ID NO 51
<211> LENGTH: 22255
<212> TYPE: DNA
<213> ORGANISM: Homo sapiens

<400> SEQUENCE: 51

| | |
|---|---|
| caacatgctt gggaccagaa gtgtttccaa tttgggattt tctcaaattt taccggttga | 60 |
| gcttccccaa tctgaaaatc tgaaatccaa catgcacggc tctgaagtct ttcactgagc | 120 |
| ctttggggga aatatttaac atcctaacag ccctaaacca acgctcaatt agcacaacag | 180 |
| tttacaatct tctctaccca gcctgatg cgaggctctg ggactagact atttagccaa | 240 |
| cagttcttgc aaaattaact gacttataag taaatagtaa tttcaacacc tcactgctaa | 300 |
| tgctgtaaca actctgcaga cctagggagc aagtacggtt tgcagagcac tgggaaggct | 360 |
| ctgaagtgac ctttgaactg ggcctcaaaa aattttgggt ttggcaaaag tcaaatctct | 420 |
| taggcttcaa attccaggca caaggattgt tgggtttgat tcattatcc agaagcaatg | 480 |
| gggatacaga attgtgatct catgtgtagg gaactgtggg ggttttttct actttaaccc | 540 |
| cagtgagact ttgtagagtg tggggtagag aaaaggctca tgaatatgcc tgaagcctaa | 600 |
| ctcagcacct ttctgaggaa ctgactgcca aaatggtaat ggagaggga aaatatgacc | 660 |
| tactttcaca agttaccttg actgcctcag ggaaacctgc tgtggtagtg tttcttctgg | 720 |
| gtgaaagacc aggtaattac ctgggtgctg gtctcagact taccagtttt gaatccctgt | 780 |
| tttaaccact cactatcgat atgaccttgg ataagttacc taacctttct cttactgtcc | 840 |
| ttttccgtaa aatggggata acagatagta gttatttcta tgagtggtta tgagaaccaa | 900 |
| gctattagat agcgggaaag cacacagtaa gcgttcaagg aactgctatt gttattaaaa | 960 |
| gcctcctttg gaagaaggac attgaggccc agagagagaa cagaacgtcc agccacacag | 1020 |
| caaatccgtg atgaagttgg gactggagta tgggtctcct gagtctcagc ccaggactct | 1080 |
| atccctcttc ccgagtcctc ggagttcccg gatggagtca catttgttca cggcagggga | 1140 |
| ggaaggtttg atggaggcct gcaggaaaca acagccaggc gcaaggcttt gggagttgaa | 1200 |
| gcatagcttc tgcgagatag aaacaaggtt gacatgggca ctcgtgcaga atgacgggct | 1260 |
| cctttggac tcccaggact acagtccctt atgcaccttg ggatctgcgg ctagcccctg | 1320 |
| cgtaaagagg gacgcgtagt cttttccctg ccccgccctg ccggggcgcc cgcctccgag | 1380 |
| gccgccctcg cttcgtcctt cccagcaagc tccgcgccgg cgccggctat tgattggctg | 1440 |
| aggcgggagc aggcggctgg ccggcagcag ttactcgggg tttccggtgc gaggccagag | 1500 |
| gtggggaagc catcggacgt cggcggtgag gtacgtgcag cggcggccgg tgggcgagac | 1560 |
| tatttgagag tgtgcgggcc gggatgttct cggcctgtgg ggaaatcacg ccaactcccc | 1620 |
| gcgtgggccg ggggctgtct ggggatatgc gcatgcgcg gcgtgcctcg cggcttgagg | 1680 |
| gcgcgcgggg cgtgggtggc tgcgcgcgcg ggggcgcac gtgggcctg aggggcgggg | 1740 |
| gcggtgccgg gagtcccgcc acgtcagtct ccggccctga gccaatcccg cgcccggcct | 1800 |

```
gccgcgaggg ggccggttgt gccgggaagt ggctccaggg agaagaggcc tcttccctca   1860
cccgctgtgg gagctgcgcc ccgaaagcct gccccggcac gtcgggctct cctgacccgc   1920
caagaccaga gagccgttgg cgccctccgc ccgggcctgc cggtccgttt attttaagaa   1980
gctttgtgcg cctgctgtgg ggatttctga tccaggctgc gaagaatttc gaagtctgga   2040
aaatagcaac tgtgtttgtt tctaaaggat cttctcctga cccagcatcg ctcatcacaa   2100
tgaagaacca agacaaaaag aacggggctg ccaaacaatc caatccaaaa agcagcccag   2160
gacaaccgga agcaggaccc gagggagccc aggagcggcc cagccaggcg gctcctgcag   2220
tagaagcaga aggtcccggc agcagccagg ctcctcggaa gccggagggt gtgtgccagc   2280
tctgcgttgc cagcgggcag ggggaggagc tgtgggtcg ccctcgcttc tggacttaca    2340
ggccgaggcc aggttgtccg ggaggaggag atgtagaatg agaggacagt gctggggggcc   2400 gcggtccccc ctgcgctctg gcgagttggc ggagctgccc cctctaagca caggaacaga   2460
gttctggaga gaagctccga cgggattaag tcaggtggca gccaaacgag gcacccagtc   2520
aggaaatcca ggtcccgtta gaaacacctc agccaccagc agctaactgc ccttcctgtt   2580
tgaggcattt ctagaatgat ctgaatggca agaaatgggt tttgtggggg ggaaggagat   2640
ggactagaag ttgctccgtg ccatccctgt gtgctgatgc tttacatact tttatgatct   2700
aacaaatatg ttcgggtggt agtgagaaat agttgtgtca ttttacaagt aaacagactt   2760
aaagaagtta ggcaacgatt actataattt cttgatttaa aagatgtttc gaatctaaat   2820
tctgacagga actagatttg ctgaatgata ctccattctt gcttctcagt ttccataaaa   2880
aaaaaagtta ggcaacattt aactcaaact gatgagtttg gctgggcctg aaaaatccca   2940
accagtggta taatcgtctt ctttctcact ctaccccctca tcctctcctg ctgtaggggc   3000
tcaagccaga acggctcagt ctggggccct tcgtgatgtc tctgaggagc tgagccgcca   3060
actggaagac atactgagca catactgtgt ggacaataac cagggggggcc ccggcgagga   3120 tggggcacag ggtgagccgg ctgaacccga agatgcagag aagtcccgga cctatgtggc   3180
aaggaatggg gagcctgaac caactccagt agtcaatgga gagaaggaac cctccaaggg   3240
ggatccaaac acagaagaga tccggcagag tgacgaggtc ggagaccgag accatcgaag   3300
gccacaggag aagaaaaaag ccaagggttt gggtgagcag agggcggctc tttgtgaagc   3360
tggtgaggag agggagtttg acttgacgt tctctgggcc agtctgttct gccaggattc    3420
aaaggaaaac ggtacttctc agagcagcaa gtcactctag tctaatcaaa gccaggatg    3480 tgggggccac ggcatagaga gatgcaggag ttaccagcac aaagccttct gggttttgga   3540
gcaactggag cttggcatgg gacctgttct ctctttgaga aaatggagac gggaggctag   3600
ggtaggctcc tgtgccagcc agtactacct gctgtgtgac cttgggtgtg tcccttctcc   3660
tctctgggtc ttagtttata tttctcttta cagtaagaaa attagactag gccagagttg   3720
aaaacccaaa tatctgcata agctgggctt ggccatgggg ccacctgaag atggaggctt   3780
tactgcttcc ctgattagtt gctctcacta gccaactgag agcaggcaaa actacaggct   3840
gggtgcagtc aggcttttt ttttttttt tttttttaaa taagaaaaag ccagaaatct    3900
agagttatgt gagaactcta gattttttca tagttagcag ctaaaatggt aagagccaaa   3960
caaaacccat ccgtgggttg gatttggcac acatgcctgc gaattgcagt ctccatgctg   4020
atctcttggg cccttctggg gaggcagagg gaaggctccc tgactcagtc acaggcaatg   4080
gggataggca agtgacagtc attttacagc agggtatgta tgtttaagag tctaggccga   4140
ggtgtggtgg ctcacgcctg taattgcagc actttgggag gccgaggcgg gtggatcacc   4200
```

-continued

```
tgagggtcag gagttcgaga acagcctggc caacatgatg aaatcccgtc tctactaaaa    4260
atacaaaaat tagctggaca tgctggcaca cgcctgtaat cccagctact gggaggctg    4320
aggcaggaga atggcttgaa cccgggaggc agaggttgca gtgaactgag attgtgccac    4380
tacatccagc ctgggtgaca agagtgaaac tctgtctcaa aaaaaaaaa aaagaatcta    4440
gaatctaagt cgagtgtcat tatatccatg ttttattcct attccctttt cccttatgt    4500
atcctcttac tttaaagagg aactttaaaa aatcttaggg acgactaggc agagtggctc    4560
acacctgtaa ctccagcact tgggaggcc aaggcaggca gattatgagg tcaggagttc    4620
gagaccagcc tggccaacat ggtgaaaccc cagttctact aaagatacaa aaaatcagcc    4680
gggcgtggtg gcacgtgcct ataatcccag atactcggga ggctgaggca ggagaatcac    4740
ttgaacccgt gaggcaaagt tttcagtgag ctgagatcat gccattgcac tccacctggg    4800
tgacagggtg agactccatc tcaaaaaaag aaaaaggaaa aatcttaac gtcacataca    4860
tggaaagatc atcttttttca ccccccaccc ccaactgaga tggagttttg ctcttgtcac    4920
ccaagctgga gtgcactggc gcgatctagc tccctgcaag ctccgcctcc cgggttcaca    4980
ccattctccc tgcctcagcc tcccgagtag ctgggactac aggctcctgc taccatgccc    5040
ggctaatttt tttgtatttt ttttagtaga cgggggttt catctgtgtt agccaggatg    5100
gttttgatct cctgacctcg tgatccgccc gcctcagcct cccaaagtgc tgggattaca    5160
ggcgtaagcc actgcacccc gccttttttt tttaattaat taattttttt agacagagtc    5220
tcgctctgtc ccaagctgga gtgcagtggc gcgatctggg ctcactgcaa cctccgcctc    5280
ctgggttcac ggcgattctc ctgcctcagc ctcccgagta gctgggacta caggctcctg    5340
ctaccatgcc cggctaattt ttttgtattt tttttagtag acgggggtt tcactgtgtt    5400
agccaggatg gttttgatct cctgacctcg tgatccgccc gcctcagcct cccaaagtcc    5460
gcctcagcct cccaaagtgc tgggattaca ggcgtaagcc actgtaccct gccttttttt    5520
tttaattaat taattttttt agacagagtc tcgctctgtc accaagctgg agtgcagtgg    5580
cgcgatttgg gctcactgca acctccgctt cttgggttca agcgattttc ctacctcagc    5640
ctccggagta actgggacta caggcgcgtg ccaccacacc aagctaattt ttttgtgtat    5700
gtctttagta gagatggggt ttcaccatgt taggatggtc tcgatctctt gacctcgtga    5760
tccgcctgcc tcggcctccc aaagtgctgg gattacaggc atgagccacc ttgcctggcc    5820
gaaagtatct tcattttaaa gttcactgtt tggctactct gttgacaaga gtttagtatt    5880
tctcaaggag gctaagatac ctattccttt ttggatccta cctctatcag gagggtgggc    5940
cttccttgca ttgaaacagt atgaaaacag tagcccctgaa ttcataagtg ggacacctt    6000
cttctattgg tagagcaggc agttttttttc tcctgccaat ggtgcctact aaggagattt    6060
cactagggta cagtcgttca tttgataagc atttgttgag catatcctct gtgatggtac    6120
tatggacagt actgggggcta tagtgagggc aggattgagt tggtccttat ggcaaggaag    6180
gcagctaatc aacaagcaaa atataaagta tgatggggag ggctgtcttc agcactcatg    6240
agtgtgagcc caggcctgga ggggacacct ggagaagagg gtgcatgtct ttgctcctgt    6300
gcttttcagg gaaggagatc acgttgctga tgcagacatt gaatactctg agtaccccag    6360
aggagaagct ggctgctctg tgcaagaagt atgctgaact ggtcagttcc cccctccgcg    6420
ggcaccttcc ctgcgttggg aaaatcagca tgccacctgg tgtaaggttg ggggtgcaga    6480
gtcaagtagg tggcttaatt cctgttcagc ttttctctga actatctgtt aaatgggaa    6540
```

-continued

| | | | | |
|---|---|---|---|---|
| tcacttccag | ccagcctctt | cagggctgtg | cagcaagagg | agaaactgca | tattccttga | 6600 |
| aagaaatttc | tcaaagaatg | attccaaggt | ggtagagccc | ttgttcctgg | cctgagtcca | 6660 |
| agacaccttg | tgatcttgat | gcttcttcct | caaatacaga | tgcatagagc | cattatcaca | 6720 |
| gttaataaaa | ctaacactag | tcacttgata | cttttttcctt | ttactccaga | gcagtcttct | 6780 |
| tgtcactgcc | tcctcatatt | ccccatgaca | ttgactttta | acagaaacta | gactagctgt | 6840 |
| cttgtaggat | gccccttct | agctttgtca | tctctgtggt | atcattttac | ttctttacct | 6900 |
| cctggtacat | gtaagtgaag | tagaagttag | ctctaaagct | tgatccaatt | cagcttcaac | 6960 |
| tttttgacaa | gaattcttca | taagtacttc | atgttccatc | acaataaatg | caaagcatgc | 7020 |
| tcttcccact | tgttgtaac | attgttcagt | gggttggggg | tggggcagcc | agattcttcc | 7080 |
| atcatcaggt | cccttgtcag | aatttgaact | aacagattta | tccattgatg | gtcacagcct | 7140 |
| gtgtatgtat | gtatgtatgt | atgtatgtat | gtatttattt | atttatttat | tttttgagac | 7200 |
| ggggtcttgc | tctgtcgccc | aggctggggt | gcagtggcac | gatctcggct | cgctgcaagc | 7260 |
| tccgccttct | gggttcatgc | cattctcctg | cctcagcctc | ccgagtagct | gggtctacag | 7320 |
| gcgcccgcca | ccatgctagg | ctattttttt | tttttttttt | tttttttagta | gagacggggt | 7380 |
| ttcaccgtgt | tagccaggat | ggtctcgatc | tcttgacctc | gtgatccgcc | cgcctcggcc | 7440 |
| tcccaaagtg | ctgggattac | aggcttgagc | caccacgcct | ggcctattta | tttatttatt | 7500 |
| cagagtcaga | gtctcgctct | gtcaccaggc | tggagtgcag | tggcgcgatc | tcggctcatt | 7560 |
| gcaacctcca | cctcccaggt | tcaagcgagt | ctcctgcctc | agcctcccga | gtagctggga | 7620 |
| ttacaggtgc | atgtcaccat | gcctggctaa | attttgtatg | ttttagtaga | gacagagttt | 7680 |
| cagtatgttg | gccaggatgg | tcttgatctc | ttggcctcgt | gatccgcccg | tctcagcctc | 7740 |
| ccaaagtgct | gggattacag | gtgtgagcca | ctgtgcctgg | cctctaagta | tttattttaa | 7800 |
| aattaattca | ttccacacac | atttattaat | attttcctgt | aaggaactt | actcatcttt | 7860 |
| aaaatgggga | atgtcatacc | tgcctaatga | cattcttgta | aggattaaat | aaaaggtata | 7920 |
| aggaagataa | gcacccttt | ggagtgatcc | agccagggga | aaattgctga | tgcaagagag | 7980 |
| gaaatgagtt | gctagagtgg | tgttgtgagt | agaggagggg | agctgaggcc | tgcccaagaa | 8040 |
| gggggcttgg | ctgtggtaac | cacatggcta | ggtctgtgtg | actggaggag | aggacgggc | 8100 |
| aggtggactg | gtagatgtgc | agcttgtgcc | cctgattctc | tagtttcttc | tgtgttttga | 8160 |
| gatttgatga | gaacgatgaa | atagttgtct | ggaaggagag | gagtgtgaat | agcatatgca | 8220 |
| ttgtattggg | attgctggtc | ttcctgaaat | tggtggccat | gaatttaaag | tgagactctt | 8280 |
| caagtagggt | tgtttatagta | ctggtgtaaa | gcaggaaggt | gctttactag | ggttgcagta | 8340 |
| ctactgggga | agggccaaga | gagttgaggg | tgtaagaaat | ccaagccagg | taatgtagtt | 8400 |
| attttaaagg | agagtggaag | gatggttgag | tcaatggatt | ggaggtccta | tagggtaaga | 8460 |
| gactttctga | ggatcacaga | tactgattgg | aatgagctaa | aaagataggt | gatggtagtc | 8520 |
| ctggactggg | atgctggaaa | ttgagatagt | gggtgtgctc | tctggtagtg | acaaatctag | 8580 |
| atctgcgctg | tccaagataa | attcgtctct | agctaattga | catgtggcca | gtttgaattt | 8640 |
| gaacatgcta | taaatgtaag | atacacatca | gcttttgaag | acttaagcaa | aaacaaagaa | 8700 |
| tataaaacat | cttttttgtga | gagagtgtct | cagtcaccca | ggctggagtg | cagtggcgtg | 8760 |
| atgtcctgct | tccaggttca | aacgattctc | ctgcctcaca | gcctcctgga | gtaactgaga | 8820 |
| ttacaggcgc | atgccaccaa | actggctact | tttttgtatt | tttttttag | tagaaacggg | 8880 |
| ttcaccatgt | tggccaggct | ggtcttgaac | tcctgacctc | aagtgatctg | cctgcctcag | 8940 |

```
cctcccaaag tgctgggatt acaggcatga gccaccactc ccggcctcac tttttttacat      9000 tgattccgtg ttgaaattgt aatgttttgg atattaggtt aaatacatat attactaaaa      9060
ttaatttcac ctgttttttta cttttttagt gcggccagta gaatatttt aattacttat      9120 gtggtttgca ttatatttct gttgtacagg cctggatagg gtcatgggag gggaactgag      9180
ctggggaaag gagtgggttt gtggaagagg tgatggactg tgaggccagg gagttagaag      9240
gattatctgt tgatactgaa gtggccacaa atgagaaaag taattgtgtt ggggagagcg      9300
ctgatgaacg cagcgctaac gttttgaagg aatgcgaggg agcgatgggg gtctgtctgt      9360
taataggcac aaggtacggt agcaggtggt ctcatcctcg ggcatgagtg tccagcaagt      9420
tggggaaatg caacagcttg aagtggctct agtggcccag agtcagagct ggaataggaa      9480
ttggcatctg ctggctgtgt ggcccctgct tgccctagtg agttaccatt tctctgtccc      9540
tacggtggag cctttggggt tattgtgagt tcatgggagg agcgtgtaag caccggcaca      9600
gcatcagccc atgagagtgc tcctggcctg agagggtaag ggtcagggca gctcaggaga      9660
ccctagacct gcatagtgat ccccccacca ggaaggcccc acaagatgct cacctgccct      9720
ccctatccct gtccccagct ggaggagcac cggaattcac agaagcagat gaagctccta      9780
cagaaaaagc agagccagct ggtgcaagag aaggaccacc tgcgcggtga gcacagcaag      9840
gccgtcctgg cccgcagcaa gcttgagagc ctatgccgtg agctgcagcg gcacaaccgc      9900
tccctcaagg taggcctggg cccctggaa caggtgactc tggtttcctt gacttccact      9960
taatgtttct ttcatgggct ttcctcttaa aaagtagtgc aggctagggc caggcgcagt     10020
ggcacacata agtgattaaa aatcttctgg ccactaaaaa acagaaatta attttagtaa     10080
tatacttaac ccaatatcca aaacattaca atttcaacat gaaatcagtg taaaaaagca     10140
aggctgggtg tggtggctca cacctgtaat cccaacactt tgggaggctg aggtggatgg     10200
atcacttgag gccaggagtt tgagaccaac ctggtcaacg cagtgaaacc ccattctact     10260
aaaaatacaa aaattagccg agtgtgctgg caaatgccta taatcccagc tactcaggtg     10320
gctcaggcat gagaattgct tgcacctggg aggctgaggt tgcagtgagc cgagattgca     10380
tcactgcatt acagcctggg caacagagtg agactcagtg tccaaaaaaa aaaaaaagta     10440
gtgcaggctt gtggcataga aatacacttt ctcaataatg ccttacgtta agagagtact     10500
gcttgtaatc atttgacatg tattagataa ggtgaaggat aaagtactaa gagaatccat     10560
aatgcactgg cgttagtatt tctcaatgaa atgacagtcc cctggtaagc ggaggcctgg     10620
ctctgacaag cagctcttgt cccagacgtt ggtcagtcag gaacctgggt ccttcccatg     10680
ttctgctgct tctatggtga ggtcagtctg tggttacacc aagtttaaat acagcctttt     10740
aactttcttt tttatatgta aaatcttaca tgtagttttt agaatgaaat tattatacat     10800
gtaccatttc atatcctgtg ccttttttc actttacata acattttcc ctatcagtat     10860 gtgtagggct atcttctcat tatatggata tattatatca gtgccctagt taaagcattt     10920
tgggggttgt ttacaatttt tcattattac atatagaact atagtgaaaa ttcttgttat     10980
atttatcact ggtcagttat atagaactta tctgtaggat aagtcatgga attgaaatgg     11040
ctaggtcaca gtatatgcag attttttcatt ttaatagatt ttgctggatt gccttccagt     11100 gaggggggcag tgtgccttcc ccatcaaaag tgttgagtgc ctaattctgc acaactttgc     11160
aaaccctggg tgttactaaa ttttaacagc ttggtctctg ggggtacaga ggggacaaat     11220
gcacattaat ctgaaatctg gaagaatagg ccttaggaga tccgacttgc ttcagaatgg     11280
```

```
cacttagcac ttacatgtgt gcatgtgtgc ctgcattttt tcttccttt tttttttttg      11340
gggacggagt cttgctctgt ggcccatcgc ccaggctgga gtgcagtggc gcgatcatag      11400
ctcaccacaa cctccgcctc ccaggttcaa atgactcctc tgcctcagcc tcccaagcag      11460
ctgggaccac aggtgcacac catcacgccg gctaattttt gtattttagt agaaacgggg      11520
tttcaccata ttggccaggc tggtctcaaa ctcctgacct cgtgatccgc ccacctcagc      11580
ctcccaaagt gctgggatta caggcgtgag ccaccgcgcc tgccatgtgc ctgcattttt      11640
ctaggggggag aatctcactt gatgtcacct gatatacaga ggggcccatt ggaacccgca     11700
ttgcacaaca tcctggagtc tggctactcc acgctttggg agcagggagg ctgttggca      11760
gagaccatct gtggactagc tgggggaccc ttgtgaggta gcagtggatg atggctctcg      11820
ggctgacttc tttgcccagg aagaaggtgt gcagcgggcc cggaggagg aggagaagcg       11880
caaggaggtg acctcgcact tccaggtgac actgaatgac attcagctgc agatggaaca      11940
gcacaatgag cgcaactcca agctgcgcca agagaacatg gagctggctg agaggctcaa      12000
gaagctgatt gagcagtatg agctgcgcga ggaggtaagg gtatcacgga cagcagtcat      12060
ggcccagaaa ttgtgaggtt ttgagtgtgt gctaggcact gggacagtac cttttcaggc      12120
ttcatcccat tctccctttc ttcctcctcc tcctccttgg gaggagagta atgttattcc      12180
tcatagataa aaacaggtg tggagaagag actcacttac agccacacag ccccaggtcc       12240
acagtgcctt gtcccaaatg actgggccag gcatcttttg gaattagaac tatccacatt      12300
ttagaatgga ggtacatgta tggactgtgt gttatatagc ccctcagca gggccttggg       12360
gaagccagac acattaatgt atttatgcag tagaacttcc aaatactcac ctacattatg      12420
ggcttacaat gatgcaggtc aagtctggct gccagcttat gacaatttcc attttcagaa      12480
cttttgtagaa tttggaattg caggggaggg gtgtacctgt gatcagtgat ggactccaga    12540
gactgtgtcc actgattcct tgctgctcct gccactcaaa aggcagaatt tatcaggctg      12600
ggcgtggtgg ctcatgcctg taatcccaac actttgggag gccaaagcgg gcggatcacc      12660
tgaggtcagg agttcaagac cagcctggcc aacatggtga aaccctgtct ctactaaaaa      12720
tacaaaaaat tagccaggtg tggtggtgca cggctgtagt cccagctact caggaggctg      12780
aggcaggaga attgcttgaa cccaggaggc agaggttgca atgagccaag attgtgctac      12840
tgcactctag cctgggtgat ataccgagac tccatctcaa aaaaaaaaa aaaaaaagc        12900
aggatgtcac tcccttttgtc actgcgttgg ctgccacccc aggcacttga atctttggat    12960
cttccctgcc agtcacctgg ctgttctggg cgcgttctca tcatgagaag ggagacctgc     13020
agcccccta cagggctggc agaggacctg ctctggatta ggccctttcc tagcccctgg      13080
ggtgtggcag tgggtgagac cgggaagatc tgccctctta ggttcatagg ccaaagtgat     13140
gatcgtgtgt gcaggaccta gagggcgctc ccctgaccca cccctttcct tgccatactt     13200
catcctctgg gaacaaagct gcttgtttgg tttgagggga gttggtttgg ttcttatccc     13260
tcagcgctga gacatagagg cttcctgggc cactacagtg agacacgaac ttcaagaatc     13320
tgaataccc cgtttctct ccccgccaag gcaaaaaagg acttagtact acctgtggag       13380
aaggaggtgc aggactacca ggccctgctg ctttgcattt acagccctcc ccagacagac     13440
acaggcaccc tcatcatacc caaactggac ttacctgcta ggcaccttcc cttcccatc      13500
caaaaaaatg gagttatttt ccctttttc agcaagtcca gttgatttta cctttgaagt     13560
agcacctgag tccttcacct tctctccatc ccttctctct cacctgacac aggtctgcag     13620
cgctcctcta gtaggcagga cagccattcc ttggggatgc acatgtctag tctttgccta     13680
```

```
gatatggcaa gtctttgcca actgagctag gctgttatgt tcttagaggc attgttttg    13740
cccattcttc ccatttacaa gagaatcagg gacacagaag tgagggcttc cagccccata    13800
ggtgatcaat cctgggtca gagatttgag tgtgtttatt gcttgccttc ttgggagcag    13860
attccatcca taaaccatgt gcttaccaag gtctgactca ctgggagaga aacgacgtga    13920
ggttggaaag ctgaccttcc agagacttgg ggcccatgtt gtgtggtaca catgggagtc    13980
catcatatca gattgagatg ggggctggg caaagtgccc tggtctgtgg ctgtggggct    14040
accctgagaa agggagcgcc tgacaagccg actgctccca ccatctttgt tgcagcatat    14100
cgacaaagtc ttcaaacaca aggacctaca acagcagctg gtggatgcca agctccagca    14160
ggcccaggag atgctaaagg aggcagaaga gcggcaccag cgggagaagg attttgtgag    14220
gctcaggccc cagggttggg gtgggggtgt gggaggagac aggctgggct ctggctcagc    14280
tcatagccgg gttatatggg agaagtctgg ccagaccagg cacagattcc ttgagtacca    14340
gtctgagagc aggaagcctc agtgggtctg gtgcttgtgg ctaaaaacca aacatagccc    14400
ctggggggctt ctgacaggat ctggggttct gtcttggaaa tagctcctga agaggcagt    14460
agagtcccag aggatgtgtg agctgatgaa gcagcaagag acccacctga agcaacaggt    14520
gagagcatat aacctgaccc tgtgccttca agtttccctc actgggcccc atcctgggggg   14580
tagtgaaatg ggaccctcat tctaggactg gctgtgtcct ggctgctatg acgccttggt    14640
tgagcttagg tgggctcaga ggacttcatt tgtagctcag aaatgtattg cttttgagga    14700
ggtaggaaca gaagagtttg aaaatcaaca taaaggcaaa ataaaagtca ccctaagtct    14760
cctactttcc aggcttagca ttttggatta tatccttcca aatatatagc tttgctttgt    14820
tttaaggaaa aatagtatct caatagaatt actggtcaga gagtcaagga cgggtctgag    14880
tgtgttgacc agagtgcctc ccagagaaac ccagtcttat ctgtgggctg ctttctcccc    14940
acagcttgcc ctatacacag agaagtttga ggagttccag aacacacttt ccaaaagcag    15000
cgaggtattc accacattca agcaggagat ggaaaaggta actgtggtcc aggccaggca    15060
tggctgctgg ggcataagct gcttcattca aaattgttgg gcctgccttc aggaagctcc    15120
catctggggt gtctcaaggg cagggctgtt aggaaggttc acagcctttc ccctcttgag    15180
gcagtatcag tggtatgtat acactccagg ttgtcccagg gaatgggggca gtcttttctg    15240
tttgtttggt ttttttgggg ggtttgttgt tgttgttgtt gttgttgttg ttgtttgaga    15300
tggagactca cctattgccc aggctggagt gcagtggcat gatctcagct cattgcagcc    15360
tttgcccccc gggttcaagt gattctcctg cctcagcctc ctgactagct ggaattacag    15420
gcgcgtgcca ccatgcctgg ctaattttt ctttctttt tttttgtatt tttagtagag    15480
acggggtttc accatgttgg ccaggctggt ctcgaactct tggcctcaag tgatctgccc    15540
gccttggcct cccaaagtgc tgggattata ggcgtgagcc accatgcctg gccccttacc    15600
attccttgtt attggtggtg gacacctctg acttcctggt ggtgaggtgg cacagagggc    15660
attgactgca tcctgtaatg ccttgcgcct tgggatcaat cattcccac cttgagaca    15720
caggtgcagt ccccaccttg gagacacaga ccttggagag gccagctctg accatttcct    15780
tctgtctgtc acataaccta gatgactaag aagatcaaga agctggagaa agaaaccacc    15840
atgtaccggt cccggtggga gagcagcaac aaggccctgc ttgagatggc tgaggaggtg    15900
ggctgtctgt gatctgcagc cagggtgggg gtgtgcactt agcgcatatc aggccctttc    15960
ctgtatgttc tacccatcag tgacacagct agcatgaggt agaggtgaga tttgcacaca    16020
```

```
atgtccaagt ccaaagttaa tgctgttctc tccccatggg aggtggtgag cccagtggta    16080
ggtctccagt gggagtgaag ggagcaaatg gaagaaagga ataaaagagc agaaaaaaac    16140
gggtgccagt gatgtgcctg gtttacatgt aaagcagccc aggtagtttg tgatttcaca    16200
gcttgtaatg tagaagaaag gaactaacga tggagcagca actgcaagcc agaccttgct    16260
gaaagttttt gggtttttt tgtcttttt gctgctgaat gttttaggt acgttgttca       16320
ttgaaccttc tcttgagctc tgaggatggt attagtagtc ctgttttata gatgagacag    16380
gctcaaaagt caagtccttt gccaaggtca cgtggtagat aaatggagga atacgttatc    16440
tccaagccgt gccccttttc tgcaccatgc tgccccacct gacagcctag tcatggcttc    16500
aactaggact gtttcctaaa gggggccagc tttggactcg gtctgctctc agccttgtta    16560
aagtgtttgc cgccaagtgg tgatggtaag tgggaggttg atggggcacg gcactgaagg    16620
tctcatttct ttccctagaa aacagtccgg gataaagaac tggagggcct gcaggtaaaa    16680
atccaacggc tggagaagct gtgccgggca ctgcagacag agcgcaatga cctgaacaag    16740
agggtacagg acctgagtgc tggtggccag ggctccctca ctgacagtgg ccctgagagg    16800
aggccagagg ggcctggggc tcaagcaccc agctccccca gggtcacaga gcgccttgc    16860
tacccaggag caccgagcac agaagcatca ggccagactg ggcctcaaga gcccacctcc    16920
gccagggcct agagagcctg tgttgggtc atgctgggaa gggagcggca gcccagccag    16980
gcctggccca taaaggctc ccatgctgag cagcccattg ctgaagccag gatgttctga    17040
cctggctggc atctggcact tgcaatttg gattttgtgg gtcagtttta cgtacatagg    17100
gcattttgca aggccttgca aatgcattta tacctgtaag tgtacagtgg gcttgcattg    17160
gggatggggg tgtgtacaga tgaagtcagt ggcttgtctg tgagctgaag agtcttgaga    17220
ggggctgtca tctgtagctg ccatcacagt gagttggcag aagtgacttg agcatttctc    17280
tgtctgattt gaggctcaga cccctccctg cccttcagag ctcaagacaa gtaatacacc    17340
caggtcttga ctgcatttgt cttgtgagca gggcttgctt ggtcagctca ggccctccta    17400
gctgctctgg aggctccttt gattctctag acctggaaaa ggtgtcccta ggcagagccc    17460
tggcagggcg ctcagagctg gggatttgct gcctggaaca agggacctgg agaatgtttt    17520
tgcgtgggat gatgtgctgg tcaggagccc cttgggcatc gcttcccctg ccctttggta    17580
gtgccaggac caggccaatg atgcttctca gtagccttat cattcacagg tgcctctcta    17640
gcctgcacaa atgattgaca agagatcacc caaaggatta tttctgaagg tgttttttc    17700
tttatttctt tttctttttt ttttttttc tttttcttt ttttttgcac atgacagtgt      17760
ttgtattgag gaccttccaa ggaagaggga tgctgtagca gtggtgcctg ggtgcctggc    17820
ctccagtgtc ccacctcctt caccacccca cttggctcct ttgccatctt gatgctgagg    17880
tttcctgttt ggtgagatca ggttgtttgt ggtaaaagaa aggaaagggc ttctgatggc    17940
tttgccacaa gcttacctgt gggtttcagt cctgagaggc caccaccagt tcccatcagc    18000
actgtctcca tgcagcagtt gctgggtccc atgtccagct gcctctttgg cttcatgggt    18060
ttttctgctt cctgccccca cccccacatg tgcaatcctc aagatttgtc ctgattctat    18120
ttcctggcac ctccctgcct gtccttgggg attctacttc ttcctgtgtg ggagcccata    18180
gctgttgtct aacaggtaag aaatgaaatt gaactattga ctgggcccca gaaatccata    18240
aaatggctgc agacagttgt ttctgtgtcc tgttctaccc ccactccagt acataactac    18300
tatgtactgt gtagagccat tctatatgct gaatgttctg ctgttgcaaa cttgccaggg    18360
tattagccag tgtttgtgcc aagcagtttt ctgggacaac agaatgactc agaccaagat    18420
```

```
ggataggatg gttagggctt tgcttcttgc tgttttctt tgaagctagt tcattgtcct    18480
gcaggtccct tcatcttcca tacctagccc actcttttag cccttacctt aaatctctca    18540
gataagttgg ttcacaaaga atgttaagta ctgaatcatg tgtgactgag accagagatg    18600
gcaaatgaat ggcacaccat ttctccttct cctgccccag ggcaggtacc actgatctgc    18660
atcagagttg cctgctattc tctggtgtat ccttcacatc taggtgccct caagcagctg    18720
tgtgagtgtt gagatctctg ccatctctgg ctgagatact gctgtcctgt gaagtgtttc    18780
ccatgacctt tttcttcccc tttgaatccc tctgtctgga gtagtccttg cctcttcctg    18840
ctccagtagg gccttttccc taccccagcc cctgtgccag gctaagctgg tacaagagct    18900
gccaacctca cagagtgttt gctaggcgag agaggtgcag ggaagaggca gaggtatgca    18960 ccttcccct tgaagagagg ggaaaggcct acagtggccc acataattgc ctgactcaca    19020
cttcagctac ctcttaatgc ctgtggaggg actggagctg ctggatccca gtgtggtggt    19080
gtaggaggcc acagtgagca ggtggcccca gctgggtttc ccaggtcagg aatgtgggcc    19140
ccaggcaagg tgcagccttt gctcacagct ccatccatgt ctagaccttc aggccagtct    19200
gcagatgagg ttccctacct ttttcttctc ttcattgacc aaatcaacca atcactacag    19260
ctgctctgct tctgctttcc aaagtagccc aggtcctggg ccagatgcag gggaggtgcc    19320
tatccatgag tgaaggccag tgtcttcctc acctgggtgg gtcccacact tgtgacctca    19380
gttttaggac caagatctgt gttggttct tagattgcta gcttttcctc caggggacca    19440
cagcaggtga agctcaagag cgcatggctc tgctaatagt aaattgtttt cagggccttg    19500
tccagctgag agcttcatgt ccaccagatt ctgagaggtg tcagcagcac tttttttttt    19560
tatttgttgt ttgttttcca tgaggttatc ggaccatggg ctgagctcag gcactttctg    19620
taggagactg ttatttctgt aaagatggtt atttaaccct tctcacccca tcacggtggc    19680
cctgagggct gacccggagg ccagtggagc tgcctggtgt ccacggggga gggccaaggc    19740
ctgctgagct gattctccag ctgctgcccc agccttccg ccttgcacag cacagaggtg    19800
gtcaccccag ggacagccag gcacctgctc tccttgccct tcctggggga agggagctgc    19860
cttctgtccc tgtaactgct ttccttatgg cccagcccgg ccactcagac ttgtttgaag    19920
ctgcactggc agcttttttg tctcctttgg gtattcacaa cagccaggga cttgattttg    19980
atgtatttta aaccacatta aataaagagt ctgttgcctt acttgttct ctcctgacct    20040 gtgtattcct ttgtttctgg atctgatcca ttcagcccct tccatcatca ctgacttgtt    20100
caggtctgct gcagagcgcc catggtggtt ccctggtatc ttacatattc cacagtgtct    20160
ttgagcagtc gccacagcct caggatgctg gcatattcac ttgagctgcc tgagtggagc    20220
ccttggcaaa gttggcaaga cccttgcctc agagaggatc acacacacac aaaaaagttt    20280
tccctgacct gggggctcac aggctagtga agggaaaagg tacttttagc tatagacagg    20340
tcaatggtgc tgagagcaga gaggaggccc ctgcccccctt cagcaaggtg agggggtgat    20400
acctggaatg gccttctgaa ccacagggca ggtagaagat gaacgtcatt tagtgattaa    20460
atggtacagc tgggaagcag gtccatggga ctgggagagg gggtgaggct gggcccagag    20520
tctgggtacc aggttaagga atgtgggcta gatccagagg gcagggggg caactgaagg    20580 tgtttcaata ggaaattgat aggctccagc agtaaggcaa aaggcatgga gccaggcata    20640
ggccatttga ggcccaggtt aagaggggtg gacactcatc actgctattt gggtctgagc    20700
tgtgggtagg ctcctatagc cctggcctgc ccaagggaat tcacagggc ctctaattgt    20760
```

```
atgcattcct taaggagagc acattctctg ttcagttttt acaccccca tttacccacc    20820 tcaagcatgg gactcctata tgggagacat gctgctggtg ccctcaccca gcaccctgtt    20880
ctctctgggt cctgggttgg tcaggcacaa aggatgatat gtgctgaatg cccaggaaat    20940
ggcagagaca acccacctgc ccttccctcc aggcctccac aaatagatgt gcccacaatg    21000
actgtgacag tcccagcaga gcctctgacc cttctagctg ggtcctgata catgttttcc    21060
atgctggcca tgttatttct agtcgcagat cctctggagg gtgtgggggg ggtgccgccc    21120
caactcttgg agattccaag caaagcagct ctgagaataa tgaggtttct gaccccccag    21180
tgaagcagct gaggatggga accacagggg tgctccctct gtcagcagca ttaccactgt    21240
ctactctagc agctccggtg gggaaggaga gggatttctg ttgtcccag tctgggcccc    21300 tggttattga aaaagttcgg aattactctt taccttgtg gagtgttctg agtgttggaa    21360
gtacccagga agaagccctg agcaggtgcc ctcaggagca gtgcccatgg ctccccacat    21420
cagccaagag gcccaacccc aggaagccac tcctgcccgg ggatggggaa ggtgggctgg    21480
gtggctgtgt gcactgccct gggccagctc acttgagcct gctgagccgc ctggccaaac    21540
atgagcctct ctcctgttgt atcagatgct gttctgggga cctgcgccag gagcctctgc    21600
cagggcttta aatagctgcc cccattgatc tggctgcagg cagcagcagt cacactgggt    21660
cagcctccat caggtgctca ggtttccctg aggactggag tcaggtgcca gggaatcgcg    21720
tggtctacct tatgacctgg tgctccccac acctgtctcc taggcctggg gggtggggag    21780
gactcctgtc acttcatctg cggcaaaata cagccccac cacttaccag agaaaactgt    21840
ctggcattgt agagagaggg gttttgccct caaaagactg ttgcttactt tcagtagaat    21900
ggggaatgac actggtatct tccttaaggg ttgttatggg gatgaaatgt atgtaaagtg    21960
ctcaataggg cactggactc actccattga tggctgtctt tgctcgaagt gtcttcctga    22020
tgctgctgct gttgctgctt gtgcttcttc tgtgcttaca ttctctctct ctcactcact    22080
cactctgtct ctcctctccc ccgccccacc ccctttctga caaagccacc accattttgt    22140
aaggaactgt agcttctctc tgaaactgcc gggaaaggga aaatctttt aaaatagaca    22200 tcacacaacc aacagggtcc cctaggttca ggcggggagg tgaggtcgag tgaga          22255
```

<210> SEQ ID NO 52
<211> LENGTH: 7
<212> TYPE: PRT
<213> ORGANISM: Artificial Sequence
<220> FEATURE:
<223> OTHER INFORMATION: Polycatonic peptide

<400> SEQUENCE: 52

Arg Arg Arg Arg Arg Arg Arg
1               5

<210> SEQ ID NO 53
<211> LENGTH: 7
<212> TYPE: PRT
<213> ORGANISM: Artificial Sequence
<220> FEATURE:
<223> OTHER INFORMATION: Polycatonic peptide
<221> NAME/KEY: VARIANT
<222> LOCATION: (1)...(7)
<223> OTHER INFORMATION: Xaa = Any Amino Acid

<400> SEQUENCE: 53

Lys Lys Leu Lys Leu Xaa Xaa
1               5

LOW DENSITY LIPOPROTEIN BINDING PROTEINS AND THEIR USE IN DIAGNOSING AND TREATING ATHEROSCLEROSIS

CROSS REFERENCE TO RELATED APPLICATIONS

This application is a divisional of U.S. patent application Ser. No. 10/671,242, filed Sep. 24, 2003, issued as U.S. Pat. No. 7,402,395 on Jul. 22, 2008, which is a continuation of U.S. patent application Ser. No. 09/616,289, filed Jul. 14, 2000, issued as U.S. Pat. No. 6,632,923 on Oct. 14, 2003, which is a continuation-in-part of U.S. patent application Ser. No. 09/517,849, filed Mar. 2, 2000, issued as U.S. Pat. No. 6,605,588 on Aug. 12, 2003, which is a continuation-in part of U.S. patent application Ser. No. 08/979,608, filed Nov. 26, 1997, issued as U.S. Pat. No. 6,355,451 on Mar. 12, 2002, which claimed priority from U.S. Provisional Application No. 60/031,930, filed Nov. 27, 1996, and U.S. Provisional Application No. 60/048,547, filed Jun. 3, 1997. These applications are incorporated herein by reference in their entirety.

FIELD OF THE INVENTION

This invention relates to novel polypeptides (LBPs) which bind to low density lipoprotein (LDL), polynucleotides which encode these polypeptides, and treatments, diagnoses and therapeutic agents for atherosclerosis.

BACKGROUND OF THE INVENTION

Atherosclerosis is the principal cause of heart attacks and strokes. It has been reported that about 50% of all deaths in the United States, Europe and Japan are due to atherosclerosis. Atherosclerotic lesions in the arterial wall characterize atherosclerosis. Cholesteryl esters (CE) are present in these atherosclerotic lesions. Low density lipoprotein (LDL) has been shown to be the major carrier of plasma CE, and has been implicated as the agent by which CE enter the atherosclerotic lesions.

Scattered groups of lipid-filled macrophages, called foam cells, are the first visible signs of atherosclerosis and are described as type I lesions. These macrophages are reported to contain CE derived from LDL. The macrophages recognize oxidized LDL, but not native LDL, and become foam cells by phagocytosing oxidized LDL. Larger, more organized collections of foam cells, fatty streaks, represent type II lesions. These lesions further develop into complex lesions called plaques, which can result in impeding the flow of blood in the artery.

It is widely believed that accumulation of LDL in the artery depends on the presence of functionally modified endothelial cells in the arterial wall. It has been reported in animal models of atherosclerosis that LDL, both native LDL and methylated LDL, accumulates focally and irreversibly only at the edges of regenerating endothelial islands in aortic lesions, where functionally modified endothelial cells are present, but not in the centers of these islands where endothelial regeneration is completed. Similarly, LDL accumulates in human atherosclerotic lesions. The mechanism by which the LDL accumulates focally and irreversibly in arterial lesions has not heretofore been understood.

SUMMARY OF THE INVENTION

It is an object of the invention to provide polypeptides which bind to LDL.

It is yet another object of the invention to provide a method for determining if an animal is at risk for atherosclerosis.

It is yet another object of the invention to provide a method for evaluating an agent for use in treating atherosclerosis. It is yet another object of the invention to provide a method for treating atherosclerosis.

Still another object of the invention is to utilize an LBP (low density lipoprotein binding protein) gene and/or polypeptide, or fragments, analogs and variants thereof, to aid in the treatment, diagnosis and/or identification of therapeutic agents for atherosclerosis.

In one aspect, the invention features an isolated polynucleotide comprising a polynucleotide encoding the polypeptide comprising the amino acid sequence as set forth in SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8; SEQ ID NO: 9; SEQ ID NO:43; SEQ ID NO:44; SEQ ID NO:47 or a polynucleotide capable of hybridizing to and which is at least about 95% identical to any of the above polynucleotides and wherein the encoded polypeptide is capable of binding to LDL; or a biologically active fragment of any of the above polynucleotides wherein the encoded polypeptide is capable of binding to LDL.

In certain embodiments, the polynucleotide comprises the nucleic acid sequence as set forth in SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17; SEQ ID NO: 18; SEQ ID NO:45; SEQ ID NO:46; SEQ ID NO:48.

Another aspect of the invention is an isolated polypeptide comprising a polypeptide having the amino acid sequence as set forth in SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8; SEQ ID NO: 9; SEQ ID NO: 43; SEQ ID NO:44; SEQ ID NO:47; or a polypeptide which is at least about 95% identical to any of the above polypeptides and wherein the polypeptide is capable of binding to LDL; or a biologically active fragment of any of the above polypeptides wherein the fragment is capable of binding to LDL.

Another aspect of the invention is a method for determining if an animal is at risk for atherosclerosis. An animal is provided. An aspect of LBP metabolism or structure is evaluated in the animal. An abnormality in the aspect of LBP metabolism or structure is diagnostic of being at risk for atherosclerosis. Another aspect of the invention is a method for evaluating an agent for use in treating atherosclerosis. A test cell, cell-free system or animal is provided. An agent is provided. The agent is administered to the test cell, cell-free system or animal in a therapeutically effective amount. The effect of the agent on an aspect of LBP metabolism or structure is evaluated. A change in the aspect of LBP metabolism or structure is indicative of the usefulness of the agent in treating atherosclerosis.

Another aspect of the invention is a method for evaluating an agent for the ability to alter the binding of LBP polypeptide to a binding molecule, e.g., native LDL, modified LDL, e.g., methylated LDL or oxidized LDL, or an arterial extracellular matrix structural component. An agent is provided. An LBP polypeptide is provided. A binding molecule is provided. The agent, LBP polypeptide and binding molecule are combined. The formation of a complex comprising the LBP polypeptide and binding molecule is detected. An alteration in the formation of the complex in the presence of the agent as compared to in the absence of the agent is indicative of the agent altering the binding of the LBP polypeptide to the binding molecule.

Another aspect of the invention is a method for evaluating an agent for the ability to bind to an LBP polypeptide. An agent is provided. An LBP polypeptide is provided. The agent is contacted with the LBP polypeptide. The ability of the agent to bind to the LBP polypeptide is evaluated.

Another aspect of the invention is a method for evaluating an agent for the ability to bind to a nucleic acid encoding an LBP regulatory sequence. An agent is provided. A nucleic acid encoding an LBP regulatory sequence is provided. The agent is contacted with the nucleic acid. The ability of the agent to bind to the nucleic acid is evaluated.

Another aspect of the invention is a method for treating atherosclerosis in an animal. An animal in need of treatment for atherosclerosis is provided. An agent capable of altering an aspect of LBP structure or metabolism is provided. The agent is administered to the animal in a therapeutically effective amount such that treatment of the atherosclerosis occurs. In certain embodiments, the agent is an LBP polypeptide, e.g., LBP-1, LBP-2 or LBP-3, or a biologically active fragment or analog thereof. In certain embodiments, the agent is a polypeptide of no more than about 100, 50, 30, 20, 10, 5, 4, 3 or 2 amino acid residues in length. In certain embodiments, the agent is a polypeptide having an amino acid sequence that includes at least about 20%, 40%, 60%, 80%, 90%, 95% or 98% acidic amino acid residues.

Another aspect of the invention is a method for treating an animal at risk for atherosclerosis. An animal at risk for atherosclerosis is provided. An agent capable of altering an aspect of LBP structure or metabolism is provided. The agent is administered to the animal in a therapeutically effective amount such that treatment of the animal occurs.

Another aspect of the invention is a method for treating a cell having an abnormality in structure or metabolism of LBP. A cell having an abnormality in structure or metabolism of LBP is provided. An agent capable of altering an aspect of LBP structure or metabolism is provided. The agent is administered to the cell in a therapeutically effective amount such that treatment of the cell occurs.

Another aspect of the invention is a pharmaceutical composition for treating atherosclerosis in an animal comprising a therapeutically effective amount of an agent, the agent being capable of altering an aspect of LBP metabolism or structure in the animal so as to result in treatment of the atherosclerosis, and a pharmaceutically acceptable carrier.

Another aspect of the invention is a vaccine composition for treating atherosclerosis in an animal comprising a therapeutically effective amount of an agent, the agent being capable of altering an aspect of LBP metabolism or structure in the animal so as to result in treatment of the atherosclerosis, and a pharmaceutically acceptable carrier.

Another aspect of the invention is a method for diagnosing atherosclerotic lesions in an animal. An animal is provided. A labeled agent capable of binding to LBP, e.g., LBP-1, LBP-2 or LBP-3, present in atherosclerotic lesions is provided. The labeled agent is administered to the animal under conditions which allow the labeled agent to interact with the LBP so as to result in labeled LBP. The localization or quantification of the labeled LBP is determined by imaging so as to diagnose the presence of atherosclerotic lesions in the animal.

Another aspect of the invention is a method for immunizing an animal against an LBP, e.g., LBP-1, LBP-2 or LBP-3, or fragment or analog thereof. An animal having LDL is provided. The LBP or fragment or analog thereof is administered to the animal so as to stimulate antibody production by the animal to the LBP or fragment or analog thereof such that binding of the LBP to the LDL is altered, e.g., decreased or increased.

Another aspect of the invention is a method of making a fragment or analog of LBP polypeptide, the fragment or analog having the ability to bind to native LDL and to modified LDL, e.g., methylated LDL, oxidized LDL, acetylated LDL, or cyclohexanedione-treated LDL. An LBP polypeptide is provided. The sequence of the LBP polypeptide is altered. The altered LBP polypeptide is tested for the ability to bind to modified LDL and native LDL.

Yet another aspect of the invention is a method for isolating a cDNA encoding an LBP. A cDNA library is provided. The cDNA library is screened for a cDNA encoding a polypeptide which binds to native LDL and modified LDL, e.g., methylated LDL or oxidized LDL. The cDNA which encodes the polypeptide is isolated, the cDNA encoding an LBP.

The above and other features, objects and advantages of the present invention will be better understood by a reading of the following specification in conjunction with the drawings.

BRIEF DESCRIPTION OF THE DRAWINGS

FIG. 1 depicts the amino acid sequence of rabbit LBP-1 (SEQ ID NO: 1). Differences in amino acids between rabbit and human LBP-1 are depicted in bold type.

FIGS. 2A-1 to 2A-3 depict the nucleotide sequence (SEQ ID NO: 48) and amino acid sequence (SEQ ID NO: 47) of rabbit LBP-2.

FIG. 2B depicts a portion of the amino acid sequence of rabbit LBP-2 (SEQ ID NO: 2). Differences in amino acids between rabbit and human LBP-2 are depicted in bold type. Where the sequences depicted in FIG. 2A and FIG. 2B differ, FIG. 2A represents the rabbit LBP-2 sequence.

FIG. 3 depicts the amino acid sequence of amino acids 319 to 550 of rabbit LBP-2 (SEQ ID NO: 3).

FIG. 4 depicts the amino acid sequence of amino acids 299 to 550 of rabbit LBP-2 (SEQ ID No: 4).

FIGS. 5A to 5B depict the amino acid sequence of rabbit LBP-3 (SEQ ID NO: 5).Differences in amino acids between rabbit and human LBP-3 are depicted in bold type.

FIG. 6 depicts the amino acid sequence of human LBP-1 (SEQ ID NO: 6). Differences in amino acids between rabbit and human LBP-1 are depicted in bold type.

FIGS. 7A-1 to 7A-3 depict the nucleotide sequence (SEQ ID NO: 45) and amino acid sequence (SEQ ID NO: 43) of human LBP-2.

FIG. 7B depicts the amino acid sequence of amino acids 322 to 538 of human LBP-2 (SEQ ID NO: 7). Differences in amino acids between rabbit and human LBP-2 are depicted in bold type.

FIGS. 8A-1 to 8A-3 depict the nucleotide sequence (SEQ ID NO: 46) and amino acid sequence (SEQ ID NO: 44) of human LBP-3.

FIGS. 8B-1 to 8B-2 depict the amino acid sequence of amino acids 17 to 546 of human LBP-3 (SEQ ID NO: 8). Differences in amino acids between rabbit and human LBP-3 are depicted in bold type. Where the sequences depicted in FIG. 8A and FIG. 8B differ, FIG. 8A represents the human LBP-3 sequence.

FIG. 9 depicts the amino acid sequence of amino acids 14 to 33 of human or rabbit LBP-1, called BHF-1 (SEQ ID NO: 9).

FIGS. 10A to 10B depict the cDNA sequence encoding rabbit LBP-1 (SEQ ID NO: 10) and the corresponding amino acid sequence (SEQ. ID NO:1). Differences in amino acids between rabbit and human LBP-1 are depicted in bold type.

FIGS. 11A to 11C depict a cDNA sequence encoding a portion of rabbit LBP-2 (SEQ ID NO: 11) and the corresponding amino acid sequence (SEQ ID NO:2). Differences in amino acids between rabbit and human LBP-2 are depicted in bold type. Where the sequences depicted in FIG. 2A and FIG. 11 differ, FIG. 2A represents the rabbit LBP-2 sequence.

FIGS. 12A to 12B depict a cDNA sequence of nucleotides 256 to 1617 (SEQ ID NO: 12) of SEQ ID NO: 11 of rabbit LBP-2 and the corresponding amino acid sequence(SEQ ID NO:3).

FIG. 13 depicts a cDNA sequence of nucleotides 196 to 1617 (SEQ ID NO: 13) of SEQ ID NO: 11 of rabbit LBP-2 and the corresponding amino acid sequence (SEQ ID NO:4).

FIGS. 14A to 14F depict the cDNA sequence encoding rabbit LBP-3 (SEQ ID NO: 14) and the corresponding amino acid sequence (SEQ ID NO: 5). Differences in amino acids between rabbit and human LBP-3 are depicted in bold type.

FIGS. 15A to 15B depict the cDNA sequence encoding human LBP-1 (SEQ ID NO: 15) and the corresponding amino acid sequence (SEQ ID NO:6). Differences in amino acids between rabbit and human LBP-1 are depicted in bold type.

FIGS. 16A to 16B depict a cDNA sequence encoding a portion of human LBP-2 (SEQ ID NO: 16) and the corresponding amino acid sequence (SEQ ID NO: 7). Differences in amino acids between rabbit and human LBP-2 are depicted in bold type.

FIGS. 17A to 17D depict a cDNA sequence encoding a portion of human LBP-3 (SEQ ID NO: 17) and the corresponding amino acid sequence (SEQ ID NO: 8). Differences in amino acids between rabbit and human LBP-3 are depicted in bold type. Where the sequences depicted in FIG. 8A and FIG. 17 differ, FIG. 8A represents the human LBP-3 sequence.

FIG. 18 depicts the cDNA sequence encoding BHF-1 (SEQ ID NO: 18) and corresponding amino acid sequence (SEQ ID NO: 9).

FIG. 19 corresponds to the amino acid sequence of rabbit LBP-1 (top sequence; SEQ ID NO: 1) in alignment with the amino acid sequence of human LBP-1 (bottom sequence; SEQ ID NO: 6).

FIG. 20 corresponds to the amino acid sequence of a portion of the amino acid sequence of rabbit LBP-2 (top sequence; amino acid residues 331-550 of SEQ ID NO: 47) in alignment with a portion of the amino acid sequence of human LBP-2 (bottom sequence; SEQ ID NO: 7).

FIG. 21 corresponds to the amino acid sequence of rabbit LBP-3 (top sequence; SEQ ID NO: 5) in alignment with the amino acid sequence of a portion of human LBP-3 (bottom sequence; SEQ ID NO: 44).

FIGS. 22A to 22E depict the genomic sequence of human LBP-1 (SEQ ID NO: 49) and corresponding amino acid sequence (SEQ ID NO: 6).

FIGS. 23A to 23F depict the genomic sequence of human LBP-2 (SEQ ID NO: 50) and corresponding amino acid sequence (SEQ ID NO: 43).

FIGS. 24A to 24I depict the genomic sequence of human LBP-3 (SEQ ID NO: 51) and corresponding amino acid sequence (SEQ ID NO: 44).

DETAILED DESCRIPTION

In accordance with aspects of the present invention, there are provided novel mature human and rabbit polypeptides, LBP-1, LBP-2 and LBP-3, and biologically active analogs and fragments thereof, and there are provided isolated polynucleotides which encode such polypeptides. LBP is an abbreviation for low density lipoprotein (LDL) binding protein. The terms polynucleotide, nucleotide and oligonucleotide are used interchangeably herein, and the terms polypeptides, proteins and peptides are used interchangeably herein.

This invention provides for an isolated polynucleotide comprising a polynucleotide encoding the polypeptide having the amino acid sequence of rabbit LBP-1 as set forth in FIG. 1 (SEQ ID NO: 1); rabbit LBP-2 as set forth in FIG. 2A (SEQ ID NO: 47); a portion of rabbit LBP-2 as set forth in FIG. 2B (SEQ ID NO: 2); 319 to 550 of rabbit LBP-2 as set forth in FIG. 3 (SEQ ID NO: 3); 299 to 550 of rabbit LBP-2 as set forth in FIG. 4 (SEQ ID NO: 4); rabbit LBP-3 as set forth in FIG. 5 (SEQ ID NO: 5); human LBP-1 as set forth in FIG. 6 (SEQ ID NO: 6); human LBP-2 as set forth in FIG. 7A (SEQ ID NO: 43); 322 to 538 of human LBP-2 as set forth in FIG. 7B (SEQ ID NO: 7); human LBP-3 as set forth in FIG. 8A (SEQ ID NO: 44); 17-546 of human LBP-3 as set forth in FIG. 8B (SEQ ID NO: 8); 14 to 33 of human (SEQ ID NO: 6) or rabbit (SEQ ID NO: 1) LBP-1, called BHF-1, as set forth in FIG. 9 (SEQ ID NO: 9); a polynucleotide capable of hybridizing to and which is at least about 80% identical, more preferably at least about 90% identical, more preferably yet at least about 95% identical, and most preferably at least about 98% identical to any of the above polynucleotides, and wherein the encoded polypeptide is capable of binding to LDL; or a biologically active fragment of any of the above polynucleotides wherein the encoded polypeptide is capable of binding to LDL.

This invention also includes an isolated polynucleotide comprising a polynucleotide encoding the polypeptide having amino acid residues 329-343 (SEQ ID NO: 19), 329-354 (SEQ ID NO: 20), 344-354 (SEQ ID NO: 21) or 529-538 (SEQ ID NO: 22) of human LBP-2 as set forth in FIG. 7A (SEQ ID NO: 43); amino acid residues 14-43 (SEQ ID NO: 23) or 38-43 (SEQ ID NO: 24) of rabbit or human LBP-1 as set forth in FIG. 1 (SEQ ID NO: 1) and FIG. 6 (SEQ ID NO: 6); amino acid residues 338-353 (SEQ ID NO: 25), 338-365 (SEQ ID NO: 26), 354-365 (SEQ ID NO: 27) or 444-453 (SEQ ID NO: 28) of rabbit LBP-2 as set forth in FIG. 2A (SEQ ID NO: 47); amino acid residues 96-110 (SEQ ID NO: 29) of rabbit LBP-3 as set forth in FIG. 5 (SEQ ID NO: 5); amino acid residues 69-75 (SEQ ID NO: 41) of human LBP-3 as set forth in FIG. 8A (SEQ ID NO: 44); a polynucleotide capable of hybridizing to and which is at least about 80% identical, more preferably at least about 90% identical, more preferably yet at least about 95% identical, and most preferably at least about 98% identical to any of the above polynucleotides, and wherein the encoded polypeptide is capable of binding to LDL; or a biologically active fragment of any of the above polynucleotides wherein the encoded polypeptide is capable of binding to LDL.

By a polynucleotide encoding a polypeptide is meant a polynucleotide which includes only coding sequence for the polypeptide, as well as a polynucleotide which includes additional coding and/or non-coding sequences. Thus, e.g., the polynucleotides which encode for the mature polypeptides of FIGS. 1-9 (SEQ ID NOS: 1-9, 43, 44 and 47) may include only the coding sequence for the mature polypeptide; the coding sequence for the mature polypeptide and additional coding sequence such as a leader or secretory sequence or a proprotein sequence; the coding sequence for the mature polypeptide (and optionally additional coding sequence) and non-coding sequence, such as introns or non-coding sequences 5' and/or 3' of the coding sequence for the mature polypeptide. The polynucleotides of the invention are also meant to include polynucleotides in which the coding sequence for the mature polypeptide is fused in the same reading frame to a polynucleotide sequence which aids in expression and/or secretion of a polypeptide from a host cell, e.g., a leader sequence. The polynucleotides are also meant to include polynucleotides in which the coding sequence is fused in frame to a marker sequence which, e.g., allows for purification of the polypeptide.

The polynucleotides of the present invention may be in the form of RNA, DNA or PNA, e.g., cRNA, cDNA, genomic DNA, or synthetic DNA, RNA or PNA. The DNA may be double-stranded or single stranded, and if single stranded may be the coding strand or non-coding (anti-sense) strand.

In preferred embodiments, the polynucleotide comprises the nucleic acid of rabbit LBP-1 as set forth in FIG. 10 (SEQ ID NO: 10); rabbit LBP-2 as set forth in FIG. 2A (SEQ ID NO:48) or FIG. 11 (SEQ ID NO:11); nucleotide 256 to 1617 of SEQ ID NO: 11 of rabbit LBP-2 as set forth in FIG. 12 (SEQ ID NO: 12); nucleotide 196 to 1617 of SEQ ID NO: 11 of rabbit LBP-2 as set forth in FIG. 13 (SEQ ID NO: 13); rabbit LBP-3 as set forth in FIG. 14 (SEQ ID NO: 14); human LBP-1 as set forth in FIG. 15 (SEQ ID NO: 15); human LBP-2 as set forth in FIG. 7A (SEQ ID NO: 45) or FIG. 16 (SEQ ID NO: 16); human LBP-3 as set forth in FIG. 8A (SEQ ID NO: 46) or FIG. 17 (SEQ ID NO: 17); or nucleotide 97 to 156 of rabbit LBP-1 or nucleotide 157 to 216 of human LBP-1, (BHF-1), as set forth in FIG. 18 (SEQ ID NO: 18).

In other preferred embodiments, the polynucleotide comprises the nucleic acid as set forth in SEQ ID NO:30 (GAA-GAGGAAGAAGATGATGATGAAGATGAA-GATGAAGAAGATGAT), SEQ ID NO:31 (GAAGAGGAAGAAGATGATGATGAAGAT-GAAGATGAAGAAGA TGAT GTGTCAGAGGGCTCT-GAAGTGCCCGAGAGTGAC), SEQ ID NO:32 (GTGTCA-GAGGGCTCTGAAGTGCCCGAGAGTGAC), SEQ ID NO:33 (GAGGATGATGACCCCGATGGCTTCTTAGGC), SEQ ID NO:34 (GTGGACGTGGATGAATATGAC-GAGAACAAGTTCGTGGACGAA GAAGATGGGGGC-GACGGCCAGGCCGGGCCCGACGAGGGC-GAGGTGGAC), SEQ ID NO:35 (GACGAGGGCGAGGTGGAC), SEQ ID NO:36 (GAG-GAGGAGGAGGAGGAGGAGGAAGACGAC-GAGGACGACG ACGACGAC), SEQ ID NO:37 (GAG-GAGGAGGAGGAGGAGGAGGAAGACGACGAGGACGACGACGACGTCGTGTCCGAGGGCTCG-GAGGTGCCCGAGAGCGAT), SEQ ID NO:38 (GTCGT-GTCCGAGGGCTCGGAGGTGCCCGAGAGCGAT), SEQ ID NO:39 (CCCCCCGGGAAGCCAGCCCTCCCAG-GAGCC), SEQ ID NO:40 (GAGGATGGGGTCCAGGGT-GAGCCCCCTGAACCTGAAGATGCA GAG), or SEQ ID NO:42 (CGTGATGTCTCTGAGGAGCTG).

The coding sequence which encodes the mature polypeptide may be identical to the coding sequences shown in FIGS. 2A, 7A, 8A and 10-18 (SEQ ID NOS: 10-18, 45, 46, and 48) or SEQ ID NOS: 30-40 or 42, or may be a different coding sequence which coding sequence, as a result of the redundancy or degeneracy of the genetic code, encodes the same mature polypeptides as the DNA of FIGS. 2A, 7A, 8A and 10-18 (SEQ ID NOS: 10-18, 45, 46, and 48) and SEQ ID NOS: 30-40 and 42.

This invention also includes recombinant vectors comprising the polynucleotides described above. The vector can be, e.g., a plasmid, a viral particle or a phage. In certain embodiments, the recombinant vector is an expression vector. The vectors may also include various marker genes which are useful in identifying cells containing such vectors.

This invention also includes a cell comprising such a recombinant vector. The recombinant vectors described herein can be introduced into a host cell, e.g., by transformation, transfection or infection.

This invention also includes a method for producing an LBP comprising culturing such a cell under conditions that permit expression of the LBP.

This invention also includes an isolated polypeptide comprising a polypeptide having the amino acid sequence as set forth in FIG. 1 (SEQ ID NO: 1); FIG. 2A (SEQ ID NO: 47); FIG. 2B (SEQ ID NO: 2); FIG. 3 (SEQ ID NO: 3); FIG. 4 (SEQ ID NO: 4); FIG. 5 (SEQ ID NO: 5); FIG. 6 (SEQ ID NO: 6); FIG. 7A (SEQ ID NO: 43); FIG. 7B (SEQ ID No: 7); FIG. 8A (SEQ ID NO: 44); FIG. 8B (SEQ ID NO: 8); or FIG. 9 (SEQ ID NO: 9); or a polypeptide which is at least about 80% identical, more preferably at least about 90% identical, more preferably yet at least about 95% identical, and most preferably at least about 98% identical to the above polypeptides, and wherein said polypeptide is capable of binding to LDL; or a biologically active fragment of any of the above polypeptides wherein the fragment is capable of binding to LDL. Differences in amino acids between the rabbit and human LBP-1, LBP-2 and LBP-3 genes are depicted in bold type in the figures. Differences in the amino acid sequences between rabbit and human LBP-1, LBP-2 and LBP-3 are also specifically shown in FIGS. 19, 20 and 21, respectively.

This invention also includes an isolated polypeptide comprising a polypeptide having amino acid residues 329-343 (SEQ ID NO: 19), 329-354 (SEQ ID NO: 20), 344-354 (SEQ ID NO: 21) or 529-538 (SEQ ID NO: 22) as set forth in FIG. 7A (SEQ ID NO: 47); amino acid residues 14-43 (SEQ ID NO: 23) or 38-43 (SEQ ID NO: 24) as set forth in FIG. 1 (SEQ ID NO:1) and FIG. 6 (SEQ ID NO: 6); amino acid residues 338-353 (SEQ ID NO: 25), 338-365 (SEQ ID NO: 26), 354-365 (SEQ ID NO: 27) or 444-453 (SEQ ID NO: 28) as set forth in FIG. 2A (SEQ ID NO: 47); amino acid residues 96-110 (SEQ ID NO: 29) as set forth in FIG. 5 (SEQ ID NO: 5); and amino acid residues 69-75 (SEQ ID NO: 41) as set forth in FIG. 8A (SEQ ID NO: 44); or a polypeptide which is at least about 80% identical, more preferably at least about 90% identical, more preferably yet at least about 95% identical, and most preferably at least about 98% identical to the above polypeptides, and wherein said polypeptide is capable of binding to LDL; or a biologically active fragment of any of the above polypeptides wherein the fragment is capable of binding to LDL.

The polypeptides of the invention are meant to include, e.g., a naturally purified product, a chemically synthesized product, and a recombinantly derived product.

The polypeptides can be used, e.g., to bind to LDL, thereby inhibiting formation of atherosclerotic plaques. The polypeptides can also be used, e.g., in gene therapy, by expression of such polypeptides in vivo. The polypeptides can also be used in pharmaceutical or vaccine compositions. The polypeptides can also be used as immunogens to produce antibodies thereto, which in turn, can be used as antagonists to the LBP polypeptides.

Without being bound by any theory, it is believed that the LBPs provide the mechanism by which atherosclerosis is promoted through LDL oxidation. The LBPs are believed to be required in order for focal, irreversible LDL binding to occur at the arterial wall, and that such binding is a critical early event in atherosclerosis because it allows the time necessary for LDL to be changed from its native state to a fully oxidized state.

Since oxidized, but not native, LDL is a foreign protein, macrophages ingest it, first becoming the foam cells of type I lesions, and subsequently forming the fatty streaks of type II lesions.

This invention also includes a method for determining if an animal is at risk for atherosclerosis. An animal is provided. An aspect of LBP metabolism or structure is evaluated in the animal. An abnormality in the aspect of LBP metabolism or structure is diagnostic of being at risk for atherosclerosis.

By atherosclerosis is meant a disease or condition which comprises several stages which blend imperceptibly into each other, including irreversible binding of LDL, LDL oxidation, macrophage recruitment, blockage of the artery and tissue death (infarction).

By animal is meant human as well as non-human animals. Nonhuman animals include, e.g., mammals, birds, reptiles, amphibians, fish, insects and protozoa. Preferably, the non-human animal is a mammal, e.g., a rabbit, a rodent, e.g., a mouse, rat or guinea pig, a primate, e.g., a monkey, or a pig. An animal also includes transgenic non-human animals. The term transgenic animal is meant to include an animal that has gained new genetic information from the introduction of foreign DNA, i.e., partly or entirely heterologous DNA, into the DNA of its cells; or introduction of a lesion, e.g., an, in vitro induced mutation, e.g., a deletion or other chromosomal rearrangement into the DNA of its cells; or introduction of homologous DNA into the DNA of its cells in such a way as to alter the genome of the cell into which the DNA is inserted, e.g., it is inserted at a location which differs from that of the natural gene or its insertion results in a knockout or replacement of the homologous host gene or results in altered and/or regulatable expression and/or metabolism of the gene. The animal may include a transgene in all of its cells including germ line cells, or in only one or some of its cells. Transgenic animals of the invention can serve as a model for studying atherosclerosis or for evaluating agents to treat atherosclerosis.

In certain embodiments, the determination for being at risk for atherosclerosis is done in a prenatal animal.

By LBP is meant a low density lipoprotein (LDL) binding protein which is capable of binding LDL and methylated LDL. By methylated LDL is meant that about 50% to about 90% of the lysine residues of LDL have a methyl group chemically attached. Methylated LDL is not recognized by previously reported cell surface receptors. See, e.g., Weisgraber et al., J. Biol. Chem. 253: 9053-9062 (1978). In certain embodiments, the LBP is also capable of binding oxidized LDL. In certain preferred embodiments, the binding of LDL to an LBP is irreversible. In certain preferred embodiments, the LBP does not transport the LDL to any intracellular compartment. Examples of LBPs are LBP-1, LBP-2 and LBP-3 described herein.

By LBP metabolism is meant any aspect of the production, release, expression, function, action, interaction or regulation of LBP. The metabolism of LBP includes modifications, e.g., covalent or non-covalent modifications, of LBP polypeptide. The metabolism of LBP includes modifications, e.g., covalent or noncovalent modifications, that LBP induces in other substances.

The metabolism of LBP also includes changes in the distribution of LBP polypeptide, and changes LBP induces in the distribution of other substances.

Any aspect of LBP metabolism can be evaluated. The methods used are standard techniques known to those skilled in the art and can be found in standard references, e.g., Auaubel et al., ed., Current Protocols in Mol. Biology, New York: John Wiley & Sons, 1990; Kriegler, M., ed., Gene Transfer and Expression, Stockton Press, New York, N.Y., 1989; pDisplay gene expression system (Invitrogen, Carlsbad, Calif.). Preferred examples of LBP metabolism that can be evaluated include the binding activity of LBP polypeptide to a binding molecule, e.g., LDL; the transactivation activity of LBP polypeptide on a target gene; the level of LBP protein; the level of LBP mRNA; the level of LBP modifications, e.g., phosphorylation, glycosylation or acylation; or the effect of LBP expression on transfected mammalian cell binding of LDL.

By binding molecule is meant any molecule to which LBP can bind, e.g., a nucleic acid, e.g., a DNA regulatory region, a protein, e.g., LDL, a metabolite, a peptide mimetic, a non-peptide mimetic, an antibody, or any other type of ligand. In certain preferred embodiments, the aspect of LBP metabolism that is evaluated is the ability of LBP to bind to native LDL and/or methylated LDL and/or oxidized LDL. Binding to LDL can be shown, e.g., by antibodies against LDL, affinity chromatography, affinity coelectrophoresis (ACE) assays, or ELISA assays. See Examples. In other embodiments, it is the ability of LBP to bind to an arterial extracellular matrix structural component that is evaluated. Examples of such components include proteoglycans, e.g., chondroitin sulfate proteoglycans and heparin sulfate proteoglycans; elastin; collagen; fibronectin; vitronectin; integrins; and related extracellular matrix molecules. Binding to arterial extracellular matrix structural components can be shown by standard methods known to those skilled in the art, e.g., by ELISA assays. Primary antibodies to the LBP are then added, followed by an enzyme-conjugated secondary antibody to the primary antibody, which produces a stable color in the presence of an appropriate substrate, and color development on the plates is measured in a microtiter plate reader.

Transactivation of a target gene by LBP can be determined, e.g., in a transient transfection assay in which the promoter of the target gene is linked to a reporter gene, e.g., β-galactosidase or luciferase, and co-transfected with an LBP expression vector. Such evaluations can be done in vitro or in vivo. Levels of LBP protein, mRNA or phosphorylation, can be measured, e.g., in a sample, e.g., a tissue sample, e.g., arterial wall, by standard methods known to those skilled in the art.

In certain embodiments, an aspect of LBP structure is evaluated, e.g., LBP gene structure or LBP protein structure. For example, primary, secondary or tertiary structures can be evaluated. For example, the DNA sequence of the gene is determined and/or the amino acid sequence of the protein is determined. Standard cloning and sequencing methods can be used as are known to those skilled in the art. In certain embodiments, the binding activity of an antisense nucleic acid with the cellular LBP mRNA and/or genomic DNA is determined using standard methods known to those skilled in the art so as to detect the presence or absence of the target mRNA or DNA sequences to which the antisense nucleic acid would normally specifically bind.

The risk for atherosclerosis that is determined can be a reduced risk or an increased risk as compared to a normal animal. For example, an abnormality which would give a reduced risk is an inactive LBP polypeptide. An abnormality which would give an increased risk would be, e.g., an LBP polypeptide that has higher activity, e.g., LDL binding activity, than native LBP polypeptide.

The invention also includes a method for evaluating an agent for use in treating atherosclerosis. A test cell, cell-free system or animal is provided. An agent is provided. The agent is administered to the test cell, cell-free system or animal in a therapeutically effective amount. The effect of the agent on an aspect of LBP metabolism or structure is evaluated. A change in the aspect of LBP metabolism or structure is indicative of the usefulness of the agent in treating atherosclerosis.

In certain embodiments, the method employs two phases for evaluating an agent for use in treating atherosclerosis, an initial in vitro phase and then an in vivo phase. The agent is administered to the test cell or cell-free system in vitro, and if a change in an aspect of LBP metabolism occurs, then the agent is further administered to a test animal in a therapeutically effective amount and evaluated in vivo for an effect of the agent on an aspect of LBP metabolism.

By cell is meant a cell or a group of cells, or a cell that is part of an animal. The cell can be a human or non-human cell. Cell is also meant to include a transgenic cell. The cell can be obtained, e.g., from a culture or from an animal. Animals are meant to include, e.g., natural animals and non-human transgenic animals. In certain embodiments, the transgenic cell or nonhuman transgenic animal has an LBP transgene, or fragment or analog thereof. In certain embodiments, the transgenic cell or non-human transgenic animal has a knockout for the LBP gene.

The test cell, cell-free system or animal can have a wild type pattern or a non-wild type pattern of LBP metabolism. A non-wild type pattern of LBP metabolism can result, e.g., from under-expression, over-expression, no expression, or a temporal, site or distribution change. Such a non-wild type pattern can result, e.g., from one or more mutations in the LBP gene, in a binding molecule gene, a regulatory gene, or in any other gene which directly or indirectly affects LBP metabolism. A mutation is meant to include, e.g., an alteration, e.g., in gross or fine structure, in a nucleic acid. Examples include single base pair alterations, e.g., missense or nonsense mutations, frameshifts, deletions, insertions and translocations. Mutations can be dominant or recessive. Mutations can be homozygous or heterozygous. Preferably, an aspect of LBP-1, LBP-2 or LBP-3 metabolism is evaluated.

An agent is meant to include, e.g., any substance, e.g., an anti-atherosclerosis drug. The agent of this invention preferably can change an aspect of LBP metabolism. Such change can be the result of any of a variety of events, including, e.g., preventing or reducing interaction between LBP and a binding molecule, e.g., LDL or an arterial extracellular matrix structural component; inactivating LBP and/or the binding molecule, e.g., by cleavage or other modification; altering the affinity of LBP and the binding molecule for each other; diluting out LBP and/or the binding molecule; preventing expression of LBP and/or the binding molecule; reducing synthesis of LBP and/or the binding molecule; synthesizing an abnormal LBP and/or binding molecule; synthesizing an alternatively spliced LBP and/or binding molecule; preventing or reducing proper conformational folding of LBP and/or the binding molecule; modulating the binding properties of LBP and/or the binding molecule; interfering with signals that are required to activate or deactivate LBP and/or the binding molecule; activating or deactivating LBP and/or the binding molecule in such a way as to prevent binding; or interfering with other receptors, ligands or other molecules which are required for the normal synthesis or functioning of LBP and/or the binding molecule. For example, the agent can block the binding site on LDL for LBPs expressed focally in the arterial wall extracellular matrix, or it could block the binding site on an LBP for LDL, or it could be bifunctional, i.e., it could block both binding sites.

Examples of agents include LBP polypeptide, e.g., LBP-1, LBP-2 or LBP-3, or a biologically active fragment or analog thereof; a nucleic acid encoding LBP polypeptide or a biologically active fragment or analog thereof; a nucleic acid encoding an LBP regulatory sequence or a biologically active fragment or analog thereof; a binding molecule for LBP polypeptide; a binding molecule for LBP nucleic acid, the LBP nucleic acid being, e.g., a nucleic acid comprising a regulatory region for LBP or a nucleic acid comprising a structural region for LBP or a biologically active fragment of LBP; an antisense nucleic acid; a mimetic of LBP or a binding molecule; an antibody for LBP or a binding molecule; a metabolite; or an inhibitory carbohydrate or glycoprotein. In certain embodiments, the agent is an antagonist, agonist or super agonist.

Knowledge of the existence of the sequence of the LBPs allows a search for natural or artificial ligands to regulate LDL levels in the treatment of atherosclerosis. In certain embodiments, the agent is a natural ligand for LBP. In certain embodiments, the agent is an artificial ligand for LBP.

By analog is meant a compound that differs from naturally occurring LBP in amino acid sequence or in ways that do not involve sequence, or both. Analogs of the invention generally exhibit at least about 80% homology, preferably at least about 90% homology, more preferably yet at least about 95% homology, and most preferably at least about 98% homology, with substantially the entire sequence of a naturally occurring LBP sequence, preferably with a segment of about 100 amino acid residues, more preferably with a segment of about 50 amino acid residues, more preferably yet with a segment of about 30 amino acid residues, more preferably yet with a segment of about 20 amino acid residues, more preferably yet with a segment of about 10 amino acid residues, more preferably yet with a segment of about 5 amino acid residues, more preferably yet with a segment of about 4 amino acid residues, more preferably yet with a segment of about 3 amino acid residues, and most preferably with a segment of about 2 amino acid residues. Non-sequence modifications include, e.g., in vivo or in vitro chemical derivatizations of LBP. Non-sequence modifications include, e.g., changes in phosphorylation, acetylation, methylation, carboxylation, or glycosylation. Methods for making such modifications are known to those skilled in the art. For example, phosphorylation can be modified by exposing LBP to phosphorylation-altering enzymes, e.g., kinases or phosphatases. Preferred analogs include LBP or biologically active fragments thereof whose sequences differ from the wild-type sequence by one or more conservative amino acid substitutions or by one or more non-conservative amino acid substitutions, deletions, or insertions which do not abolish LBP biological activity. Conservative substitutions typically include the substitution of one amino acid for another with similar characteristics, e.g., substitutions within the following groups: valine, glycine; glycine, alanine; valine, isoleucine, leucine; aspartic acid, glutamic acid; asparagine, glutamine; serine, threonine; lysine, arginine; and phenylalanine, tyrosine. Other examples of conservative substitutions are shown in Table 1.

TABLE 1

CONSERVATIVE AMINO ACID SUBSTITUTIONS

| For Amino Acid | Code | Replace with any of |
|---|---|---|
| Alanine | A | D-Ala, Gly, beta-Ala, L-Cys, D-Cys |
| Arginine | R | D-Arg, Lys, D-Lys, homo-Arg, D-homo-Arg, Met, Ile, D-Met, D-Ile, Orn, D-Orn, L-NMMA, L-NAME |
| Asparagine | N | D-Asn, Asp, D-Asp, Glu, D-Glu, Gln, D-Gln |
| Aspartic Acid | D | D-Asp, D-Asn, Asn, Glu, D-Glu, Gln, D-Gln |
| Cysteine | C | D-Cys, S-Me-Cys, Met, D-Met, Thr, D-Thr |
| Glutamine | Q | D-Gln, Asn, D-Asn, Glu, D-Glu, Asp, D-Asp |
| Glutamic Acid | E | D-Glu, D-Asp, Asp, Asn, D-Asn, Gln, D-Gln |
| Glycine | G | Ala, D-Ala, Pro, D-Pro, β-Ala Acp |
| Histidine | H | D-His |
| Isoleucine | I | D-Ile, Val, D-Val, Leu, D-Leu, Met, D-Met |
| Leucine | L | D-Leu, Val, D-Val, Leu, D-Leu, Met, D-Met |
| Lysine | K | D-Lys, Arg, D-Arg, homo-Arg, D-homo-Arg, Met, D-Met, Ile, D-Ile, Orn, D-Orn |
| Methionine | M | D-Met, S-Me-Cys, Ile, D-Ile, Leu, D-Leu, Val, D-Val |

TABLE 1-continued

CONSERVATIVE AMINO ACID SUBSTITUTIONS

| For Amino Acid | Code | Replace with any of |
|---|---|---|
| Phenylalanine | F | D-Phe, Tyr, D-Thr, L-Dopa, His, D-His, Trp, D-Trp, Trans-3,4, or 5-phenylproline, cis-3,4, or 5-phenylproline |
| Proline | P | D-Pro, L-I-thioazolidine-4-carboxylic acid, D- or L-1-oxazolidine-4-carboxylic acid |
| Serine | S | D-Ser, Thr, D-Thr, allo-Thr, Met, D-Met, Met(O), D-Met(O), L-Cys, D-Cys |
| Threonine | T | D-Thr, Ser, D-Ser, allo-Thr, Met, D-Met, Met(O), D-Met(O), Val, D-Val |
| Tryptophan | W | D-Trp, Phe, D-Phe, Tyr, D-Tyr |
| Tyrosine | Y | D-Tyr, Phe, D-Phe, L-Dopa, His, D-His |
| Valine | V | D-Val, Leu, D-Leu, Ile, D-Ile, Met, D-Met |

Amino acid sequence variants of a protein can be prepared by any of a variety of methods known to those skilled in the art. For example, random mutagenesis of DNA which encodes a protein or a particular domain or region of a protein can be used, e.g., PCR mutagenesis (using, e.g., reduced Taq polymerase fidelity to introduce random mutations into a cloned fragment of DNA; Leung et al., BioTechnique 1: 11-15 (1989)), or saturation mutagenesis (by, e.g., chemical treatment or irradiation of single-stranded DNA in vitro, and synthesis of a complementary DNA strand; Mayers et al., Science 229: 242 (1985)). Random mutagenesis can also be accomplished by, e.g., degenerate oligonucleotide generation (using, e.g., an automatic DNA synthesizer to chemically synthesize degenerate sequences; Narang, Tetrahedron 39: 3 (1983); Itakura et al., Recombinant DNA, Proc. 3rd Cleveland Sympos. Macromolecules, ed. A. G. Walton, Amsterdam: Elsevier, pp. 273-289 (1981)). Non-random or directed mutagenesis can be used to provide specific sequences or mutations in specific regions. These techniques can be used to create variants which include, e.g., deletions, insertions, or substitutions, of residues of the known amino acid sequence of a protein. The sites for mutation can be modified individually or in series, e.g., by (i) substituting first with conserved amino acids and then with more radical choices depending upon results achieved, (ii) deleting the target residue, (iii) inserting residues of the same or a different class adjacent to the located site, or (iv) combinations of the above. For example, analogs can be made by in vitro DNA sequence modifications of the sequences of FIGS. 2A, 7A, 8A, 10-18 (SEQ ID NOS: 10-18, 45, 46, and 48). For example, in vitro mutagenesis can be used to convert any of these DNA sequences into a sequence which encodes an analog in which one or more amino acid residues has undergone a replacement, e.g., a conservative replacement as described in Table 1.

Methods for identifying desirable mutations include, e.g., alanine scanning mutagenesis (Cunningham and Wells, Science 244: 1081-1085 (1989)), oligonucleotide-mediated mutagenesis (Adelman et al., DNA, 2: 183 (1983)); cassette mutagenesis (Wells et al., Gene 34: 315 (1985)), combinatorial mutagenesis, and phage display libraries (Ladner et al., PCT International Appln. No. WO88/06630). The LBP analogs can be tested, e.g., for their ability to bind to LDL and/or to an arterial extracellular matrix component, as described herein. Other analogs within the invention include, e.g., those with modifications which increase peptide stability. Such analogs may contain, e.g., one or more non-peptide bonds (which replace the peptide bonds) in the peptide sequence. Also included are, e.g.: analogs that include residues other than naturally occurring L-amino acids, e.g., D-amino acids or nonnaturally occurring or synthetic amino acids, e.g., β or γ amino acids; and cyclic analogs.

Analogs are also meant to include peptides in which structural modifications have been introduced into the peptide backbone so as to make the peptide non-hydrolyzable. Such peptides are particularly useful for oral administration, as they are not digested. Peptide backbone modifications include, e.g., modifications of the amide nitrogen, the α-carbon, the amide carbonyl, or the amide bond, and modifications involving extensions, deletions or backbone crosslinks. For example, the backbone can be modified by substitution of a sulfoxide for the carbonyl, by reversing the peptide bond, or by substituting a methylene for the carbonyl group. Such modifications can be made by standard procedures known to those skilled in the art. See, e.g., Spatola, A. F., "Peptide Backbone Modifications: A Structure-Activity Analysis of Peptides Containing Amide Bond Surrogates, Conformational Constraints, and Related Backbone Replacements," in Chemistry and Biochemistry of Amino Acids, Peptides and Proteins, Vol. 7, pp. 267-357, B. Weinstein (ed.), Marcel Dekker, Inc., New York (1983).

An analog is also meant to include polypeptides in which one or more of the amino acid residues include a substituent group, or polypeptides which are fused with another compound, e.g., a compound to increase the half-life of the polypeptide, e.g., polyethylene glycol.

By fragment is meant some portion of the naturally occurring LBP polypeptide. Preferably, the fragment is at least about 100 amino acid residues, more preferably at least about 50 amino acid residues, more preferably yet at least about 30 amino acid residues, more preferably yet at least about 20 amino acid residues, more preferably yet at least about 5 amino acid residues, more preferably yet at least about 4 amino acid residues, more preferably yet at least about 3 amino acid residues, and most preferably at least about 2 amino acid residues in length. Fragments include, e.g., truncated secreted forms, proteolytic fragments, splicing fragments, other fragments, and chimeric constructs between at least a portion of the relevant gene, e.g., LBP-1, LBP-2 or LBP-3, and another molecule. Fragments of LBP can be generated by methods known to those skilled in the art. In certain embodiments, the fragment is biologically active. The ability of a candidate fragment to exhibit a biological activity of LBP can be assessed by methods known to those skilled in the art. For example, LBP fragments can be tested for their ability to bind to LDL and/or to an arterial extracellular matrix structural component, as described herein. Also included are LBP fragments containing residues that are not required for biological activity of the fragment or that result from alternative mRNA splicing or alternative protein processing events.

Fragments of a protein can be produced by any of a variety of methods known to those skilled in the art, e.g., recombinantly, by proteolytic digestion, or by chemical synthesis. Internal or terminal fragments of a polypeptide can be generated by removing one or more nucleotides from one end (for a terminal fragment) or both ends (for an internal fragment) of a nucleic acid which encodes the polypeptide. Expression of the mutagenized DNA produces polypeptide fragments. Digestion with "end-nibbling" endonucleases can thus generate DNAs which encode an array of fragments. DNAs which encode fragments of a protein can also be generated; e.g., by random shearing, restriction digestion or a combination of the above-discussed methods. For example, fragments of LBP can be made by expressing LBP DNA which has been manipulated in vitro to encode the desired fragment, e.g., by restriction digestion of any of the DNA sequences of FIGS. 2A, 7A, 8A, 10-18 (SEQ ID NOS: 10-18, 45, 46, and 48).

Fragments can also be chemically synthesized using techniques known in the art, e.g., conventional Merrifield solid phase f-Moc or t-Boc chemistry for example, peptides of the present invention can be arbitrarily divided into fragments of desired length with no overlap of the fragments, or divided into overlapping fragments of a desired length.

An LBP or a biologically active fragment or analog thereof, or a binding molecule or a biologically active fragment or analog thereof, can, e.g., compete with its cognate molecule for the binding site on the complementary molecule, and thereby reduce or eliminate binding between LBP and the cellular binding molecule. LBP or a binding molecule can be obtained, e.g., from purification or secretion of naturally occurring LBP or binding molecule, from recombinant LBP or binding molecule, or from synthesized LBP or binding molecule.

Therefore, methods for generating analogs and fragments and testing them for activity are known to those skilled in the art.

An agent can also be a nucleic acid used as an antisense molecule. Antisense therapy is meant to include, e.g., administration or in situ generation of oligonucleotides or their derivatives which specifically hybridize, e.g., bind, under cellular conditions, with the cellular mRNA and/or genomic DNA encoding an LBP polypeptide, or mutant thereof, so as to inhibit expression of the encoded protein, e.g., by inhibiting transcription and/or translation. The binding may be by conventional base pair complementarity, or, for example, in the case of binding to DNA duplexes, through specific interactions in the major groove of the double helix.

In certain embodiments, the antisense construct binds to a naturally-occurring sequence of an LBP gene which, e.g., is involved in expression of the gene. These sequences include, e.g., promoter, start codons, stop codons, and RNA polymerase binding sites. In other embodiments, the antisense construct binds to a nucleotide sequence which is not present in the wild type gene. For example, the antisense construct can bind to a region of an LBP gene which contains an insertion of an exogenous, non-wild type sequence. Alternatively, the antisense construct can bind to a region of an LBP gene which has undergone a deletion, thereby bringing two regions of the gene together which are not normally positioned together and which, together, create a non-wild type sequence. When administered in vivo to a subject, antisense constructs which bind to non-wild type sequences provide the advantage of inhibiting the expression of a mutant LBP gene, without inhibiting expression of any wild type LBP gene.

An antisense construct of the present invention can be delivered, e.g., as an expression plasmid which, when transcribed in the cell, produces RNA which is complementary to at least a unique portion of the cellular mRNA which encodes an LBP polypeptide. An alternative is that the antisense construct is an oligonucleotide which is generated ex vivo and which, when introduced into the cell causes inhibition of expression by hybridizing with the mRNA (duplexing) and/or genomic sequences (triplexing) of an LBP gene. Such oligonucleotides are preferably modified oligonucleotides which are resistant to endogenous nucleases, e.g. exonucleases and/or endonucleases, and are therefore stable in vivo. Exemplary nucleic acid molecules for use as antisense oligonucleotides are phosphoramidate, phosphothioate, phosphorodithioates and methylphosphonate analogs of DNA and peptide nucleic acids (PNA). (See also U.S. Pat. Nos. 5,176,996; 5,264,564; and 5,256,775). Additionally, general approaches to constructing oligomers useful in antisense therapy have been reviewed. (See, e.g., Van der Krol et al., Biotechniques 6: 958-976, (1988); Stein et al., Cancer Res. 48: 2659-2668 (1988)).

By mimetic is meant a molecule which resembles in shape and/or charge distribution LBP or a binding molecule. The mimetic can be a peptide or a non-peptide. Mimetics can act as therapeutic agents because they can, e.g., competitively inhibit binding of LBP to a binding molecule. By employing, e.g., scanning mutagenesis, e.g., alanine scanning mutagenesis, linker scanning mutagenesis or saturation mutagenesis, to map the amino acid residues of a particular LBP polypeptide involved in binding a binding molecule, peptide mimetics, e.g., diazepine or isoquinoline derivatives, can be generated which mimic those residues in binding to a binding molecule, and which therefore can inhibit binding of the LBP to a binding molecule and thereby interfere with the function of LBP. Non-hydrolyzable peptide analogs of such residues can be generated using, e.g., benzodiazepine (see, e.g., Freidinger et al., in Peptides: Chemistry and Biology, G. R. Marshall ed., ESCOM Publisher: Leiden, Netherlands (1988)); azepine (see, e.g., Huffman et al., in Peptides: Chemistry and Biology, G. R. Marshall ed., ESCOM Publisher: Leiden, Netherlands (1988)); substituted gamma lactam rings (see, e.g., Garvey et al., in Peptides: Chemistry and Biology, G. R. Marshall ed., ESCOM Publisher: Leiden, Netherlands (1988)); keto-methylene pseudopeptides (see, e.g., Ewenson et al., J. Med. Chem. 29: 295 (1986); Ewenson et al., in Peptides: Structure and Function (Proceedings of the 9th American Peptide Symposium) Pierce Chemical Co. Rockland, Ill. (1985)); β-turn dipeptide cores (see, e.g., Nagai et al., Tetrahedron Lett. 26: 647 (1985); Sato et al., J. Chem. Soc. Perkin Trans. 1: 1231 (1986)); or β-aminoalcohols (see, e.g., Gordon et al., Biochem. Biophys. Res. Commun. 126:419 (1985); Dann et al., Biochem. Biophys. Res. Commun. 134: 71 (1986)).

Antibodies are meant to include antibodies against any moiety that directly or indirectly affects LBP metabolism. The antibodies can be directed against, e.g., LBP or a binding molecule, or a subunit or fragment thereof. For example, antibodies include anti-LBP-1, LBP-2 or LBP-3 antibodies; and anti-binding molecule antibodies. Antibody fragments are meant to include, e.g., Fab fragments, Fab' fragments, F(ab')$_2$ fragments, F(v) fragments, heavy chain monomers, heavy chain dimers, heavy chain trimers, light chain monomers, light chain dimers, light chain trimers, dimers consisting of one heavy and one light chain, and peptides that mimic the activity of the anti-LBP or anti-binding molecule antibodies. For example, Fab$_2$' fragments of the inhibitory antibody can be generated through, e.g., enzymatic cleavage. Both polyclonal and monoclonal antibodies can be used in this invention. Preferably, monoclonal antibodies are used. Natural antibodies, recombinant antibodies or chimeric-antibodies, e.g., humanized antibodies, are included in this invention. Preferably, humanized antibodies are used when the subject is a human. Most preferably, the antibodies have a constant region derived from a human antibody and a variable region derived from an inhibitory mouse monoclonal antibody. Production of polyclonal antibodies to LBP is described in Example 6. Monoclonal and humanized antibodies are generated by standard methods known to those skilled in the art. Monoclonal antibodies can be produced, e.g., by any technique which provides antibodies produced by continuous cell lines cultures. Examples include the hybridoma technique (Kohler and Milstein, Nature 256: 495-497 (1975), the trioma technique, the human B-cell hybridoma technique (Kozbor et al., Immunology Today 4:72 (1983)), and the EBV-hybridoma technique to produce human monoclonal antibodies (Cole et al., in Monoclonal Antibodies and Cancer Therapy, A. R. Lisa, Inc., pp. 77-96 (1985)). Preferably, humanized antibodies are raised through conventional production and harvesting techniques (Berkower, I., Curr. Opin. Biotechnol. 7:622-628 (1996); Ramharayan and Skaletsky, Am. Biotechnol. Lab 13:26-28 (1995)). In certain preferred embodiments, the antibodies are raised against the LBP, preferably the LDL-binding site, and the Fab fragments produced. These antibodies, or fragments derived therefrom, can be used, e.g., to block the LDL-binding sites on the LBP molecules.

Agents also include inhibitors of a molecule that are required for synthesis, post-translational modification, or functioning of LBP. and/or a binding molecule, or activators of a molecule that inhibits the synthesis or functioning of LBP and/or the binding molecule. Agents include, e.g., cytokines, chemokines, growth factors, hormones, signaling components, kinases, phosphatases, homeobox proteins, transcription factors, editing factors, translation factors and post-translation factors or enzymes. Agents are also meant to include ionizing radiation, non-ionizing radiation, ultrasound and toxic agents which can, e.g., at least partially inactivate or destroy LBP and/or the binding molecule.

An agent is also meant to include an agent which is not entirely LBP specific. For example, an agent may alter other genes or proteins related to arterial plaque formation. Such overlapping specificity may provide additional therapeutic advantage.

The invention also includes the agent so identified as being useful in treating atherosclerosis.

The invention also includes a method for evaluating an agent for the ability to alter the binding of LBP polypeptide to a binding molecule. An agent is provided. An LBP polypeptide is provided. A binding molecule is provided. The agent, LBP polypeptide and binding molecule are combined. The formation of a complex comprising the LBP polypeptide and binding molecule is detected. An alteration in the formation of the complex in the presence of the agent as compared to in the absence of the agent is indicative of the agent altering the binding of the LBP polypeptide to the binding molecule.

In preferred embodiments, the LBP polypeptide is LBP-1, LBP-2 or LBP-3. Examples of a binding molecule include native LDL, modified LDL, e.g., methylated LDL or oxidized LDL, and arterial extracellular matrix structural components.

Altering the binding includes, e.g., inhibiting or promoting the binding. The efficacy of the agent can be assessed, e.g., by generating dose response curves from data obtained using various concentrations of the agent. Methods for determining formation of a complex are standard and are known to those skilled in the art, e.g., affinity coelectrophoresis (ACE) assays or ELISA assays as described herein.

The invention also includes the agent so identified as being able to alter the binding of an LBP polypeptide to a binding molecule.

The invention also includes a method for evaluating an agent for the ability to bind to an LBP polypeptide. An agent is provided. An LBP polypeptide is provided. The agent is contacted with the LBP polypeptide. The ability of the agent to bind to the LBP polypeptide is evaluated. Preferably, the LBP polypeptide is LBP-1, LBP-2 or LBP-3. Binding can be determined, e.g., by measuring formation of a complex by standard methods known to those skilled in the art, e.g., affinity coelectrophoresis (ACE) assays or ELISA assays as described herein.

The invention also includes the agent so identified as being able to bind to LBP polypeptide.

The invention also includes a method for evaluating an agent for the ability to bind to a nucleic acid encoding an LBP regulatory sequence. An agent is provided. A nucleic acid encoding an LBP regulatory sequence is provided. The agent is contacted with the nucleic acid. The ability of the agent to bind to the nucleic acid is evaluated. Preferably, the LBP regulatory sequence is an LBP-1, LBP-2 or LBP-3 regulatory sequence. Binding can be determined, e.g., by measuring formation of a complex by standard methods known to those skilled in the art, e.g., DNA mobility shift assays, DNase I footprint analysis Molecular Biology, The invention being able to bind sequence. (Ausubel et al., ed., Current Protocols in John Wiley & Sons, New York, N.Y., (1989)).

The invention also includes the agent so identified as to a nucleic acid encoding an LBP regulatory sequence.

The invention also includes a method for treating atherosclerosis in an animal. An animal in need of treatment for atherosclerosis is provided. An agent capable of altering an aspect of LBP structure or metabolism is provided. The agent is administered to the animal in a therapeutically effective amount such that treatment of the atherosclerosis occurs.

In certain preferred embodiments, the agent is an LBP polypeptide, e.g., LBP-1, LBP-2 or LBP-3, or a biologically active fragment or analog thereof. The agent can be, e.g., the polypeptide as set forth in SEQ ID NOS: 1-9, 43, 44, and 47. Preferably, the agent is a polypeptide of no more than about 100 amino acid residues in length, more preferably of no more than about 50 amino acid residues, more preferably yet of no more than about 30 amino acid residues, more preferably yet of no more than about 20 amino acid residues, more preferably yet of no more than about 10 amino acid residues, more preferably yet of no more than about 5 amino acid residues, more preferably yet of no more than about 4 amino acid residues, more preferably yet of no more than about 3 amino acid residues, and most preferably of no more than about 2 amino acid residues. Preferably, the polypeptide includes at least about 20% acidic amino acid residues, more preferably yet at least about 40% acidic amino acid residues, more preferably yet at least about 60% acidic amino acid residues, more preferably yet at least about 80% acidic amino acid residues, more preferably yet at least about 90% acidic amino acid residues, more preferably yet at least about 95% acidic amino acid residues, and most preferably at least about 98% acidic amino acid residues. Acidic amino acid residues include aspartic acid and glutamic acid. An example of such an LBP poly-peptide is BHF-1, which is a 20 amino acid length fragment of human or rabbit LBP-1 which contains amino acid residues 14 through 33. See FIG. 9 (SEQ ID NO: 9). 45% of the amino acid residues of BHF-1 are acidic. The invention also includes biologically active fragments and analogs of BHF-1.

Other preferred acidic regions from the LBPs are amino acid residues 329 through 343 (SEQ ID NO: 19), 329 through 354 (SEQ ID NO: 20), 344 through 354 (SEQ ID NO: 21), and 529 through 538 (SEQ ID NO: 22) of human LBP-2 as depicted in FIG. 7A (SEQ. ID NO: 43); amino acid residues 14 through 43 (SEQ ID NO: 23) and 38 through 43 (SEQ ID NO: 24) of rabbit or human LBP-1 as depicted in FIG. 1 (SEQ ID NO: 1) and FIG. 6 (SEQ ID NO: 6); amino acid residues 338 through 353 (SEQ ID NO: 25), 338 through 365 (SEQ ID NO: 26), 354 through 365 (SEQ ID NO: 27), and 444 through 453 (SEQ ID NO: 28) of rabbit LBP-2 as depicted in FIG. 2A (SEQ ID NO: 47); amino acid residues 96 through 110 (SEQ ID NO: 29) of rabbit LBP-3 as depicted in FIG. 5 (SEQ ID NO: 5); and amino acid residues 69-75 (SEQ ID NO: 41) of human LBP-3 as depicted in FIG. 8A (SEQ ID NO: 44). The invention is also meant to include biologically active fragments and analogs of any of these polypeptides.

Other examples of agents include homopolymers and heteropolymers of any amino acid or amino acid analog. In certain preferred embodiments, the agent is a homopolymer of an acidic amino acid or analog thereof. In certain embodiments, the agent is a heteropolymer of one or more acidic amino acids and one or more other amino acids, or analogs thereof. For example, agents include poly(glu), poly(asp), poly(glu asp), poly(glu N), poly(asp N) and poly(glu asp N). By N is meant any amino acid, or analog thereof, other than glu or asp. By poly(glu asp) is meant all permutations of glu and asp for a given length peptide. A preferred peptide is poly(glu) of no more than about 10 amino acids in length, preferably about 7 amino acids in length.

In certain preferred embodiments, the agent is an LBP nucleic acid or a biologically active fragment or analog thereof, e.g., a nucleic acid encoding LBP-1, LBP-2 or LBP-3 polypeptide, or a biologically active fragment or analog thereof. The agent can be, e.g., a nucleic acid comprising a nucleotide sequence as set forth in SEQ ID NOS: 10-18, 45, 46, and 48. In other embodiments, the agent is an antisense molecule, e.g., one which can bind to an LBP gene sequence.

Treating is meant to include, e.g., preventing, treating, reducing the symptoms of, or curing the atherosclerosis. Administration of the agent can be accomplished by any method which allows the agent to reach the target area, e.g., a target cell or the extracellular matrix. These methods include, e.g., injection, deposition, implantation, suppositories, oral ingestion, inhalation, topical administration, or any other method of administration where access to the target area by the agent is obtained. Injections can be, e.g., intravenous, intradermal, subcutaneous, intramuscular or intraperitoneal. Implantation includes inserting implantable drug delivery systems, e.g., microspheres, hydrogels, polymeric reservoirs, cholesterol matrices, polymeric systems, e.g., matrix erosion and/or diffusion systems and non-polymeric systems, e.g., compressed, fused or partially fused pellets. Suppositories include glycerin suppositories. Oral ingestion doses can be enterically coated. Inhalation includes administering the agent with an aerosol in an inhalator, either alone or attached to a carrier that can be absorbed.

Administration of the agent can be alone or in combination with other therapeutic agents. In certain embodiments, the agent can be combined with a suitable carrier, incorporated into a liposome, or incorporated into a polymer release system.

In certain embodiments of the invention, the administration can be designed so as to result in sequential exposures to the agent over some time period, e.g., hours, days, weeks, months or years. This can be accomplished by repeated administrations of the agent by one of the methods described above, or alternatively, by a controlled release delivery system in which the agent is delivered to the animal over a prolonged period without repeated administrations. By a controlled release delivery system is meant that total release of the agent does not occur immediately upon administration, but rather is delayed for some time. Release can occur in bursts or it can occur gradually and continuously. Administration of such a system can be, e.g., by long acting oral dosage forms, bolus injections, transdermal patches or subcutaneous implants.

Examples of systems in which release occurs in bursts include, e.g., systems in which the agent is entrapped in liposomes which are encapsulated in a polymer matrix, the liposomes being sensitive to a specific stimulus, e.g., temperature, pH, light, magnetic field, or a degrading enzyme, and systems in which the agent is encapsulated by an ionically-coated microcapsule with a microcapsule core-degrading enzyme. Examples of systems in which release of the agent is gradual and continuous include, e.g., erosional systems in which the agent is contained in a form within a matrix, and diffusional systems in which the agent permeates at a controlled rate, e.g., through a polymer. Such sustained release systems can be, e.g., in the form of pellets or capsules.

The agent can be suspended in a liquid, e.g., in dissolved form or colloidal form. The liquid can be a solvent, partial solvent or non-solvent. In many cases water or an organic liquid can be used.

The agent can be administered prior to or subsequent to the appearance of atherosclerosis symptoms. In certain embodiments, the agent is administered to patients with familial histories of atherosclerosis, or who have phenotypes that may indicate a predisposition to atherosclerosis, or who have been diagnosed as having a genotype which predisposes the patient to atherosclerosis, or who have other risk factors, e.g., hypercholesterolemia, hypertension or smoking.

The agent is administered to the animal in a therapeutically effective amount. By therapeutically effective amount is meant that amount which is capable of at least partially preventing or reversing atherosclerosis. A therapeutically effective amount can be determined on an individual basis and will be based, at least in part, on consideration of the species of animal, the animal's size, the animal's age, the agent used, the type of delivery system used, the time of administration relative to the onset of atherosclerosis symptoms, and whether a single, multiple, or controlled release dose regimen is employed. A therapeutically effective amount can be determined by one of ordinary skill in the art employing such factors and using no more than routine experimentation.

Preferably, the concentration of the agent is at a dose of about 0.1 to about 1000 mg/kg body weight/day, more preferably at about 0.1 to about 500 mg/kg/day, more preferably yet at about 0.1 to about 100 mg/kg/day, and most preferably at about 0.1 to about 5 mg/kg/day. The specific concentration partially depends upon the particular agent used, as some are more effective than others. The dosage concentration of the agent that is actually administered is dependent at least in part upon the final concentration that is desired at the site of action, the method of administration, the efficacy of the particular agent, the longevity of the particular agent, and the timing of administration relative to the onset of the atherosclerosis symptoms. Preferably, the dosage form is such that it does not substantially deleteriously affect the animal. The dosage can be determined by one of ordinary skill in the art employing such factors and using no more than routine experimentation.

In certain embodiments, various gene constructs can be used as part of a gene therapy protocol to deliver nucleic acids encoding an agent, e.g., either an agonistic or antagonistic form of an LBP polypeptide. For example, expression vectors can be used for in vivo transfection and expression of an LBP polypeptide in particular cell types so as to reconstitute the function of, or alternatively, abrogate the function of, LBP polypeptide in a cell in which non-wild type LBP is expressed. Expression constructs of the LBP polypeptide, and mutants thereof, may be administered in any biologically effective carrier, e.g., any formulation or composition capable of effectively delivering the LBP gene to cells in vivo. Approaches include, e.g., insertion of the subject gene in viral vectors including, e.g., recombinant retroviruses, adenovirus, adeno-associated virus, and herpes simplex virus-1, or recombinant bacterial or eukaryotic plasmids. Viral vectors infect or transduce cells directly; plasmid DNA can be delivered with the help of, for example, cationic liposomes (Lipofectin™ (Life Technologies, Inc., Gaithersburg, Md.) or derivatized (e.g. antibody conjugated), polylysine conjugates, gramacidin S, artificial viral envelopes or other such intracellular carriers, as well as direct injection of the gene construct or $Ca_3(PO_4)_2$ precipitation carried out in vivo. The above-described methods are known to those skilled in the art and can be performed without undue experimentation. Since transduction of appropriate target cells represents the critical first step in gene therapy, choice of the particular gene delivery system will depend on such factors as the phenotype of the intended target and the route of administration, e.g., locally or systemically. Administration can be directed to one or more cell types, and to one or more cells within a cell type, so as to be therapeutically effective, by methods that are known to those skilled in the art. In a preferred embodiment, the agent is administered to arterial wall cells of the animal. For example, a genetically engineered LBP gene is administered to arterial wall cells. In certain embodiments, administration is done in a prenatal animal or embryonic cell. It will be recognized that the particular gene construct provided for in vivo transduction of LBP expression is also useful for in vitro transduction of cells, such as for use in the diagnostic assays described herein.

In certain embodiments, therapy of atherosclerosis is performed with antisense nucleotide analogs of the genes which code for the LBPs. Preferably, the antisense nucleotides have non-hydrolyzable "backbones," e.g., phosphorothioates, phosphorodithioates or methylphosphonates. The nucleoside base sequence is complementary to the sequence of a portion of the gene coding for, e.g., LBP-1, 2 or 3. Such a sequence might be, e.g., ATTGGC if the gene sequence for the LBP is TAACCG. One embodiment of such therapy would be incorporation of an antisense analog of a portion of one of the LBP genes in a slow release medium, e.g., polyvinyl alcohol, which is administered, e.g., by subcutaneous injection, so as to release the antisense nucleotide analog over a period of weeks or months. In another embodiment, the antisense analog is incorporated into a polymeric matrix, e.g., polyvinyl alcohol, such that the gel can be applied locally to an injured arterial wall to inhibit LBP synthesis and prevent LDL accumulation, e.g., after angioplasty or atherectomy.

The invention also includes a method for treating an animal at risk for atherosclerosis. An animal at risk for atherosclerosis is provided. An agent capable of altering an aspect of LBP structure or metabolism is provided. The agent is administered to the animal in a therapeutically effective amount such that treatment of the animal occurs. Being at risk for atherosclerosis can result from, e.g., a family history of atherosclerosis, or phenotypic symptoms which predispose to atherosclerosis, e.g., having hypercholesterolemia, hypertension or smoking.

The invention also includes a method for treating a cell having an abnormality in structure or metabolism of LBP. A cell having an abnormality in structure or metabolism of LBP is provided. An agent capable of altering an aspect of LBP structure or metabolism is provided. The agent is administered to the cell in a therapeutically effective amount such that treatment of the cell occurs.

In certain embodiments, the cell is obtained from a cell culture or tissue culture or an embryo fibroblast. The cell can be, e.g., part of an animal, e.g., a natural animal or a nonhuman transgenic animal. Preferably, the LBP is LBP-1, LBP-2 or LBP-3.

The invention also includes a pharmaceutical composition for treating atherosclerosis in an animal comprising a therapeutically effective amount of an agent, the agent being capable of altering an aspect of LBP metabolism or structure in the animal so as to result in treatment of the atherosclerosis, and a pharmaceutically acceptable carrier. Pharmaceutically acceptable carriers include, e.g., saline, liposomes and lipid emulsions.

In certain preferred embodiments, the agent of the pharmaceutical composition is an LBP polypeptide, e.g., LBP-1, LBP-2 or LBP-3, or a biologically active fragment or analog thereof. The agent can be, e.g., the polypeptide as set forth in SEQ ID NOS: 1-9, 43, 44, and 47. Preferably, the agent is a polypeptide of no more than about 100 amino acid residues in length, more preferably of no more than about 50 amino acid residues, more preferably yet of no more than about 30 amino acid residues, more preferably yet of no more than about 20 amino acid residues, more preferably yet of no more than about 10 amino acid residues, more preferably yet of no more than about 5 amino acid residues, more preferably yet of no more than about 4 amino acid residues, more preferably yet of no more than about 3 amino acid residues, and most preferably of no more than about 2 amino acid residues. Preferably, the polypeptide includes at least about 20% acidic amino acid residues, more preferably yet at least about 40% acidic amino acid residues, more preferably yet at least about 60% acidic amino acid residues, more preferably yet at least about 80% acidic amino acid residues, more preferably yet at least about 90% acidic amino acid residues, more preferably yet at least about 95% acidic amino acid residues, and most preferably at least about 98% acidic amino acid residues.

In certain preferred embodiments, the agent is an LBP nucleic acid, e.g., a nucleic acid encoding LBP-1, LBP-2 or LBP-3 polypeptide, or a biologically active fragment or analog thereof. The agent can be, e.g., a nucleic acid comprising a nucleotide sequence as set forth in SEQ ID NOS: 10-18, 45, 46, and 48.

The invention also includes a vaccine composition for treating atherosclerosis in an animal comprising a therapeutically effective amount of an agent, the agent being capable of altering an aspect of LBP metabolism or structure in the animal so as to result in treatment of the atherosclerosis, and a pharmaceutically acceptable carrier.

The invention also includes a method for diagnosing atherosclerotic lesions in an animal. An animal is provided. A labeled agent capable of binding to LBP present in atherosclerotic lesions is provided. The labeled agent is administered to the animal under conditions which allow the labeled agent to interact with the LBP so as to result in labeled LBP. The localization or quantification of the labeled LBP is determined by imaging so as to diagnose the presence of atherosclerotic lesions in the animal.

Preferably, the LBP is LBP-1, LBP-2 or LBP-3. The imaging can be performed by standard methods known to those skilled in the art, including, e.g., magnetic resonance imaging, gamma camera imaging, single photon emission computed tomographic (SPECT) imaging, or positron emission tomography (PET).

Preferably, agents that bind tightly to LBPs in atherosclerotic lesions are used for atherosclerotic imaging and diagnosis. The agent is radiolabeled with, e.g., $^{99m}Tc$ or another isotope suitable for clinical imaging by gamma camera, SPECT, PET scanning or other similar technology. Since LBPs occur in very early lesions, such imaging is more sensitive than angiography or ultrasound for locating very early lesions which do not yet impinge on the arterial lumen to cause a visible bulge or disturbed flow. In addition to locating both early and more developed lesions, the imaging agents which bind to LBPs can also be used to follow the progress of atherosclerosis, as a means of evaluating the effectiveness of both dietary and pharmacological treatments.

Thus, a diagnostic embodiment of the invention is the adaptation of, e.g., a peptide complementary to one of the LBPs, by radiolabeling it and using it as an injectable imaging agent for detection of occult atherosclerosis. The peptide is selected from those known to bind to LBPs, e.g., RRRRRRR (SEQ ID NO: 52) or KKLKLXX (SEQ ID NO: 53), or any other polycationic peptide which binds to the highly electronegative domains of the LBPs. For extracorporeal detection with a gamma scintillation (Anger) camera, technetium-binding ligands, e.g., CGC, GGCGC, or GGCGCF, can be incorporated into the peptides at the N-terminus or C-terminus for 99mWc labeling. For external imaging by magnetic resonance imaging (MRI), e.g., the gadolinium-binding chelator, diethylene triamine penta-acetic acid (DTPA), is covalently bound to the N- or C-terminus of the peptides. In yet other embodiments, the LBP-binding peptides are covalently bound, e.g., to magnetic ion oxide particles by standard methods known to those skilled in the art, e.g., conjugating the peptides with activated polystyrene resin beads containing magnetic ion oxide.

The invention also includes a method for immunizing an animal against an LBP, e.g., LBP-1, LBP-2 or LBP-3, or fragment or analog thereof. An animal having LDL is provided. An LBP or fragment or analog thereof is provided. The LBP or fragment or analog thereof is administered to the animal so as to stimulate antibody production by the animal to the LBP or fragment or analog thereof such that binding of the LBP to The LDL is altered, e.g., decreased or increased.

The invention also includes a method of making a fragment or analog of LBP polypeptide, the fragment or analog having the ability to bind to modified LDL and native LDL. An LBP polypeptide is provided. The sequence of the LBP polypeptide is altered. The altered LBP polypeptide is tested for the ability to bind to modified LDL, e.g., methylated LDL, oxidized LDL, acetylated LDL, cyclohexanedione-treated LDL (CHD-LDL), and to native LDL.

The fragments or analogs can be generated and tested for their ability to bind to these modified LDLs and to native LDL, by methods known to those skilled in the art, e.g., as described herein. Preferably, they are tested for their ability to bind to methylated LDL and native LDL. The binding activity of the fragment or analog can be greater or less than the binding activity of the native LBP. Preferably, it is greater. In preferred embodiments, the LBP is LBP-1, LBP-2 or LBP-3.

The invention also includes a method for isolating a cDNA encoding an LBP. A cDNA library is provided. The cDNA library is screened for a cDNA encoding a polypeptide which binds to native LDL and modified LDL, e.g., methylated LDL or oxidized LDL. The cDNA which encodes this polypeptide is isolated, the cDNA encoding an LBP.

Atherosclerosis in a hyperlipidemic subject can be reduced following the generation of an immune response in the subject by immunization with LBPs. Numerous immunotherapeutic products can be used to generate antibodies that will block the binding between LDL and LBPs.

The injection of one or more LBPs can result in the production of anti-LBP antibodies, resulting in a reduction in, e.g., aortic atherosclerosis. This effect is thought to be mediated by an inhibition of LBP binding to LDL. LBP immunogens that can be used in the invention include human LBPs, non-human LBPs, recombinant LBPs, and proteins structurally related to the LBPs described herein, e.g. non-naturally occurring proteins that differ from a naturally occurring LBP at one or more amino acid residues. In addition to full length proteins, injecting one or more peptides that include an LBP domain can generate an effective immune response. For example, the injection of a peptide comprising an LBP domain having LDL-binding activity can cause an organism to make antibodies to the LBP binding sites for LDL. These peptide immunogens can include sequences derived from human LBPs, non-human LBPs, recombinant LBPs, and proteins structurally related to the LBPs described herein.

Modifications can be made to a protein or peptide immunogen of the invention to increase its immunogenicity. The immunogen can be conjugated or coupled with a carrier, e.g. a Cholera toxin B chain or monoclonal antibodies. The immunogen can be precipitated with aluminum salts or cross-linked with formaldehyde or other aldehydes. The protein may be mixed with a physiologically acceptable diluent such as water, phosphate buffered saline, or saline. The composition may further include an adjuvant. In addition to RIBI adjuvant, adjuvants such as incomplete Freund's adjuvant, aluminum phosphate, aluminum hydroxide are all well known in the art. Adjustments in the adjuvant of the invention can be made to affect the immunogenicity of the peptide or protein. Examples of such modifications include using: aluminum salts; cytokines; MF59 (microfluidized emulsion of oil and surfactants); SAF-1 (oil-based emulsion); saponin derivatives; polymers (such as polyphosphazene); and bacterial toxins. Additional descriptions of antigenic protein-adjuvant combinations are described in WO 99/54452 (herein incorporated by reference) and WO 99/49890 (herein incorporated by reference).

In addition to delivery of the proteins and peptides described above, numerous other delivery systems can be used to generate the anti-atherosclerotic immunity of the invention. The LBP immunogen can be delivered either directly as a protein antigen or alternatively as a nucleic acid that encodes the protein antigen. The immunotherapeutic products of the invention, either protein or nucleic acid, can be delivered by numerous delivery routes. These include injection, deposition, implantation, suppositories, oral ingestion, inhalation (e.g., delivery via a nasal spray), and topical administration (e.g., delivery via a skin patch).

A nucleic acid encoding an immunogen of the invention can be directly administered, for example by injection, to tissues and expressed as a protein. The DNA or RNA can be either associated with a delivery vehicle (e.g., viruses, bacteria, liposomes, and gold beads) or naked (free from association with transfection-facilitating proteins, viral particles, liposomal formulations, charged lipids and calcium phosphate precipitating). The nucleic acid can optionally include a promoter, e.g. a viral promoter. The immunogen encoded by the nucleic acid is produced in the host, resulting in the generation of an immune response. Methods for the delivery of nucleic acid sequences encoding therapeutic proteins and peptides are described in detail by Felgner et al. (U.S. Pat. No. 5,580,859; herein incorporated by reference) and Barbet et al. (U.S. Pat. No. 6,025,338; herein incorporated by reference). Vaccine compositions of viral liposomes comprising a nucleic acid, e.g. an RNA, encoding a protein antigen are described in WO 99/52503 (herein incorporated by reference). Proteins and nucleic acids encoding peptides can also be delivered to an individual by their encapsulation in liposomes, microparticles, and ISCOMS, all of which are well known in the art (see, e.g., U.S. Pat. No. 6,013,258, herein incorporated by reference).

A nucleic acid encoding an immunogen of the invention can also be included in the genome of a plant, so as to result in the production of the immunogen by plant tissues. The genetically modified plant may then consumed by an individual, resulting in the ingestion of the immunogen and the generation of an anti-LBP immune response. Methodology for the generation and usage of edible plant vaccines is described in WO 99/54452 (herein incorporated by reference).

Numerous plants may be useful for the production of an edible vaccine, including: tobacco, tomato, potato, eggplant, pepino, yam, soybean, pea, sugar beet, lettuce, bell pepper, celery, carrot, asparagus, onion, grapevine, muskmelon, strawberry, rice, sunflower, rapeseed/canola, wheat, oats, maize, cotton, walnut, spruce/conifer, poplar and apple. The edible vaccine can include a plant cell transformed with a nucleic acid construct comprising a promoter and a sequence encoding an LBP. The sequence may optionally encode a chimeric protein, comprising a cholera toxin subunit B peptide fused to the LBP peptide. Preferred plant promoters of the invention include CaMV 35S, patatin, mas, and granule-bound starch synthase promoters. Additional useful promoters and enhancers are described in WO 99/54452.

The edible vaccine of the invention can be administered to a mammal suffering from or at risk of atherosclerosis. Preferably, an edible vaccine is administered orally, e.g. consuming a transgenic plant of the invention. The transgenic plant can be in the form of a plant part, extract, juice, liquid, powder, or tablet. The edible vaccine can also be administered via an intranasal route.

Microorganisms, e.g., attenuated viruses or bacteria, can be used in the invention by including a nucleic acid encoding an LBP immunogen in the genome of the microorganism. This modified vector can then be delivered to a host, resulting in the in vivo production of the immunogen. The immune response generated by these vectors is expected to result in anti-atherosclerotic immunity. Nucleic acid molecules are inserted into microorganism genomes by standard methods known in the art (U.S. Pat. No. 5,866,136 and U.S. Pat. No. 6,025,164, both of which are herein incorporated by reference)

The anti-atherosclerotic methods of the invention are directed to treating a subject, e.g., a human, primate, horse, dog, cat, or goat, at risk for atherosclerosis by stimulating an anti-LBP response in the subject by immunotherapy. The LBP proteins and peptides of the invention may be delivered to the subject by the numerous delivery systems described herein. The immunotherapy may comprise an initial immunization followed by additional, e.g. one, two, or three, boosters.

The invention also includes a method of treating a subject at risk for atherosclerosis by (1) providing a subject at risk for atherosclerosis and (2) administering to the subject one or more of the following: (a) an LBP protein or fragment or analog thereof and an adjuvant; (b) a nucleic acid encoding an LBP protein; (c) a virus or bacteria comprising a nucleic acid encoding an LBP protein; and (d) an edible plant comprising a nucleic acid encoding an LBP protein. The LBP protein used in this method can be any LBP described herein, e.g., LBP-1, LBP-2, or LBP-3. A combination of more than one nucleic acid or LBP protein or fragment or analog thereof can be administered to the subject. For example, combinations of LBP proteins, or nucleic acids encoding LBP proteins, include: (1) LBP-1 and LBP-2; (2) LBP-1 and LBP-3; (3) LBP-2 and LBP-3; and (4) LBP-1, LBP-2, and LBP-3. This method optionally includes a step of diagnosing the subject as being at risk for atherosclerosis.

Also provided by the invention is a method of treating a subject at risk for atherosclerosis whereby a non-autologous LBP protein or a nucleic acid encoding a non-autologous LBP protein is delivered to the subject to generate an immune response to an autologous LBP. Specifically, this method entails identifying one or more autologous LBP proteins, e.g., LBP-1, LBP-2, or LBP-3, produced by the subject. The identification can by, e.g., DNA sequence analysis, protein sequence analysis, antibody reactivity, hybridization analysis, or nucleic acid amplification. Next, a non-autologous LBP protein, e.g., allogeneic, xenogeneic, or a genetically modified, non-naturally occurring protein that differs at one or more amino acid residues from the one or more LBP proteins, is administered to the subject. Alternatively, a nucleic acid encoding a non-autologous LBP protein is administered to the subject. The anti-atherosclerotic effectiveness of this immunotherapeutic product is determined by its ability to induce an immune response against one or more autologous LBP proteins when administered to the subject. It is therefore expected that extensive differences between a non-autologous and autologous LBP protein will not result in cross immunoreactivity. This method optionally includes a step of diagnosing the subject as being at risk for atherosclerosis.

Another method of the invention is a method of treating a subject at risk for atherosclerosis by increasing the levels of one or more LBP proteins circulating in the plasma. According to this method, either autologous or non-autologous LBP levels may be increased. Non-autologous LBP proteins include, e.g., allogeneic LBP, xenogeneic LBP, and genetically modified LBP. The plasma levels of one or more LBP proteins can be increased by the delivery of a nucleic acid encoding an LBP protein. Because LBP generally does not normally occur as a circulating protein, the endogenous molecule is expected to be susceptible to immune recognition when delivered in a soluble form. This method optionally includes a step of diagnosing the subject as being at risk for atherosclerosis.

Also included in the invention is a pharmaceutical composition containing one or more LBP proteins, e.g., LBP-1, LBP-2, or LBP-3, mixed with an adjuvant, suitable for use in humans. The pharmaceutical composition can contain a combination of more than one LBP protein. For example, compositions can include any of the following: (1) LBP-1 and LBP-2; (2) LBP-1 and LBP-3; (3) LBP-2 and LBP-3; and (4) LBP-1, LBP-2, and LBP-3.

Also included in the invention is a cell therapy system, whereby a cell expressing an LBP is delivered to a subject at risk for atherosclerosis. This cell can be engineered to express either an autologous or non-autologous LBP protein or peptide of the invention. Delivery of this engineered cell to a subject results in the in vivo production of an LBP protein and the associated immunotherapy produced when either the protein or a nucleic acid encoding the protein is provided to an individual. Cell therapy methods are described in U.S. Pat. No. 5,955,095 (herein incorporated by reference).

The following non-limiting examples further illustrate the present invention.

EXAMPLES

Example 1

Construction of a Rabbit cDNA Library

This example illustrates the construction of a rabbit cDNA library using mRNA from balloon-deendothelialized healing rabbit abdominal aorta. Balloon-catheter deendothelialized rabbit aorta has been shown to be a valid model for atherosclerosis (Minick et al., Am. J. Pathol. 95:131-158 (1979).

The mRNA was obtained four weeks after ballooning to maximize focal LDL binding in the ballooned rabbit aorta. First strand cDNA synthesis was carried out in a 50 µl reaction mixture containing 4 μg mRNA; 2 μg oligo d(T)primer; methylation dNTP mix (10 mM each); 10 mM DTT; 800 units superscript II RT (Life Technologies, Gaithersburg, Md.); 1× first strand cDNA synthesis buffer (50 mM Tris-HCl, pH 8.3; 75 mM KCl; 5 mM $MgCl_2$), which was incubated for 1 hr at 37° C. The reaction mixture was then adjusted to 250 μl through the addition of 1× second strand buffer (30 mM Tris-HCl, pH 7.5; 105 mM KCl; 5.2 mM $MgCl_2$); 0.1 mM DTT; methylation dNTP mix (10 mM each); 50 units E. coli DNA polymerase I, 3 units RNase H; 15 units E. coli DNA ligase (all enzymes from Life Technologies), which was incubated for an additional 2.5 hr at 15° C. The resulting double-stranded cDNAs (dscDNA) were then treated with 1.5 units T4 DNA polymerase (Novagen Inc., Madison, Wis.) for 20 min at 11° C. to make blunt-ended dscDNA. These were then concentrated by ethanol precipitation and EcoR1/Hind III linkers were attached to the ends by T4 DNA ligase (Novagen Inc.). The linker-ligated cDNAs were treated with EcoR1 and Hind111 restriction enzymes to produce EcoR1 and Hind III recognition sequences at their 5' and 3' ends, respectively. After the removal of linker DNA by gel exclusion chromatography, the dscDNAs were inserted into λEXlox phage arms (Novagen Inc.) in a unidirectional manner by T4 DNA ligase and packaged into phage particles according to the manufacturer's protocol (Novagen Inc.). A phage library of cDNAs containing $2 \times 10^6$ independent clones was established from 4 μg of mRNA.

Example 2

Identification of Rabbit cDNAs Encoding LDL Binding Proteins (LBPs)

This example illustrates a method of functionally screening a rabbit cDNA library so as to identify cDNAs encoding LBPs which bind to both native LDL and methyl LDL. Methyl LDL is not recognized by previously reported cell surface receptors. See, e.g., Weisgraber et al., J. Biol. Chem. 253:9053-9062 (1978).

A fresh overnight culture of E. coli ER1647 cells (Novagen Inc.) was infected with the cDNA phage obtained from Example 1, and plated at a density of $2 \times 10^4$ plaque-forming units (pfu) in 150 mm diameter plates containing 2×YT agar. A total of 50 plates, equivalent to $1 \times 10^6$ phage, were plated and incubated at 37° C. until the plaques reached 1 mm in diameter (5-6 hr). A dry nitrocellulose membrane, which had previously been saturated with 10 mM IPTG solution, was layered on top of each plate to induce the production of recombinant protein, as well as to immobilize the proteins on the membranes. The plates were incubated at 37° C. for an additional 3-4 hr, and then overnight at 4° C.

The next day, the membranes were lifted from each plate and processed as follows. Several brief rinses in TBST solution (10 mM Tris-HCl, pH 8.0; 150 mM NaCl, 0.05% Tween 20); two 10-min rinses with 6M guanidine-HCl in HBB (20 mM HEPES, pH 7.5; 5 mM $MgCl_2$, 1 mM DTT, and 5 mM KCl); two 5-min rinses in 3M guanidine-HCl in HBB; a final brief rinse in TBSEN (TBS, 1 mM EDTA, 0.02% $NaN_3$).

The membranes were then blocked for 30 min at room temperature in a solution of TBSEN with 5% non-fat dry milk, followed by 10 min in TBSEN with 1% non-fat dry milk. Following blocking, the membranes were incubated with native human LDL (obtained as described in Example 11 or methylated human LDL (meLDL) (see Weisgraber et al., J. Biol. Chem. 253:9053-9062 (1978)), at a concentration of 4 μg/ml, in a solution containing 1×TBSEN, 1% non-fat dry milk, 1 mM PMSF, 0.5× protease inhibitor solution (1 mM ε-amino caproic acid/1 mM benzamidine). Incubation was for 4 hr at room temperature in a glass Petri dish with gentle stirring on a stirring table, followed by overnight at 4° C. with no stirring.

Specifically bound meLDL and native LDL were detected on the nitrocellulose membranes by antibodies against human LDL. Sheep anti-human LDL polyclonal antibodies (Boehringer Mannheim, Indianapolis, Ind.) were adsorbed with E. coli plys E cell extracts to abolish background. For adsorption, E. coli plys E cells were grown to log phase, spun down and resuspended in PBS containing 1 mM PMSF, 2 mM ε-amino caproic acid, and 1 mM benzamidine. The cell suspension then underwent 8 freeze-thaw cycles via immersion in liquid nitrogen and cold running tap water, respectively. The anti LDL antibodies/cell extract solution were incubated with gentle stirring for 1 hr at 4° C. (1 ml of antibody solution/3 mg crude cell extract). Following incubation, the mixture was centrifuged (10,000×g; 10 min; 4° C.) and the supernatant was stored at 4° C. in the presence of 0.02% $NaN_3$, until use. The membranes were processed for immunoscreening as follows: (i) three 5-min washes at room temperature in TBSEN containing 1% gelatin; (ii) 30 min incubation in PBS, pH 7.4 with 1% gelatin; (iii) two-hr room temperature incubation with gentle stirring in fresh PBS/gelatin solution containing adsorbed sheep anti-human LDL antibodies (Boehringer Manheim, Indianapolis, Ind.) (1:1000 dilution); (iv) three brief washes in TBS, pH 7.4; (v) one-hr room temperature incubation with gentle stirring in PBS/gelatin solution containing donkey anti-sheep alkaline phosphatase-conjugated antibodies (Sigma, St. Louis, Mo.) (1:10,000 dilution); (vi) three brief washes with TBS, PH 7.4; and (vii) development according to the manufacturer's instructions, using an alkaline phosphatase substrate development kit (Novagen Inc.). Phage plaques which produced LBPs appeared as blue-colored "donuts" on the membranes.

The phage from Example 1 containing the LBP cDNAs were plaque-purified and converted into plasmid subclones by following a protocol called "Autosubcloning by Cre-mediated Plasmid Excision" provided by Novagen Inc. DNA sequences were obtained by the dideoxynucleotide chain-termination method (Sanger et al., Proc. Natl. Acad. Sci., USA 74: 5463-5467 (1977), and analyzed by an Applied Biosystems automated sequencer. The open reading frame (ORF) of each cDNA was determined from consensus sequences obtained from both the sense and antisense strands of the cDNAs. Sequencing confirmed that three previously unknown genes had been isolated. Since the genes were selected by functional screening for LDL binding, the proteins coded by these genes were termed LDL binding proteins (LBPs), specifically, LBP-1, LBP-2 and LBP-3. The cDNA sequences for rabbit LBP-1, LBP-2 and LBP-3 and the corresponding proteins are set forth in SEQ ID NOS: 10-14 and 48.

Based on their respective cDNA coding sequences, the sizes of the recombinant proteins were determined to be 16.2 kDa for LBP-1, 40 kDa for LBP-2, and 62.7 kDa for LBP-3.

Example 3

Northern Blot Analysis of Rabbit RNA Using LBP cDNA or cRNA

This example illustrates the size and tissue distribution of LBP mRNAs. Total RNA was isolated from different rabbit tissues: adrenals, thoracic aorta, abdominal aorta, ballooned and reendothelialized abdominal aorta, heart, kidney, smooth muscle cells, lung and liver, by Trizol reagent (Life Technologies) and concentrated by ethanol precipitation. Gel electrophoresis of RNA was carried out in 1.2% agarose gel containing 1×MOPS buffer (0.2M MOPS, pH 7.0; 50 mM sodium acetate; 5 mM EDTA, pH 8.0) and 0.37M formaldehyde. Gels were loaded with 20 μg total RNA from each tissue examined and electrophoresed at 100 volts for 2 hr in 1×MOPS buffer. RNAs were blotted onto supported nitrocellulose membranes (Schleicher & Schuell, Keene, N.H.) and immobilized by baking at 80° C. for 2 hr. Hybridization to radiolabeled LBP-1, LBP-2 and LBP-3 cDNA or cRNA probes was carried out by standard procedures known to those skilled in the art (see, e.g., Ausubel et al., Current Protocols in Molecular Biology; John Wiley & Sons (1989)); signals were detected by autoradiography.

The results were as follows: the sizes of the mRNAs were about 1.3 kb for LBP-1, about 2.3-2.5 kb for LBP-2, and about 4.7 kb for LBP-3. LBP-1, LBP-2 and LBP-3 mRNA were found in all tissues tested, but the highest amount was in ballooned abdominal aorta.

Example 4

Isolation of Human LBP cDNAs and Genomic Clones

This example illustrates isolation of human LBP cDNAs. Human LBP cDNA clones were isolated from three cDNA libraries. A human fetal brain cDNA library was obtained from Stratagene, LaJolla, Calif., a human liver and a human aorta cDNA library were obtained from Clontech, Palo Alto, Calif., and screened with a radiolabeled cDNA probe derived from rabbit LBP-1, LBP-2 or LBP-3, according to the method described in Law et al., Gene Expression 4:77-84 (1994). Several strongly hybridizing clones were identified and plaque-purified. Clones were confirmed to be human LBP-1, LBP-2 and LBP-3, by DNA sequencing using the dideoxynucleotide chain-termination method and analysis by an Applied Biosystems automated sequencer. The cDNA sequences and the corresponding proteins for human LBP-1, LBP-2 and LBP-3 are set forth in SEQ ID NOS: 15, 16 and 17, respectively.

A human genomic library was screened with each of the LBP-1, LBP-2, and LBP-3 clones obtained from the cDNA library screening. Clones hybridizing to each of the three cDNAs were isolated and sequenced. The genomic sequence for LBP-1, LBP-2, and LBP-3 are set forth in FIGS. 22-24, respectively. The LBP-1 open reading frame spans four exons of the LBP-1 gene (FIG. 22; SEQ ID NO:49). The LBP-1 protein predicted by the genomic sequence is identical to that predicted by the cDNA clone described above. The LBP-2 open reading frame spans five exons of the LBP-2 gene (FIG. 23; SEQ ID NO:50). The LBP-2 protein predicted by the genomic sequence differs from that predicted by the cDNA clone in that it contains an additional 321 amino acids at its amino terminus (the LBP-2 cDNA is a 5' truncation). The LBP-3 open reading frame spans ten exons of the LBP-3 gene (FIG. 24; SEQ ID NO:51). The LBP-3 protein predicted by the genomic sequence differs from that predicted by the cDNA clone in that it contains an additional 16 amino acids at its amino terminus (the LBP-3 cDNA is a 5' truncation) and an Asn at amino acid position 130 (the cDNA predicts a Tyr at this position). A comparison between the corresponding LBP-1, LBP-2 and LBP-3 protein sequences for rabbit and human are shown in FIGS. 19, 20 and 21.

Example 5

Isolation of Recombinant LBP-1, LBP-2 and LBP-3 Rabbit Proteins from *E. coli*

LBP cDNA was isolated from the original pEXlox plasmids obtained as described in Examples 1 and 2, and subcloned into the pPROEX-HT vector (Life Technologies) for recombinant protein expression. Induction of the recombinant protein by IPTG addition to transformed *E. coli* DH10B cultures resulted in the expression of recombinant protein containing a 6-histidine tag (N-terminal). This tagged protein was then purified from whole cell proteins by binding to Ni-NTA (nickel nitrilo-triacetic acid) as described in the protocol provided by the manufacturer (Qiagen, Inc., Santa Clara, Calif.). The preparation obtained after the chromatography step was approximately 90% pure; preparative SDS-PAGE was performed as the final purification step.

When required by the characterization procedure, iodination of LBPs was carried out using Iodobeads (Pierce, Rockford, Ill.). The Iodobeads were incubated with 500 μCi of $Na^{125}I$ solution (17 Ci/mg) (New England Nuclear, Boston, Mass.) in a capped microfuge tube for 5 min at room temperature. The protein solution was added to the Iodobeads-$Na^{125}I$ microfuge tube and incubated for 15 min at room temperature. At the end of this incubation, aliquots were removed for the determination of total soluble and TCA precipitable counts. The radiolabeled protein was then precipitated with cold acetone (2.5 vol; −20° C.; 2.5 hr). Following this incubation, precipitated protein was collected by centrifugation (14,000 g; 1 hr; room temperature) and resuspended in sample buffer (6 M urea/50 mM Tris, pH 8.0/2 mM EDTA). Integrity of the protein preparation was assessed by SDS-PAGE.

The identities of the recombinant LBPs were confirmed using standard protein sequencing protocols known to those skilled in the art. (A Practical Guide for Protein and Peptide Purification for Microsequencing, Matsudaira, ed., Academic Press, Inc., 2d edition (1993)). Analysis was performed using an Applied Biosystems Model 477A Protein Sequencer with on-line Model 120 PTH amino acid analyzer.

Example 6

Production of Antibodies to LBP-1, LBP-2 and LBP-3

This example illustrates the production of polyclonal antibodies to LBP-1, LBP-2 and LBP-3. A mixture of purified recombinant LBP protein (0.5 ml; 200 μg) and RIBI adjuvant (RIBI ImmunoChem. Research, Inc., Hamilton, Mont.) was injected subcutaneously into male guinea pigs (Dunkin Hartley; Hazelton Research Products, Inc., Denver, Pa.) at 3-5 sites along the dorsal thoracic and abdominal regions of the guinea pig. Blood was collected by venipuncture on days 1 (pre-immune bleeding), 28, 49 and 70. Booster injections were administered on days 21 (100 μg; SC), 42 (50 μg; SC), and 63 (25 μg; SC). The titer of the guinea pig antiserum was evaluated by serial dilution "dot blotting." Preimmune antiserum was evaluated at the same time. After the third booster of LBP protein, the titer against the recombinant protein reached a maximal level with a detectable calorimetric response on a dot blot assay of 156 pg.

Specificity of the polyclonal antibody for recombinant LBP-1, LBP-2 or LBP-3 was demonstrated using Western blot analysis. (Towbin et al., Proc. Natl. Acad. Sci. USA 76: 4350 (1979)). The protein-antibody complex was visualized immunochemically with alkaline phosphatase-conjugated goat antiguinea pig IgG, followed by staining with nitro blue tetrazolium (BioRad Laboratories, Hercules, Calif.). Nonspecific binding was blocked using 3% non-fat dry milk in Tris buffered saline (100 mM Tris; 0.9% NaCl, pH 7.4).

Example 7

Immunohistochemical Characterization

This example illustrates the presence of LBPs in or on endothelial cells covering plaques, in or on adjacent smooth muscle cells, and in the extracellular matrix. In addition, co-localization of LDL and LBPs was demonstrated. These results were obtained by examining ballooned rabbit arterial lesions and human atherosclerotic plaques by immunohistochemical methods.

Ballooned deendothelialized aorta was obtained from rabbits which had received a bolus injection of human LDL (3 mg; i.v.) 24 hr prior to tissue collection. Human aortas containing atherosclerotic plaques were obtained from routine autopsy specimens. Tissues were fixed in 10% buffered formalin ($\leq$24 hr) and imbedded in paraffin using an automated tissue-imbedding machine. Tissue sections were cut (5-7µ) and mounted onto glass slides by incubating for 1 hr at 60° C. Sections were deparaffinized. After a final wash with deionized $H_2O$, endogenous peroxidase activity was eliminated by incubating the sections with 1% $H_2O_2/H_2O$ buffer for 5 min at room temperature. Sections were rinsed with phosphate buffered saline (PBS) for 5 min at room temperature and nonspecific binding was blocked with 5% normal goat serum or 5% normal rabbit serum depending on the source of the secondary antibody (Sigma, St. Louis, Mo.) (1 hr; room temperature). Sections were then incubated with a 1:50 dilution (in 5% normal goat serum/PBS) of a guinea pig polyclonal antibody against the rabbit form of recombinant LBP-1, LBP-2 or LBP-3. Controls included preimmune serum as well as specific antisera to LBP-1, LBP-2, or LBP-3 in which the primary antibody was completely adsorbed and removed by incubation with recombinant LBP-1, LBP-2 or LBP-3 followed by centrifugation prior to incubation with the tissue sections. An affinity purified rabbit polyclonal antibody against human apolipoprotein B (Polysciences Inc.; Warrington, Pa.) was used at a dilution of 1:100 (in 5% normal rabbit serum/PBS). Sections were incubated for 2 hr at room temperature in a humidified chamber. At the end of incubation, sections were rinsed with PBS and incubated with a 1:200 dilution (in 5% normal goat serum/PBS) of goat anti-guinea pig biotinylated IgG conjugate (Vector Laboratories, Burlingame, Calif.) or a 1:250 dilution (in 5% normal rabbit serum/PBS) of rabbit anti-goat biotinylated IgG conjugate (Vector Laboratories, Burlingame, Calif.) for 1 hr at room temperature in a humidified chamber. Sections were then rinsed with PBS and antigen-antibody signal amplified using avidin/biotin HRP conjugate (Vectastain ABC kit; Vector Laboratories, Burlingame, Calif.). Sections were developed using DAB substrate (4-6 min; room temperature) and counterstained with hematoxylin. In the ballooned rabbit artery, immunohistochemistry with the anti-LBP-1, LBP-2 and LBP-3 antibodies showed that LBP-1, LBP-2 and LBP-3 were located in or on functionally modified endothelial cells at the edges of regenerating endothelial islands, the same location in which irreversible LDL binding has been demonstrated (Chang et al., Arteriosclerosis and Thrombosis 12:1088-1098 (1992)). LBP-1, LBP-2 and LBP-3 were also found in or on intimal smooth muscle cells underneath the functionally modified endothelial cells, and to a lesser extent, in extracellular matrix. No LBP-1, LBP-2 or LBP-3 was detected in still deendothelialized areas, where LDL binding had been shown to be reversible (Chang et al., Arteriosclerosis and Thrombosis 12:1088-1098 (1992)). Immunohistochemistry of ballooned rabbit aorta with anti-human apolipoprotein B antibodies showed the presence of LDL at the same locations as that found for LBP-1, LBP-2 and LBP-3.

In the human atherosclerotic plaques taken at routine autopsies, immunohistochemistry with the anti-LBP-1, anti-LBP-2 and anti-LBP-3 antibodies showed that LBP-1, LBP-2, and LBP-3 were also found in or on endothelial cells covering plaques and in or on adjacent smooth muscle cells. In the human tissue, there was greater evidence of LBP-1, LBP-2 and LBP-3 in extracellular matrix.

The results obtained with paraffin sections were identical to those of frozen sections.

Example 8

Affinity Coelectrophoresis (ACE) Assays of LBPs and LDL or HDL

This example illustrates that binding occurs between LBP-1, LBP-2 or LBP-3 and LDL, and that this binding is specific, as illustrated by the fact that binding does not occur between LBP-1, LBP-2 or LBP-3 and HDL (high density lipoprotein). Analysis of the affinity and specificity of recombinant rabbit LBP-1, LBP-2 or LBP-3 binding to LDL was carried out using the principle of affinity electrophoresis (Lee and Lander, Proc. Natl. Acad. Sci. USA 88:2768-2772 (1991)). Melted agarose (1%; 65° C.) was prepared in 50 mM sodium MOPS, pH 7.0; 125 mM sodium acetate, 0.5% CHAPS. A teflon comb consisting of nine parallel bars (45×4×4 mm/3 mm spacing between bars) was placed onto GelBond film (FMC Bioproducts, Rockland, Me.) fitted to a plexiglass casting tray with the long axis of the bars parallel to the long axis of the casting tray. A teflon strip (66×1×1 mm) was placed on edge with the long axis parallel to the short axis of the casting tray, at a distance of 4 mm from the edge of the teflon comb. Melted agarose (>65° C.) was then poured to achieve a height of approximately 4 mm. Removal of the comb and strip resulted in a gel containing nine 45×4×4 mm rectangular wells adjacent to a 66×1 mm slot. LDL or HDL samples were prepared in gel buffer (50 mM sodium MOPS, pH 7.0, 125 mM sodium acetate) at twice the desired concentration. Samples were then mixed with an equal volume of melted agarose (in 50 mM MOPS, pH 7.0; 125 mM sodium acetate; 50° C.), pipetted into the appropriate rectangular wells and allowed to gel. The binding affinity and specificity of LBP-1 and LBP-3 was tested using several concentrations of LDL (540 to 14 nM) and HDL (2840177 nM). A constant amount (0.003 nM-0.016 nM) of $^{125}$I-labeled LBP-1, LBP-2 or LBP-3 (suspended in 50 mM sodium MOPS, pH 7.0; 125 mM sodium acetate; 0.5% bromophenol blue; 6% (wt/vol) sucrose) was loaded into the slot. Gels were electrophoresed at 70 v/2 hr/20° C. At the end of the run, the gels were air dried and retardation profiles were visualized by exposure of X-ray films to the gels overnight at −70° C., with intensifying screens.

LDL retarded LBP-1, LBP-2 and LBP-3 migration through the gel in a concentration-dependent, saturable manner, indicating that LBP-1, LBP-2 and LBP-3 binding to LDL was highly specific. This conclusion is supported by the fact that HDL did not retard LBP-1, LBP-2 or LBP-3. A binding curve generated from the affinity coelectrophoresis assay indicated that LBP-1 binds to LDL with a $K_d$ of 25.6 nM, that LBP-2 (rabbit clone 26) binds to LDL with a $K_d$ of 100 nM, and that LBP-3 (80 kDa fragment) binds to LDL with a $K_d$ of 333 nM.

In addition to testing affinity and specificity of LBP-1, LBP-2 and LBP-3 binding to LDL, the ability of "cold" (i.e., non-radiolabeled) LBP-1, LBP-2 or LBP-3 to competitively inhibit radiolabeled LBP-1, LBP-2 or LBP-3 binding to LDL, respectively, was tested. Competition studies were carried out using fixed concentrations of cold LDL and radiolabeled LBP-1 and increasing amounts of cold recombinant LBP-1 (6-31 µM). The ACE assay samples and gel were prepared as described herein. Cold LBP-1 inhibited binding of radiolabeled LBP-1 to LDL in a concentration-dependent manner, cold LBP-2 inhibited binding of radiolabeled LBP-2 to LDL in a concentration-dependent manner, and cold LBP-3 inhibited binding of radiolabeled LBP-3 to LDL in a concentration-dependent manner.

Rabbit and human LBP-2 contain a long stretch of acidic amino acids at the amino terminal (rabbit LBP-2 amino acid residues 338 through 365 and human LBP-2 amino acid residues 329 through 354). The possibility that this segment of LBP-2 was the LDL binding domain was tested by subcloning two rabbit LBP-2 clones which differ from each other by the presence or absence of this acidic region (clone 26 and clone 45, respectively) into expression vectors, by standard methods known to those skilled in the art. ACE assays were then conducted in order to assess the affinity and specificity of the binding of these two clones to LDL. LDL retarded clone 26 derived radiolabeled LBP-2 migration through the gel in a concentration-dependent, saturable, manner while clone 45 derived radiolabeled LBP-2 migration was not retarded.

Competition studies using fixed concentrations of cold LDL and clone 26 derived radiolabeled LBP-2 and increasing concentrations of cold recombinant LBP-2/clone 26 and LBP-a/clone 45 were carried out. Cold clone 26 derived LBP-2 inhibited binding of clone 26 derived radiolabeled LBP-2 to LDL in a concentration-dependent manner. Clone 45 derived LBP-2, on the other hand, did not affect the binding of clone 26 derived radiolabeled LBP-2 to LDL. These results indicate that the long stretch of acidic amino acids contain a binding domain of LBP-2 to LDL.

Example 9

Affinity Coelectrophoreses (ACE) Assays of LBP-1 or LBP-2 and LDL in the Presence of Inhibitors This example illustrates that binding between LBP-1 or LBP-2 and LDL is inhibited by polyglutamic acid or BHF-1. The ability of a third compound to inhibit binding between two proteins previously shown to interact was tested by a modification of the ACE assays described in Example 8. The third compound was added to the top or wells together with the radiolabeled protein. If the third compound inhibited binding, the radiolabeled protein would run through the gel. If the third compound did not inhibit binding, migration of the radiolabeled protein was retarded by the protein cast into the gel.

Inhibition of LBP-1/LDL or LBP-2/LDL binding by polyglutamic acid (average MW about 7500, corresponding to about 7 monomers) was shown by casting a constant amount of LDL (148 nM) in all the rectangular lanes. A constant amount (1 µl) of $^{125}$I-labeled LBP-1 or LBP-2 (0.003 nM-0.016 nM) was loaded in the wells at the top of the gel, together with increasing concentrations of polyglutamic acid (obtained from Sigma) (0-0.4 nM). The gel was electrophoresed at 70 volts for 2 hr, dried and placed on X-ray film, with intensifying screens, overnight at −70° C. before the film was developed to determine the retardation profile of LBP-1 and LBP-2. As the concentration of polyglutamic acid increased, retardation of radiolabeled LBP-1 and LBP-2 migration by LDL decreased in a concentration-dependent manner, which showed that polyglutamic acid inhibited binding between LBP-1, LBP-2 and LDL.

Inhibition of LBP-1/LDL binding by BHF-1 was shown by casting a constant amount of LDL (148 nM) in all the rectangular lanes. A constant amount of $^{125}$I-labeled LBP-1 (0.003 nM-0.016 nM) was loaded in the wells at the top of the gel, together with increasing concentrations of BHF-1 (0-10 nM), obtained as described in Example 15. The gel was electrophoresed at 70 volts for 2 hr, dried and placed on X-ray film, with intensifying screens, overnight at −70° C. The film was then developed to determine the retardation profile of $^{125}$I-LBP-1. As the concentration of BHF-1 increased, retardation of LBP-1 by LDL decreased in a concentration-dependent manner, which demonstrated that BHF-1 inhibited binding between LBP-1 and LDL.

Example 10

Affinity Coelectrophoreses (ACE) Assays for Identifying Fragments Analogs and Mimetics of LBPs which Bind to LDL This example illustrates a method for identifying fragments, analogs or mimetics of LBPs which bind to LDL, and which thus can be used as inhibitors of LDL binding to LBP in the arterial walls, by occupying binding sites on LDL molecules, thereby rendering these sites unavailable for binding to LBP in the arterial wall.

Fragments of LBPs are generated by chemical cleavage or synthesized from the known amino acid sequences. Samples of these fragments are individually added (cold) to radiolabeled LBP as described in Example 8, to assess the inhibitory potency of the various fragments. By iterative application of this procedure on progressively smaller portions of fragments identified as inhibitory, the smallest active polypeptide fragment or fragments are identified. In a similar manner, analogs of the LBPs are tested to identify analogs which can act as inhibitors by binding to LDL. And, similarly, mimetics of LBP (molecules which resemble the conformation and/or charge distributions of the LDL-binding sites on LBP molecules) are tested in a similar fashion to identify molecules exhibiting affinities for the LDL-binding sites on LBP.

The affinities of the inhibitors so identified are at least as strong as the affinity of LDL itself for the LDL-binding sites on LBP. The inhibitors bind at least competitively, and some irreversibly and preferentially as well, to the LDL-binding sites, thereby rendering such sites unavailable for binding to humoral LDL.

Example 11

ELISA Assays

This example illustrates the use of ELISA plate assays for the quantification of a test compound's capacity to inhibit the binding of LDL to a specific LBP.

In one example, the ELISA assay was carried out as follows: LDL was diluted in 50 mM $Na_2HCO_3$, pH 9.6/0.02% $NaN_3$ and added to the wells of a 96-well plate (ImmunoWare 96-Well Reacti-Bind EIA Polystyrene Plates; Pierce (Rockford, Ill.)) to achieve a final concentration ranging from 0.1 to 1 µg/well. The plates were incubated for 6 hr at room temperature. At the end of the incubation period, the wells were washed 3 times with Tris-buffered saline, pH 7.4 (TBS), and blocked overnight with 200 µl of 1% bovine serum albumin (BSA) in TBS/0.02% $NaN_3$ (Sigma; St. Louis Mo.) at room temperature. The wells were then incubated with 200 µl of LBP protein (5-10 µg/well) in TBS and varying concentrations of the test compound. Plates were incubated for 1 hr at room temperature. The wells were then washed three times with TBS and blocked for 2 hr with 200 µl of 1% BSA in TBS/0.02% $NaN_3$ at room temperature. At the end of the incubation period, the wells were washed 3 times with TBS and a 1:1000 dilution (in TBS/0.05% Tween 20) of the appropriate guinea pig anti-LBP protein polyclonal antibody was added to the wells and incubated for 1 hr at room temperature. The wells were then washed 3 times with TBS/0.05% Tween 20; a 1:30,000 dilution of goat anti-guinea pig IgG alkaline phosphatase conjugate (Sigma) was added to each well. Plates were incubated for 1 hr at room temperature. The wells were washed 3 times with TBS/0.05% Tween 20 and a calorimetric reaction was carried out by adding 200 ml of p-nitrophenyl phosphate substrate (Sigma; St. Louis Mo.) to the wells. The reaction was allowed to proceed for 30 min at room temperature and stopped with 50 µl of 3N NaOH. The absorbance was determined at 405 nm using an ELISA plate reader. The test compound's effectiveness in blocking the binding of LDL to the recombinant protein was assessed by comparing the absorbance values of control and treated groups.

In a second example, the ELISA assay was carried out as follows: LDL was diluted in Tris-buffered saline, pH 7.4 (TBS) and added to the wells of a 96-well plate (ImmunoWare 96-Well Reacti-Bind EIA Polystyrene Plates; Pierce (Rockford, Ill.)) to give a plate-saturating concentration of 0.2 µg/well. The plate was incubated for 1 hr at room temperature, after which the wells were washed three times with TBS, before being blocked for 1 hr at room temperature with 1% bovine serum albumin (BSA in TBS). The wells were then washed twice with TBS before LBP-1 or LBP-2 (0.025 µg/well), or LBP-3 (0.01 µg/well) were added, without and with varying concentrations of the test inhibitor compound. Each condition was set up in quadruplicate. The plate was incubated for 1 hr at room temperature, then washed three times with TBS/0.02% Tween 20 (TBS/Tween). An appropriate dilution of guinea pig anti-LBP polyclonal antibody (1:750 to 1:1500, depending on the antibody) was added to three wells for each condition and incubated for 1 hr. Anti-LBP antibody was replaced by buffer for the fourth well of each condition, as a negative control. After 1 hr, the plate was again washed three times with TBS/Tween before a 1:10,000 dilution (in TBS/Tween) of goat anti-guinea pig IgG alkaline phosphatase-conjugated antibody (Sigma) was added to each well. The plate was incubated for 1 hr at room temperature, then washed three times with TBS/Tween. A fresh solution of substrate was prepared from an Alkaline Phosphatase Substrate Kit (Bio-Rad, Hercules, Calif.) as follows: Mix 1 ml 5× concentrated diethanolamine buffer with 4 ml distilled water. Add one tablet of p-nitrophenylphosphate (5 mg) and vortex until tablet is completely dissolved. Substrate solution was added to wells immediately. Increasing concentrations of diluted alkaline phosphatase-conjugated goat anti-guinea pig IgG (1:100,000 dilution in TBS/Tween) were added to five empty wells, followed by substrate, as a positive control. Following addition of substrate, the plate was immediately placed in an ELISA plate reader, allowed to stand at 37° C., generally for 75 min, before absorbance was measured at 405 nm. Incubation in the ELISA reader at 37° C. was sometimes adjusted to optimize absorbance (60-90 min). The effectiveness of the test inhibitor was determined, after subtracting absorbance of negative controls, by comparing absorbance in wells where an LBP was mixed with test inhibitor to absorbance in wells containing LBP with no inhibitor.

Alternatively, LBPs, rather than LDL, were bound to the plate. Recombinant LBP protein binding to LDL and the effect of varying concentration of the inhibitor on LBP-LDL binding was determined through the use of antibodies against LDL. This interaction was visualized through the use of a secondary antibody conjugated to a reporter enzyme (e.g. alkaline phosphatase).

ELISA plate assays were used to screen agents which can affect the binding of LBP proteins to LDL. For example, peptides derived from LBP-1 and human LBP-3 protein sequences (BHF-1 and BHF-2, respectively) were synthesized and have been shown to reduce the binding of LDL to recombinant LBP-1 and LBP-2 in this format. These results were in agreement with those obtained with the ACE assays.

Example 12

Administration of Humanized Antibodies Against LBPs so as to Block LDL-Binding Sites on the LBPs This example illustrates administration to patients of humanized antibodies against LBP-1, LBP-2 or LBP-3 so as to block LDL-binding sites on arterial LBP molecules. Mouse monoclonal antibodies are humanized by recombinant DNA techniques and produced by standard procedures known to those skilled in the art (Berkower, I., Curr. Opin. Biotechnol. 7:622-628 (1996); Ramharayan and Skaletsky, Am. Biotechnol. Lab 13: 26-28 (1995)) against LBPs and/or the LDL-binding sites on the LBPs. The corresponding Fab fragments are also produced, as described in Goding, J. W., Monoclonal Antibodies: Principles and Practice, Academic Press, New York, N.Y. (1986). These antibodies are administered parenterally in sufficient quantity so as to block LDL-binding sites on the LBP molecules, i.e., 1-10 mg/kg daily. This prevents the irreversible arterial uptake of LDL that is required to facilitate oxidation of the LDL.

Example 13

Preparation of LDL

This example illustrates the preparation of LDL. LDL was prepared from the plasma of normolipemic donors (Chang et al., Arterioscler. Thromb. 12:1088-1098 (1992)). 100 ml of whole blood was placed into tubes containing 100 mM disodium EDTA. Plasma was separated from red blood cells by low-speed centrifugation (2,000 g; 30 min; 4° C.). Plasma density was adjusted to 1.025 gm/ml with a solution of KBr and centrifuged for 18-20 hr, 100,000×g, 12° C. Very low density lipoproteins (VLDL) were removed from the tops of the centrifuge tubes with a Pasteur pipette. The density of the infranate was raised to 1.050 gm/ml with KBr solution and centrifuged for 22-24 hr, 100,000×g, 12° C. LDL was removed from the tops of the centrifuge tubes with a drawn out Pasteur pipette tip. Purity of the LDL preparation was checked by Ouchterlony double immunodiffusion against antibodies to human LDL, human HDL, human immunoglobulins, and human albumin. KBr was removed from the LDL solution by dialysis (1 L, ×2, approximately 16 hr) against 0.9% saline, pH 9.0, containing 1 mM EDTA and 10 µM butylated hydroxytoluene (BHT), the latter to prevent oxidation of LDL. Following dialysis, LDL protein was measured by the method of Lowry (Lowry et al., J. Biol. Chem. 193: 265-275 (1951)), and the LDL was stored at 4° C. until use. LDL preparations were kept for no more than 4-6 weeks.

Example 14

Preparation of HDL

This example illustrates the preparation of HDL. HDL was prepared from plasma of normolipemic donors. 100 ml of whole blood was placed into tubes containing 100 mM disodium EDTA and plasma was collected by centrifugation (2000 g; 30 min; 4° C.). Apolipoprotein B containing lipoproteins present in plasma were then precipitated by the sequential addition of sodium heparin (5,000 units/ml) and $MnCl_2$ (1M) to achieve a final concentration of 200 units/ml and 0.46 M, respectively (Warnick and Albers, J. Lipid Res. 19:65-76 (1978)). Samples were then centrifuged, (2000 g; 1 hr; 4° C.). The supernatant was collected and density adjusted to 1.21 g/ml by the slow addition of solid KBr. HDL was separated by ultracentrifugation (100,000 g; >46 hr; 12° C.). Purity of the HDL preparation was assessed via Ouchterlony double immunodiffusion test using antibodies against human HDL, human LDL, human immunoglobulins, and human albumin. HDL samples were dialyzed against saline pH 9.0/1 mM EDTA/10 μM BHT (4 L; 24 hr/4° C.) and total protein was determined by the Lowry protein assay (Lowry et al., J. Biol. Chem. 193:265-275 (1951)). HDL was stored at 4° C. until use. HDL preparations were kept for no longer than 2 weeks.

Example 15

Synthesis of BHF-1

This example illustrates the synthesis of BHF-1, a fragment of human or rabbit LBP-1 which contains amino acid residues 14 through 33. BHF-1 was synthesized using an Applied Biosystems Model 430A peptide synthesizer with standard T-Boc NMP chemistry cycles. The sequence of BHF-1 is as follows:

```
                                         (SEQ ID NO: 9)
val-asp-val-asp-glu-tyr-asp-glu-asn-lys-phe-val-
asp-glu-glu-asp-gly-gly-asp-gly.
```

After synthesis, the peptide was cleaved with hydrofluoric acid/anisole (10/1 v/v) for 30 min at −10° C. and then incubated for 30 min at 0° C. BHF-1 was then precipitated and washed three times with cold diethyl ether. Amino acid coupling was monitored with the ninhydrin test (>99%).

The BHF-1 peptide was purified to homogeneity by high performance liquid chromatography on a reverse phase Vydac $C_4$ column (2.24×25 cm) using a linear gradient separation (2-98% B in 60 min) with a flow rate of 9 ml/min. Buffer A consisted of 0.1% trifluoroacetic acid (TFA)/Milli Q water and Buffer B consisted of 0.085% TFA/80% acetonitrile. The gradient was run at room temperature and absorbance monitored at 210 and 277 nm.

Fast atom bombardment-mass spectrometry gave a protonated molecular ion peak $(M+H)^+$ at m/z=2290.2, in good agreement with the calculated value. On amino acid analysis, experimental values for the relative abundance of each amino acid in the peptide were in good agreement with theoretical values. The lyophilized peptide was stored at −20° C.

Example 16

In Vitro Screening for Agents which Inhibit Binding Between LDL and LBPs

This example illustrates in vitro screening for agents which inhibit binding between LDL and LBPs.

A candidate polypeptide for being an agent is chosen, e.g., LBP-1, LBP-2, LBP-3, BHF-1 or any other polypeptide. The shortest fragment of the polypeptide that inhibits LDL binding to LBPs in vitro is determined. Peptides are synthesized by standard techniques described herein. Inhibition assays are performed using standard ELISA techniques for screening, and affinity coelectrophoresis (ACE) assays to confirm the ELISA results, as described herein. Additional assays that can be used in this screening method include, e.g., fluorescence polarization and pulsed ultra-filtration electrospray mass spectrometry. Short peptides ranging, e.g., from dimers to 20-mers are constructed across sequences of the candidate polypeptide whose chemical characteristics make them likely LDL binding sites, e.g., acidic regions. The ability of shorter and shorter lengths of the peptides to inhibit LDL binding in vitro and to mammalian cells in culture is tested. For example, the effect of the peptide on inhibiting LDL binding in mammalian cells transfected to express an LBP gene is tested. Each of the peptides so identified as an inhibitor is tested with each of LBP-1, LBP-2 and LBP-3, to determine whether a single inhibitor works against all three LBPs.

Once the minimum active sequence is determined, the peptide backbone is modified so as to inhibit proteolysis, as discussed herein. For example, modification is accomplished by substitution of a sulfoxide for the carbonyl, by reversing the peptide bond, by substituting a methylene for the carbonyl group, or other similar standard methodology. See Spatola, A. F., "Peptide Backbone Modifications: A Structure-Activity Analysis of Peptides Containing Amide Bond Surrogates, Conformational Constraints, and Related Backbone Replacements," in Chemistry and Biochemistry of Amino Acids, Peptides and Proteins, Vol. 7, pp. 267-357, B. Weinstein (ed.), Marcel Dekker, Inc., New York (1983). The ability of these analogs to inhibit LDL binding to the LBPs in vitro is tested in a similar manner as for the natural peptides described above, e.g., by ELISA, ACE, fluorescence polarization, and/or pulsed ultra-filtration electrospray mass spectrometry.

Example 17

In Vitro Screening with Cultured Mammalian Cells for Agents which Inhibit Binding Between LDL and LBPs This example illustrates cell-based in vitro screening of agents which have been shown by in vitro tests such as ACE assay and ELISA to be potential inhibitors of binding between LDL and LBPs.

Mammalian cells, such as 293 cells, which are commonly used for expression of recombinant gene constructs, are used to develop cell lines which express LBPs on the cell surface. This is done by subcloning LBP open reading frames (ORFS) into a mammalian expression plasmid vector, pDisplay (Invitrogen, Carlsbad, Calif.), which is designed to express the gene of interest on the cell surface. The use of mammalian cells to produce LBPs allows for their expression in a functionally active, native conformation. Therefore, stably transfected mammalian cell lines with surface expression of LBPs individually, or in combination, are particularly suitable for assaying and screening inhibitors that block LDL binding in cell culture, as well as to evaluate the cytotoxicity of these compounds.

Specifically, LBP ORFs are amplified by PCR (Perkin Elmer, Foster City, Calif.) from cDNA templates using Taq polymerase (Perkin Elmer) and appropriate primers. The amplified LBP ORFs are purified by agarose gel electrophoresis and extracted from gel slices with the Bio-Rad DNA Purification kit (Bio-Rad, Hercules, Calif.). The purified DNAs are then cut with the restriction enzymes Bgl II and Sal I (New England Biolabs, Beverly, Mass.) to generate cohesive ends, and purified again by agarose gel electrophoresis and DNA extraction as described above. The LBP ORFs are then subcloned into the Bgl II/Sal I sites in the mammalian expression vector, pDisplay (Invitrogen) by ligation. Recombinant plasmids are established by transformation in $E.$ $coli$ strains TOP10 (Invitrogen) or DH5α (Life Technologies, Grand Island, N.Y.). Recombinant pDisplay/LBP plasmid DNA is isolated from overnight $E.$ $coli$ cultures with the Bio-Rad Plasmid Miniprep kit, cut with Bgl II/Sal I, and analyzed by agarose gel electrophoresis. LBP ORFs in successfully transformed clones are verified by automated dideoxy DNA sequencing. To transfect human kidney 293 cells, 1-2 µg of DNA is mixed with 6 µl lipofectamine reagent (Life Technologies) and incubated with the cells as described in the Life Technologies protocol. LBP expression in transfected cells is confirmed by Western blot analysis of cell extracts obtained 48 hr after transfection. To select for stably transfected 293 cells, the antibiotic G418 (Life Technologies) is added to the growth medium at a concentration of 800 µg/ml. Colonies resistant to G418 are tested for recombinant LBP expression by Western blot, and recombinant clones expressing LBPs are expanded, assayed for LDL binding and used to test compounds for their ability to inhibit LDL binding.

Example 18

In Vivo Screening for Agents which Inhibit Binding Between LDL and LBPs

This example illustrates in vivo screening of agents which have been shown by in vitro tests to be promising candidate inhibitors of binding between LDL and LBPs.

In vivo inhibitory activity is first tested in the healing balloon-catheter deendothelialized rabbit aorta model of arterial injury (Roberts et al., J. Lipid Res. 24:1160-1167 (1983); Chang et al., Arterioscler. Thromb. 12:1088-1098 (1992)). This model was shown to be an excellent analog for human atherosclerotic lesions. Other useful animal models for human atherosclerosis include Apo E knockout mice and LDL receptor knockout mice. Both of these mouse models are characterized by high levels of plasma cholesterol and the development of naturally-occurring atherosclerotic-like lesions.

Each candidate inhibitor is tested in five to ten ballooned rabbits, while an equal number of rabbits receive a control peptide, or placebo. Four weeks following aortic deendothelialization, when reendothelialization (healing) is partially complete, daily parenteral (intravenous or subcutaneous) or intragastric administration of the peptides and the analogs begins at an initial concentration of 10 mg/kg body weight, which is varied down, or up to 100 mg/kg depending on results. 30 min later, a bolus of intravenously injected $^{125}$I (or $^{99m}$Tc-) labeled LDL is given to test the candidate inhibitor's ability in short term studies to inhibit LDL sequestration in healing arterial lesions. If $^{125}$I-LDL is used, the animals are sacrificed 8-24 hr later, the aortas excised, washed and subjected to quantitative autoradiography of excised aortas, as previously described (Roberts et al., J. Lipid Res. 24:1160-1167 (1983); Chang et al., Arterioscler. Thromb. 12:1088-1098 (1992)). If $^{99m}$Tc-LDL is used, analysis is by external gamma camera imaging of the live anesthetized animal at 2-24 hr, as previously described (Lees and Lees, Syndromes of Atherosclerosis, in Fuster, ed., Futura Publishing Co., Armonk, N.Y., pp. 385-401 (1996)), followed by sacrifice, excision and imaging of the excised aorta. Immediately before the end of testing, the animals have standard toxicity tests, including CBC, liver enzymes, and urinalysis.

The compounds which are most effective and least toxic are then tested in short term studies of rabbits fed a 2% cholesterol diet (Schwenke and Carew, Arteriosclerosis 9:895-907 (1989)). Each candidate inhibitor is tested in five to ten rabbits, while an equal number of rabbits receive a control peptide, or placebo. Animals receive one or more doses per day of the candidate inhibitor, or placebo, for up to two weeks. Daily frequency of doses is determined by route of administration. If active drug or placebo are administered parenterally, they are given 1-3 times daily and the 2% cholesterol diet is continued. If drug or placebo are given orally, they are mixed with the 2% cholesterol diet. Schwenke and Carew (Arteriosclerosis 9:895-907 (1989)) have shown that the LDL concentration in lesion-prone areas of the rabbit aorta is increased 22-fold above normal in rabbits fed a 2% cholesterol diet for 16 days, and that the increased LDL content precedes the histological evidence of early atherosclerosis. Therefore, analysis of the effect of the candidate inhibitors is tested two weeks after the start of cholesterol feeding by injecting $^{125}$I-LDL, allowing it to circulate for 8-24 hr, and then performing quantitative autoradiography on the excised aortas of both test and control animals. If appropriate, quantitation of aortic cholesterol content is also carried out (Schwenke and Carew, Arteriosclerosis 9:895-907 (1989); Schwenke and Carew, Arteriosclerosis 9:908-918 (1989).

The above procedures identify the most promising candidate inhibitors, as well as the best route and frequency of their administration. Inhibitors so identified are then tested in long-term studies of cholesterol-fed rabbits. These tests are carried out in the same way as the short-term cholesterol feeding studies, except that inhibitor effectiveness is tested by injection of $^{125}$I-LDL at longer intervals following the initiation of cholesterol feeding, and lesion-prone areas of the aorta are examined histologically for evidence of atherosclerosis. Testing times are at two, four, and six months. Major arteries are examined grossly and histologically or evidence and extent of atherosclerosis. If necessary, other accepted animal models, such as atherosclerosis-susceptible primates (Williams et al., Arterioscler. Thromb. Vast. Biol. 15:827-836 (1995)), genetically altered mice, and/or Watanabe rabbits are tested with short- and long-term cholesterol feeding.

Example 19

In Vivo Inhibition of Radiolabeled LDL Accumulation in the Ballooned Deendothelialized Rabbit Aorta Via Induction of Active Immunity Against LBP Protein This example illustrates the effect that induction of immunity against LBP protein has on the accumulation of radiolabeled LDL in the ballooned deendothelialized rabbit aorta model of atherosclerosis.

Immunity was induced in male New Zealand White rabbits (Hazelton Research Products, Denver, Pa.) as follows: A mixture of purified human recombinant LBP-2 or BHF-1 peptide (1 ml; 1 mg) and RIBI adjuvant (RIBI ImmunoChem Research, Inc., Hamilton, Mont.) was injected subcutaneously at 2-5 sites along the dorsal thoracic and abdominal regions of the rabbits. Blood was collected by venipuncture on days 1 (preimmune bleeding), 35, 63, and 91. Booster injections were administered on days 28 (500 µg; SC), 56 (250 µg; SC), and 84 (125 µg; SC).

The titer of the rabbits was evaluated by serial dilution using an ELISA plate format. Preimmune serum was evaluated at the same time. After the third booster of LBP protein or peptide, the titer reached a maximal level with a detectable calorimetric response on an ELISA plate of 156 pg. Titer is defined as the maximum dilution of antibody which generates an absorbance reading of 0.5 above control in 30 min. Specificity of the polyclonal antibodies was demonstrated using Western blot analysis as described in Example 6.

On day 93, the abdominal aorta of immunized and control rabbits was deendothelialized using a Fogarty number 4 embolectomy catheter (Chang et al., Arteriosclerosis and Thrombosis 12:1088-1098 (1992)). Four weeks after ballooning, rabbits received a bolus injection of $^{125}$I-labeled LDL (1 ml; i.v.). Blood samples were collected at 1 hr intervals for 8 hr, and 24 hr post injection. Blood samples were centrifuged for 30 min at 2000 rpm (40° C.) and total activity present in the serum was determined using a Gamma counter. Total TCA precipitable counts were determined by addition of TCA to the serum to a final concentration of 10% followed by incubation for 10 min at 4° C. Serum samples were then centrifuged (2000 rpm; 30 min; 40° C.) and total activity present in the supernate was determined. TCA precipitable counts were calculated by subtraction: total soluble counts minus counts present in the supernate after TCA precipitation. Blood samples for the determination of antibody titers were collected prior to the injection of the radiolabeled LDL.

After 24 hr, the rabbits were injected intravenously with 5% Evan's blue dye which was allowed to circulate for 15 min. Areas of the aorta in which the endothelial covering is absent stain blue while those areas covered by endothelium remain unstained. At the end of the incubation period, the rabbits were euthanized and the abdominal and thoracic aorta were dissected out, rinsed, and fixed overnight in 10% TCA at room temperature. The aortas were then rinsed exhaustively with physiological saline, weighed, counted, blotted dry and placed onto X-ray film in order to visualize the pattern of radiolabeled LDL accumulation in the deendothelialized rabbit abdominal aorta.

Immunization of rabbits against recombinant human LBP-2 or BHF-1 peptide altered the pattern of radiolabeled LDL accumulation in the ballooned deendothelialized abdominal aorta. When corrected for dosage, and percent reendothelialization, immunized-ballooned rabbits had lower accumulation of radiolabeled LDL compared to nonimmune-ballooned rabbits. These results indicate that active immunization against LBP provides an effective means by which the accumulation of LDL in the injured arterial wall can be modified.

Example 20

Screening Agents in Humans which Inhibit Binding Between LDL and LBPs

Human studies are carried out according to standard FDA protocols for testing of new drugs for safety (Phase I), efficacy (Phase II), and efficacy compared to other treatments (Phase III). Subjects, who are enrolled into studies after giving informed consent, are between the ages of 18 and 70. Women who are pregnant, or likely to become pregnant, or subjects with diseases other than primary atherosclerosis, such as cancer, liver disease, or diabetes, are excluded. Subjects selected for study in FDA Phase II and Phase III trials have atherosclerotic disease previously documented by standard techniques, such as ultrasound and/or angiography, or are known to be at high risk of atherosclerosis by virtue of having at least one first degree relative with documented atherosclerosis. Subjects themselves have normal or abnormal plasma lipids. Initial testing includes 20-50 subjects on active drug and 20-50 subjects, matched for age, sex, and atherosclerotic status, on placebo. The number of subjects is pre-determined by the number needed for statistical significance. Endpoints for inhibitor efficacy includes ultrasound measurements of carotid artery thickness in high risk subjects, as well as in subjects with known carotid or coronary disease; atherosclerotic events; atherosclerotic deaths; and all-cause deaths in all subjects. Non-invasive analysis (carotid artery thickness by ultrasound) as per Stadler (Med. and Biol. 22:25-34 (1996)) are carried out at 6- to 12-month intervals for 3 years. Atherosclerotic events and deaths, as well as all-cause deaths are tabulated at 3 years.

Oral dosage of drug in FDA Phase I trials ranges from 0.01 to 10 gm/day, and is determined by results of animal studies, extrapolated on a per kg basis. Based on data obtained from Phase I studies, the dose range and frequency are narrowed in Phase II and III trials. If parenteral administration of drug is determined by animal studies to be the only effective method, parenteral administration in human subjects is tested by injection, as well as by the transdermal and nasal insufflation routes. Testing of parenteral drug follows the same outline as that for oral administration.

The optimal treatment schedule and dosage for humans is thus established.

Example 21

Treating an Individual Having Atherosclerosis with BHF-1

This example illustrates a method for treating an individual having atherosclerosis with an LBP fragment, e.g., BHF-1, so as to decrease the levels of arterially bound LDL in the individual. BHF-1 is obtained as described herein. The BHF-1 is administered to the mammal intravenously as a bolus or as an injection at a concentration of 0.5-10 mg/kg body weight. Such administrations are repeated indefinitely in order to prevent the development or progression of symptomatic atherosclerosis, just as is done currently with cholesterol lowering drugs. Stable subjects are examined twice yearly to evaluate the extent of any atherosclerotic disease by physical exam and non-invasive studies, such as carotid artery thickness, ultrasound, and/or gamma camera imaging of the major arteries, to determine if atherosclerotic lesions are present, and, if previously present, have regressed or progressed. Such a regimen results in treatment of the atherosclerosis.

Example 22

In Vivo Reduction of Atherosclerosis in Apo E Knockout Mice by Immunization with LBPs Separate immunization experiments were performed with each of LBP-1, LBP-2, and LBP-J. Immunity was induced by injecting apo E knockout mice with the LBP protein (LBP-1, LBP-2, or LBP-3) together with an RIBI adjuvant (RIBI ImmunoChem Research, Inc., Hamilton, Mont.). Apo E knockout mice (Jackson Laboratories, Bar Harbor, Me.) are hyperlipidemic and thus a model for human atherosclerosis. Apo E knockout mice have high levels of plasma cholesterol and develop naturally-occurring atherosclerotic-like lesions.

Four week old apo E knockout mice (Jackson Laboratories, Bar Harbor, Me.) were ear tagged, randomly assigned to different cages and weighed. Body weights were determined weekly. Animals were allowed to habituate for 1 week. Normal rodent chow was provided ad libitum and animals were maintained in a 12:12 light:dark cycle. The following four groups of mice were treated with either recombinant LBP proteins (40 μg of recombinant protein/mouse) plus RIBI adjuvant or RIBI adjuvant alone (control group).

LBP-1: Immunized with rabbit recombinant LBP-1 (6-His tag).

LBP-2: Immunized with rabbit recombinant LBP-2 clone 26 (6-His tag).

LBP-3: Immunized with rabbit recombinant LBP-3 (6-His tag).

Control: Received adjuvant.

Blood samples (pre-immune serum) were collected prior to the initial injection of recombinant protein and RIBI adjuvant (as described in the manufacturer's manual). After 21 days, mice received a booster injection (half-initial dose) and were then bled seven days later. Titer was defined as the maximum dilution of serum that yielded a change in absorbance equivalent to 2× that of control serum (60 min; 37° C.). The amount of recombinant protein per well was 100 ng.

Booster injections took place at 21 day intervals until an average titer value of 1:10,000 was reached. At this time, mice were switched to western type diet (Harland Teklad, Madison, Wis.) and fed ad libitum. Blood samples were collected at this time (retro-orbital sinus bleeding technique) and monthly thereafter.

Blood samples were analyzed for total cholesterol, HDL cholesterol, and triglyceride concentration with a commercially available total cholesterol and triglycerides assay kits (Sigma; St. Louis Mo.) using an ELISA format. HDL concentration was determined after Apo B containing lipoproteins were precipitated using heparin/$MnCl_2$.

Apo E knockout mice were sacrificed at 26 weeks of age. The mice were anesthetized with methoxyfluorane and exanguinated via cardiac puncture. A midline thoracotomy was performed, a cannula inserted into the right ventricle and perfusate allowed unrestricted flow via an incision into the right atrium. The mice were perfused with saline, followed by 10% phosphate buffered formalin until fasciculations stopped. At this time, the aorta was exposed and adventitial fat removed in situ. The aorta was then removed from the heart down to the iliac bifurcation and placed in 10% phosphate buffered formalin overnight.

The aorta was stained as follows: after a brief 70% ethanol rinse, it was immersed in a filtered solution of 0.5% (weight/volume) Sudan IV in 35% ethanol/50% acetone with continuous shaking for 10 minutes at room temperature. Unbound dye was removed by incubating the aorta in an 80% ethanol solution with shaking until the background color was clear. The vessel was then rinsed in distilled water, placed in physiological saline and opened longitudinally from the aortic arch down to the iliac bifurcation. The vessel was pinned out and photographed. Photographs were then digitized using an Astra 1200S scanner (UMAX Technologies Inc., Freemont, Calif.) and a commercially available graphics program (Canvas; Deneba Software, Miami Fla.). Total and lesion areas were determined using the signal processing toolbox of MAT-LAB (The Mathworks Inc., Natick, Mass.). Percent involvement was calculated by dividing lesion area by total area.

A second analysis was done to measure aortic atherosclerosis by a cholesterol extraction method whereby cholesterol is determined as a unit weight of artery. This method may be more accurate in measuring lesion size than attempting to measure the thickness of many sections. Specifically, the weight of an artery was measured, then the cholesterol was extracted. Aortic cholesterol content was then measured by gas-liquid chromatography. The amount of cholesterol per unit weight of artery was then determined.

After the first booster injection, some of the apo E knockout mice immunized against LBP-1 had relatively high anti-LBP-1 titers ($\leq 1:5000$) while others in the same group exhibited moderate levels (>1:500 to <1:1000). LBP-2/26 titers were low in the apoE knockout mice (<1:500) at this time. LBP-3 titers ranged from moderate to low ($\geq 1:500$ to <1:1000) to low (<1:500) in the apoE knockout mice.

After the second booster injection, Apo E knockout mice immunized against LBP-1 had moderate to high titers (>1:1000 to $\leq 1:8000$). Apo E knockout mice immunized against LBP-2/26 had moderate titer levels (>1:2000). LBP-3 titers range from moderate to high (>1:1000 to >1:8000) in the Apo knockout mice.

After the third booster injection, most of the mice immunized against LBP-1 had relatively high titers (>1:10,000) while others had moderate to high titers (>1000 to <1:10,000). Some of the Apo E knockout mice had moderate (<1:5000) to low (<1:1000) titers. LBP-3 titers ranged from high (>1:5000 to $\leq 1:10,000$) to moderate (>1:1000 to <1:5000).

Data were analyzed using T-tests and Wilcoxons. Immunization against LBP-1, LBP-2/26 or LBP-3 did not have a significant effect (P>0.05) on body weight of Apo E knockout mice. Due to the small sample size and the large variability present in the Apo E knockout mice, it was not possible to determine whether immunization against LBP-1, LBP-2/26 or LBP-3 had an effect on total cholesterol, HDL cholesterol or triglycerides concentration, but it did not appear to.

Immunization against LBP-1 or LBP-3 did not have a significant effect (P>0.05) on lesions of the apo E knockout mice or LDL receptor negative knockout mice. However, immunization of the apo E knockout mice against LBP-2 had a significant effect on lesion area (Table 2), and, once outliers were deleted, a significant effect on arterial wall cholesterol content (Table 3). The LBP-2 immunized apo E knockout mice had significantly reduced aortic atherosclerosis as compared to the control, non-immunized mice. Without being bound to any particular theory, the circulating antibodies generated against LBP-2 proteins are thought to block LDL binding to the artery wall.

TABLE 2

Lesion Area in LBP-Immunized Apo E Mice

| Apo E Mice | Lesion Area % Coverage | Treated Area Change | P-Value Wilcoxon |
|---|---|---|---|
| Control | 9.40 | | |
| LBP-1 | 6.05 | −0.36% | 0.07 |
| LBP-2 | 6.01 | −0.36% | 0.01 |
| LBP-3 | 7.14 | −0.24% | 0.36 |

TABLE 3

Arterial Cholesterol Content in LBP-Immunized Apo E Mice

| Apo E Mice | Arterial Wall Cholesterol (ug cholesterol/mg aorta) | Treated Area Cholesterol Change | P-Value Wilcoxon |
|---|---|---|---|
| Control | 6.33 | | |
| LBP-1 | 3.82 | −0.40% | 0.14 |
| LBP-2 | 3.28 | −0.48% | 0.07 |
| LBP-2 (outliers deleted) | 1.83 | −0.71% | 0.01 |
| LBP-3 | 4.48 | −0.29% | 0.20 |

Example 23

In Vivo Reduction of Atherosclerosis in LDL Receptor Knockout Mice by Immunization with BHF-1

An immunization experiment was performed with the BHF-1 peptide. LDL receptor (LDLR) knockout mice (B6, 129S-Ldlr$^{tm1Her}$, Jackson Laboratories, Bar Harbor, Me.) were injected with the BHF-1 peptide (see Example 15 for methods of synthesizing the BHF-1 peptide) together with an RIBI adjuvant (RIBI ImmunoChem Research, Inc., Hamilton, Mont.). LDLR knockout mice are hyperlipidemic and thus a model for human atherosclerosis. LDLR knockout mice have high levels of plasma cholesterol and develop naturally-occurring atherosclerotic-like lesions.

Four week old LDLR knockout mice were ear tagged, randomly assigned to different cages and weighed. Body weights were subsequently determined weekly. Animals were allowed to habituate for one week prior to experimentation. Normal rodent chow was provided ad libitum and animals were maintained in a 12:12 light:dark cycle. Animals were divided into experimental and control groups, as follows: (1) experimental, 16 mice were immunized with the BHF-1.20.L peptide; (2) control, 8 mice were immunized against bovine serum albumin.

Mice in the experimental group received subcutaneous injections (9.99 μg/g body weight; 200 μl final volume) of the BHF-1.20.L peptide daily for 2 weeks, from 5 to 7 weeks of age, prior to the initial injection with the peptide and adjuvant. Blood samples (pre-immune serum) were collected prior to the initial injection of BHF-1.20.L and RIBI adjuvant (50 μg of peptide/mouse) (as described in the manufacturer's manual) at 7 weeks of age. After 21 days, mice received a booster injection (half-initial dose) and were then bled 7 days later. Titer was defined as the maximum dilution of serum that yielded a change in absorbance equivalent to 2× that of control serum (60 min; 37° C.). The amount of peptide per well was 100 ng. Booster injections took place at 21 days interval.

Blood samples were analyzed for total cholesterol, HDL cholesterol, and triglyceride concentration, using commercially available total cholesterol and triglycerides assay kits (Sigma, St. Louis Mo.) (ELISA). HDL concentration was determined after Apo B containing lipoproteins were precipitated using heparin/MnCl$_2$.

When fed a normal rodent chow, total serum cholesterol concentration in LDLR knockout mice remains relatively low. A high fat diet, on the other hand, results in an increase in total serum cholesterol concentration in these mice. The animals were thus switched at 16 weeks of age to a modified "Western Type" diet (0.1% cholesterol content) (Harland Teklad, Madison, Wis.) and fed ad libitum. This diet was expected to increase the total serum cholesterol concentration to a range of 600-800 mg/dl, thereby increasing the rate of lesion formation. Blood samples were collected at 18 weeks of age (retro-orbital sinus bleeding technique) and monthly thereafter.

At 30 weeks of age, the mice were sacrificed and aorta were removed as described in Example 22. Aortic atherosclerosis was measured by the cholesterol extraction method described in Example 22, whereby cholesterol is determined as a unit weight of artery.

Immunization against BHF-1.20.L had no effect on body weight of LDLR knockout mice. Consumption of the modified "Western Type" diet for 12 weeks significantly ($P<0.05$) increased total serum cholesterol, HDL cholesterol and triglycerides in both experimental and control animals. Levels of total serum cholesterol, HDL serum cholesterol and serum triglyceride concentration were not significantly different ($P>0.05$) between experimental and control animals.

Mice that were immunized with the BHF-1 peptide had 24% less aortic cholesterol content ($P>0.037$) as compared to the control, non-immunized mice. Without being bound to any particular theory, the immunization is thought to generate circulating antibodies against the BHF-1 peptide. These antibodies are thought to block LDL binding to the artery wall, thereby reducing aortic cholesterol content.

Those skilled in the art will be able to ascertain using no more than routine experimentation, many equivalents of the specific embodiments of the invention described herein. These and all other equivalents are intended to be encompassed by the following claims.

The invention claimed is:

1. A method for identifying a candidate agent that inhibits the binding of low density lipoprotein binding protein-2 (LBP-2) to an LBP-2 binding molecule, the method comprising:
   contacting in vitro an LBP-2 polypeptide, an LBP-2 binding molecule and a candidate agent, wherein the LBP-2 polypeptide comprises an amino acid sequence that binds to LDL and (i) has at least 80% sequence identity to the amino acid sequence of SEQ ID NO: 7; (ii) is identical to a fragment of at least ten amino acid residues of SEQ ID NO:7; or (iii) differs by one or more conservative amino acid substitutions from the amino acid sequence of SEQ ID NO:7; and
   measuring the formation of a complex containing the LBP-2 polypeptide and the LBP-2 binding molecule, wherein a reduction in the formation of the complex in the presence of the candidate agent as compared with in the absence of the candidate agent indicates that the candidate agent inhibits the binding of LBP-2 to the LBP-2 binding molecule.

2. The method of claim 1, wherein the LBP-2 binding molecule is low density lipoprotein (LDL).

3. The method of claim 2, wherein the LDL is native LDL.

4. The method of claim 2, wherein the LDL is modified LDL.

5. The method of claim 4, wherein the modified LDL is methylated LDL or oxidized LDL.

6. The method of claim 1, wherein the LBP-2 binding molecule is an extracellular matrix component.

7. The method of claim 6, wherein the extracellular matrix component is a proteoglycan.

8. The method of claim 1, wherein the formation of the complex is measured by an affinity coelectrophoresis (ACE) assay.

9. The method of claim 1, wherein the formation of the complex is measured by an enzyme-linked immunosorbent assay (ELISA).

10. The method of claim 1, wherein the LBP-2 polypeptide comprises the amino acid sequence of SEQ ID NO: 19, SEQ ID NO: 20, SEQ ID NO: 21, or SEQ ID NO: 22.

11. The method of claim 1, wherein the LBP-2 polypeptide comprises an amino acid sequence that has at least 80% sequence identity to the amino acid sequence of SEQ ID NO:7.

12. The method of claim 1, wherein the LBP-2 polypeptide comprises an amino acid sequence that has at least 90% sequence identity to the amino acid sequence of SEQ ID NO:7.

13. The method of claim 1, wherein the LBP-2 polypeptide comprises an amino acid sequence that has at least 95% sequence identity to the amino acid sequence of SEQ ID NO:7.

14. The method of claim 1, wherein the LBP-2 polypeptide comprises the amino acid sequence of SEQ ID NO: 7.

15. The method of claim 1, wherein the LBP-2 polypeptide comprises an amino acid sequence that is identical to a fragment of at least ten amino acid residues of SEQ ID NO:7.

16. The method of claim 1, wherein the LBP-2 polypeptide comprises an amino acid sequence that differs by one or more conservative amino acid substitutions from the amino acid sequence of SEQ ID NO:7.

17. The method of claim 1, wherein the candidate agent is a nucleic acid, antibody, metabolite, carbohydrate, glycoprotein, peptide, or non-peptide mimetic.

18. The method of claim 1, wherein the LBP-2 polypeptide is immobilized on a surface during the contacting step.

19. The method of claim 1, wherein the LBP-2 binding molecule is immobilized on a surface during the contacting step.

20. The method of claim 1, wherein the LBP-2 polypeptide is expressed on the surface of a cell.

21. The method of claim 20, wherein the cell is a cell line transfected with an expression vector encoding a protein comprising the LBP-2 polypeptide.

22. A method for identifying a candidate agent that inhibits the binding of low density lipoprotein binding protein-2 (LBP-2) to an LBP-2 binding molecule, the method comprising:
   contacting in vitro an LBP-2 polypeptide, an LBP-2 binding molecule and a candidate agent, wherein the LBP-2 polypeptide comprises an amino acid sequence that binds to LDL and (i) has at least 80% sequence identity to the amino acid sequence of SEQ ID NO:43; (ii) is identical to a fragment of at least ten amino acid residues of SEQ ID NO:43; or (iii) differs by one or more conservative amino acid substitutions from the amino acid sequence of SEQ ID NO:43; and
   measuring the formation of a complex containing the LBP-2 polypeptide and the LBP-2 binding molecule, wherein a reduction in the formation of the complex in the presence of the candidate agent as compared with in the absence of the candidate agent indicates that the candidate agent inhibits the binding of LBP-2 to the LBP-2 binding molecule.

23. The method of claim 22, wherein the LBP-2 binding molecule is low density lipoprotein (LDL).

24. The method of claim 23, wherein the LDL is native LDL.

25. The method of claim 23, wherein the LDL is modified LDL.

26. The method of claim 25, wherein the modified LDL is methylated LDL or oxidized LDL.

27. The method of claim 22, wherein the LBP-2 binding molecule is an extracellular matrix component.

28. The method of claim 27, wherein the extracellular matrix component is a proteoglycan.

29. The method of claim 22, wherein the formation of the complex is measured by an affinity coelectrophoresis (ACE) assay.

30. The method of claim 22, wherein the formation of the complex is measured by an enzyme-linked immunosorbent assay (ELISA).

31. The method of claim 22, wherein the LBP-2 polypeptide comprises an amino acid sequence that has at least 80% sequence identity to the amino acid sequence of SEQ ID NO:43.

32. The method of claim 22, wherein the LBP-2 polypeptide comprises an amino acid sequence that has at least 90% sequence identity to the amino acid sequence of SEQ ID NO:43.

33. The method of claim 22, wherein the LBP-2 polypeptide comprises an amino acid sequence that has at least 95% sequence identity to the amino acid sequence of SEQ ID NO:43.

34. The method of claim 22, wherein the LBP-2 polypeptide comprises the amino acid sequence of SEQ ID NO: 43.

35. The method of claim 22, wherein the LBP-2 polypeptide comprises an amino acid sequence that is identical to a fragment of at least ten amino acid residues of SEQ ID NO:43.

36. The method of claim 22, wherein the LBP-2 polypeptide comprises an amino acid sequence that differs by one or more conservative amino acid substitutions from the amino acid sequence of SEQ ID NO:43.

37. The method of claim 22, wherein the candidate agent is a nucleic acid, antibody, metabolite, carbohydrate, glycoprotein, peptide, or non-peptide mimetic.

38. The method of claim 22, wherein the LBP-2 polypeptide is immobilized on a surface during the contacting step.

39. The method of claim 22, wherein the LBP-2 binding molecule is immobilized on a surface during the contacting step.

40. The method of claim 22, wherein the LBP-2 polypeptide is expressed on the surface of a cell.

41. The method of claim 40, wherein the cell is a cell line transfected with an expression vector encoding a protein comprising the LBP-2 polypeptide.

* * * * *